US009267162B2

(12) United States Patent
Burgard et al.

(10) Patent No.: US 9,267,162 B2
(45) Date of Patent: Feb. 23, 2016

(54) MICROORGANISMS AND METHODS FOR THE PRODUCTION OF CAPROLACTONE

(71) Applicant: Genomatica, Inc., San Diego, CA (US)

(72) Inventors: Anthony P. Burgard, Bellefonte, PA (US); Robin E. Osterhout, San Diego, CA (US); Priti Pharkya, San Diego, CA (US); Mark J. Burk, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

(21) Appl. No.: 14/596,072

(22) Filed: Jan. 13, 2015

(65) Prior Publication Data

US 2015/0353975 A1   Dec. 10, 2015

Related U.S. Application Data

(63) Continuation of application No. 13/668,117, filed on Nov. 2, 2012, now Pat. No. 8,940,509.

(60) Provisional application No. 61/554,920, filed on Nov. 2, 2011.

(51) Int. Cl.
*C08G 63/02* (2006.01)
*C12P 17/08* (2006.01)
*C12N 15/70* (2006.01)
*C07D 313/04* (2006.01)

(52) U.S. Cl.
CPC ............... *C12P 17/08* (2013.01); *C07D 313/04* (2013.01); *C12N 15/70* (2013.01)

(58) Field of Classification Search
CPC .......... C08G 63/08; A61L 31/06; C08L 67/04
USPC .......................... 435/135; 528/354, 355, 357
See application file for complete search history.

(56) References Cited

U.S. PATENT DOCUMENTS

| | | | |
|---|---|---|---|
| 5,686,276 | A | 11/1997 | Laffend et al. |
| 5,958,745 | A | 9/1999 | Gruys et al. |
| 6,790,645 | B2 | 9/2004 | Brzostowicz et al. |
| 7,105,296 | B2 | 9/2006 | Bramucci et al. |
| 7,127,379 | B2 | 10/2006 | Palsson et al. |
| 7,229,804 | B2 | 6/2007 | Huisman et al. |
| 7,799,545 | B2 | 9/2010 | Burgard et al. |
| 7,947,483 | B2 | 5/2011 | Burgard et al. |
| 2002/0012939 | A1 | 1/2002 | Palsson et al. |
| 2002/0168654 | A1 | 11/2002 | Maranas et al. |
| 2003/0059792 | A1 | 3/2003 | Palsson et al. |
| 2003/0224363 | A1 | 12/2003 | Park et al. |
| 2003/0233218 | A1 | 12/2003 | Schilling et al. |
| 2004/0009466 | A1 | 1/2004 | Maranas et al. |
| 2004/0029149 | A1 | 2/2004 | Palsson et al. |
| 2004/0072723 | A1 | 4/2004 | Palsson et al. |
| 2008/0033138 | A1 | 2/2008 | Carr et al. |
| 2009/0047719 | A1 | 2/2009 | Burgard et al. |
| 2011/0008861 | A1 | 1/2011 | Berry et al. |
| 2011/0091944 | A1 | 4/2011 | Wu et al. |
| 2011/0183393 | A1 | 7/2011 | Dundon et al. |
| 2011/0201089 | A1 | 8/2011 | Burgard et al. |

FOREIGN PATENT DOCUMENTS

| | | |
|---|---|---|
| WO | WO 03/106998 | 12/2003 |
| WO | WO 2004/024876 | 3/2004 |
| WO | WO 2004/056963 | 7/2004 |
| WO | WO 2007/141208 | 12/2007 |
| WO | WO 2008/080124 | 7/2008 |
| WO | WO 2008/137403 | 11/2008 |
| WO | WO 2010/068953 | 6/2010 |
| WO | WO 2011/022651 | 2/2011 |

OTHER PUBLICATIONS

Adams et al., "Oxidoreductase-type Enzymes and Redox Proteins Involved in Fermentative Metabolisms of Hyperthermophilic Archaea," Archaea. Adv. Protein Chem. 48:101-180 (1996).
Agnihotri et al., "Enoyl-CoA Hydratase: Reaction, Mechanism, and Inhibition," Bioorg.Med.Chem. 11:9-20 (2003).
Aharoni et al., "Directed evolution of mammalian paraoxonases PON1 and PON3 for bacterial expression and catalytic specialization," Proc.Natl.Acad.Sci.U.S.A 101:482-487 (2004).
Alber et al., "Malonyl-Coenzyme A Reductase in the Modified 3-Hydroxypropionate Cycle for Autotrophic Carbon Fixation in Archaeal Metallosphaera and *Sulfolobus* spp.," J. Bacteriol. 188:8551-8559 (2006).
Alber et al., "Study of an alternate glyoxylate cycle for acetate assimilation by Rhodobacter sphaeroides," Mol.Microbiol 61:297-309 (2006).
Altmiller et al., "Purification and Properties of Dihydroxy Acid Dehydratase from Soluble and Mitochondrial Fractions of Neurospora crassa," Arch.Biochem.Biophys. 138:160-170 (1970).
Aoshima and Igarashi, "Nondecarboxylating and Decarboxylating Isocitrate Dehydrogenases: Oxalosuccinate Reductase as an Ancestral Form of Isocitrate Dehydrogenase," J. Bacteriol. 190:2050-2055 (2008).
Aoshima and Igarashi, "A novel oxalosuccinate-forming enzyme involved in the reductive carboxylation of 2-oxoglutarate in Hydrogenobacter thermophilus TK-6," Mol. Microbiol. 62:748-759 (2006).
Aoshima et al., "A novel enzyme, citryl-CoA synthetase, catalysing the first step of the citrate cleavage reaction in Hydrogenobacter thermophilus TK-6," Mol. Micrbiol. 52:751-761 (2004).
Aoshima et al., "A novel biotin protein required for reductive carboxylation of 2-oxoglutarate by isocitrate dehydrogenase in Hydrogenobacter thermophilus TK-6," Mol. Microbiol. 51:791-798 (2004).

(Continued)

*Primary Examiner* — Terressa Boykin
(74) *Attorney, Agent, or Firm* — Jones Day

(57) ABSTRACT

The invention provides non-naturally occurring microbial organisms containing caprolactone pathways having at least one exogenous nucleic acid encoding a butadiene pathway enzyme expressed in a sufficient amount to produce caprolactone. The invention additionally provides methods of using such microbial organisms to produce caprolactone by culturing a non-naturally occurring microbial organism containing caprolactone pathways as described herein under conditions and for a sufficient period of time to produce caprolactone.

20 Claims, 9 Drawing Sheets

(56) References Cited

OTHER PUBLICATIONS

Aoshima et al., "A novel enzyme, citryl-CoA lyase, catalysing the second step of the citrate cleavage reaction in Hydrogenobacter thermophilus TK-6," Mol. Microbiol. 52:763-770 (2004).
Aoshima, M., "Novel enzyme reactions related to the tricarboxylic acid cycle: phylogenetic/functional implications and biotechnological applications," Appl. Microbiol. Biotechnol. 75:249-255 (2007).
Arikawa et al., "Soluble fumarate reductase isoenzymes from *Saccharomyces cerevisiae* are required for anaerobic growth," FEMS Microbiol. Lett. 165:111-116 (1998).
Armstrong et al., "Stereoselectivity and Stereospecificity of the α,β-Dihydroxy Acid Dehydratase From *Salmonella typhimurium*," Biochim.Biophys.Acta 498:282-293 (1977).
Arps et al., "Genetics of Serine Pathway Enzymes in Methylobacterium extorquens AM1: Phosphoenolpyruvate Carboxylase and Malyl Coenzyme A Lyase," J. Bacteriol. 175:3776-3783 (1993).
Atsumi et al., "Metabolic engineering of *Escherichia coli* for 1-butanol production," Metab Eng 10:305-311 (2008).
Atsumi et al., "Non-fermentative pathways for synthesis of branched-chain higher alcohols as biofuels," Nature 451:86-89 (2008).
Autor et al., "The Interactions of Acetoacetate Decarboxylase with Carbonyl Compounds, Hydrogen Cyanide, and an Organic Mercurial," J Biol.Chem. 245:5214-5222 (1970).
Ay et al, "Cloning, purification and characterization of a thermostable carboxylesterase from *Anoxybacillus* sp. PDF1," Prot Expr Purif 80:74-9 (2011).
Bartsch et al., "Only plant-type (GLYK) glycerate kinases produce D-glycerate 3-phosphate," FEBS Lett. 582:3025-3028 (2008).
Bekal et al., "Purification of Leuconostoc mesenteroides Citrate Lyase and Cloning and Characterization of the citCDEFG Gene Cluster," J. Bacteriol. 180:647-654 (1998).
Benner and Rozzell, "Stereospecificity and Stereochemical Infidelity of Acetoacetate Decarboxylase," J.Am.Chem.Soc. 103:993-994 (1981).
Berg et al., "A 3-Hydroxypropionate/4-Hydroxybutyrate Autotrophic Carbon Dioxide Assimilation Pathway in Archaea," Science 318:1782-1786 (2007).
Bergquist and Gibbs, "Degenerate Oligonucleotide Gene Shuffling," Methods Mol.Biol 352:191-204 (2007).
Bergquist et al., "Degenerate oligonucleotide gene shuffling (DOGS) and random drift mutagenesis (RNDM): Two complementary techniques for enzyme evolution," Biomol. Eng. 22:63-72 (2005).
Berman et al., "The Pathway of myo-Inositol Degradation in Aerobacter aerogenes," J Biol.Chem. 241:800-806 (1966).
Bernhard et al., "Functional and structural role of the cytochrome b subunit of the membrane-bound hydrogenase complex of Alcaligenes eutrophus H16," Eur. J. Biochem. 248, 179-186 (1997).
Bianchi et al., "*Escherichia coli* Ferredoxin NADP+ Reductase: Activation of *E. coli* Anaerobic Ribonucleotide Reduction, Cloning of the Gene (fpr), and Overexpression of the Protein," J Bacteriol. 175:1590-1595 (1993).
Billecke et al., "Human Serum Paraoxonase (PON1) Isozymes Q and R Hydrolyze Lactones and Cyclic Carbonate Esters," Drug Metab Dispos. 28:1335-1342 (2000).
Binieda et al., "Purification, characterization, DNA sequence and cloning of a pimeloyl-CoA synthetase from Pseudomonas mendocina 35," Biochem.J 340 ( Pt 3):793-801 (1999).
Binstock et al., "Fatty Acid Oxidation Complex from *E. coli*," Methods Enzymol. 71 Pt C:403-411 (1981).
Bisswanger, "Substrate Specificity of the Pyruvate Dehydrogenase Complex from *Escherichia coli*," J. Biol. Chem. 256:815-82 (1981).
Blaschkowski et al., "Routes of Flavodoxin and Ferredoxin Reduction in *Escheichia coli*," Eur. J. Biochem. 123:563-569 (1982).
Bobik et al., "Propanediol Utilization Genes (pdu) of *Salmonella typhimurium*: Three Genes for the Propanediol Dehydratase," J Bacteriol. 179:6633-6639 (1997).
Bock et al., "Purification and Characterization of Two Extremely Thermostable Enzymes, Phosphate Acetyltransferase and Acetate Kinase, from the Hyperthermophilic Eubacterium Thermotoga maritime," J Bacteriol. 181:1861-1867 (1999).
Bott and Dimroth, "Klebsiella pneumonia genes for citrate lyase and citrate lyase ligase: localization, sequencing, and expression," Mol. Microbiol. 14:347-356 (1994).
Bott, "Anaerobic citrate metabolism and its regulation in enterobacteria," Arch. Microbiol. 167: 78-88 (1997).
Bower et al., "Cloning, Sequencing, and Characterization of the Bacillus subtilis Biotin Biosynthetic Operon," J Bacteriol 178(14):4122-4130 (1996).
Boynton et al., "Cloning, Sequencing, and Expression of Clustered Genes Encoding b-Hydroxybutyryl-Coenzyme A (CoA) Dehydrogenase, Crotonase, and Butyryl-CoA Dehydrogenase from Clostridium acetobutylicum ATCC 824," J Bacteriol. 178:3015-3024 (1996).
Brasen and Schonheit, "Unusual ADP-forming acetyl-coenzyme A synthetases from the mesophilic halophilic euryarchaeon Haloarcula marismortui and from the hyperthermophilic crenarchaeon Pyrobaculum aerophilum," Arch. Microbiol. 182:277-287 (2004).
Bravo et al., "Reliable, Sensitive, Rapid and Quantitative Enzyme-Based Assay for Gamma-Hydroxybutyric Acid (GHB)," J Forens Sci, 49:379-387 (2004).
Breitkreuz et al., "A Novel-Hydroxybutyrate Dehydrogenase," J Biol Chem, 278:41552-41556 (2003).
Bremer, "Pyruvate Dehydrogenase, Substrate Specificity and Product Inhibition," Eur. J. Biochem. 8:535-540 (1969).
Brown et al., "The Enzymatic Introconversion of Acetate and Acetyl-coenzyme A in *Escherichia coli*," J. Gen. Microbiol. 102:327-336 (1977).
Brzostowicz et al, "mRNA Differential Display in a Microbial Enrichment Culture: Simultaneous Identification of Three Cyclohexanone Monooxygenases from Three Species," AEM 69:334-42 (2003).
Buck et al., "Primary Structure of the Succinyl-CoA Synthetase of *Escherichia coli*," Biochemistry 24:6245-6252 (1985).
Buckel et al., "Glutaconate CoA-Transferase from Acidaminococcus fermentans," Eur.J Biochem. 118:315-321 (1981).
Burgard et al., "OptKnock: A Bilevel Programming Framework for Identifying Gene Knockout Strategies for Microbial Strain Optimization," Biotechnol. Bioeng. 84:647-657 (2003).
Burgard et al., "Minimal Reaction Sets for *Escherichia coli* Metabolism under Different Growth Requirements and Uptake Environments," Biotechnol. Prog. 17:791-797 (2001).
Burgdorf, "The Soluble NAD-Reducing [NiFe]-Hydrogenase from Ralstonia eutropha H16 Consists of Six Subunits and Can Be Specifically Activated by NADPH," J. Bact. 187(9) 3122-3132(2005).
Buu et al., "Functional Characterization and Localization of Acetyl-CoA Hydrolase, Ach1p, in *Saccharomyces cerevisiae*," J.Biol.Chem. 278:17203-17209 (2003).
Campbell et al., "A new *Escherichia coli* metabolic competency: growth on fatty acids by a novel anaerobic b-oxidation pathway," Mol.Microbiol 47:793-805 (2003).
Cary et al., "Cloning and Expression of Clostridium acetobutylicum ATCC 824 Acetoacetyl-Coenzyme A:Acetate/Butyrate: Coenzyme A-Transferase in *Escherichia coli*," Appl Environ Microbiol 56:1576-1583 (1990).
Charrier et al., "A novel class of CoA-transferase involved in shortchain fatty acid metabolism in butyrate-producing human colonic bacteria," Microbiology 152, 179-185 (2006).
Chen et al., "The Control Region of the pdu/cob Regulon in *Salmonella typhimurium*," J Bacteriol. 176:5474-5482 (1994).
Cheng et al., "Genetic Analysis of a Gene Cluster for Cyclohexanol Oxidation in *Acinetobacter* sp. Strain SE19 by In Vitro Transposition," J Bacteriol. 182:4744-4751 (2000).
Clark, "Molybdenum cofactor negative mutants of *Escherichia coli* use citrate anaerobically," FEMS Microbiol. Lett. 55:245-249 (1990).
Coco et al., "DNA shuffling method for recombined genes and evolved enzymes," Nat. Biotechnol. 19:354-359 (2001).
Colonna et al., "Synthesis and radiocarbon evidence of terephthalate polyesters completely prepared from renewable resources," Green Chemistry, 13:2543-2548 (2011).

(56) References Cited

OTHER PUBLICATIONS

Conrad et al., "D- and L-Isoleucine Metabolism and Regulation of Their Pathways in Pseudomonas putida," J Bacteriol. 118:103-111 (1974).
Coppi, "The hydrogenases of Geobacter sulfurreducens: a comparative genomic perspective," Microbiology 151, 1239-1254 (2005)).
Corthesy-Theulaz et al., "Cloning and Characterization of Helicobacter pylori Succinyl CoA:Acetoacetate CoA-transferase, a Novel Prokaryotic Member of the CoA-transferase Family," J Biol. Chem. 272:25659-25667 (1997).
Cracknell, et al., "A kinetic and thermodynamic understanding of O2 tolerance in [NiFe]-hydrogenases," Proc Nat Acad Sci, 106(49) 20681-20686 (2009).
Cunningham et al., "Transcriptional regulation of the aconitase genes (acnA and acnB) of *Escherichia coli*," Microbiology 143 (Pt 12):3795-3805 (1997).
Currie et al., "Authentication and dating of biomass components of industrial materials; links to sustainable technology," Nuclear Instruments and Methods in Physics Research B, 172:281-287 (2000).
Dangel et al., "Enzyme reactions involved in anaerobic cyclohexanol metabolism by a denitrifying *Pseudomonas* species," 152:271-279 (1989).
Dartois et al., "Cloning, nucleotide sequence and expression in *Escherichia coli* of a lipase gene from Bacillus subtilis 168," Biochim.Biophys.Acta 1131:253-260 (1992).
Davey et al., "The Metabolism of trans-Cyclohexan-1,2-diol by an *Acinetobacter* Species," Eur.J Biochem. 74:115-127 (1977).
de Vries et al, "Functional Characterization of Mitochondrial Carnitine almitoyltransferases I and II Expressed in the Yeast Pichia pastoris," Biochem 36:5285-92 (1997).
Deana R., "Substrate Specificity of a Dicarboxyl-CoA: Dicarboxylic Acid Coenzyme a Transferase from Rat Liver Mitochondria," Biochem Int 26:767-773 (1992).
Denk et al, "L-Cysteine Biosynthesis in *Escherichia cok* Nucleotide Sequence and Expression of the Serine Acetyltransferase (cysE) Gene from the Wild-type and a Cysteine-excreting Mutant," J Gen Microbiol 133:515-25 (1987).
Di Gennaro et al., "Styrene lower catabolic pathway in Pseudomonas Xuorescens ST: identiWcation and characterization of genes for phenylacetic acid degradation," Arch.Microbiol 188:117-125 (2007).
Diao et al., "Crystallization of butyrate kinase 2 from Thermotoga maritima mediated by vapor diffusion of acetic acid," Acta Crystallogr.D.Biol.Crystallogr. 59:1100-1102 (2003).
Diao et al., "Crystal Structure of Butyrate Kinase 2 from Thermotoga maritima, a Member of the ASKHA Superfamily of Phosphotransferases," J Bacteriol. 191:2521-2529 (2009).
Diaz et al., "Characterization of the hca Cluster Encoding the Dioxygenolytic Pathway for Initial Catabolism of 3-Phenylpropionic Acid in *Escherichia coli*K-12," J. Bacteriol. 180:2915-2923 (1998).
Dobbek et al., "Crystal Structure of a Carbon Monoxide Dehydrogenase Reveals a [Ni-4Fe-5S] Cluster," Science 293:1281-1285 (2001).
Doo et al, "Productivity of cyclohexanone oxidation of the recombinant Corynebacterium glutamicum expressing chnB of Acinetobacter calcoaceticus," J Biotechnol 142:164-9 (2009).
Dorner and Boll, "Properties of 2-Oxoglutarate:Ferredoxin Oxidoreductase from Thauera aromatica and Its Role in Enzymatic Reduction of the Aromatic Ring," J. Bacteriol. 184 (14), 3975-83 (2002).
Doten et al., "Cloning and Genetic Organization of the pca Gene Cluster from Acinetobacter calcoacetius," J Bacteriol. 169:3168-3174 (1987).
Doughty et al., "Purification and Properties of D-Glycerate 3-Kinase from *Escherichia coli*," J Biol.Chem. 241:568-572 (1966).
Draganov et al., "Human paraoxonases (PON1, PON2, and PON3) are lactonases with overlapping and distinct substrate specificities," J.Lipid Res. 46:1239-1247 (2005).
Drake and Daniel, "Physiology of the thermophilic acetogen Moorella thermoacetica," Res. Microbiol. 155:869-883 (2004).

Drake, H. L., "Demonstration of Hydrogenase in Extracts of the Homoacetate-Fermenting Bacterium Clostridium thermoaceticum," J. Bacteriol. 150:702-709 (1982).
Driscoll et al., "Sequence Organization and Regulation of the Bacillus subtilis menBE Operon," J. Batceriol. 174:5063-5071 (1992).
Duncan et al., "Acetate Utilization and Butyryl Coenzyme A (CoA):Acetate-CoA Transferase in Butyrate-Producing Bacteria from the Human Large Intestine," 68:5186-5190 (2002).
Eberhard et al., "Evolution of Function in the Crotonase Superfamily: The Stereochemical Course of the Reaction Catalyzed by 2-Ketocyclohexanecarboxyl-CoA Hydrolase," J. Am. Chem. Soc. 126:7188-7189 (2004).
Efe et al., "Options for Biochemical Production of 4-Hydroxybutyrate and Its Lactone as a Substitute for Petrochemical Production," Biotechnol.Bioeng. 99:1392-1406 (2008).
Egland et al., "A cluster of bacterial genes for anaerobic benzene ring biodegradation," Proc. Natl. Acad. Sci U.S.A. 94:6484-6489 (1997).
Eikmanns et al., "The phosphoenolpyruvate carboxylase gene of Corynebacterium glutamicum: Molecular cloning, nucleotide sequence, and expression," Mol. Gen. Genet. 218:330-339 (1989).
Eisen et al., "The complete genome sequence of Chlorobium tepidum TLS, a photosynthetic, anaerobic, green-sulfur bacterium," Proc. Natl. Acad. Sci. USA 99(14): 9509-14 (2002).
Ekiel et al., "Acetate and CO2 Assimilation by Methanothrix concilii," J. Bacteriol. 162:905-908 (1985).
Elshahed et al., "Metabolism of Benzoate, Cyclohex-1-ene Carboxylate, and Cyclohexane Carboxylate by "Syntrophus aciditrophicus" Strain SB in Syntrophic Association with H2-Using Microorganisms," Appl. Environ. Microbiol. 67:1728-1738 (2001).
Enomoto et al., "Cloning and Sequencing of the Gene Encoding the Soluble Fumarate Reductase from *Saccharomyces cerevisiae*," DNA Res. 3:263-267 (1996).
Evans et al., "A New Ferredoxin-Dependent Carbon Reduction Cycle in a Photosynthetic Bacterium," Proc. Natl. Acad. Sci. U.S.A. 55:928-934 (1966).
Fernandez-Valverde et al., "Purification of Pseudomonas putida Acyl Coenzyme A Ligase Active with a Range of Aliphatic and Aromatic Substrates," Appl. Environ. Microbiol. 59:1149-1154 (1993).
Fishbein et al., "Purification and Properties of an Enzyme in Human Blood and Rat Liver Microsomes Catalyzing the Formation and Dydrolysis of y-Lactones," J Biol Chem 241:4835-4841 (1966).
Flint et al., "The Role and Properties of the Iron—Sulfur Cluster in *Escherichia coli* Dihydroxy-Acid Dehydratase," J.Biol.Chem. 268:14732-14742 (1993).
Ford et al., "Molecular properties of the lysl gene and the regulation of aminoadipate reductase in Schizosaccharomyces pombe," Curr. Genet. 28:131-137 (1995).
Fox and Roseman, "Isolation and Characterization of Homogeneous Acetate Kinase from *Salmonella typhimurium* and *Escherichia coli*," J. Biol. Chem. 261:13487-13497 (1986).
Fox et al., "Characterization of the Region Encoding the CO-Induced Hydrogenase of Rhodospirillum rubrum," J Bacteriol. 178:6200-6208 (1996).
Fujii et al., "Error-prone rolling circle amplification: the simplest random mutagenesis protocol," Nat. Protoc. 1:2493-2497 (2006).
Fujii et al., "One-step random mutagenesis by error-prone rolling circle amplification," Nucleic Acids Res. 32:e145 (2004).
Fujinaga and Meyer, "Cloning and Expression in *Escherichia coli* of the Gene Encoding the [2Fe-2S] Ferredoxin from Clostridium Pasteurianum," Biochemical and Biophysical Research Communications, 192(3):1115-1122 (1993).
Fukao et al., "Succinyl-CoA:3-Ketoacid CoA Transferase (SCOT): Cloning of the Human SCOT Gene, Tertiary Structural Modeling of the Human SCOT Monomer and Characterization of Three Pathogenic Mutations," Genomics 68(2):144-151 (2000).
Fukuda and Wakagi, "Substrate recognition by 2-oxoacid:ferredoxin oxidoreductase from *Sulfolobus* sp. strain 7," Biochim. Biophys. Acta 1597:74-80 (2002).
Fukuda et al., "Role of a highly conserved YPITP motif in 2-oxoacid:ferredoxin Oxidoreductase," Eur. J. Biochem. 268:5639-5646 (2001).

(56) References Cited

OTHER PUBLICATIONS

Furdui and Ragsdale, "The Role of Pyruvate Ferredoxin Oxidoreductase in Pyruvate Synthesis during Autotrophic Growth by the Wood-Ljungdahl Pathway," J. Biol. Chem. 275:28494-28499 (2000).

Gangloff et al., "Molecular Cloning of the Yeast Mitochondrial Aconitase Gene (ACOI) and Evidence of a Synergistic Regulation of Expression by Glucose plus Glutamate," Mol. Cell. Biol. 10:3551-3561 (1990).

Germer, "Overexpression, Isolation, and Spectroscopic Characterization of the Bidirectional [NiFe] Hydrogenase from *Synechocystis* sp. PCC 6803," J. Biol. Chem. 284(52), 36462-36472 (2009).

Gibbs et al., "Degenerate oligonucleotide gene shuffling (DOGS): a method for enhancing the frequency of recombination with family shuffling," Gene 271:13-20 (2001).

Gibson and McAlister-Henn, "Physical and Genetic Interactions of Cytosolic Malate Dehydrogenase with Other Gluconeogenic Enzymes," J. Biol. Chem. 278:25628-25636 (2003).

Gobel et al., "Degradation of Aromatics and Chloroaromatics by *Pseudomonas* sp. Strain B13: Cloning, Characterization, and Analysis of Sequences Encoding 3-Oxoadipate:Succinyl-Coenzyme A (CoA) Transferase and 3-Oxoadipyl-CoA Thiolase," J Bacteriol. 184:216-223 (2002).

Gong et al., "Specificity Determinants for the Pyruvate Dehydrogenase Component Reaction Mapped with Mutated and Prosthetic Group Modified Lipoyl Domains," J. Biol. Chem. 275:13645-13653 (2000).

Gonzalez and Robb, "Genetic analysis of Carboxydothermus hydrogenoformans carbon monoxide dehydrogenase genes cooF and coos," FEMS Microbiol Lett. 191:243-247 (2000).

Gonzalez et al., "Characterization of a (2R,3R)-2,3-Butanediol Dehydrogenase as the *Saccharomyces cerevisiae* YAL060W Gene Product," 275:35876-35885 (2000).

Guengerich et al., "Epdxide Hydrolase: Properties and Metabolic Roles," Rev. Biochem. Toxicol. 4:5-30, (1982).

Guest et al., "The Fumarase Genes of *Escherichia coli*: Location of the funB Gene and Discovery of a New Gene," J. Gen. Microbiol. 131:2971-2984 (1985).

Gulick et al., "The 1.75 Å Crystal Structure of Acetyl-CoA Synthetase Bound to Adenosine-5'-propylphosphate and Coenzyme A," Biochemistry 42:2866-2873 (2003).

Guo et al., "Site-directed mutational analysis of the novel catalytic domains of a-aminoadipate reductase (Lys2p) from Candida albicans," Mol.Genet.Genomics 269:271-279 (2003).

Guo et al., "Posttranslational activation, site-directed mutation and phylogenetic analyses of the lysine biosynthesis enzymes α-aminoadipate reductase Lyslp (AAR) and the phosphopantetheinyl transferase Lys1p (PPTase) from Schizosaccharomyces pombe," Yeast 21:1279-1288 (2004).

Guterman et al. "Generation of phenylpropanoid pathway-derived volatiles in transgenic plants: rose alcohol acetyltransferase produces phenylethyl acetate and benzyl acetate in petunia flowers," Plant Mol Biol 60: 555-563 (2006).

Haller et al., "Discovering New Enzymes and Metabolic Pathways: Conversion of Succinate to Propionate by *Escherichia coli*," Biochemistry, 39(16):4622-4629 (2000).

Hanai et al., "Engineered Synthetic Pathway for Isopropanol Production in *Escherichia coli*," Appl Environ Microbiol 73:7814-7818 (2007).

Hansen et al., "De Novo Biosynthesis of Vanillin in Fission Yeast (*Schizosaccharomyces pombe*) and Baker's Yeast (*Saccharomyces cerevisiae*)," Appl.Environ.Microbiol 75:2765-2774 (2009).

Harder, "Anaerobic degradation of cyclohexane-1,2-diol by a new *Azoarcus* species," J., Arch. Microbiol. 168:199-203 (1997).

Harrison et al., "The pimFABCDE operon from Rhodopseudomonas palustris mediates dicarboxylic acid degradation and participates in anaerobic benzoate degradation," Microbiology 151:727-736 (2005).

Hartmanis, M.G., "Butyrate Kinase from Clostridium acetobutylicum," J. Biol. Chem. 262:617-621 (1987).

Harwood et al., "Identification of the pcaRKF Gene Cluster from Pseudomonas putida: Involvement in Chemotaxis, Biodegradation and Transport of 4-Hydroxybenzoate," J Bacteriol. 176:6479-6488 (1994).

Hasegawa et al., "Transcriptional regulation of ketone body-utilizing enzyme, acetoacetyl-CoA synthetase, by C/EBPα during adipocyte differentiation," Biochim Biophys Acta 1779:414-419 (2008).

Haselbeck and McAlister-Henn, "Isolation, Nucleotide Sequence, and Disruption of the *Saccharomyces cerevisiae* Gene Encoding Mitochondrial NADPH(H)-specific Isocitrate Dehydrogenase," J. Biol. Chem. 266:2339-2345 (1991).

Hayes et al., "Combining computational and experimental screening for rapid optimization of protein properties," Proc. Natl. Acad. Sci. USA 99:15926-15931 (2002).

Haywood et al., "4-Acetamidobutyrate Deacetylase in the Yeast Candida boidinii Grown on Putrescine or Spermidine as Sole Nitrogen Source and Its Probable Role in Polyamine Catabolism," FEMS Microbiology Letters 52:91-96 (1988).

Heidlas et al., "Purification and properties of two oxidoreductases catalyzing the enantioselective reduction of diacetyl and other diketones from baker's yeast," Eur.J Biochem. 188:165-174 (1990).

Herrmann et al., "Energy Conservation via Electron-Transferring Flavoprotein in Anaerobic Bacteria," J. Bacteriol. 190:784-791 (2008).

Hesslinger et al., "Novel keto acid formate-lyase and propionate kinase enzymes are components of an anaerobic pathway in *Escherichia coli* that degrades L-threonine to propionate," Mol. Microbiol 27:477-492 (1998).

Hibbert et al., "Directed evolution of biocatalytic processes," Biomol.Eng 22:11-19 (2005).

Hijarrubia et al., "Domain Structure Characterization of the Multifunctional-Aminoadipate Reductase from Penicillium chrysogenum by Limited Proteolysis," J Biol.Chem. 278:8250-8256 (2003).

Hillmer and Gottschalk, "Solubilization and Partial Characterization of Particulate Dehydrogenases from Clostridium kluyveri," Biochim. Biophys. Acta 3334:12-23 (1974).

Hillmer et al., "Particulate Nature of Enzymes Involved in the Fermenation of Ethanol and Acetate by Clostridium kluyveri," FEBS Lett. 21:351-354 (1972).

Hiser et al., "ERG10 from *Saccharomyces cerevisiae* Encodes Acetoacetyl-CoA Thiolase," J.Biol.Chem. 269:31383-31389 (1994).

Hoffmeister et al., "Mitochondrial trans-2-Enoyl-CoA Reductase of Wax Ester Fermentation from Euglena gracilis Defines a New Family of Enzymes Involved in Lipid Synthesis," J. Biol. Chem. 280:4329-4338 (2005).

Holtzapple,E. and Schmidt-Dannert,C., "Biosynthesis of Isoprenoid Wax Ester in Marinobacter hydrocarbonoclasticus DSM 8798: Identification and Characterization of Isoprenoid Coenzyme A Synthetase and Wax Ester Synthases," J. Bacteriol. 189 (10), 3804-3812 (2007).

Horswill and Escalante-Semerena, "In Vitro Conversion of Propionate to Pyruvate by *Salmonella enterica* Enzymes: 2-Methylcitrate Dehydratase (PrpD) and Aconitase Enzymes Catalyze the Conversion of 2-Methylcitrate to 2-Methylisocitrate," Biochemistry 40:4703-4713 (2001).

Huang et al., "Identification and Characterization of a Second Butyrate Kinase from Clostridium acetobutylicum ATCC 824," J Mol.Microbiol Biotechnol 2:33-38 (2000).

Hughes et al., "Helicobacter pylori porCDAB and oorDABC Genes Encode Distinct Pyruvate:Flavodoxin and 2-Oxoglutarate:Acceptor Oxidoreductases Which Mediate Electron Transport to NADP," J. Bacteriol. 180:1119-1128 (1998).

Hugler et al., "Autotrophic CO2 fixation via the reductive tricarboxylic acid cycle in different lineages within the phylum Aquificae: evidence for two ways of citrate cleavage," Environ. Microbiol. 9:81-92 (2007).

Hugler et al., "Evidence for Autotrophic CO2 Fixation via the Reductive Tricarboxylic Acid Cycle by Members of the Subdivision of Proteobacteria," J. Bacteriol. 187:3020-3027 (2005).

Hugler, "Malonyl-Coenzyme A Reductase from Chloroflexus aurantiacus, a Key Enzyme of the 3-Hydroxypropionate Cycle for Autotrophic CO2 Fixation," J. Bacteriol. 184:2404-2410 (2002).

(56) References Cited

OTHER PUBLICATIONS

Huisman and Lalonde, "Enzyme Evolution for Chemical Process Applications," In Biocatalysis in the pharmaceutical and biotechnology industries pp. 717-742 (2007).
Hynes and Murray, "ATP-Citrate Lyase Is Required for Production of Cytosolic Acetyl Coenzyme A and Development in Aspergillus nidulans," Eukaryotic Cell, July: 1039-1048, (2010).
Ikeda et al., "Anabolic five subunit-type pyruvate:ferredoxin oxidoreductase from Hydrogenobacter thermophilus TK-6," Biochem. Biophys. Res. Commun. 340:76-82 (2006).
Ingram-Smith and Smith, "AMP-forming acetyl-CoA synthetases in Archaea show unexpected diversity in substrate utilization," Archaea 2:95-107 (2007).
Ingram-Smith et al., "Characterization of the Acetate Binding Pocket in the Methanosarcina thermophila Acetate Kinase," J. Bacteriol. 187:2386-2394 (2005).
Ishige et al., "Wax Ester Production from n-Alkanes by *Acinetobacter* sp. Strain M-1: Ultrastructure of Cellular Inclusions and Role of Acyl Coenzyme A Reductase," Appl. Environ. Microbiol. 68:1192-1195 (2002).
Ismail et al., "Functional genomics by NMR spectroscopy," Eur.J Biochem. 270:3047-3054 (2003).
Iverson et al., "Structure of the *Escherichia coli* Fumarate Reductase Respiratory Complex," Science 284:1961-1966 (1999).
Iwaki et al, "Identification of a Transcriptional Activator (ChnR) and a 6-Oxohexanoate Dehydrogenase (ChnE) in the Cyclohexanol Catabolic Pathway in *Acinetobacter* sp. Strain NCIMB 9871 and Localization of the Genes That Encode Them," AEM 65:5158-62 (1999).
Iwakura et al., "Studies on Regulatory Functions of Malic Enzymes," J. Biochem. 85(5):1355-65 (1979).
Jacobi et al., "The hyp operon gene products are required for the maturation of catalytically active hydrogenase isoenzymes in *Escherichia coli*," Arch.Microbiol 158:444-451 (1992).
Jeon et al., "Heterologous expression of the alcohol dehydrogenase (adhI) gene from Geobacillus thermoglucosidasius strain M10EXG," J Biotechnol 135:127-133 (2008).
Jogl and Tong, "Crystal Structure of Yeast Acetyl-Coenzyme A Synthetase in Complex with AMP," Biochemistry 43:1425-1431 (2004).
Johanson et al., "Strain engineering for stereoselective bioreduction of dicarbonyl compounds by yeast reductases," FEMS Yeast Res. 5:513-525 (2005).
Johnston et al., "Structure of naphthoate synthase (MenB) from *Mycobacterium tuberculosis* in both native and product-bound forms," Acta Crstyallogr. D. Biol. Crystallogr. 61:1199-1206 (2005).
Jojima et al., "Production of isopropanol by metabolically engineered *Escherichia coli*," Appl Microbiol Biotechnol 77:1219-1224 (2008).
Jones et al., "Acetone-Butanol Fermentation Revisited," Microbiol Rev. 50:484-524 (1986).
Kai et al., "Phosphoenolpyruvate carboxylase: three-dimensional structure and molecular mechanisms," Arch. Biochem. Biophys. 414:170-179 (2003).
Kalscheuer et al., "A Novel Bifunctional Wax Ester Synthase/Acyl-CoA:Diacylglycerol Acyltransferase Mediates Wax Ester and Triacylglycerol Biosynthesis in Acinetobacter calcoaceticus ADP1," AJ Biol Chem 278: 8075-8082 (2003).
Kalscheuer et al., "Analysis of Storage Lipid Accumulation in Alcanivorax borkumensis: Evidence for Alternative Triacylglycerol Biosynthesis Routes in Bacteria," J Bacteriol 189: 918-928 (2007).
Kanajunia et al., "Cloning, expression, purification, crystallization and preliminary X-ray crystallographic study of DHNA synthetase from Geobacillus kaustophilus," Acta Crstyallogr. Sect. F. Struct. Biol. Cyst. Commun.63:103-105 (2007).
Kanao et al., "Characterization of isocitrate dehydrogenase from the green sulfur bacterium Chlorobium limicola," Eur. J. Biochem. 269:1926-1931 (2002).
Kanao et al., "Kinetic and biochemical analyses on the reaction mechanism of a bacterial ATP-citrate lyase," Eur. J. Biochem. 269:3409-3416 (2002).

Karlen et al., "Absolute determination of the activity of two C" dating Standards," Arkiv Geofysik, 4:465-471 (1968).
Kaschabek et al., "Degradation of Aromatics and Chloroaromatics by *Pseudomonas* sp. Strain B13: Purification and Characterization of 3-Oxoadipate:Succinyl-Coenzyme A (CoA) Transferase and 3-Oxoadipyl-CoA Thiolase," J Bacteriol. 184:207-215 (2002).
Katz et al., "Screening of two complementary collections of *Saccharomyces cerevisiae* to identify enzymes involved in stereo-selective reductions of specific carbonyl compounds: an alternative to protein purification," 33:163-172 (2003).
Kazahaya, "Aerobic Dissimilation of Glucose by Heterolactic Bacteria," J. Gen. Appl. Microbiol. 18:43-55 (1972).
Kellum and Drake, "Effects of Cultivation Gas Phase on Hydrogenase of the Acetogen Clostridium thermoaceticum," J. Bacteriol. 160:466-469 (1984).
Keng et al., "Specificity of Aspartokinase III from *Escherichia coli* and an Examination of Important Catalytic Residues," Arch Biochem Biophys 335:73-81 (1996).
Khalameyzer et al., "Screening, Nucleotide Sequence, and Biochemical Characterization of an Esterase from Pseudomonas fluorescens with High Activity towards Lactones," Appl.Environ. Microbiol. 65:477-482 (1999).
Kim and Tabita, "Both Subunits of ATP-Citrate Lyase from Chlorobium tepidum Contribute to Catalytic Activity," J. Bacteriol. 188:6544-6552 (2006).
Kim et al., "Effect of Overexpression of Actinobacillus succinogenes Phosphoenolpyruvate Carboxykinase on Succinate Production in *Escherichia coli*," Appl. Environ. Microbiol. 70:1238-1241 (2004).
Kim et al., "Construction of an *Escherichia coli* K-12 Mutant for Homoethanologenic Fermentation of Glucose or Xylose without Foreign Genes," Appl. Environ. Microbiol. 73:1766-1771 (2007).
Kim et al., "Dihydrolipoamide Dehydrogenase Mutation Alters the NADH Sensitivity of Pyruvate Dehydrogenase Complex of *Escherichia coli* K-12," J. Bacteriol. 190:3851-3858 (2008).
Kim et al., "Catalytic Promiscuity in Dihydroxy-Acid Dehydratase from the Thermoacidophilic Archaeon Sulfolobus solfataricus," J.Biochem. 139:591-596 (2006).
Kinoshita et al., "Purification of two alcohol dehydrogenases from Zymomonas mobilis and their properties," Appl Microbiol Biotechnol 22:249-254 (1985).
Knappe and Sawers, "A radical-chemical route to acetyl-CoA: the anaerobically induced pyruvate formate-lyase system of *Escherichia coli*," FEMS.Microbiol Rev. 6:383-398 (1990).
Kobayashi et al., "Physicochemical, Catalytic, and Immunochemical Properties of Fumarases Crystallized Separately from Mitochondrial and Cytosolic Fractions of Rat Livers," J. Biochem. 89:1923-1931 (1981).
Koland and Gennis, "Proximity of Reactive Cysteine Residue and Flavin in *Escherichia coli* Pyruvate Oxidase as Estimated by Fluorescence Energy Transfer," Biochemistry 21:4438-4442 (1982).
Koo et al., "Cloning and characterization of the bifunctional alcohol/acetaldehyde dehydrogenase gene (adhE) in Leuconostoc mesenteroides isolated from kimchi," Biotechnol Lett. 27:505-510 (2005).
Korolev et al., "Autotracing of *Escherichia coli* acetate CoA-transferase a-subunit structure using 3.4 ÅE MAD and 1.9 ÅE native data," Acta Crystallogr.D.Biol.Crystallogr. 58:2116-2121 (2002).
Kosaka et al., "Characterization of the sol Operon in Butanol-Hyperproducing Clostridium saccharoperbutylacetonicum Strain N1-4 and Its Degeneration Mechanism," Biosci Biotechnol Biochem., 71:58-68 (2007).
Kowalchuk et al., "Contrasting patterns of evolutionary divergence within the Acinetobacter calcoaceticus pca operon," Gene 146:23-30 (1994).
Kretz et al., "Gene Site Saturation Mutagenesis: A Comprehensive Mutagenesis Approach," Methods Enzymol. 388:3-11 (2004).
Kumari et al., "Cloning, Characterization, and Functional Expression of acs, the Gene Which Encodes Acetyl Coenzyme A Synthetase in *Escherichia coli*," J. Bacteriol. 177:2878-2886 (1995).
Kuznetsova, et al., "Enzyme genomics: Application of general enzymatic screens to discover new enzymes," FEMS Microbiol Rev, 2005, 29(2):263-279.

(56) References Cited

OTHER PUBLICATIONS

Kwon et al., "Brain 4-Aminobutyrate Aminotransferase," J. Microbiol. Biotechnol. 16:1448-1452 (2006).
Laivenieks et al., "Cloning, Sequencing, and Overexpression of the Anaerobiospirillum succiniciproducens Phosphoenolpyruvate Carboxykinase (pckA) Gene," Appl. Environ. Microbiol. 63:2273-2280 (1997).
Lamas-Maceiras et al., "Amplification and disruption of the phenylacetyl-CoA ligase gene of Penicillium chrysogenum encoding an aryl-capping enzyme that supplies phenylacetic acid to the isopenicillin N-acyltransferase," Biochem.J 395:147-155 (2006).
Langin et al., "The MET2 gene of Succbwzyces cerevisiue: molecular cloning and nucleotide sequence," Gene 49:283-93 (1986).
Lardizabal et al. "Purification of a Jojoba Embryo Wax Synthase, Cloning of its cDNA, and Production of High Levels of Wax in Seeds of Transgenic Arabidopsis," Plant Physiology 122: 645-655 (2000).
Leal, "PduP is a coenzyme-a-acylating propionaldehyde dehydrogenase associated with the polyhedral bodies involved in B12-dependent 1,2-propanediol degradation by *Salmonella enterica* serovar Typhimurium LT2," Arch. Microbiol. 180:353-361 (2003).
Lee et al., "Cloning and Characterization of Mannheimia succiniciproducens MBEL55E Phosphoenolpyruvate Carboxykinase (pckA) Gene," Biotechnol. Bioprocess Eng. 7:95-99 (2002).
Lee et al., "A new approach to directed gene evolution by recombined extension on truncated templates (RETT)," J. Molec. Catalysis 26:119-129 (2003).
Leutwein and Heider, "Succinyl-CoA:(R)-Benzylsuccinate CoA-Transferase: an Enzyme of the Anaerobic Toluene Catabolic Pathway in Denitrifying Bacteria," J. Bact. 183(14) 4288-4295 (2001).
Lin et al., "Fed-Batch Culture of a Metabolically Engineered *Escherichia coli* Strain Designed for High-Level Succinate Production and Yield Under Aerobic Conditions," Biotechnol. Bioeng. 90:775-779 (2005).
Louis et al., "Restricted Distribution of the Butyrate Kinase Pathway among Butyrate-Producing Bacteria from the Human Colon," J. Bacteriol. 186:2099-2106 (2004).
Low et al., "Mimicking Somatic Hypermutation: Affinity Maturation of Antibodies Displayed on Bacteriophage Using a Bacterial Mutator Strain," J. Mol. Biol. 260:359-3680 (1996).
Lu et al, "Topology and Active Site of PlsY the Bacterial Acylphosphate:Glycerol-3-Phosphate Acyltransferase," J Biol Chem 282:11339-46 (2007).
Lukey et al., "How *Escherichia coli* Is Equipped to Oxidize Hydrogen under Different Redox Conditions," J. Biol. Chem. 285(6):3928-3938 (2010).
Lutz et al., "Rapid generation of incremental truncation libraries for protein engineering using—phosphothioate nucleotides," Nucleic Acids Res 29:E16 (2001).
Lutz et al., "Creating multiple-crossover DNA libraries independent of sequence identity," Proc. Natl. Acad. Sci. USA 98:11248-11253 (2001).
Macis et al., "Properties and sequence of the coenzyme B12-dependent glycerol dehydratase of Clostridium pasteurianum," FEMS Microbiol Lett. 164:21-28 (1998).
Mack et al., "Location of the tow genes encoding glutaconate coenzyme A-transferase at the beginning of the hydroxyglutarate operon in Acidaminococcus fermentans," 226:41-51 (1994).
Mack et al., "Converion of glutaconate CoA-transferase from Acidaminococcus fermentans into an acyl-CoA hydrolase by site-directed mutagenesis," FEBS.Lett. 405:209-212 (1997).
Maeda et al., "*Escherichia coli* hydrogenase 3 is a reversible enzyme possessing hydrogen uptake and synthesis activities," Appl Microbiol Biotechnol 76(5):1035-42 (2007).
Mann, "An International Reference Material for Radiocarbon Dating," Radiocarbon, 25(2):519-527 (1983).
Marco-Marin et al., "Site-directed Mutagenesis of*Escherichia coli* Acetylglutamate Kinase and Aspartokinase III Probes the Catalytic and Substrate-binding Mechanisms of these Amino Acid Kinase Family Enzymes and Allows Three-dimensional Modelling of Aspartokinase," 334:459-476 (2003).

Marolewski et al., "Cloning and Characterization of a New Purine Biosynthetic Enzyme: A Non-Folate Glycinamide Ribonucleotide Transformylase from *E. coli*," Biochemistry 33:2531-2537 (1994).
Martin et al., "Nematode.net update 2008: improvements enabling more efficient data mining and comparative nematode genomics," Appl.Environ.Microbiol. (2009).
Martin et al., "Engineering a mevalonate pathway in *Escherichia coli* for production of terpenoids," Nat.Biotechnol 21:796-802 (2003).
Martinez-Blanco et al., "Purification and Biochemical Characterization of Phenylacetyl-CoA Ligase from Pseudomonas putida," J Biol Chem 265:7084-7090 (1990).
Mason et al., "Alcohol acetyltransferases and the significance of ester synthesis in yeast," Yeast 16: 1287-1298 (2000).
Matiasek et al., "Volatile Ketone Formation in Bacteria: Release of 3-Oxopentanoate by Soil Pseudomonads During Growth on Heptanoate," Curr.Microbiol 42:276-281 (2001).
Matthies et al., "Reciprocal Isomerization of Butyrate and Isobutyrate by the Strictly Anaerobic Bacterium Strain WoG13 and Methanogenic Isobutyrate Degradation by a Defined Triculture," Appl Environ.Microbiol 58:1435-1439 (1992).
McAlister-Henn and Thompson, "Isolation and Expression of the Gene Encoding Yeast Mitochondrial Malate Dehydrogenase," J. Bacteriol. 169:5157-5166 (1987).
McInerney et al., "The genome of Syntrophus aciditrophicus: Life at the thermodynamic limit of microbial growth," Proc. Natl Acad. Sci U.S. A. 104:7600-7605 (2007).
Meijer et al., "Gene deletion of cytosolic ATP: citrate lyase leads to altered organic acid production in Aspergillus niger," J. Ind. Microbiol. Biotechnol. 36:1275-1280 (2009).
Melchiorsen et al., "The level of pyruvate-formate lyase controls the shift from homolactic to mixed-acid product formation in Lactococcus lactis," Appl Microbiol Biotechnol 58:338-344 (2002).
Menon and Ragsdale, "Mechanism of the *Clostridium thermoaceticum* Pyruvate:Ferredoxin Oxidoreductase: Evidence for the Common Catalytic Intermediacy of the Hydroxyethylthiamine Pyropyrosphate Radical," Biochemistry 36:8484-8494 (1997).
Minard and McAlister-Henn, "Isolation, Nucleotide Sequence Analysis, and Disruption of the MDH2 Gene from *Saccharomyces cerevisiae*: Evidence for Three Isozymes of Yeast Malate Dehydrogenase," Mol. Cell. Biol. 11:370-380 (1991).
Mizobata et al., "Purification and Characterization of a Thermostable Class II Fumarase from Thermus thermophilus," Arch. Biochem. Biophys. 355:49-55 (1998).
Mori et al., "Characterization, Sequencing, and Expression of the Genes Encoding a Reactivating Factor for Glycerol-inactivated Adenosylcobalamin-dependent Diol Dehydratase," J Biol.Chem. 272:32034-32041 (1997).
Morris et al., "Nucleotide sequence of the LYS2 gene of *Saccaromyces cerevisiae*: homology to Bacillus brevis tyrocidine synthetase 1," Gene 98:141-145 (1991).
Mouttaki et al., "Cyclohexane Carboxylate and Benzoate Formation from Crotonate in Syntrophus aciditrophicus," Appl. Environ. Micobiol. 73:930-938 (2007).
Mukhopadhyay and Purwantini, "Pyruvate carboxylase from *Mycobacterium smegmatis*: stabilization, rapid purification, molecular and biochemical characterization and regulation of the cellular level," Biochim. Biophys. Acta 1475:191-206 (2000).
Mukhopadhyay et al., "The fdxA Ferredoxin Gene Can Down-Regulate frxA Nitroreductase Gene Expression and Is Essential in Many Strains of Helicobacter pylori," J Bacteriol. 185:2927-2935 (2003).
Muller et al., "Nucleotide exchange and excision technology (NExT) DNA shuffling: a robust method for DNA fragmentation and directed evolution," Nucleic Acids Res. 33:e117 (2005).
Mullins et al., "A Specialized Citric Acid Cycle Requiring Succinyl-Coenzyme A (CoA):Acetate CoA-Transferase (AarC) Confers Acetic Acid Resistance on the Acidophile Acetobacter aceti," J. Bacteriol. 190(14):4933-4940 (2008).
Muratsubaki et al., "One of the Fumarate Reductase Isoenzymes from *Saccharomyces cerevisiae* Is Encoded by the OSM1 Gene," Arch. Biochem. Biophys. 352:175-181 (1998).
Musfeldt et al., "Novel Type of ADP-Forming Acetyl Coenzyme A Synthetase in Hyperthermophilic Archaea: Heterologous Expression and Characterization of Isoenzymes from the Sulfate Reducer

(56) References Cited

OTHER PUBLICATIONS

Archaeoglobus fulgidus and the Methanogen Methanococcus jannaschii," J Bacteriol. 184:636-644 (2002).
Naggert et al., "Cloning, Sequencing, and Characterization of *Escherichia coli* Thioesterase II," J Biol Chem 266:11044-11050 (1991).
Nakahigashi et al., "Nucleotide sequence of the fadA and fadB genes from *Escherichia coli*," Nucleic Acids Res. 18:4937 (1990).
Nakano et al., "Characterization of Anaerobic Fermentative Growth of Bacillus subtilis: Identification of Fermentation End Products and Genes Required for Growth," J. Bacteriol. 179:6749-6755 (1997).
Nardi et al. "The EstA esterase is responsible for the main capacity of Lactococcus lactis to synthesize short chain fatty acid esters in vitro," J. Appl. Microbiol. 93:994-1002 (2002).
Ness et al., "Synthetic shuffling expands functional protein diversity by allowing amino acids to recombine independently," Nat. Biotechnol. 20:1251-1255 (2002).
Nilekani and SivaRaman, "Purification and Properties of Citrate Lyase from *Escherichia coli*," Biochemistry 22:4657-4663 (1983).
Nimmo, "Kinetic mechanism of *Escherichia coli* isocitrate dehydrogenase and its inhibition by glyoxylate and oxaloacetate," Biochem. J. 234:317-2332 (1986).
Nishizawa et al., "Gene expression and characterization of two 2-oxoacid:ferredoxin oxidoreductases from Aeropyrum pernix K1," FEBS Lett. 579:2319-2322 (2005).
Nogales et al., "Characterization of the last step of the aerobic phenylacetic acid degradation pathway," Microbiology 153:357-365 (2007).
Noichinda et al. "Subcellular Localization of Alcohol Acetyltransferase in Strawberry Fruit," FoodSci Technol Res 5: 239-242 (1999).
Nowrousian et al., "The fungal acl1 and acl2 genes encode two polypeptides with homology to the N- and C-terminal parts of the animal ATP citrate lyase polypeptide," Curr. Genet. 37:189-93 (2000).
O'Brien and Gennis, "Studies of the Thiamin Pyrophosphate Binding Siotef *Escherichia coli* Pyruvate Oxidase," J. Biol. Chem. 255:3302-3307 (1980).
O'Brien et al., "Regulation by Lipids of Cofactor Binding to a Peripheral Membrand Enzyme: Binding of Thiamin Pyrophosphate to Pyruvate Oxidase," Biochemistry 16:3105-3109 (1977).
O'Brien et al., "Insight into the Mechanism of the B12-Independent Glycerol Dehydratase from Clostridium butyricum: Preliminary Biochemical and Structural Characterization," Biochemistry 43:4635-4645 (2004).
Ohgami et al., "Expression of acetoacetyl-CoA synthetase, a novel cytosolic ketone body-utilizing enzyme, in human brain," Biochem. Pharmacol. 65:989-994 (2003).
Olivera et al., "Molecular characterization of the phenylacetic acid catabolic pathway in Pseudomonas putida U: The phenylacetyl-CoA catabolon," Proc.Natl.Acad.Sci U.S.A 95:6419-6424 (1998).
Ostermeier et al., "A combinatorial approach to hybrid enzymes independent of DNA homology," Nat. Biotechnol. 17:1205-1209 (1999).
Ostermeier et al., "Combinatorial protein engineering by incremental truncation," Proc. Natl. Acad. Sci. USA 96:3562-3567 (1999).
Otten et al., "Directed evolution: selecting today's biocatalyst," CRC Press; Often and Quax. Biomol.Eng 22:1-9 (2005).
Park et al., "Biosynthesis of Poly(3-hydroxybutyrateco-3-hydroxyalkanoates) by Metabolically Engineered *Escherichia coli* Strains," Appl.Biochem.Biotechnol 113-116:335-346 (2004).
Park et al., "Identification and Characterization of a New Enoyl Coenzyme A Hydratase Involved in Biosynthesis of Medium-Chain-Length Polyhydroxyalkanoates in Recombinant *Escherichia coli*," J Bacteriol. 185:5391-5397 (2003).
Park et al., "New FadB Homologous Enzymes and Their Use in Enhanced Biosynthesis of Medium-Chain-Length Polyhydroxyalkanoates in fadB Mutant *Escherichia coli*," Biotechnol Bioeng 86:681-686 (2004).

Park et al., "Purifications and Characterizations of a Ferredoxin and Its Related 2-Oxoacid:Ferredoxin Oxidoreductase from the Hyperthermophilic Archaeon, Sulfolobus solfataricus P1," J Biochem Mol Biol. 39:46-54 (2006).
Parkin et al., "Rapid and Efficient Electrocatalytic CO2/CO Interconversions by Carboxydothermus hydrogenoformans CO Dehydrogenase I on an Electrode," J Am.Chem.Soc. 129:10328-10329 (2007).
Parsot et al., "Nucleotide sequence of *Escherichia coli* argB and argC genes: comparison of N-N-acetylglutamate kinase and N-acetylglutamate-y-semialdehyde dehydrogenase with homologous and analogous enzymes," Gene 68:275-283 (1988).
Pauli et al., "ato Operon: a Highly Inducible System for Acetoacetate and Butyrate Degradation in *Escherichia coli*," Eur.J Biochem. 29:553-562 (1972).
Pauwels et al., "The N-acetylglutamate synthase/N-acetylglutamate kinase metabolon of *Saccharomyces cerevisiae* allows co-ordinated feedback regulation of the first two steps in arginine biosynthesis," Eur.J Biochem. 270:1014-1024 (2003).
Pelletier et al., "2-Ketocyclohexanecarboxyl Coenzyme A Hydrolase, the Ring Cleavage Enzyme Required for Anaerobic Benzoate Degradation by Rhodopseudomonas palustris," J. Bacteriol. 180:2330-2336 (1998).
Peoples et al., "Fine structural analysis of the Zoogloea ramigera phbA-phbB locus encoding β-ketothiolase and acetoacetyl-CoA reductase: nucleotide sequence of phbB," Mol.Microbiol 3:349-357 (1989).
Perez et al., "*Escherichia coli* YqhD Exhibits Aldehyde Reductase Activity and Protects from the Harmful Effect of Lipid Peroxidation-derived Aldehydes," J Biol.Chem. 283:7346-7353 (2008).
Pieulle et al., "Isolation and Analysis of the Gene Encoding the Pyruvate-Ferredoxin Oxidoreductase of Desulfovibrio africanus, Production of the Recombinant Enzyme in *Escherichia coli*, and Effect of Carboxy-Terminal Deletions on Its Stability," J. Bacteriol. 179:5684-5692 (1997).
Ploux et al., "Investigation of the first step of biotin biosynthesis in Bacillus sphaericus," Biochem.J 287 ( Pt 3):685-690 (1992).
Ploux et al., "The NADPH-linked acetoacetyl-CoA reductase from Zoogloea ramigera," Eur.J Biochem. 174:177-182 (1988).
Pohl et al., "Remarkably Broad Substrate Tolerance of Malonyl-CoA Synthetase, an Enzyme Capable of Intracellular Synthesis of Polyketide Precursors," J.Am.Chem.Soc. 123:5822-5823 (2001).
Powlowski, "Purification and Properties of the Physically Associated meta-Cleavage Pathway Enzymes 4-Hydroxy-2-Ketovalerate Aldolase and Aldehyde Dehydrogenase (Acylating) from *Pseudomonas* sp. Strain CF600," J. Bacteriol. 175:377-385 (1993).
Priefert and Steinbuchel, "Identification and Molecular Characterization of the Acetyl Coenzyme A Synthetase Gene (acoE) of Alcaligenes eutrophus," J. Bacteriol. 174:6590-6599 (1992).
Pritchard et al., "A general model of error-prone PCR," J Theor.Biol. 234:497-509 (2005).
Qi et al., "Saturation-mutagenesis in two positions distant from active site of a Klebsiella pneumoniae glycerol dehydratase identifies some highly active mutants," J.Biotechnol. 144:43-50 (2009).
Rado et al., "Phosphotransacetylase from Bacillus Subtilis: Purification and Physiological Studies," Biochim.Biophys.Acta 321:114-125 (1973).
Ragsdale, "Enzymology of the Wood-Ljungdahl Pathway of Acetogenesis," Annals of the New York Academy of Sciences 1125: 129-136 (2008).
Ragsdale, S.W., "Pyruvate Ferredoxin Oxidoreductase and Its Radical Intermediate," Chem. Rev. 103:2333-2346 (2003).
Rajpal et al., "A general method for greatly improving the affinity of antibodies by using combinatorial libraries," Proc. Natl. Acad. Sci. USA 102:8466-8471 (2005).
Rakhely, "Cyanobacterial-Type, Heteropentameric, NAD-Reducing NiFe Hydrogenase in the Purple Sulfur Photosynthetic Bacterium Thiocapsa roseopersicina," Appl. Environ. Microbiol. 70(2) 722-728 (2004).
Ramon-Maiques et al., "Structure of Acetylglutamate Kinase, a Key Enzyme for Arginine Biosynthesis and a Prototype for the Amino Acid Kinase Enzyme Family, during Catalysis," Structure. 10:329-342 (2002).

(56) References Cited

OTHER PUBLICATIONS

Ramos-Vera et al., "Autotrophic Carbon Dioxide Assimilation in Thermoproteales Revisited," J Bacteriol, 191:4286-4297 (2009).
Rangarajan et al., "Structure of [NiFe] Hydrogenase Maturation Protein HypE from *Escherichia coli* and Its Interaction with HypF," J. Bacteriol. 190:1447-1458 (2008).
Ravagnani et al., "Spo0A directly controls the switch from acid to solvent production in solvent-forming clostridia," Mol.Microbiol 37:1172-1185 (2000).
Raynaud et al., "Molecular characterization of the 1,3-propanediol (1,3-PD) operon of Clostridium butyricum," Proc.Natl.Acad.Sci U.S.A 100:5010-5015 (2003).
Reetz et al., "Directed Evolution of an Enantioselective Enzyme through Combinatorial Multiple-Cassette Mutagenesis," Angew. Chem. Int. Ed Engl. 40:3589-3591 (2001).
Reetz et al., "Iterative Saturation Mutagenesis on the Basis of B Factors as a Strategy for Increasing Protein Thermostability," Angew. Chem. Int. Ed Engl. 45:7745-7751 (2006).
Reetz et al., "Iterative saturation mutagenesis (ISM) for rapid directed evolution of functional enzymes," Nat. Protoc. 2:891-903 (2007).
Regev-Rudzki et al., "Yeast Aconitase in Two Locations and Two Metabolic Pathways: Seeing Small Amounts Is Believing," Mol. Biol. Cell. 16:4163-4171 (2005).
Reidhaar-Olson et al., "Random Mutagenesis of Protein Sequences Using Oligonucleotide Cassettes," Methods Enzymol. 208:564-586 (1991).
Reidhaar-Olson et al., "Combinatorial Cassette Mutagenesis as a Probe of the Informational Content of Protein Sequences," Science 241:53-57 (1988).
Reiser, "Isolation of mutants of Acinetobacter calcoaceticus deficient in wax ester synthesis and complementation of one mutation with a gene encoding a fatty acyl coenzyme A reductase," Journal of Bacteriology 179:2969-2975 (1997).
Riviere et al., "Acetyl:Succinate CoA-transferase in Procyclic Trypanosoma brucei," J. Biol. Chem. 279(44):45337-45346 (2004).
Roberts et al., "The Role of Enoyl-CoA Hydratase in the Metabolism of Isoleucine by Pseudomonas putida," Arch.Microbiol 117:99-108 (1978).
Robinson et al., "Studies on Rat Brain Acyl-Coenzyme a Hydrolase (Short Chain)" Biochem.Biophys.Res.Commun. 71:959-965 (1976).
Rochu et al., "Stabilization of the active form(s) of human paraoxonase by human phosphate-binding protein," Biochem.Soc. Trans. 35:1616-1620 (2007).
Rozzel et al., "Sterochemical Imperative in Enzymic Decarboxylations" J.Am.Chem.Soc. 106:4937-4941 (1984).
Sass et al., "Folding of Fumarase during Mitochondrial Import Determines its Dual Targeting in Yeast," J. Biol. Chem. 278:45109-45116 (2003).
Sato et al., "Poly[(R)-3-Hydroxybutyrate] Formation in *Escherichia coli* from Glucose through an Enoyl-CoA Hydratase-Mediated Pathway," J Biosci.Bioeng 103:38-44 (2007).
Sauvageot et al., "Characterisation of the diol dehydratase pdu operon of Lactobacillus collinoides," FEMS Microbiol Lett. 209:69-74 (2002).
Sawers and Boxer, "Purification and properties of membrand bound hydrogenase isoenzyme 1 from anaerobically grown *Escherichia coli* K12," Eur.J Biochem. 156:265-275 (1986).
Sawers et al., "Differential Expression of Hydrogenase Isoenzymes in *Escherichia coli* K-12: Evidence for a Third Isoenzyme," J Bacteriol. 164:1324-1331 (1985).
Sawers et al., "Characterization and Physiological Roles of Membrane-Bound Hydrogenase Isoenzymes from *Slamonella typhimurium*," J Bacteriol. 168:398-404 (1986).
Sawers, G., "The hydrogenases and formate dehydrogenases of *Escherichia coli*," Antonie Van Leeuwenhoek, 66:57-88 (1994).
Schink and Schlegel, "The membrane-bound hydrogenase of alcaligenes eutrophus," Biochim. Biophys. Acta, 567, 315-324 (1979).

Schneider and Schlegel, "Purification and properties of soluble hydrogenase from alcaligenes eutrphus H16," Biochim. Biophys. Acta 452, 66-80 (1976).
Schneider et al., "Biosynthesis of the Prosthetic Group of Citrate Lyase," Biochemistry 39:9438-9450 (2000).
Schweiger and Buckel, "On the dehydration of (R)-lactate in the fermentation of alanine to propionate by Clostridium propionicum," FEBS Letters, 171(1) 79-84 (1984).
Seedorf et al., "The genome of Clostridium kluyveri, a strict anaerobe with unique metabolic features," Proc.Natl.Acad.Sci U.S.A 105:2128-2133 (2008).
Selifonova et al., "Rapid Evolution of Novel Traits in Microorganisms," Appl. Environ. Microbiol. 67:3645-3649 (2001).
Selmer et al., "Propionate CoA-transferase from Clostridium propionicum Cloning of the gene and identi® cation of glutamate 324 at the active site," Eur J Biochem 269, 372-380 (2002).
Sen et al., "Developments in Directed Evolution for Improving Enzyme Functions," Appl Biochem.Biotechnol 143:212-223 (2007)).
Seravalli et al., "Evidence That NiNi Acetyl-CoA Synthase Is Active and That the CuNi Enzyme Is Not," Biochemistry 43:3944-3955 (2004).
Seyfried et al., "Cloning, Sequencing, and Overexpression of the Genes Encoding Coenzyme B12-Dependent Glycerol Dehydratase of Citrobacter freundii," J Bacteriol. 178:5793-5796 (1996).
Shao et al., "Random-priming in vitro recombination: an effective tool for directed evolution," Nucleic Acids Res 26:681-683 (1998).
Sharma et al., "Menaquinon (Vitamin K2) Biosynthesis: Nucleotide Sequence and Expression of the menB Gene from *Escherichia coli*," J. Bacteriol. 174:5057-5062 (1992).
Shiba et al., "The CO2 assimilation via the reductive tricarboxylic acid cycle in an obligatory autotrophic, aerobic hydrogen-oxidizing bacterium, Hydrogenobacter thermophilus," Arch Microbiol, 141:198-203 (1985).
Shimomura et al., "Purification and Partial Characterization of 3-Hydroxyisobutyryl-coenzyme A Hydrolase of Rat Liver," J Biol Chem. 269:14248-14253 (1994).
Shimomura et al., "3-Hydroxyisobutyryl-CoA Hydrolase," Methods Enzymol. 324:229-240 (2000).
Shimoyama et al., "MmcBC inPelotomaculum thermopropionicum represents a novel group of prokaryotic fumarases," FEMS Microbiol. Lett. 270:207-213 (2007).
Sieber et al., "Libraries of hybrid proteins from distantly related sequences," Nat. Biotechnol. 19:456-460 (2001).
Siebers et al., "Reconstruction of the Central Carbohydrate Metabolism of Thermoproteus tenax by Use of Genomic and Biochemical Data," J. Bacteriol. 186:2179-2194 (2004).
Skarstedt et al., "*Escherichia coli* Acetate Kinase Mechanism Studied by Net Initial Rate, Equilibrium, and Independent Isotopic Exchange Kinetics," J.Biol.Chem. 251:6775-6783 (1976).
Slater et al., "Multiple b-Ketothiolases Mediate Poly(b-Hydroxyalkanoate) Copolymer Synthesis in Ralstonia eutropha," J.Bacteriol. 180:1979-1987 (1998).
Smith et al., "Fumarate metabolism and the microaerophily of *Campylobacter* species," Int. J. Biochem. Cell. Biol. 31:961-975 (1999).
Smith et al., "Purification and Characteristics of y-Glutamyl Kinase Involved in *Escherichia coli* Proline Biosynthesis," J.Bacteriol. 157:545-551 (1984).
Sohling et al., "Molecular Analysis of the Anaerobic Succinate Degradation Pathway in Clostridium kluyveri," J Bacteriol. 178:871-880 (1996).
Song et al., "Structure, Function, and Mechanism of the Phenylacetate Pathway Hot Dog-fold Thioesterase PaaI," J Biol Chem. 281(16):11028-38 (2006).
Sramek et al., "Purification and Properties of *Escherichia coli* Coenzyme A-Transferase," Arch Biochem Biophys 171:14-26 (1975).
St. Maurice et al., "Flavodoxin:Quinone Reductase (FqrB): a Redox Partner of Pyruvate:Ferredoxin Oxidoreductase That Reversibly Couples Pyruvate Oxidation to NADPH Production in Helicobacter pylori and Campylobacter jejuni," J Bacteriol. 189(13):4764-4773 (2007).

(56) References Cited

OTHER PUBLICATIONS

Stadtman, "Phosphotransacetylase from Clostridium kluyveri," Methods Enzymol 1:596-599 (1955).
Starai et al., "Residue Leu-641 of Acetyl-CoA Synthetase is Critical for the Acetylation of Residue Lys-609 by the Protein Acetyltransferase Enzyme of Salmonella enteric," J. Biol. Chem. 280:26200-26205 (2005).
Starai et al., "Acetate excretion during growth of Salmonella enterica on ethanolamine requires phosphotransacetylase (EutD) activity, and acetate recapture requires acetyl-CoA synthetase (Acs) and phosphotransacetylase (PTA) activities," Microbiology 151:3793-3801 (2005).
Steffan and McAlister-Henn, "Isolation and Characterization of the Yeast Gene Encoding the MDH3 Isozyme of Malate Dehydrogenase," J. Biol. Chem. 267:24708-24715 (1992).
Stemmer, "Rapid evoluslion of a protein in vitro by DNA shuffling," Nature 370:389-391 (1994).
Stemmer, "DNA shuffling by random fragmentation and reassembly: In vitro recombination for molecular evolution," Proc Natl Acad Sci USA 91:10747-10751 (1994).
Stirling et al., "Purification and properties of a nicotinamide adenine dinucleotide-linked cyclohexanol dehydrogenase from a nocardia species," 4:37-40 (1980).
Stols and Donnelly, "Production of Succinic Acid through Overexpression of NAD1-Dependent Malic Enzyme in an Escherichia coli Mutant," Appl. Environ. Microbiol. 63(7) 2695-2701 (1997).
Stols et al., "Expression of Ascaris suum Malic Enzyme in a Mutant Escherichia coli Allows Production of Succinic Acid from Glucose," Appl. Biochem. Biotechnol. 63-65(1), 153-158 (1997).
Stols et al., "New vectors for co-expression of proteins: Structure of Bacillus subtilis ScoAB obtained by high-throughput protocols," Protein Expr.Purif. 53:396-403 (2007).
Sulzenbacher et al., "Crystal Structure of E. coli Alcohol Dehydrogenase YqhD: Evidence of a Covalently Modified NADP Coenzyme," 342:489-502 (2004).
Suzuki, et al., "GriC and GriD Constitute a Carboxylic Acid Reductase Involved in Grixazone Biosynthesis in Streptomyces griseus," J. Antibiot. 60(6):380-387 (2007).
Suzuki, T., "Phosphotransacetylase of Escherichia coli B, Activation by pyruvate and inhibition by NADH and Certain Nucleotides," Biochim. Biophys. Acta 191:559-569 (1969).
Svetlitchnyi et al., "Two Membrane-Associated NiFeS—Carbon Monoxide Dehydrogenases from the Anaerobic Carbon-Monoxide-Utilizing Eubacterium Carboxydothermus hydrogenoformans," J Bacteriol. 183:5134-5144 (2001).
Tae-Kang et al., "Purification and Characterization of a Cyclohexanol Dehydrogenase from Rhodococcus sp. TK6," J.Microbiol.Biotechnol. 12:39-45 (2002).
Takahashi and Nakamura, "Functional Assignment of the OKF2-iscS-iscU-iscA-hscB-hscA-fdx-0RF3 Gene Cluster Involved in the Assembly of Fe—S Clusters in Escherichia coli," J Biochem. 126:917-926 (1999).
Takahashi, "Metabolic Pathways for Cytotoxic End Product Formation from Glutamate- and Aspartate-Containing Peptides by Porphyromonas gingivalis," J. Bacteriol 182:4704-4710 (2000).
Takahashi-Abbe et al., "Biochemical and functional properties of a pyruvate formate-lyase (PFL)-activating system in Streptococcus mutans," Oral.Microbiol Immunol 18:293-297 (2003).
Takeo, "Existence and Properties fo Two Malic Enzymes in Escherichia coli," J. Biochem. 66:379-387 (1969).
Tan et al., "Cloning, Expression, and Nucleotide Sequence of a Lipase Gene from Pseudomonas fluorescens B52," Appl.Environ. Microbiol. 58:1402-1407 (1992).
Tanaka et al., "Cloning and characterization of a human orthologue of testis-specific succinyl CoA: 3-oxo acid CoA transferase (Scot-t) cDNA," Mol. Hum. Reprod. 8(1):16-23 (2001).
Tang et al., "Microbial Conversion of Glycerol to 1,3-Propanediol by an Engineered Strain of Escherichia coli," Appl.Environ.Microbiol. 75:1628-1634 (2009).
Tani et al., "Thermostable NADP1-Dependent Medium-Chain Alcohol Dehydrogenase from Acinetobacter sp. Strain M-1: Purification and Characterization and Gene Expression in Escherichia coli," Appl.Environ.Microbiol. 66:5231-5235 (2000).
Thauer, "A Fifth Pathway of Carbon Fixation," Science 318:1732-1733 (2007).
Thiery et al., "Acyltransferase Activity of the Wide Spectrum Amidase of Brevibacterium sp. R312," J. Gen. Microbiol., 132:2205-8 (1986).
Tobimatsu et al., "Molecular Cloning, Sequencing and Characterization of the Genes for Adenosylcobalamin-dependent Diol Dehydratase of Klebsiella pneumonia," Biosci.Biotechnol Biochem. 62:1774-1777 (1998).
Tobimatsu et al., "Molecular Cloning, Sequencing and Expression of the Genes Encoding Adenosylcobalamin-dependent Diol Dehydrase of Klebsiella oxytoca," J Biol.Chem. 270:7142-7148 (1995).
Toraya et al., "Substrate Specificity of Coenzyme B12 Dependent Diol Dhydrase: Glycerol as Both a Good Substrate and a Potent Inactivator," Biochem.Biophys.Res.Commun. 69:475-480 (1976).
Toth, "The ald Gene, Encoding a Coenzyme A-Acylating Aldehyde Dehydrogenase, Distinguishes Clostridium beijerinckii and Two Other Solvent-Producing Clostridia from Clostridium acetobutylicum," Appl. Environ. Microbiol. 65:4973-4980 (1999).
Trower et al., "Isolation and Characterization of a Cyclohexane-Metabolizing Xanthobacter," 49:1282-1289 (1985).
Tseng et al., "Oxygen- and Growth Rate-Dependent Regulation of Escherichia coli Fumarase (FumA, FumB, and FumC) Activity," J. Bacteriol. 183:461-467 (2001).
Twarog et al., "Role of Butyryl Phosphate in the Energy Metabolism of Clostridium Tetanomorphum," J Bacteriol. 86:112-117 (1963).
Ulaganathan et al., "Structure of Staphylococcus aureus 1,4-dihydroxy-2-naphthoyl-CoA synthase (MenB) in complex with acetoacetyl-CoA," Acta Crstyallogr. Sect. F. Struct. Biol. Cyst. Commun. 63:908-913 (2007).
Valdes-Hevia et al., "Isolation and characterization of the gene encoding phosphoenolpyruvate carboxykinase from Saccharomyces cerevisiae," FEBS Lett. 258:313-316 (1989).
Vamecq et al., "The Microsomal Dicarboxylyl-CoA Synthetase," Biochem.J 230:683-693 (1985).
Van Beilen et al., "Cloning of Baeyer-Villiger monooxygenases from Comamonas, Xanthobacter and Rhodococcus using polymerase chain reaction with highly degenerate primers," 5:174-182 (2003).
van Grinsven et al., "Acetate:Succinate CoA-transferase in the Hydrogenosomes of Trichomonas vaginalis," J Biol Chem. 283:1411-1418 (2008).
van Vliet et al., "The iron-induced ferredoxin FdxA of Campylobacter jejuni is involved in aerotolerance," FEMS Microbiol Lett. 196:189-193 (2001).
Vanderwinkel et al., "Growth of Escherichia Coli on Fatty Acids: Requirement for Coenzyme a Tansferase Activity," Biochem. Biophys.Res.Commun. 33:902-908 (1968).
Vazquez et al., "Phosphotransbutyrylase Expression in Bacillus megaterium," Curr.Microbiol 42:345-349 (2001).
Venkitasubramanian et al., "Reduction of Carboxylic Acids by Nocardia Aldehyde Oxidoreductase Requires a Phosphopantetheinylated Enzyme," J Biol.Chem. 282:478-485 (2007).
Vey et al., "Structural basis for glycyl radical formation by pyruvate formate-lyase activating enzyme," Proc.Natl. Acad. Sci. U.S.A. 105:16137-16141 (2008).
Vita et al., "Disulfide Bond-Dependent Mechanism of Protection against Oxidative Stress in Pyruvate-Ferredoxin Oxidoreductase of Anaerobic DesulfoVibrio Bacteria," Biochemistry, 47: 957-64 (2008).
Volkov et al, "Recombination and chimeragenesis by in vitro heteroduplex formation and in vivo repair," Nucleic Acids Res. 27:e18 (1999).
Volkov et al., "Random Chimeragenesis by Heteroduplex Recombination," Methods Enzymol. 328:456-463 (2000).
Wakil et al., "Studies on the Fatty Acid Oxidizing System of Animal Tissues," J Biol.Chem. 207:631-638 (1954).

(56) References Cited

OTHER PUBLICATIONS

Walker et al., "Yeast Pyruvate Carboxylase: Identification of Two Genes Encoding Isoenzymes," Biochem. Biophys. Res. Commun. 176:1210-1217 (1991).
Walter et al., "Molecular Characterization of Two Clostridium acetobutylicum ATCC 824 Butanol Dehydrogenase Isozyme Genes," Journal of Bacteriology, 174:7149-7158 (1992).
Walter et al., "Sequence and arrangement of two genes of the butyrate-synthesis pathway of Clostridium acetobutylicum ATCC 824," Gene 134:107-111 (1993).
Wang et al., "Molecular cloning and functional identification of a novel phenylacetyl-CoA ligase gene from Penicillium chrysogenum," Biochemical and Biophysical Research Communications, 360:453-458 (2007).
Weidner et al., "Molecular Characterization of the Genes Encoding Pyruvate Formate-Lyase and Its Activating Enzyme of Clostridium pasteurianum," J Bacteriol. 178:2440-2444 (1996).
Westin et al., "The Identification of a Succinyl-CoA Thioesterase Suggests a Novel Pathway for Succinate Production in Peroxisomes," J.Biol.Chem. 280:38125-38132 (2005).
Wiesenborn et al., "Phosphotransbutyrylase from *Clostridium acetobutylicum* ATCC 824 and Its Role in Acidogenesis," App. Environ. Microbiol. 55:317-322 (1989).
Wiesenborn et al., "Coenzyme A Transferase from Clostridum acetobutylicum ATCC 824 abd Uts Rike ub the Uptake of Acids," Appl Environ Microbiol 55:323-329 (1989).
Winzer et al., "Differential Regulation of Two Thiolase Genes from Clostridium acetobutylicum DSM 792," J.Mol.Microbiol Biotechnol 2:531-541 (2000).
Winzer et al., "Acetate kinase from Clostridium acetobutylicum: a highly specific enzyme that is actively transcribed during acidogenesis and solventogenesis," Microbioloy 143 (Pt 10):3279-3286 (1997).
Wolff et al., "Purification and Characterization of the Oxygen-Sensitive 4-Hydroxybutanoate Dehydrogenase from Clostridium kluyveri," Protein Expr.Purif. 6:206-212 (1995).
Wong et al., "Sequence saturation mutagenesis with tunable mutation frequencies," Anal. Biochem. 341:187-189 (2005).
Wong et al., "Transversion-enriched sequence saturation mutagenesis (SeSaM-Tv+): A random mutagenesis method with consecutive nucleotide exchanges that complements the bias of error-prone PCR," Biotechnol. J. 3:74-82 (2008).
Wong et al., "Sequence saturation mutagenesis (SeSaM): a novel method for directed evolution," Nucleic Acids Res. 32:e26 (2004).
Wood et al., "A challenge for 21st century molecular biology and biochemistry: what are the causes of obligate autotrophy and methanotrophy?," FEMS Microbiol. Rev. 28:335-352 (2004).
Woods et al., "Two biochemically distinct classes of fumarase in *Escherichia coli*," Biochim. Biophys. Acta 954:14-26 (1988).
Wu et al., "Life in Hot Carbon Monoxide: The Complete Genome Sequence of Carboxydothermus hydrogenoformans Z-2901," PLoS Genet. 1:e65 (2005).

Yabutani et al., "Analysis of β-ketothiolase and acetoacetyl-CoA reductase genes of a methylotrophic bacterium, Paracoccus denitrificans, and their expression in *Escherichia coli*," FEMS Microbiol Lett. 133:85-90 (1995).
Yakunin and Hallenbeck, "Purification and characterization of pyruvate axidoreductase from the photosynthetic bacterium Rhodobacter capsulatus," Biochimica et Biophysica Acta 1409 (1998) 39-49 (1998).
Yamamoto et al., "Carboxylation reaction catalyzed by 2-oxoglutarate:ferredoxin oxidoreductases from Hydrogenobacter thermophilus," Extremophiles 14:79-85 (2010).
Yang et al., "Nucleotide sequence of the promoter and fadB gene of the fadBA operon and primary structure of the multifunctional fatty acid oxidation protein from *Escherichia coli*," Biochemistry 30:6788-6795 (1991).
Yang, "*E Coli* Map," J Bacteriol. 173:7405-7406 (1991).
Ylianttila et al., "Site-directed mutagenesis to enable and improve crystallizability of Candida tropicalis (3R)-hydroxyacyl-CoA dehydrogenase," Biochem Biophys Res Commun 324:25-30 (2004).
Ylianttila et al., "Crystal Structure of Yeast Peroxisomal Multifunctional Enzyme: Structural Basis for Substrate Specificity of (3R)-hydroxyacyl-CoA Dehydrogenase Units," J Mol Biol 358:1286-1295 (2006).
Yoshida et al., "Identification of a Functional 2-keto-myo-Inositol Dehydratase Gene of Sinorhizobium fredii USDA191 Required for myo-Inositol Utilization," Biosci.Biotechnol.Biochem. 70:2957-2964 (2006).
Yoshida et al., "The fifth gene of the iol operon of Bacillus subtilis, iolE, encodes 2-keto-myoinositol dehydratase," Microbiology 150:571-580 (2004).
Yoshioka and Hashimoto, "Ester Formation by Alcohol Acetyltransferase from Brewers' Yeast," Agricul and Biol Chem, 45:2183-2191 (1981).
Youngleson et al., "Homology between Hydroxybutyryl and Hydroxyacyl Coenzyme A Dehydrogenase Enzymes from Clostridium acetobutylicum Fermentation and Vertebrate Fatty Acid 1-Oxidation Pathways," J Bacteriol. 171:6800-6807 (1989).
Yun et al., : The Genes for Anabolic 2-Oxoglutarate: Ferredoxin Oxidoreductase from Hydrogenobacter thermophilus TK-6, Biochem. Biophys. Res. Commun. 282:589-594 (2001).
Yun et al., "A Novel Five-Subunit-Type 2-Oxoglutalate:Ferredoxin Oxidoreductases from Hydrogenobacter thermophilus TK-6," Biochem. Biophys. Res. Commun. 292:280-286 (2002).
Zeiher et al., "Identification and Characterization of Mitochondrial Acetyl-Coenzyme a Hydrolase from Pisum sativum L. Seelings," Plant.Physiol. 94:20-27 (1990).
Zhang et al., "Isolation and properties of a levo-lactonase from Fusarium proliferatum ECU2002: a robust biocatalyst for production of chiral lactones," Appl Microbiol Biotechnol 75:1087-1094 (2007).
Zhao et al., "Molecular evolution by staggered extension process (StEP) in Vitro recombination," Nat. Biotechnol. 16:258-261 (1998).
Zhou et al., "Engineering a native homoethanol pathway in *Escherichia coli* B for ethanol production," Biotechnol. Lett. 30:335-342 (2008).

MICROORGANISMS AND METHODS FOR THE PRODUCTION OF CAPROLACTONE

This application is a continuation of U.S. patent application Ser. No. 13/668,117 (now U.S. Pat. No. 8,940,509), filed Nov. 2, 2012 which claims the benefit of priority of U.S. Provisional application Ser. No. 61/554,920, filed Nov. 2, 2011, both of which are incorporated herein by reference in their entirety and for all purposes.

BACKGROUND OF THE INVENTION

The present invention relates generally to biosynthetic processes, and more specifically to organisms having caprolactone capability.

Caprolactone (ε-Caprolactone) is a cyclic ester with a seven-membered ring having the formula $(CH_2)_5CO_2$. This colorless liquid is miscible with most organic solvents. It is produced as a precursor to caprolactam. The caprolactone monomer is used in the manufacture of highly specialized polymers because of its ring-opening potential. Ring-opening polymerization, for example, results in the production of polycaprolactone. Caprolactone is typically prepared by oxidation of cyclohexanone with peracetic acid.

Caprolactone undergoes reactions typical for primary alcohols. Downstream applications of these product groups include protective and industrial coatings, polyurethanes, cast elastomers, adhesives, colorants, pharmaceuticals and many more. Other useful properties of caprolactone include high resistance to hydrolysis, excellent mechanical properties, and low glass transition temperature.

Thus, there exists a need for methods for effectively producing compounds such as caprolactone. The present invention satisfies this need and provides related advantages as well.

SUMMARY OF INVENTION

The invention provides non-naturally occurring microbial organisms containing caprolactone pathways having at least one exogenous nucleic acid encoding a butadiene pathway enzyme expressed in a sufficient amount to produce caprolactone. The invention additionally provides methods of using such microbial organisms to produce caprolactone by culturing a non-naturally occurring microbial organism containing caprolactone pathways as described herein under conditions and for a sufficient period of time to produce caprolactone.

DETAILED DESCRIPTION OF THE INVENTION

Figure 1:
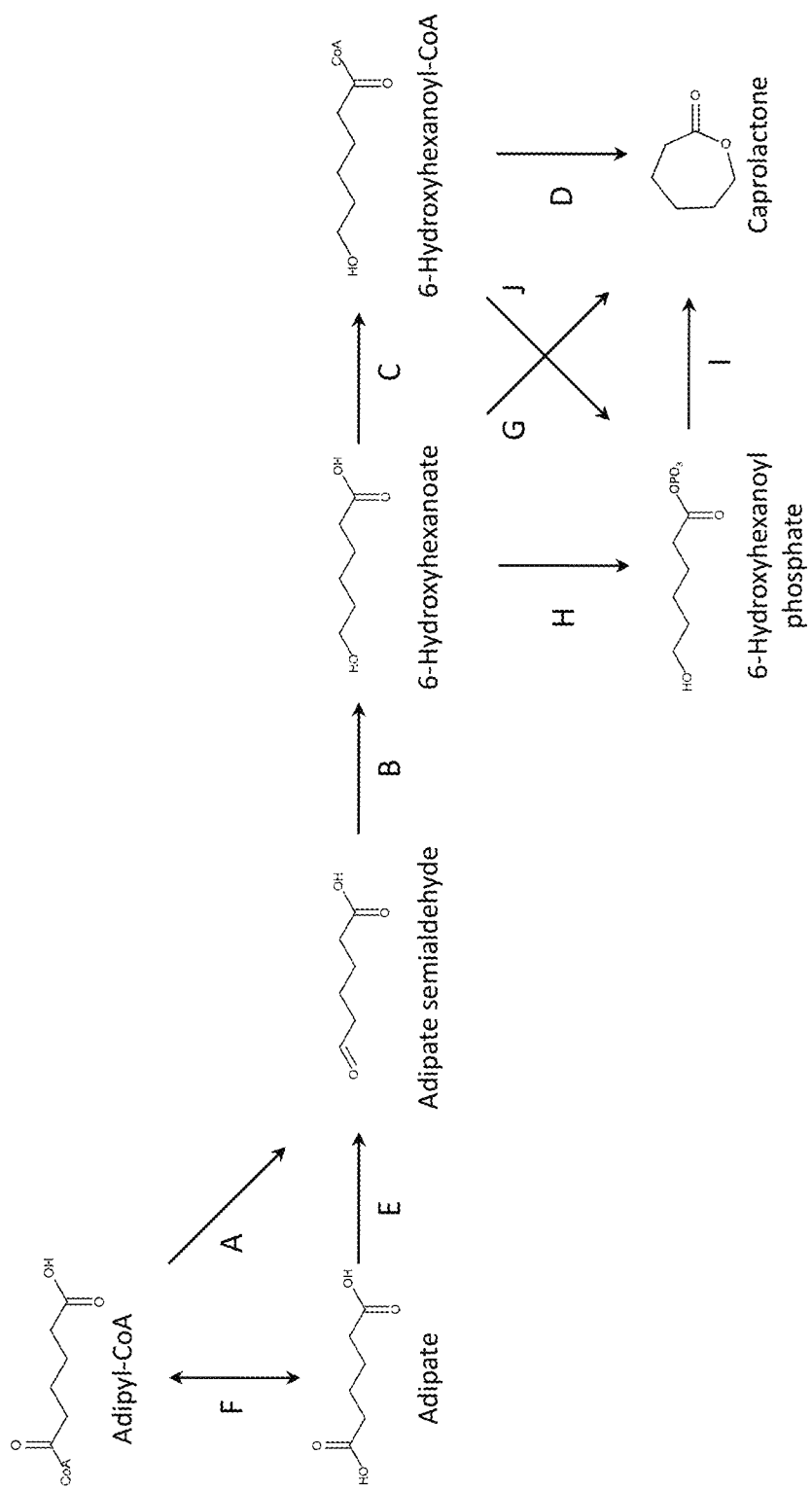
FIG. 1 shows exemplary pathways from adipate or adipyl-CoA to caprolactone. Enzymes are A. adipyl-CoA reductase, B. adipate semialdehyde reductase, C. 6-hydroxyhexanoyl-CoA transferase or synthetase, D. 6-hydroxyhexanoyl-CoA cyclase or spontaneous cyclization, E. adipate reductase, F. adipyl-CoA transferase, synthetase or hydrolase, G. 6-hydroxyhexanoate cyclase, H. 6-hydroxyhexanoate kinase, I. 6-hydroxyhexanoyl phosphate cyclase or spontaneous cyclization, J. phosphotrans-6-hydroxyhexanoylase.

The present invention is directed to the design and production of cells and organisms having biosynthetic production capabilities for caprolactone. The invention, in particular, relates to the design of microbial organism capable of producing caprolactone by introducing one or more nucleic acids encoding a caprolactone pathway enzyme.

In one embodiment, the invention utilizes in silico stoichiometric models of *Escherichia coli* metabolism that identify metabolic designs for biosynthetic production of caprolactone. The results described herein indicate that metabolic pathways can be designed and recombinantly engineered to achieve the biosynthesis of caprolactone in *Escherichia coli* and other cells or organisms. Biosynthetic production of caprolactone, for example, for the in silico designs can be confirmed by construction of strains having the designed metabolic genotype. These metabolically engineered cells or organisms also can be subjected to adaptive evolution to further augment caprolactone biosynthesis, including under conditions approaching theoretical maximum growth.

In certain embodiments, the caprolactone biosynthesis characteristics of the designed strains make them genetically stable and particularly useful in continuous bioprocesses. Separate strain design strategies were identified with incorporation of different non-native or heterologous reaction capabilities into *E. coli* or other host organisms leading to caprolactone producing metabolic pathways from either adipyl-CoA, adipate, 4-hydroxybutyryl-CoA, adipate semialdehyde and pimeloyl-CoA. In silico metabolic designs were identified that resulted in the biosynthesis of caprolactone in microorganisms from each of these substrates or metabolic intermediates.

Strains identified via the computational component of the platform can be put into actual production by genetically engineering any of the predicted metabolic alterations, which lead to the biosynthetic production of caprolactone or other intermediate and/or downstream products. In yet a further embodiment, strains exhibiting biosynthetic production of these compounds can be further subjected to adaptive evolution to further augment product biosynthesis. The levels of product biosynthesis yield following adaptive evolution also can be predicted by the computational component of the system.

The maximum theoretical caprolactone yield from glucose is 0.80 mol/mol (0.51 g/g), according to the equation:

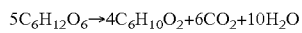

The pathways presented in FIGS. 1-5 achieve a yield of 0.80 moles caprolactone per mole of glucose utilized. Increasing product yields is possible if cells are capable of fixing $CO_2$ through pathways such as the reductive TCA cycle or the Wood-Ljungdahl pathway and additional reducing equivalents are provided.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a caprolactone biosynthetic pathway.

A metabolic modification refers to a biochemical reaction that is altered from its naturally occurring state. Therefore, non-naturally occurring microorganisms can have genetic modifications to nucleic acids encoding metabolic polypeptides, or functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

It is understood that when more than one exogenous nucleic acid is included in a microbial organism that the more than one exogenous nucleic acids refers to the referenced encoding nucleic acid or biosynthetic activity, as discussed above. It is further understood, as disclosed herein, that such more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

The non-naturally occurring microbial organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as *E. coli* and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having caprolactone biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionally related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

In some embodiments, the invention provides a non-naturally occurring microbial organism having a caprolactone pathway and including at least one exogenous nucleic acid encoding a caprolactone pathway enzyme expressed in a sufficient amount to produce caprolactone. In some aspects of the invention, the caprolactone pathway includes a pathway selected from: (1) 1A, 1B, 1C and 1D; (2) 1E, 1B, 1C and 1D; (3) 1F, 1A, 1B, 1C and 1D; (4) 1F, 1E, 1B, 1C and 1D; (5) 1A, 1B and 1G; (6) 1E, 1B and 1G; (7) 1F, 1A, 1B and 1G; (8) 1F, 1E, 1B and 1G; (9) 1A, 1B, 1C, 1J and 1I; (10) 1E, 1B, 1C, 1J and 1I; (11) 1F, 1A, 1B, 1C, 1J and 1I; (12) 1F, 1E, 1B, 1C, 1J and 1I; (13) 1A, 1B, 1H and 1I; (14) 1E, 1B, 1H and 1I; (15) 1F, 1A, 1B, 1H and 1I; (16) 1F, 1E, 1B, 1H and 1I; (17) 2A, 2B, 2C, 2D, 2E and 2F; (18) 2A, 2B, 2C, 2D and 2G; (19) 2A, 2B, 2C, 2D, 2E, 2J and 2I; (20) 2A, 2B, 2C, 2D, 2H and 2I; (21) 4A, 4B, 4C, 4D and 3A; and (22) 5A, 5B, 5C an 3A, wherein 1A is an adipyl-CoA reductase, wherein 1B is an adipate semialdehyde reductase, wherein 1C is a 6-hydroxyhexanoyl-CoA transferase or a 6-hydroxyhexanoyl-CoA synthetase, wherein 1D is a 6-hydroxyhexanoyl-CoA cyclase or spontaneous cyclization, wherein 1E is an adipate reductase, wherein 1F is an adipyl-CoA transferase, an adipyl-CoA synthetase or an adipyl-CoA hydrolase, wherein 1G is a 6-hydroxyhexanoate cyclase, wherein 1H is a 6-hydroxyhexanoate kinase, wherein 1I is a 6-hydroxyhexanoyl phosphate cyclase or spontaneous cyclization, wherein 1J is a phosphotrans-6-hydroxyhexanoylase, wherein 2A is a 4-hydroxybutyryl-CoA:acetyl-CoA acyltransferase, wherein 2B is a 3-oxo-6-hydroxyhexanoyl-CoA reductase, wherein 2C is a 3,6-dihydroxyhexanoyl-CoA dehydratase, wherein 2D is a 6-hydroxyhex-2-enoyl-CoA reductase, wherein 2E is a 6-hydroxyhexanoyl-CoA transferase, a 6-hydroxyhexanoyl-CoA synthetase or a 6-hydroxyhexanoyl-CoA hydrolase, wherein 2F is a 6-hydroxyhexanoate cyclase, wherein 2G is a 6-hydroxyhexanoyl-CoA cyclase or spontaneous cyclization, wherein 2H is a phosphotrans-6-hydroxyhexanoylase, wherein 2I is a 6-hydroxyhexanoyl phosphate cyclase or spontaneous cyclization, wherein 2J is a 6-hydroxyhexanoate kinase, wherein 3A is a cyclohexanone monooxygenase, wherein 4A is an adipate semialdehyde dehydratase, wherein 4B is a cyclohexane-1,2-dione reductase, wherein 4C is a 2-hydroxycyclohexanone reductase, wherein 4D is a cyclohexane-1,2-diol dehydratase, wherein 5A is a 2-ketocyclohexane-1-carboxyl-CoA hydrolase (acting on C-C), wherein 5B is a 2-ketocyclohexane-1-carboxoyl-CoA transferase, a 2-ketocyclohexane-1-carboxoyl-CoA synthetase or a 2-ketocyclohexane-1-carboxoyl-CoA hydrolase, and wherein 5C is a 2-ketocyclohexane-1-carboxylate decarboxylase.

In one embodiment, the invention provides a non-naturally occurring microbial organism as described herein, wherein the microbial organism includes two, three, four, five, six or seven exogenous nucleic acids each encoding a caprolactone pathway enzyme. For example, the microbial organism can include exogenous nucleic acids encoding each of the enzymes of at least one of the pathways selected from (1)-(22) as described above.

In one embodiment, at least one exogenous nucleic acid included within the microbial organism is a heterologous nucleic acid. In another aspect, the non-naturally occurring microbial organism as disclosed herein is in a substantially anaerobic culture medium.

In one embodiment, the non-naturally occurring microbial organism as disclosed herein further includes (i) a reductive TCA pathway comprising at least one exogenous nucleic acid encoding a reductive TCA pathway enzyme, wherein said at least one exogenous nucleic acid is selected from an ATP-citrate lyase, citrate lyase, a fumarate reductase, and an alpha-ketoglutarate:ferredoxin oxidoreductase; (ii) a reductive TCA pathway comprising at least one exogenous nucleic acid encoding a reductive TCA pathway enzyme, wherein said at least one exogenous nucleic acid is selected from a pyruvate:ferredoxin oxidoreductase, a phosphoenolpyruvate carboxylase, a phosphoenolpyruvate carboxykinase, a CO dehydrogenase, and an $H_2$ hydrogenase; or (iii) at least one exogenous nucleic acid encodes an enzyme selected from a CO dehydrogenase, an $H_2$ hydrogenase, and combinations thereof.

In another aspect of the invention, non-naturally occurring microbial organism having (i) above, further includes an exogenous nucleic acid encoding an enzyme selected from a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, ferredoxin, and combinations thereof. In another aspect, the non-naturally occurring microbial organism including (ii) as described above further includes an exogenous nucleic acid encoding an enzyme selected from an aconitase, an isocitrate dehydrogenase, a succinyl-CoA synthetase, a succinyl-CoA transferase, a fumarase, a malate dehydrogenase, and combinations thereof.

In one aspect of the invention, the non-naturally occurring microbial organism having (i) as described above further comprises four exogenous nucleic acids encoding an ATP-citrate lyase, citrate lyase, a fumarate reductase, and an alpha-ketoglutarate:ferredoxin oxidoreductase. In one aspect of the invention, the non-naturally occurring microbial organism having (ii) as described above further comprises five exogenous nucleic acids encoding a pyruvate:ferredoxin oxidoreductase, a phosphoenolpyruvate carboxylase, a phosphoenolpyruvate carboxykinase, a CO dehydrogenase, and an $H_2$ hydrogenase. In one aspect of the invention, the non-naturally occurring microbial organism having (iii) as described above further comprises two exogenous nucleic acids encoding a CO dehydrogenase and an $H_2$ hydrogenase.

In an additional embodiment, the invention provides a non-naturally occurring microbial organism having a caprolactone pathway, wherein the non-naturally occurring microbial organism comprises at least one exogenous nucleic acid encoding an enzyme or protein that converts a substrate to a product selected from the group consisting of adipyl-CoA to adipate, adipyl-CoA to adipate semialdehyde, adipate to adipate semialdehyde, adipate semialdehyde to 6-hydroxyhexanoate, 6-hydroxyhexanoate to 6-hydroxyhexanoyl-CoA, 6-hydroxyhexanoate to 6-hydroxyhexanoyl-phosphate, 6-hydroxyhexanoate to caprolactone, 6-hydroxyhexanoyl-CoA to 6-hydroxyhexanoyl phosphate, 6-hydroxyhexanoyl phosphate to caprolactone, 6-hydroxyhexanoyl-CoA to caprolactone, 4-hydroxybutyryl-CoA to 3-oxo-6-hydroxy hexanoyl-CoA, to 3-oxo-6-hydroxy hexanoyl-CoA to 3,6-dihydroxy hexanoyl-CoA, 3,6-dihydroxy hexanoyl-CoA to 6-hydroxyhex-2-enoyl-CoA, 6-hydroxyhex-2-enoyl-CoA to 6-hydroxyhexanoyl-CoA, 6-hydroxyhexanoyl-CoA to 6-hydroxyhexanoate, cyclohexanon to caprolactone, adipate semialdehyde to cyclohexane-1,2-dione, cyclohexane-1,2-dione to 2-hydroxycyclohexanone, to 2-hydroxycyclohexanone to cyclohexane-1,2-diol, cyclohexane-1,2-diol to cyclohexone, pimeloyl-CoA to 2-ketocyclohexone-1-carboxoyl-CoA, 2-ketocyclohexone-1-carboxoyl-CoA to 2-ketocyclohexane-1-carboxylate, and 2-ketocyclohexane-1-carboxylate to cyclohexanone. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, the invention provides a non-naturally occurring microbial organism containing at least one exogenous nucleic acid encoding an enzyme or protein, where the enzyme or protein converts the substrates and products of a caprolactone pathway, such as that shown in FIGS. 1-5.

While generally described herein as a microbial organism that contains a caprolactone pathway, it is understood that the invention additionally provides a non-naturally occurring microbial organism comprising at least one exogenous nucleic acid encoding a caprolactone pathway enzyme expressed in a sufficient amount to produce an intermediate of a caprolactone pathway. For example, as disclosed herein, a caprolactone pathway is exemplified in FIGS. 1-5. Therefore, in addition to a microbial organism containing a caprolactone pathway that produces caprolactone, the invention additionally provides a non-naturally occurring microbial organism comprising at least one exogenous nucleic acid encoding a caprolactone pathway enzyme, where the microbial organism produces a caprolactone pathway intermediate, for example, 6-hydroxyhexanoate, 6-hydroxyhexanoyl-CoA, 6-hydroxyhexanoyl phosphate, 3-oxo-6-hydroxy hexanoyl-CoA, 3,6-dihydroxy hexanoyl-CoA, 6-hydroxyhex-2-enoyl-CoA, cyclohexanone, cyclohexane-1,2-dione, 2-hydroxycyclohexanone, cyclohexane-1,2-diol, 2-ketocyclohexane-1-carboxyoyl-CoA, or 2-ketocyclohexane-1-carboxylate.

It is understood that any of the pathways disclosed herein, as described in the Examples and exemplified in the Figures, including the pathways of FIGS. 1-5, can be utilized to generate a non-naturally occurring microbial organism that produces any pathway intermediate or product, as desired. As disclosed herein, such a microbial organism that produces an intermediate can be used in combination with another microbial organism expressing downstream pathway enzymes to produce a desired product. However, it is understood that a non-naturally occurring microbial organism that produces a caprolactone pathway intermediate can be utilized to produce the intermediate as a desired product.

This invention is also directed, in part to engineered biosynthetic pathways to improve carbon flux through a central metabolism intermediate en route to caprolactone. The present invention provides non-naturally occurring microbial organisms having one or more exogenous genes encoding enzymes that can catalyze various enzymatic transformations en route to caprolactone. In some embodiments, these enzymatic transformations are part of the reductive tricarboxylic acid (RTCA) cycle and are used to improve product yields, including but not limited to, from carbohydrate-based carbon feedstock.

In numerous engineered pathways, realization of maximum product yields based on carbohydrate feedstock is hampered by insufficient reducing equivalents or by loss of reducing equivalents and/or carbon to byproducts. In accordance with some embodiments, the present invention increases the yields of caprolactone by (i) enhancing carbon fixation via the reductive TCA cycle, and/or (ii) accessing additional reducing equivalents from gaseous carbon sources and/or syngas components such as CO, $CO_2$, and/or $H_2$. In addition to syngas, other sources of such gases include, but are not limited to, the atmosphere, either as found in nature or generated.

Figure 6:
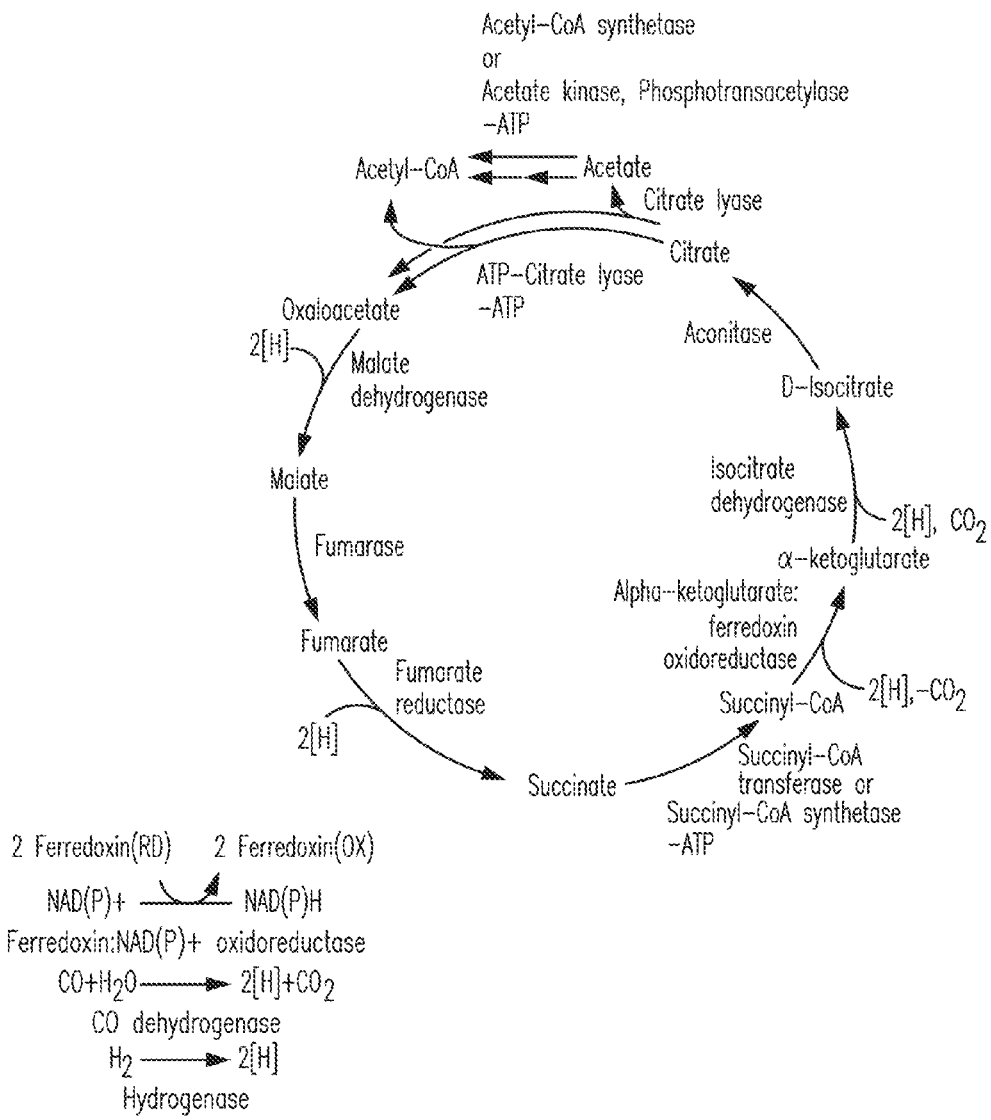
FIG. 6 shows the reverse TCA cycle for fixation of $CO_2$ on carbohydrates as substrates. The enzymatic transformations are carried out by the enzymes as shown.

The $CO_2$-fixing reductive tricarboxylic acid (RTCA) cycle is an endergenic anabolic pathway of $CO_2$ assimilation which uses reducing equivalents and ATP (FIG. 6). One turn of the RTCA cycle assimilates two moles of $CO_2$ into one mole of acetyl-CoA, or four moles of $CO_2$ into one mole of oxaloacetate. This additional availability of acetyl-CoA improves the maximum theoretical yield of product molecules derived from carbohydrate-based carbon feedstock. Exemplary carbohydrates include but are not limited to glucose, sucrose, xylose, arabinose and glycerol.

In some embodiments, the reductive TCA cycle, coupled with carbon monoxide dehydrogenase and/or hydrogenase enzymes, can be employed to allow syngas, $CO_2$, CO, $H_2$, and/or other gaseous carbon source utilization by microorganisms. Synthesis gas (syngas), in particular is a mixture of primarily $H_2$ and CO, sometimes including some amounts of $CO_2$, that can be obtained via gasification of any organic feedstock, such as coal, coal oil, natural gas, biomass, or waste organic matter. Numerous gasification processes have been developed, and most designs are based on partial oxidation, where limiting oxygen avoids full combustion, of organic materials at high temperatures (500-1500° C.) to provide syngas as a 0.5:1-3:1 $H_2$/CO mixture. In addition to coal, biomass of many types has been used for syngas production and represents an inexpensive and flexible feedstock for the biological production of renewable chemicals and fuels. Carbon dioxide can be provided from the atmosphere or in condensed from, for example, from a tank cylinder, or via sublimation of solid $CO_2$. Similarly, CO and hydrogen gas can be provided in reagent form and/or mixed in any desired ratio. Other gaseous carbon forms can include, for example, methanol or similar volatile organic solvents.

The components of synthesis gas and/or other carbon sources can provide sufficient $CO_2$, reducing equivalents, and ATP for the reductive TCA cycle to operate. One turn of the RTCA cycle assimilates two moles of $CO_2$ into one mole of acetyl-CoA and requires 2 ATP and 4 reducing equivalents.

CO and/or $H_2$ can provide reducing equivalents by means of carbon monoxide dehydrogenase and hydrogenase enzymes, respectively. Reducing equivalents can come in the form of NADH, NADPH, FADH, reduced quinones, reduced ferredoxins, reduced flavodoxins and thioredoxins. The reducing equivalents, particularly NADH, NADPH, and reduced ferredoxin, can serve as cofactors for the RTCA cycle enzymes, for example, malate dehydrogenase, fumarate reductase, alpha-ketoglutarate:ferredoxin oxidoreductase (alternatively known as 2-oxoglutarate:ferredoxin oxidoreductase, alpha-ketoglutarate synthase, or 2-oxoglutarate synthase), pyruvate:ferredoxin oxidoreductase and isocitrate dehydrogenase. The electrons from these reducing equivalents can alternatively pass through an ion-gradient producing electron transport chain where they are passed to an acceptor such as oxygen, nitrate, oxidized metal ions, protons, or an electrode. The ion-gradient can then be used for ATP generation via an ATP synthase or similar enzyme.

The reductive TCA cycle was first reported in the green sulfur photosynthetic bacterium *Chlorobium limicola* (Evans et al., *Proc. Natl. Acad. Sci. U.S.A.* 55:928-934 (1966)). Similar pathways have been characterized in some prokaryotes (proteobacteria, green sulfur bacteria and thermophilic Knallgas bacteria) and sulfur-dependent archaea (Hugler et al., *J. Bacteriol.* 187:3020-3027 (2005; Hugler et al., *Environ. Microbiol.* 9:81-92 (2007). In some cases, reductive and oxidative (Krebs) TCA cycles are present in the same organism (Hugler et al., supra (2007); Siebers et al., *J. Bacteriol.* 186: 2179-2194 (2004)). Some methanogens and obligate anaerobes possess incomplete oxidative or reductive TCA cycles that may function to synthesize biosynthetic intermediates (Ekiel et al., *J. Bacteriol.* 162:905-908 (1985); Wood et al., *FEMS Microbiol. Rev.* 28:335-352 (2004)).

The key carbon-fixing enzymes of the reductive TCA cycle are alpha-ketoglutarate:ferredoxin oxidoreductase, pyruvate:ferredoxin oxidoreductase and isocitrate dehydrogenase. Additional carbon may be fixed during the conversion of phosphoenolpyruvate to oxaloacetate by phosphoenolpyruvate carboxylase or phosphoenolpyruvate carboxykinase or by conversion of pyruvate to malate by malic enzyme.

Many of the enzymes in the TCA cycle are reversible and can catalyze reactions in the reductive and oxidative directions. However, some TCA cycle reactions are irreversible in vivo and thus different enzymes are used to catalyze these reactions in the directions required for the reverse TCA cycle. These reactions are: (1) conversion of citrate to oxaloacetate and acetyl-CoA, (2) conversion of fumarate to succinate, and (3) conversion of succinyl-CoA to alpha-ketoglutarate. In the TCA cycle, citrate is formed from the condensation of oxaloacetate and acetyl-CoA. The reverse reaction, cleavage of citrate to oxaloacetate and acetyl-CoA, is ATP-dependent and catalyzed by ATP-citrate lyase, or citryl-CoA synthetase and citryl-CoA lyase. Alternatively, citrate lyase can be coupled to acetyl-CoA synthetase, an acetyl-CoA transferase, or phosphotransacetylase and acetate kinase to form acetyl-CoA and oxaloacetate from citrate. The conversion of succinate to fumarate is catalyzed by succinate dehydrogenase while the reverse reaction is catalyzed by fumarate reductase. In the TCA cycle succinyl-CoA is formed from the NAD(P)$^+$ dependent decarboxylation of alpha-ketoglutarate by the alpha-ketoglutarate dehydrogenase complex. The reverse reaction is catalyzed by alpha-ketoglutarate:ferredoxin oxidoreductase.

Figure 7:
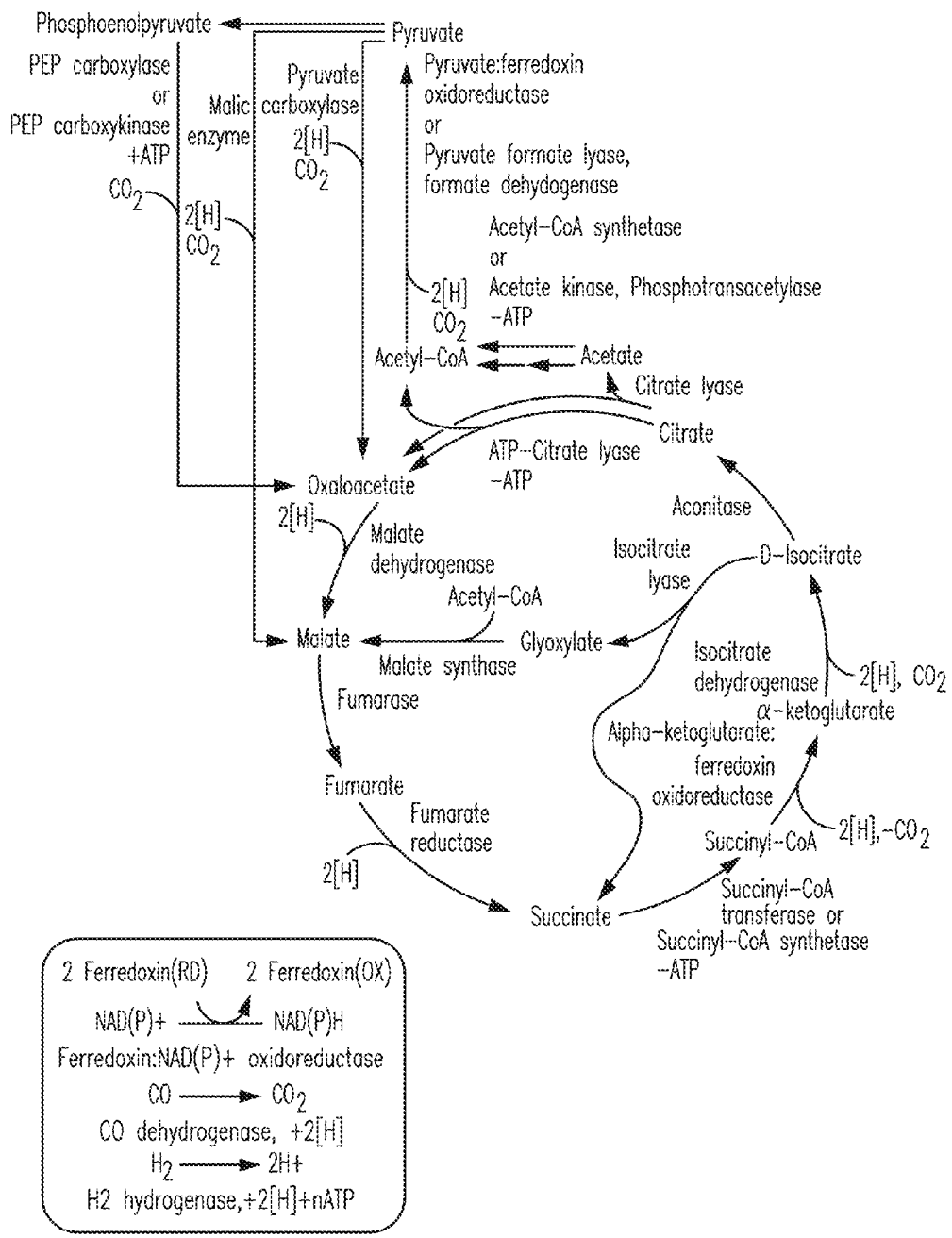
FIG. 7 shows the pathway for the reverse TCA cycle coupled with carbon monoxide dehydrogenase and hydrogenase for the conversion of syngas to acetyl-CoA.

An organism capable of utilizing the reverse tricarboxylic acid cycle to enable production of acetyl-CoA-derived products on 1) CO, 2) $CO_2$ and $H_2$, 3) CO and $CO_2$, 4) synthesis gas comprising CO and $H_2$, and 5) synthesis gas or other gaseous carbon sources comprising CO, $CO_2$, and $H_2$ can include any of the following enzyme activities: ATP-citrate lyase, citrate lyase, aconitase, isocitrate dehydrogenase, alpha-ketoglutarate:ferredoxin oxidoreductase, succinyl-CoA synthetase, succinyl-CoA transferase, fumarate reductase, fumarase, malate dehydrogenase, acetate kinase, phosphotransacetylase, acetyl-CoA synthetase, acetyl-CoA transferase, pyruvate:ferredoxin oxidoreductase, NAD(P)H:ferredoxin oxidoreductase, carbon monoxide dehydrogenase, hydrogenase, and ferredoxin (see FIG. 7). Enzymes and the corresponding genes required for these activities are described herein.

Carbon from syngas or other gaseous carbon sources can be fixed via the reverse TCA cycle and components thereof. Specifically, the combination of certain carbon gas-utilization pathway components with the pathways for formation of caprolactone from acetyl-CoA results in high yields of these products by providing an efficient mechanism for fixing the carbon present in carbon dioxide, fed exogenously or produced endogenously from CO, into acetyl-CoA.

In some embodiments, a caprolactone pathway in a non-naturally occurring microbial organism of the invention can utilize any combination of (1) CO, (2) $CO_2$, (3) $H_2$, or mixtures thereof to enhance the yields of biosynthetic steps involving reduction, including addition to driving the reductive TCA cycle.

In some embodiments a non-naturally occurring microbial organism having an caprolactone pathway includes at least one exogenous nucleic acid encoding a reductive TCA pathway enzyme. The at least one exogenous nucleic acid is selected from an ATP-citrate lyase, citrate lyase, a fumarate reductase, isocitrate dehydrogenase, aconitase, and an alpha-ketoglutarate:ferredoxin oxidoreductase; and at least one exogenous enzyme selected from a carbon monoxide dehydrogenase, a hydrogenase, a NAD(P)H:ferredoxin oxidoreductase, and a ferredoxin, expressed in a sufficient amount to allow the utilization of (1) CO, (2) $CO_2$, (3) $H_2$, (4) $CO_2$ and $H_2$, (5) CO and $CO_2$, (6) CO and $H_2$, or (7) CO, $CO_2$, and $H_2$.

In some embodiments a method includes culturing a non-naturally occurring microbial organism having a caprolactone pathway also comprising at least one exogenous nucleic acid encoding a reductive TCA pathway enzyme. The at least one exogenous nucleic acid is selected from an ATP-citrate lyase, citrate lyase, a fumarate reductase, isocitrate dehydrogenase, aconitase, and an alpha-ketoglutarate:ferredoxin oxidoreductase. Additionally, such an organism can also include at least one exogenous enzyme selected from a carbon monoxide dehydrogenase, a hydrogenase, a NAD(P)H:ferredoxin oxidoreductase, and a ferredoxin, expressed in a sufficient amount to allow the utilization of (1) CO, (2) $CO_2$, (3) $H_2$, (4) $CO_2$ and $H_2$, (5) CO and $CO_2$, (6) CO and $H_2$, or (7) CO, $CO_2$, and $H_2$ to produce a product.

In some embodiments a non-naturally occurring microbial organism having an caprolactone pathway further includes at least one exogenous nucleic acid encoding a reductive TCA pathway enzyme expressed in a sufficient amount to enhance carbon flux through acetyl-CoA. The at least one exogenous nucleic acid is selected from an ATP-citrate lyase, citrate lyase, a fumarate reductase, a pyruvate:ferredoxin oxidoreductase, isocitrate dehydrogenase, aconitase and an alpha-ketoglutarate:ferredoxin oxidoreductase.

In some embodiments a non-naturally occurring microbial organism having a caprolactone pathway includes at least one exogenous nucleic acid encoding an enzyme expressed in a sufficient amount to enhance the availability of reducing equivalents in the presence of carbon monoxide and/or hydrogen, thereby increasing the yield of redox-limited products via carbohydrate-based carbon feedstock. The at least one exogenous nucleic acid is selected from a carbon monoxide dehydrogenase, a hydrogenase, an NAD(P)H:ferredoxin oxidoreductase, and a ferredoxin. In some embodiments, the present invention provides a method for enhancing the availability of reducing equivalents in the presence of carbon monoxide or hydrogen thereby increasing the yield of redox-limited products via carbohydrate-based carbon feedstock, such as sugars or gaseous carbon sources, the method includes culturing this non-naturally occurring microbial organism under conditions and for a sufficient period of time to produce caprolactone.

In some embodiments, the non-naturally occurring microbial organism having an caprolactone pathway includes two exogenous nucleic acids, each encoding a reductive TCA pathway enzyme. In some embodiments, the non-naturally occurring microbial organism having an caprolactone pathway includes three exogenous nucleic acids each encoding a reductive TCA pathway enzyme. In some embodiments, the non-naturally occurring microbial organism includes three exogenous nucleic acids encoding an ATP-citrate lyase, a fumarate reductase, and an alpha-ketoglutarate:ferredoxin oxidoreductase. In some embodiments, the non-naturally occurring microbial organism includes three exogenous nucleic acids encoding a citrate lyase, a fumarate reductase, and an alpha-ketoglutarate:ferredoxin oxidoreductase. In some embodiments, the non-naturally occurring microbial organism includes four exogenous nucleic acids encoding a pyruvate:ferredoxin oxidoreductase; a phosphoenolpyruvate carboxylase or a phosphoenolpyruvate carboxykinase, a CO dehydrogenase; and an $H_2$ hydrogenase. In some embodiments, the non-naturally occurring microbial organism includes two exogenous nucleic acids encoding a CO dehydrogenase and an $H_2$ hydrogenase.

In some embodiments, the non-naturally occurring microbial organisms having an caprolactone pathway further include an exogenous nucleic acid encoding an enzyme selected from a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, and combinations thereof.

In some embodiments, the non-naturally occurring microbial organism having an caprolactone pathway further includes an exogenous nucleic acid encoding an enzyme selected from carbon monoxide dehydrogenase, acetyl-CoA synthase, ferredoxin, NAD(P)H:ferredoxin oxidoreductase and combinations thereof.

In some embodiments, the non-naturally occurring microbial organism having an caprolactone pathway utilizes a carbon feedstock selected from (1) CO, (2) $CO_2$, (3) $CO_2$ and $H_2$, (4) CO and $H_2$, or (5) CO, $CO_2$, and $H_2$. In some embodiments, the non-naturally occurring microbial organism having an caprolactone pathway utilizes hydrogen for reducing equivalents. In some embodiments, the non-naturally occurring microbial organism having an caprolactone pathway utilizes CO for reducing equivalents. In some embodiments, the non-naturally occurring microbial organism having an caprolactone pathway utilizes combinations of CO and hydrogen for reducing equivalents.

In some embodiments, the non-naturally occurring microbial organism having an caprolactone pathway further includes one or more nucleic acids encoding an enzyme selected from a phosphoenolpyruvate carboxylase, a phosphoenolpyruvate carboxykinase, a pyruvate carboxylase, and a malic enzyme.

In some embodiments, the non-naturally occurring microbial organism having an caprolactone pathway further includes one or more nucleic acids encoding an enzyme selected from a malate dehydrogenase, a fumarase, a fumarate reductase, a succinyl-CoA synthetase, and a succinyl-CoA transferase.

In some embodiments, the non-naturally occurring microbial organism having an caprolactone pathway further includes at least one exogenous nucleic acid encoding a citrate lyase, an ATP-citrate lyase, a citryl-CoA synthetase, a citryl-CoA lyase an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, and a ferredoxin.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

As disclosed herein, the product 6-hydroxyhexanoate or 2-ketocyclohexane-1-carboxylate, as well as other intermediates, are carboxylic acids, which can occur in various ionized forms, including fully protonated, partially protonated, and fully deprotonated forms. Accordingly, the suffix "-ate," or the acid form, can be used interchangeably to describe both the free acid form as well as any deprotonated form, in particular since the ionized form is known to depend on the pH in which the compound is found. It is understood that carboxylate products or intermediates includes ester forms of carboxylate products or pathway intermediates, such as O-carboxylate and S-carboxylate esters. O- and S-carboxylates can include lower alkyl, that is C1 to C6, branched or straight chain carboxylates. Some such O- or S-carboxylates include, without limitation, methyl, ethyl, n-propyl, n-butyl, i-propyl, sec-butyl, and tert-butyl, pentyl, hexyl O- or S-carboxylates, any of which can further possess an unsaturation, providing for example, propenyl, butenyl, pentyl, and hexenyl O- or S-carboxylates. O-carboxylates can be the product of a biosynthetic pathway. Exemplary O-carboxylates accessed via biosynthetic pathways can include, without limitation, methyl 6-hydroxyhexanoate, ethyl 6-hydroxyhexanoate, and n-propyl 6-hydroxyhexanoate. Other biosynthetically accessible O-carboxylates can include medium to long chain groups, that is C7-C22, O-carboxylate esters derived from fatty alcohols, such heptyl, octyl, nonyl, decyl, undecyl, lauryl, tridecyl, myristyl, pentadecyl, cetyl, palmitolyl, heptadecyl, stearyl, nonadecyl, arachidyl, heneicosyl, and behenyl alcohols, any one of which can be optionally branched and/or contain unsaturations. O-carboxylate esters can also be accessed via a biochemical or chemical process, such as esterification of a free carboxylic acid product or transesterification of an O- or S-carboxylate. S-carboxylates are exemplified by CoA S-esters, cysteinyl S-esters, alkylthioesters, and various aryl and heteroaryl thioesters.

The non-naturally occurring microbial organisms of the invention can be produced by introducing expressible nucleic acids encoding one or more of the enzymes or proteins participating in one or more caprolactone biosynthetic pathways. Depending on the host microbial organism chosen for biosynthesis, nucleic acids for some or all of a particular caprolactone biosynthetic pathway can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve caprolactone biosynthesis. Thus, a non-naturally occurring microbial organism of the invention can be produced by introducing exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as caprolactone.

Host microbial organisms can be selected from, and the non-naturally occurring microbial organisms generated in, for example, bacteria, yeast, fungus or any of a variety of other microorganisms applicable or suitable to fermentation processes. Exemplary bacteria include any species selected from the order Enterobacteriales, family Enterobacteriaceae, including the genera *Escherichia* and *Klebsiella*; the order Aeromonadales, family Succinivibrionaceae, including the genus *Anaerobiospirillum*; the order Pasteurellales, family Pasteurellaceae, including the genera *Actinobacillus* and *Mannheimia*; the order Rhizobiales, family Bradyrhizobiaceae, including the genus *Rhizobium*; the order Bacillales, family Bacillaceae, including the genus *Bacillus*; the order Actinomycetales, families Corynebacteriaceae and Streptomycetaceae, including the genus *Corynebacterium* and the genus *Streptomyces*, respectively; order Rhodospirillales, family Acetobacteraceae, including the genus *Gluconobacter*; the order Sphingomonadales, family Sphingomonadaceae, including the genus *Zymomonas*; the order Lactobacillales, families Lactobacillaceae and Streptococcaceae, including the genus *Lactobacillus* and the genus *Lactococcus*, respectively; the order Clostridiales, family Clostridiaceae, genus *Clostridium*; and the order Pseudomonadales, family Pseudomonadaceae, including the genus *Pseudomonas*. Non-limiting species of host bacteria include *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida*.

Similarly, exemplary species of yeast or fungi species include any species selected from the order Saccharomycetales, family Saccaromycetaceae, including the genera *Saccharomyces, Kluyveromyces* and *Pichia*; the order Saccharomycetales, family Dipodascaceae, including the genus *Yarrowia*; the order Schizosaccharomycetales, family Schizosaccaromycetaceae, including the genus *Schizosaccharomyces*; the order Eurotiales, family Trichocomaceae, including the genus *Aspergillus*; and the order Mucorales, family Mucoraceae, including the genus *Rhizopus*. Non-limiting species of host yeast or fungi include *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizopus oryzae, Yarrowia lipolytica*, and the like. *E. coli* is a particularly useful host organism since it is a well characterized microbial organism suitable for genetic engineering. Other particularly useful host organisms include yeast such as *Saccharomyces cerevisiae*. It is understood that any suitable microbial host organism can be used to introduce metabolic and/or genetic modifications to produce a desired product.

Depending on the caprolactone biosynthetic pathway constituents of a selected host microbial organism, the non-naturally occurring microbial organisms of the invention will include at least one exogenously expressed caprolactone pathway-encoding nucleic acid and up to all encoding nucleic acids for one or more caprolactone biosynthetic pathways. For example, caprolactone biosynthesis can be established in a host deficient in a pathway enzyme or protein through exogenous expression of the corresponding encoding nucleic acid. In a host deficient in all enzymes or proteins of a caprolactone pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of caprolactone can be included, such as an adipyl-CoA reductase, an adipate semialdehyde reductase, a 6-hydroxyhexanoyl-CoA transferase or synthetase, and a 6-hydroxyhexanoyl-CoA cyclase.

Given the teachings and guidance provided herein, those skilled in the art will understand that the number of encoding nucleic acids to introduce in an expressible form will, at least, parallel the caprolactone pathway deficiencies of the selected host microbial organism. Therefore, a non-naturally occurring microbial organism of the invention can have one, two, three, four, five, six, seven up to all nucleic acids encoding the enzymes or proteins constituting a caprolactone biosynthetic pathway disclosed herein. In some embodiments, the non-naturally occurring microbial organisms also can include other genetic modifications that facilitate or optimize caprolactone biosynthesis or that confer other useful functions onto the host microbial organism. One such other functionality can include, for example, augmentation of the synthesis of one or more of the caprolactone pathway precursors such as adipyl-CoA, adipate, adipate semialdehyde, 4-hydroxybutyryl-CoA, cyclohexanone, or pimeloyl-CoA.

Generally, a host microbial organism is selected such that it produces the precursor of a caprolactone pathway, either as a naturally produced molecule or as an engineered product that either provides de novo production of a desired precursor or increased production of a precursor naturally produced by the host microbial organism. For example, adipyl-CoA is produced naturally in a host organism such as *E. coli*. A host organism can be engineered to increase production of a precursor, as disclosed herein. In addition, a microbial organism that has been engineered to produce a desired precursor can be used as a host organism and further engineered to express enzymes or proteins of a caprolactone pathway.

In some embodiments, a non-naturally occurring microbial organism of the invention is generated from a host that contains the enzymatic capability to synthesize caprolactone. In this specific embodiment it can be useful to increase the synthesis or accumulation of a caprolactone pathway product to, for example, drive caprolactone pathway reactions toward caprolactone production. Increased synthesis or accumulation can be accomplished by, for example, overexpression of nucleic acids encoding one or more of the above-described caprolactone pathway enzymes or proteins. Overexpression of the enzyme or enzymes and/or protein or proteins of the caprolactone pathway can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing caprolactone, through overexpression of one, two, three, four, five, six, seven, that is, up to all nucleic acids encoding caprolactone biosynthetic pathway enzymes or proteins. In addition, a non-naturally occurring organism can be generated by mutagenesis of an endogenous gene that results in an increase in activity of an enzyme in the caprolactone biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods of the invention, any of the one or more exogenous nucleic acids can be introduced into a microbial organism to produce a non-naturally occurring microbial organism of the invention. The nucleic acids can be introduced so as to confer, for example, a caprolactone biosynthetic pathway onto the microbial organism. Alternatively, encoding nucleic acids can be introduced to produce an intermediate microbial organism having the biosynthetic capability to catalyze some of the required reactions to confer caprolactone biosynthetic capability. For example, a non-naturally occurring microbial organism having a caprolactone biosynthetic pathway can comprise at least two exogenous nucleic acids encoding desired enzymes or proteins, such as the combination of adipyl-CoA reductase and a 6-hydroxyhexanoate cyclase, or alternatively a 6-hydroxyhexanoate kinase and a 6-hydroxyhexanoyl phosphate cyclase, or alternatively a 3,6-dihydroxyhexanoyl-CoA dehydratase and a 6-hydroxyhex-2-enoyl-CoA reductase, or alternatively a cyclohexane-1,2-diol dehydratase and a cyclohexanone monooxygenase, and the like. Thus, it is understood that any combination of two or more enzymes or proteins of a biosynthetic pathway can be included in a non-naturally occurring microbial organism of the invention. Similarly, it is understood that any combination of three or more enzymes or proteins of a biosynthetic pathway can be included in a non-naturally occurring microbial organism of the invention, for example, an adipyl-CoA reductase, an adipate semialdehyde reductase and a 6-hydroxyhexanoate cyclase, or alternatively an adipate semialdehyde reductase, a 6-hydroxyhexanoyl-CoA transferase, and a 6-hydroxyhexanoyl-CoA cyclase, or alternatively a 3-oxo-6-hydroxyhexanoyl-CoA reductase, a 6-hydroxyhex-2-enoyl-CoA reductase and a 6-hydroxyhexanoate cyclase, and so forth, as desired, so long as the combination of enzymes and/or proteins of the desired biosynthetic pathway results in production of the corresponding desired product. Similarly, any combination of four, five, six, seven or more enzymes or proteins of a biosynthetic pathway as disclosed herein can be included in a non-naturally occurring microbial organism of the invention, as desired, so long as the combination of enzymes and/or proteins of the desired biosynthetic pathway results in production of the corresponding desired product.

In addition to the biosynthesis of caprolactone as described herein, the non-naturally occurring microbial organisms and methods of the invention also can be utilized in various combinations with each other and with other microbial organisms and methods well known in the art to achieve product biosynthesis by other routes. For example, one alternative to produce caprolactone other than use of the caprolactone producers is through addition of another microbial organism capable of converting a caprolactone pathway intermediate to caprolactone. One such procedure includes, for example, the fermentation of a microbial organism that produces a caprolactone pathway intermediate. The caprolactone pathway intermediate can then be used as a substrate for a second microbial organism that converts the caprolactone pathway intermediate to caprolactone. The caprolactone pathway intermediate can be added directly to another culture of the second organism or the original culture of the caprolactone pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, caprolactone. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of caprolactone can be accomplished by constructing a microbial organism that contains biosynthetic pathways for conversion of one pathway intermediate to another pathway intermediate or the product. Alternatively, caprolactone also can be biosynthetically produced from microbial organisms through co-culture or co-fermentation using two organisms in the same vessel, where the first microbial organism produces a caprolactone intermediate and the second microbial organism converts the intermediate to caprolactone.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce caprolactone.

Sources of encoding nucleic acids for a caprolactone pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Acinetobacter* sp. NCIMB9871, *Acetobacter aceti, Acidaminococcus fermentans, Acinetobacter baylyi, Acinetobacter calcoaceticus, Acinetobacter* sp NCIMB9871, *Acinetobacter* sp. ADP1, *Acinetobacter* sp. NCIMB9871, *Acinetobacter* sp. SE19, *Acinetobacter* sp. strain M-1, *Actinobacillus succinogenes, Aeropyrum pernix, Allochromatium vinosum* DSM 180, *Anaerobiospirillum succiniciproducens, Aquifex aeolicus, Arabidopsis thaliana, Archaeoglobus fulgidus, Aromatoleum aromaticum* EbN1, *Arthrobacter* sp. BP2, *Ascaris suum, Aspergillus nidulans, Aspergillus terreus* NIH2624, *Azoarcus* sp. Strain 22Lin, *Azoarcus* sp. T, *Azotobacter vinelandii* DJ, *Bacillus cereus, Bacillus megaterium, Bacillus megaterium* WSH-002, *Bacillus sphaericus, Bacillus subtilis, Balnearium lithotrophicum, Bos taurus, Brevibacerium* sp. HCU, *Burkholderia ambifaria* AMMD, *Burkholderia phymatum*, butyrate producing bacterium L2-50, butyrate producing bacterium L2-50, *Campylobacter curvus* 525.92, *Campylobacter jejuni, Candida albicans, Candida tropicalis, Carboxydothermus hydrogenoformans, Chlorobium phaeobacteroides* DSM 266, *Chlorobium limicola, Chlorobium tepidum, Citrobacter freundii, Citrobacter youngae, Citrobacter youngae* ATCC 29220, *Clostridium acetobutylicum, Clostridium beijerinckii, Clostridium botulinum, Clostridium butyricum, Clostridium carboxidivorans* P7, *Clostridium carboxidivorans* P7, *Clostridium cellulolyticum* H10, *Clostridium kluyveri, Clostridium kluyveri* DSM 555, *Clostridium novyi* NT, *Clostridium pasteurianum, Clostridium propionicum, Clostridium saccharoperbutylacetonicum, Clostridium symbiosum, Comamonas testosterone, Corynebacterium glutamicum, Cupriavidus taiwanensis, Cyanobium* PCC7001, *Desulfarculus baarsii* DSM 2075, *Desulfovibrio africanus, DesulfoVibrio desulfuricans* G20, *Desulfovibrio desulfuricans* subsp. *desulfuricans* str. ATCC 27774, *Desulfovibrio fructosovorans* JJ, *Desulfovibrio vulgaris* str. Hildenborough, *Dictyostelium discoideum* AX4, *Escherichia coli* K12 sp. MG1655, *Eubacterium rectale, Fusobacterium nucleatum, Geobacillus kaustophilus, Geobacillus thermoglucosidasius, Geobacter metallireducens* GS-15, *Geobacter sulfurreducens, Haemophilus influenza, Haloarcula marismortui, Helicobacter pylori, Helicobacter pylori* 26695, *Homo sapiens, Hydrogenobacter thermophilus, Klebsiella oxytoca, Klebsiella pneumoniae, Klebsiella pneumoniae* subsp. *rhinoscleromatis, Lactobacillus collinoides, Leuconostoc mesenteroides, Mannheimia succiniciproducens, Metallosphaera sedula, Methanosarcina thermophila, Methanothermobacter thermautotrophicus, Methylobacterium extorquens, Moorella thermoacetica, Mus musculus, Mycobacterium avium* subsp. *paratuberculosis* K-10, *Mycobacterium bovis* BCG, *Mycobacterium marinum* M, *Mycobacterium smegmatis, Mycobacterium smegmatis* MC2 155, *Mycobacterium tuberculosis, Neurospora crassa, Nocardia farcinica* IFM 10152, *Nocardia iowensis, Nostoc* sp. PCC 7120, *Oryza sativa, Paracoccus denitrificans, Pelobacter carbinolicus* DSM 2380, *Pelotomaculum thermopropionicum, Penicillium chrysogenum. Porphyromonas gingivalis, Pseudomonas aeruginosa* PA01, *Pseudomonas fluorescens, Pseudomonas knackmussii, Pseudomonas knackmussii* (B13), *Pseudomonas mendocina, Pseudomonas putida, Pseudomonas* sp, *Pyrobaculum aerophilum* str. IM2, *Ralstonia eutropha, Ralstonia eutropha* H16, *Ralstonia metallidurans, Ralstonia metallireducens, Rattus norvegicus, Rhizobium leguminosarum, Rhodobacter capsulatus, Rhodobacter sphaeroides, Rhodococcus* sp. PhiI, *Rhodococcus* sp. Phi2, *Rhodopseudomonas palustris, Rhodopseudomonas palustris* CGA009, *Rhodospirillum rubrum, Roseburia intestinalis, Roseburia inulinivorans, Roseburia* sp. A2-183, *Saccharomyces cerevisiae, Salmonella enteric, Salmonella enterica* subsp. *arizonae serovar, Salmonella typhimurium, Salmonella typhimurium* LT2, *Schizosaccharomyces pombe, Sinorhizobium fredii, Sordaria macrospora, Staphylococcus aureus, Streptomyces coelicolor, Streptomyces griseus* subsp. *griseus* NBRC 13350, *Sulfolobus acidocalarius, Sulfolobus solfataricus, Sulfolobus* sp. strain 7, *Sulfolobus tokodaii, Sulfurihydrogenibium subterraneum, Sulfurimonas denitrificans, Synechocystis* str. PCC 6803, *Syntrophus aciditrophicus, Thauera aromatic, Thermocrinis albus, Thermoproteus neutrophilus, Thermotoga maritima, Thermus thermophilus, Thiobacillus denitrificans, Thiocapsa roseopersicina, Trichomonas vaginalis* G3, *Trypanosoma brucei, Tsukamurella paurometabola* DSM 20162, *Xanthobacter flavus, Yarrowia lipolytica, Yersinia intermedia, Yersinia intermedia* ATCC 29909, *Zea mays, Zoogloea ramigera, Zymomonas mobilis*, as well as other exemplary species disclosed herein or available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite caprolactone biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of caprolactone described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative caprolactone biosynthetic pathway exists in an unrelated species, caprolactone biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize caprolactone.

Methods for constructing and testing the expression levels of a non-naturally occurring caprolactone-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Exogenous nucleic acid sequences involved in a pathway for production of caprolactone can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280: 4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more caprolactone biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

In one embodiment, the invention provides a method for producing caprolactone, by culturing the non-naturally occurring microbial organism as described herein under conditions and for a sufficient period of time to produce caprolactone. In some embodiments, the method includes a non-naturally occurring microbial organism having a caprolactone pathway, wherein the microbial organism includes at least one exogenous nucleic acid encoding a caprolactone pathway enzyme expressed in a sufficient amount to produce caprolactone. In some aspects of the invention, the caprolactone pathway includes a pathway selected from: (1) 1A, 1B, 1C and 1D; (2) 1E, 1B, 1C and 1D; (3) 1F, 1A, 1B, 1C and 1D; (4) 1F, 1E, 1B, 1C and 1D; (5) 1A, 1B and 1G; (6) 1E, 1B and 1G; (7) 1F, 1A, 1B and 1G; (8) 1F, 1E, 1B and 1G; (9) 1A, 1B, 1C, 1J and 1I; (10) 1E, 1B, 1C, 1J and 1I; (11) 1F, 1A, 1B, 1C, 1J and 1I; (12) 1F, 1E, 1B, 1C, 1J and 1I; (13) 1A, 1B, 1H and 1I; (14) 1E, 1B, 1H and 1I; (15) 1F, 1A, 1B, 1H and 1I; (16) 1F, 1E, 1B, 1H and 1I; (17) 2A, 2B, 2C, 2D, 2E and 2F; (18) 2A, 2B, 2C, 2D and 2G; (19) 2A, 2B, 2C, 2D, 2E, 2J and 2I; (20) 2A, 2B, 2C, 2D, 2H and 2I; (21) 4A, 4B, 4C, 4D and 3A; and (22) 5A, 5B, 5C an 3A, wherein 1A is an adipyl-CoA reductase, wherein 1B is an adipate semialdehyde reductase, wherein 1C is a 6-hydroxyhexanoyl-CoA transferase or a 6-hydroxyhexanoyl-CoA synthetase, wherein 1D is a 6-hydroxyhexanoyl-CoA cyclase or spontaneous cyclization, wherein 1E is an adipate reductase, wherein 1F is an adipyl-CoA transferase, an adipyl-CoA synthetase or an adipyl-CoA hydrolase, wherein 1G is a 6-hydroxyhexanoate cyclase, wherein 1H is a 6-hydroxyhexanoate kinase, wherein 1I is a 6-hydroxyhexanoyl phosphate cyclase or spontaneous cyclization, wherein 1J is a phosphotrans-6-hydroxyhexanoylase, wherein 2A is a 4-hydroxybutyryl-CoA:acetyl-CoA acyltransferase, wherein 2B is a 3-oxo-6-hydroxyhexanoyl-CoA reductase, wherein 2C is a 3,6-dihydroxyhexanoyl-CoA dehydratase, wherein 2D is a 6-hydroxyhex-2-enoyl-CoA reductase, wherein 2E is a 6-hydroxyhexanoyl-CoA transferase, a 6-hydroxyhexanoyl-CoA synthetase or a 6-hydroxyhexanoyl-CoA hydrolase, wherein 2F is a 6-hydroxyhexanoate cyclase, wherein 2G is a 6-hydroxyhexanoyl-CoA cyclase or spontaneous cyclization, wherein 2H is a phosphotrans-6-hydroxyhexanoylase, wherein 2I is a 6-hydroxyhexanoyl phosphate cyclase or spontaneous cyclization, wherein 2J is a 6-hydroxyhexanoate kinase, wherein 3A is a cyclohexanone monooxygenase, wherein 4A is an adipate semialdehyde dehydratase, wherein 4B is a cyclohexane-1,2-dione reductase, wherein 4C is a 2-hydroxycyclohexanone reductase, wherein 4D is a cyclohexane-1,2-diol dehydratase, wherein 5A is a 2-ketocyclohexane-1-carboxoyl-CoA hydrolase (acting on C-C), wherein 5B is a 2-ketocyclohexane-1-carboxoyl-CoA transferase, a 2-ketocyclohexane-1-carboxoyl-CoA synthetase or a 2-ketocyclohexane-1-carboxoyl-CoA hydrolase, and wherein 5C is a 2-ketocyclohexane-1-carboxylate decarboxylase.

In one embodiment, the invention provides a method for producing caprolactone using a non-naturally occurring microbial organism as described herein, wherein the microbial organism includes two, three, four, five, six or seven exogenous nucleic acids each encoding a caprolactone pathway enzyme. For example, the microbial organism can include exogenous nucleic acids encoding each of the enzymes of at least one of the pathways selected from (1)-(22) as described above.

In one embodiment, the invention provides a method for producing caprolactone using a microbial organism wherein at least one exogenous nucleic acid is a heterologous nucleic acid. In another aspect, the non-naturally occurring microbial organism as disclosed herein is in a substantially anaerobic culture medium.

In one embodiment, the invention provides a method for producing caprolactone wherein the non-naturally occurring microbial organism as disclosed herein further includes (i) a reductive TCA pathway comprising at least one exogenous nucleic acid encoding a reductive TCA pathway enzyme, wherein said at least one exogenous nucleic acid is selected from an ATP-citrate lyase, citrate lyase, a fumarate reductase, and an alpha-ketoglutarate:ferredoxin oxidoreductase; (ii) a reductive TCA pathway comprising at least one exogenous nucleic acid encoding a reductive TCA pathway enzyme, wherein said at least one exogenous nucleic acid is selected from a pyruvate:ferredoxin oxidoreductase, a phosphoenolpyruvate carboxylase, a phosphoenolpyruvate carboxykinase, a CO dehydrogenase, and an $H_2$ hydrogenase; or (iii) at least one exogenous nucleic acid encodes an enzyme selected from a CO dehydrogenase, an $H_2$ hydrogenase, and combinations thereof.

In one embodiment, the invention provides a method for producing caprolactone wherein the non-naturally occurring microbial organism having (i) above, further includes an exogenous nucleic acid encoding an enzyme selected from a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, ferredoxin, and combinations thereof. In another aspect, the non-naturally occurring microbial organism including (ii) as described above further includes an exogenous nucleic acid encoding an enzyme selected from an aconitase, an isocitrate dehydrogenase, a succinyl-CoA synthetase, a succinyl-CoA transferase, a fumarase, a malate dehydrogenase, and combinations thereof.

In one embodiment, the invention provides a method for producing caprolactone wherein the non-naturally occurring microbial organism having (i) as described above further comprises four exogenous nucleic acids encoding an ATP-citrate lyase, citrate lyase, a fumarate reductase, and an alpha-ketoglutarate:ferredoxin oxidoreductase. In one aspect of the invention, the non-naturally occurring microbial organism having (ii) as described above further comprises five exogenous nucleic acids encoding a pyruvate:ferredoxin oxidoreductase, a phosphoenolpyruvate carboxylase, a phosphoenolpyruvate carboxykinase, a CO dehydrogenase, and an $H_2$ hydrogenase. In one aspect of the invention, the non-naturally occurring microbial organism having (iii) as described above further comprises two exogenous nucleic acids encoding a CO dehydrogenase and an $H_2$ hydrogenase.

Suitable purification and/or assays to test for the production of caprolactone can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art.

The caprolactone can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the caprolactone producers can be cultured for the biosynthetic production of caprolactone. Accordingly, in some embodiments, the invention provides culture medium having the caprolactone or caprolactone pathway intermediate described herein. In some aspects, the culture mediums can also be separated from the non-naturally occurring microbial organisms of the invention that produced the caprolactone or caprolactone pathway intermediate. Methods for separating a microbial organism from culture medium are well known in the art. Exemplary methods include filtration, flocculation, precipitation, centrifugation, sedimentation, and the like.

For the production of caprolactone, the recombinant strains are cultured in a medium with carbon source and other essential nutrients. It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in United State publication 2009/0047719, filed Aug. 10, 2007. Fermentations can be performed in a batch, fed-batch or continuous manner, as disclosed herein. Fermentations can also be conducted in two phases, if desired. The first phase can be aerobic to allow for high growth and therefore high productivity, followed by an anaerobic phase of high caprolactone yields.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can include, for example, any carbohydrate source which can supply a source of carbon to the non-naturally occurring microorganism. Such sources include, for example, sugars such as glucose, xylose, arabinose, galactose, mannose, fructose, sucrose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of caprolactone.

In addition to renewable feedstocks such as those exemplified above, the caprolactone microbial organisms of the invention also can be modified for growth on syngas as its source of carbon. In this specific embodiment, one or more proteins or enzymes are expressed in the caprolactone producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, *Acetogenesis*, pp. 3-60 Chapman and Hall, New York, (1994)). This can be summarized by the following equation:

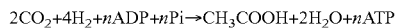

$$2CO_2 + 4H_2 + nADP + nPi \rightarrow CH_3COOH + 2H_2O + nATP$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes or proteins: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: methyltetrahydrofolate:corrinoid protein methyltransferase (for example, AcsE), corrinoid iron-sulfur protein, nickel-protein assembly protein (for example, AcsF), ferredoxin, acetyl-CoA synthase, carbon monoxide dehydrogenase and nickel-protein assembly protein (for example, CooC). Following the teachings and guidance provided herein for introducing a sufficient number of encoding nucleic acids to generate a caprolactone pathway, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the microbial organisms of the invention such that the modified organism contains the complete Wood-Ljungdahl pathway will confer syngas utilization ability.

Additionally, the reductive (reverse) tricarboxylic acid cycle coupled with carbon monoxide dehydrogenase and/or hydrogenase activities can also be used for the conversion of CO, $CO_2$ and/or $H_2$ to acetyl-CoA and other products such as acetate. Organisms capable of fixing carbon via the reductive TCA pathway can utilize one or more of the following enzymes: ATP citrate-lyase, citrate lyase, aconitase, isocitrate dehydrogenase, alpha-ketoglutarate:ferredoxin oxidoreductase, succinyl-CoA synthetase, succinyl-CoA transferase, fumarate reductase, fumarase, malate dehydrogenase, NAD(P)H:ferredoxin oxidoreductase, carbon monoxide dehydrogenase, and hydrogenase. Specifically, the reducing equivalents extracted from CO and/or $H_2$ by carbon monoxide dehydrogenase and hydrogenase are utilized to fix $CO_2$ via the reductive TCA cycle into acetyl-CoA or acetate. Acetate can be converted to acetyl-CoA by enzymes such as acetyl-CoA transferase, acetate kinase/phosphotransacetylase, and acetyl-CoA synthetase. Acetyl-CoA can be converted to the caprolactone precursors, glyceraldehyde-3-phosphate, phosphoenolpyruvate, and pyruvate, by pyruvate:ferredoxin oxidoreductase and the enzymes of gluconeogenesis. Following the teachings and guidance provided herein for introducing a sufficient number of encoding nucleic acids to generate a caprolactone pathway, those skilled in the art will understand that the same engineering design also can be performed with respect to introducing at least the nucleic acids encoding the reductive TCA pathway enzymes or proteins absent in the host organism. Therefore, introduction of one or more encoding nucleic acids into the microbial organisms of the invention such that the modified organism contains a reductive TCA pathway can confer syngas utilization ability.

Accordingly, given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, caprolactone and any of the intermediate metabolites in the caprolactone pathway. All that is required is to engineer in one or more of the required enzyme or protein activities to achieve biosynthesis of the desired compound or intermediate including, for example, inclusion of some or all of the caprolactone biosynthetic pathways. Accordingly, the invention provides a non-naturally occurring microbial organism that produces and/or secretes caprolactone when grown on a carbohydrate or other carbon source and produces and/or secretes any of the intermediate metabolites shown in the caprolactone pathway when grown on a carbohydrate or other carbon source. The caprolactone producing microbial organisms of the invention can initiate synthesis from an intermediate, for example, 6-hydroxyhexanoate, 6-hydroxyhexanoyl-CoA, 6-hydroxyhexanoyl phosphate, 3-oxo-6-hydroxy hexanoyl-CoA, 3,6-dihydroxy hexanoyl-CoA, 6-hydroxyhex-2-enoyl-CoA, cyclohexanone, cyclohexane-1,2-dione, 2-hydroxycyclohexanone, cyclohexane-1,2-diol, 2-ketocyclohexane-1-carboxyoyl-CoA, or 2-ketocyclohexane-1-carboxylate.

The non-naturally occurring microbial organisms of the invention are constructed using methods well known in the art as exemplified herein to exogenously express at least one nucleic acid encoding a caprolactone pathway enzyme or protein in sufficient amounts to produce caprolactone. It is understood that the microbial organisms of the invention are cultured under conditions sufficient to produce caprolactone.

Following the teachings and guidance provided herein, the non-naturally occurring microbial organisms of the invention can achieve biosynthesis of caprolactone resulting in intracellular concentrations between about 0.1-200 mM or more. Generally, the intracellular concentration of caprolactone is between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. publication 2009/0047719, filed Aug. 10, 2007. Any of these conditions can be employed with the non-naturally occurring microbial organisms as well as other anaerobic conditions well known in the art. Under such anaerobic or substantially anaerobic conditions, the caprolactone producers can synthesize caprolactone at intracellular concentrations of 5-10 mM or more as well as all other concentrations exemplified herein. It is understood that, even though the above description refers to intracellular concentrations, caprolactone producing microbial organisms can produce caprolactone intracellularly and/or secrete the product into the culture medium.

In addition to the culturing and fermentation conditions disclosed herein, growth condition for achieving biosynthesis of caprolactone can include the addition of an osmoprotectant to the culturing conditions. In certain embodiments, the non-naturally occurring microbial organisms of the invention can be sustained, cultured or fermented as described herein in the presence of an osmoprotectant. Briefly, an osmoprotectant refers to a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethylslfoniopropionate, 3-dimethylsulfonio-2-methylpropionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

In some embodiments, the carbon feedstock and other cellular uptake sources such as phosphate, ammonia, sulfate, chloride and other halogens can be chosen to alter the isotopic distribution of the atoms present in caprolactone or any caprolactone pathway intermediate. The various carbon feedstock and other uptake sources enumerated above will be referred to herein, collectively, as "uptake sources." Uptake sources can provide isotopic enrichment for any atom present in the product caprolactone or caprolactone pathway intermediate, or for side products generated in reactions diverging away from a caprolactone pathway. Isotopic enrichment can be achieved for any target atom including, for example, carbon, hydrogen, oxygen, nitrogen, sulfur, phosphorus, chloride or other halogens.

In some embodiments, the uptake sources can be selected to alter the carbon-12, carbon-13, and carbon-14 ratios. In some embodiments, the uptake sources can be selected to alter the oxygen-16, oxygen-17, and oxygen-18 ratios. In some embodiments, the uptake sources can be selected to alter the hydrogen, deuterium, and tritium ratios. In some embodiments, the uptake sources can be selected to alter the nitrogen-14 and nitrogen-15 ratios. In some embodiments, the uptake sources can be selected to alter the sulfur-32, sulfur-33, sulfur-34, and sulfur-35 ratios. In some embodiments, the uptake sources can be selected to alter the phosphorus-31, phosphorus-32, and phosphorus-33 ratios. In some embodiments, the uptake sources can be selected to alter the chlorine-35, chlorine-36, and chlorine-37 ratios.

In some embodiments, the isotopic ratio of a target atom can be varied to a desired ratio by selecting one or more uptake sources. An uptake source can be derived from a natural source, as found in nature, or from a man-made source, and one skilled in the art can select a natural source, a man-made source, or a combination thereof, to achieve a desired isotopic ratio of a target atom. An example of a man-made uptake source includes, for example, an uptake source that is at least partially derived from a chemical synthetic reaction. Such isotopically enriched uptake sources can be purchased commercially or prepared in the laboratory and/or optionally mixed with a natural source of the uptake source to achieve a desired isotopic ratio. In some embodiments, a target atom isotopic ratio of an uptake source can be achieved by selecting a desired origin of the uptake source as found in nature. For example, as discussed herein, a natural source can be a biobased derived from or synthesized by a biological organism or a source such as petroleum-based products or the atmosphere. In some such embodiments, a source of carbon, for example, can be selected from a fossil fuel-derived carbon source, which can be relatively depleted of carbon-14, or an environmental or atmospheric carbon source, such as $CO_2$, which can possess a larger amount of carbon-14 than its petroleum-derived counterpart.

The unstable carbon isotope carbon-14 or radiocarbon makes up for roughly 1 in $10^{12}$ carbon atoms in the earth's atmosphere and has a half-life of about 5700 years. The stock of carbon is replenished in the upper atmosphere by a nuclear reaction involving cosmic rays and ordinary nitrogen ($^{14}N$). Fossil fuels contain no carbon-14, as it decayed long ago. Burning of fossil fuels lowers the atmospheric carbon-14 fraction, the so-called "Suess effect".

Methods of determining the isotopic ratios of atoms in a compound are well known to those skilled in the art. Isotopic enrichment is readily assessed by mass spectrometry using techniques known in the art such as accelerated mass spectrometry (AMS), Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC), high performance liquid chromatography (HPLC) and/or gas chromatography, and the like.

In the case of carbon, ASTM D6866 was developed in the United States as a standardized analytical method for determining the biobased content of solid, liquid, and gaseous samples using radiocarbon dating by the American Society for Testing and Materials (ASTM) International. The standard is based on the use of radiocarbon dating for the determination of a product's biobased content. ASTM D6866 was first published in 2004, and the current active version of the standard is ASTM D6866-11 (effective Apr. 1, 2011). Radiocarbon dating techniques are well known to those skilled in the art, including those described herein.

The biobased content of a compound is estimated by the ratio of carbon-14 ($^{14}C$) to carbon-12 ($^{12}C$). Specifically, the Fraction Modern (Fm) is computed from the expression: Fm=(S−B)/(M−B), where B, S and M represent the $^{14}C/^{12}C$ ratios of the blank, the sample and the modern reference, respectively. Fraction Modern is a measurement of the deviation of the $^{14}C/^{12}C$ ratio of a sample from "Modern." Modern is defined as 95% of the radiocarbon concentration (in AD 1950) of National Bureau of Standards (NBS) Oxalic Acid I (i.e., standard reference materials (SRM) 4990b) normalized to $\delta^{13}C_{VPDB}$=−19 per mil (Olsson, *The use of Oxalic acid as a Standard*. in, *Radiocarbon Variations and Absolute Chronology*, Nobel Symposium, 12th Proc., John Wiley & Sons, New York (1970)). Mass spectrometry results, for example, measured by ASM, are calculated using the internationally agreed upon definition of 0.95 times the specific activity of NBS Oxalic Acid I (SRM 4990b) normalized to $\delta^{13}C_{VPDB}$=−19 per mil. This is equivalent to an absolute (AD 1950) $^{14}C/^{12}C$ ratio of 1.176±0.010×10$^{-12}$ (Karlen et al., *Arkiv Geofysik*, 4:465-471 (1968)). The standard calculations take into account the differential uptake of one isotope with respect to another, for example, the preferential uptake in biological systems of $C^{12}$ over $C^{13}$ over $C^{14}$, and these corrections are reflected as a Fm corrected for $\delta^{13}$.

An oxalic acid standard (SRM 4990b or HOx 1) was made from a crop of 1955 sugar beet. Although there were 1000 lbs made, this oxalic acid standard is no longer commercially available. The Oxalic Acid II standard (HOx 2; N.I.S.T designation SRM 4990 C) was made from a crop of 1977 French beet molasses. In the early 1980's, a group of 12 laboratories measured the ratios of the two standards. The ratio of the activity of Oxalic acid II to 1 is 1.2933±0.001 (the weighted mean). The isotopic ratio of HOx II is −17.8 per mile. ASTM D6866-11 suggests use of the available Oxalic Acid II standard SRM 4990 C (Hox2) for the modern standard (see discussion of original vs. currently available oxalic acid standards in Mann, *Radiocarbon*, 25(2):519-527 (1983)). A Fm=0% represents the entire lack of carbon-14 atoms in a material, thus indicating a fossil (for example, petroleum based) carbon source. A Fm=100%, after correction for the post-1950 injection of carbon-14 into the atmosphere from nuclear bomb testing, indicates an entirely modern carbon source. As described herein, such a "modern" source includes biobased sources.

As described in ASTM D6866, the percent modern carbon (pMC) can be greater than 100% because of the continuing but diminishing effects of the 1950s nuclear testing programs, which resulted in a considerable enrichment of carbon-14 in the atmosphere as described in ASTM D6866-11. Because all sample carbon-14 activities are referenced to a "pre-bomb" standard, and because nearly all new biobased products are produced in a post-bomb environment, all pMC values (after correction for isotopic fraction) must be multiplied by 0.95 (as of 2010) to better reflect the true biobased content of the sample. A biobased content that is greater than 103% suggests that either an analytical error has occurred, or that the source of biobased carbon is more than several years old.

ASTM D6866 quantifies the biobased content relative to the material's total organic content and does not consider the inorganic carbon and other non-carbon containing substances present. For example, a product that is 50% starch-based material and 50% water would be considered to have a Biobased Content=100% (50% organic content that is 100% biobased) based on ASTM D6866. In another example, a product that is 50% starch-based material, 25% petroleum-based, and 25% water would have a Biobased Content=66.7% (75% organic content but only 50% of the product is biobased). In another example, a product that is 50% organic carbon and is a petroleum-based product would be considered to have a Biobased Content=0% (50% organic carbon but from fossil sources). Thus, based on the well known methods and known standards for determining the biobased content of a compound or material, one skilled in the art can readily determine the biobased content and/or prepared downstream products that utilize of the invention having a desired biobased content.

Applications of carbon-14 dating techniques to quantify bio-based content of materials are known in the art (Currie et al., *Nuclear Instruments and Methods in Physics Research B*, 172:281-287 (2000)). For example, carbon-14 dating has been used to quantify bio-based content in terephthalate-containing materials (Colonna et al., *Green Chemistry*, 13:2543-2548 (2011)). Notably, polypropylene terephthalate (PPT) polymers derived from renewable 1,3-propanediol and petroleum-derived terephthalic acid resulted in Fm values near 30% (i.e., since 3/11 of the polymeric carbon derives from renewable 1,3-propanediol and 8/11 from the fossil end member terephthalic acid) (Currie et al., supra, 2000). In contrast, polybutylene terephthalate polymer derived from both renewable 1,4-butanediol and renewable terephthalic acid resulted in bio-based content exceeding 90% (Colonna et al., supra, 2011).

Accordingly, in some embodiments, the present invention provides caprolactone or a caprolactone pathway intermediate that has a carbon-12, carbon-13, and carbon-14 ratio that reflects an atmospheric carbon, also referred to as environmental carbon, uptake source. For example, in some aspects the caprolactone or a caprolactone pathway intermediate can have an Fm value of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or as much as 100%. In some such embodiments, the uptake source is $CO_2$. In some embodiments, the present invention provides caprolactone or a caprolactone pathway intermediate that has a carbon-12, carbon-13, and carbon-14 ratio that reflects petroleum-based carbon uptake source. In this aspect, the caprolactone or a caprolactone pathway intermediate can have an Fm value of less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 2% or less than 1%. In some embodiments, the present invention provides caprolactone or a caprolactone pathway intermediate that has a carbon-12, carbon-13, and carbon-14 ratio that is obtained by a combination of an atmospheric carbon uptake source with a petroleum-based uptake source. Using such a combination of uptake sources is one way by which the carbon-12, carbon-13, and carbon-14 ratio can be varied, and the respective ratios would reflect the proportions of the uptake sources.

Further, the present invention relates to the biologically produced caprolactone or caprolactone pathway intermediate as disclosed herein, and to the products derived therefrom, wherein the caprolactone or a caprolactone pathway intermediate has a carbon-12, carbon-13, and carbon-14 isotope ratio of about the same value as the $CO_2$ that occurs in the environment. For example, in some aspects the invention provides bioderived caprolactone or a bioderived caprolactone intermediate having a carbon-12 versus carbon-13 versus carbon-14 isotope ratio of about the same value as the $CO_2$ that occurs in the environment, or any of the other ratios disclosed herein. It is understood, as disclosed herein, that a product can have a carbon-12 versus carbon-13 versus carbon-14 isotope ratio of about the same value as the $CO_2$ that occurs in the environment, or any of the ratios disclosed herein, wherein the product is generated from bioderived caprolactone or a bioderived caprolactone pathway intermediate as disclosed herein, wherein the bioderived product is chemically modified to generate a final product. Methods of chemically modifying a bioderived product of caprolactone, or an intermediate thereof, to generate a desired product are well known to those skilled in the art, as described herein. The invention further provides a polymer, a resin, a protective or industrial coating, polyurethane, a cast elastomer, an adhesive, a colorant, or a pharmaceutical having a carbon-12 versus carbon-13 versus carbon-14 isotope ratio of about the same value as the $CO_2$ that occurs in the environment, wherein the polymer, resin, protective or industrial coating, polyurethane, cast elastomer, adhesive, colorant, or pharmaceutical is generated directly from or in combination with bioderived caprolactone or a bioderived caprolactone pathway intermediate as disclosed herein.

Caprolactone is a chemical used in commercial and industrial applications. Non-limiting examples of such applications include production of a polymer, a resin, a protective or industrial coating, polyurethane, a cast elastomer, an adhesive, a colorant, or a pharmaceutical. Accordingly, in some embodiments, the invention provides a biobased polymer, resin, protective or industrial coating, polyurethane, cast elastomer, adhesive, colorant, or pharmaceutical comprising one or more bioderived caprolactone or bioderived caprolactone pathway intermediate produced by a non-naturally occurring microorganism of the invention or produced using a method disclosed herein.

As used herein, the term "bioderived" means derived from or synthesized by a biological organism and can be considered a renewable resource since it can be generated by a biological organism. Such a biological organism, in particular the microbial organisms of the invention disclosed herein, can utilize feedstock or biomass, such as, sugars or carbohydrates obtained from an agricultural, plant, bacterial, or animal source. Alternatively, the biological organism can utilize atmospheric carbon. As used herein, the term "biobased" means a product as described above that is composed, in whole or in part, of a bioderived compound of the invention. A biobased or bioderived product is in contrast to a petroleum derived product, wherein such a product is derived from or synthesized from petroleum or a petrochemical feedstock.

In some embodiments, the invention provides a polymer, a resin, a protective or industrial coating, polyurethane, a cast elastomer, an adhesive, a colorant, or a pharmaceutical comprising bioderived caprolactone or bioderived caprolactone pathway intermediate, wherein the bioderived caprolactone or bioderived caprolactone pathway intermediate includes all or part of the caprolactone or caprolactone pathway intermediate used in the production of the polymer, resin, protective or industrial coating, polyurethane, cast elastomer, adhesive, colorant, or pharmaceutical. For example, the final polymer, resin, protective or industrial coating, polyurethane, cast elastomer, adhesive, colorant, or pharmaceutical can contain the bioderived caprolactone, caprolactone pathway intermediate, or a portion thereof that is the result of the manufacturing of polymer, resin, protective or industrial coating, polyurethane, cast elastomer, adhesive, colorant, or pharmaceutical. Such manufacturing can include chemically reacting the bioderived caprolactone or bioderived caprolactone pathway intermediate (e.g. chemical conversion, chemical functionalization, chemical coupling, oxidation, reduction, polymerization, copolymerization and the like) into the final polymer, protective or industrial coating, polyurethane, cast elastomer, adhesive, colorant, or pharmaceutical. For example, a portion of bioderived caprolactone can be a repeating unit in the polymer, resin, protective or industrial coating, polyurethane, cast elastomer, adhesive, colorant, or pharmaceutical. Thus, in some aspects, the invention provides a composition including for example, a biobased polymer, resin, protective or industrial coating, polyurethane, cast elastomer, adhesive, colorant, or pharmaceutical comprising at least 1%, at least 2%, at least 3%, at least 4%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% (w/v) bioderived caprolactone or bioderived caprolactone pathway intermediate as disclosed herein. In some aspects, the invention provides a process for producing a biobased polymer or resin disclosed herein by chemically reacting the bioderived caprolactone with itself or another compound in a polymer producing or a resin producing reaction. It is understood that such process are well known in the art.

Additionally, in some embodiments, the invention provides a composition having a bioderived caprolactone or caprolactone pathway intermediate disclosed herein and a compound other than the bioderived caprolactone or caprolactone pathway intermediate. For example, in some aspects, the invention provides a biobased polymer, resin, protective or industrial coating, polyurethane, cast elastomer, adhesive, colorant, or pharmaceutical wherein the caprolactone or caprolactone pathway intermediate used in its production is a combination of bioderived and petroleum derived caprolactone or caprolactone pathway intermediate. For example, a biobased polymer, resin, protective or industrial coating, polyurethane, cast elastomer, adhesive, colorant, or pharmaceutical can be produced using 50% bioderived caprolactone and 50% petroleum derived caprolactone or other desired ratios such as 60%/40%, 70%/30%, 80%/20%, 90%/10%, 95%/5%, 100%/0%, 40%/60%, 30%/70%, 20%/80%, 10%/90% of bioderived/petroleum derived precursors, so long as at least a portion of the product comprises a bioderived product produced by the microbial organisms disclosed herein. It is understood that methods for producing a polymer, resin, a protective or industrial coating, polyurethane, a cast elastomer, an adhesive, a colorant, or a pharmaceutical using the bioderived caprolactone or bioderived caprolactone pathway intermediate of the invention are well known in the art.

In another aspect, the compound other than the bioderived caprolactone in a composition of the invention is a trace amount of a cellular portion of a non-naturally occurring microbial organism having a caprolactone pathway of the invention disclosed here. A cellular portion of a microbial organism includes without limitation proteins, polypeptides, peptides, amino acids, nucleic acids, polynucleotides, components of the cell wall or a cellular membrane including, for example, peptidoglycans, glycoproteins, and polysaccharides, or any other cellular component. A "trace amount" as used herein refers to the presence of a compound or material in the composition, but in a quantity approaching a detectable limit. Such trace amounts can be so small as to not be accurately measured.

In some embodiments, the invention provides a molded product obtained by molding a biobased polymer or resin disclosed herein. Such molded products may be produced in to any number of industrially desirable forms including for example, a pellet.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of caprolactone includes anaerobic culture or fermentation conditions. In certain embodiments, the non-naturally occurring microbial organisms of the invention can be sustained, cultured or fermented under anaerobic or substantially anaerobic conditions. Briefly, an anaerobic condition refers to an environment devoid of oxygen. Substantially anaerobic conditions include, for example, a culture, batch fermentation or continuous fermentation such that the dissolved oxygen concentration in the medium remains between 0 and 10% of saturation.

Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of caprolactone. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of caprolactone. Generally, and as with non-continuous culture procedures, the continuous and/or near-continuous production of caprolactone will include culturing a non-naturally occurring caprolactone producing organism of the invention in sufficient nutrients and medium to sustain and/or nearly sustain growth in an exponential phase. Continuous culture under such conditions can include, for example, growth for 1 day, 2, 3, 4, 5, 6 or 7 days or more. Additionally, continuous culture can include longer time periods of 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of caprolactone can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the caprolactone producers of the invention for continuous production of substantial quantities of caprolactone, the caprolactone producers also can be, for example, simultaneously subjected to chemical synthesis procedures to convert the product to other compounds or the product can be separated from the fermentation culture and sequentially subjected to chemical or enzymatic conversion to convert the product to other compounds, if desired.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of caprolactone.

One computational method for identifying and designing metabolic alterations favoring biosynthesis of a desired product is the OptKnock computational framework (Burgard et al., *Biotechnol. Bioeng.* 84:647-657 (2003)). OptKnock is a metabolic modeling and simulation program that suggests gene deletion or disruption strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that allow an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. publication 2009/0047719, filed Aug. 10, 2007.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

As disclosed herein, a nucleic acid encoding a desired activity of a caprolactone pathway can be introduced into a host organism. In some cases, it can be desirable to modify an activity of a caprolactone pathway enzyme or protein to increase production of caprolactone. For example, known mutations that increase the activity of a protein or enzyme can be introduced into an encoding nucleic acid molecule. Additionally, optimization methods can be applied to increase the activity of an enzyme or protein and/or decrease an inhibitory activity, for example, decrease the activity of a negative regulator.

One such optimization method is directed evolution. Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (for example, >$10^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened. Numerous directed evolution technologies have been developed (for reviews, see Hibbert et al., *Biomol. Eng* 22:11-19 (2005); Huisman and Lalonde, In Biocatalysis in the pharmaceutical and biotechnology industries pgs. 717-742 (2007), Patel (ed.), CRC Press; Otten and Quax. *Biomol. Eng* 22:1-9 (2005).; and Sen et al., *Appl Biochem. Biotechnol* 143:212-223 (2007)) to be effective at creating diverse variant libraries, and these methods have been successfully applied to the improvement of a wide range of properties across many enzyme classes. Enzyme characteristics that have been improved and/or altered by directed evolution technologies include, for example: selectivity/specificity, for conversion of non-natural substrates; temperature stability, for robust high temperature processing; pH stability, for bioprocessing under lower or higher pH conditions; substrate or product tolerance, so that high product titers can be achieved; binding ($K_m$), including broadening substrate binding to include non-natural substrates; inhibition ($K_i$), to remove inhibition by products, substrates, or key intermediates; activity (kcat), to increases enzymatic reaction rates to achieve desired flux; expression levels, to increase protein yields and overall pathway flux; oxygen stability, for operation of air sensitive enzymes under aerobic conditions; and anaerobic activity, for operation of an aerobic enzyme in the absence of oxygen.

A number of exemplary methods have been developed for the mutagenesis and diversification of genes to target desired properties of specific enzymes. Such methods are well known to those skilled in the art. Any of these can be used to alter and/or optimize the activity of a caprolactone pathway enzyme or protein. Such methods include, but are not limited to EpPCR, which introduces random point mutations by reducing the fidelity of DNA polymerase in PCR reactions (Pritchard et al., *J Theor. Biol.* 234:497-509 (2005)); Error-prone Rolling Circle Amplification (epRCA), which is similar to epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats (Fujii et al., *Nucleic Acids Res.* 32:e145 (2004); and Fujii et al., *Nat. Protoc.* 1:2493-2497 (2006)); DNA or Family Shuffling, which typically involves digestion of two or more variant genes with nucleases such as Dnase I or EndoV to generate a pool of random fragments that are reassembled by cycles of annealing and extension in the presence of DNA polymerase to create a library of chimeric genes (Stemmer, *Proc Natl Acad Sci USA* 91:10747-10751 (1994); and Stemmer, *Nature* 370:389-391 (1994)); Staggered Extension (StEP), which entails template priming followed by repeated cycles of 2 step PCR with denaturation and very short duration of annealing/extension (as short as 5 sec) (Zhao et al., *Nat. Biotechnol.* 16:258-261 (1998)); Random Priming Recombination (RPR), in which random sequence primers are used to generate many short DNA fragments complementary to different segments of the template (Shao et al., *Nucleic Acids Res* 26:681-683 (1998)).

Additional methods include Heteroduplex Recombination, in which linearized plasmid DNA is used to form heteroduplexes that are repaired by mismatch repair (Volkov et al, *Nucleic Acids Res.* 27:e18 (1999); and Volkov et al., *Methods Enzymol.* 328:456-463 (2000)); Random Chimeragenesis on Transient Templates (RACHITT), which employs Dnase I fragmentation and size fractionation of single stranded DNA (ssDNA) (Coco et al., *Nat. Biotechnol.* 19:354-359 (2001)); Recombined Extension on Truncated templates (RETT), which entails template switching of unidirectionally growing strands from primers in the presence of unidirectional ssDNA fragments used as a pool of templates (Lee et al., *J. Molec. Catalysis* 26:119-129 (2003)); Degenerate Oligonucleotide Gene Shuffling (DOGS), in which degenerate primers are used to control recombination between molecules; (Bergquist and Gibbs, *Methods Mol. Biol* 352:191-204 (2007); Bergquist et al., *Biomol. Eng* 22:63-72 (2005); Gibbs et al., *Gene* 271:13-20 (2001)); Incremental Truncation for the Creation of Hybrid Enzymes (ITCHY), which creates a combinatorial library with 1 base pair deletions of a gene or gene fragment of interest (Ostermeier et al., *Proc. Natl. Acad. Sci. USA* 96:3562-3567 (1999); and Ostermeier et al., *Nat. Biotechnol.* 17:1205-1209 (1999)); Thio-Incremental Truncation for the Creation of Hybrid Enzymes (THIO-ITCHY), which is similar to ITCHY except that phosphothioate dNTPs are used to generate truncations (Lutz et al., *Nucleic Acids Res* 29:E16 (2001)); SCRATCHY, which combines two methods for recombining genes, ITCHY and DNA shuffling (Lutz et al., *Proc. Natl. Acad. Sci. USA* 98:11248-11253 (2001)); Random Drift Mutagenesis (RNDM), in which mutations made via epPCR are followed by screening/selection for those retaining usable activity (Bergquist et al., *Biomol. Eng.* 22:63-72 (2005)); Sequence Saturation Mutagenesis (SeSaM), a random mutagenesis method that generates a pool of random length fragments using random incorporation of a phosphothioate nucleotide and cleavage, which is used as a template to extend in the presence of "universal" bases such as inosine, and replication of an inosine-containing complement gives random base incorporation and, consequently, mutagenesis (Wong et al., *Biotechnol. J.* 3:74-82 (2008); Wong et al., *Nucleic Acids Res.* 32:e26 (2004); and Wong et al., *Anal. Biochem.* 341:187-189 (2005)); Synthetic Shuffling, which uses overlapping oligonucleotides designed to encode "all genetic diversity in targets" and allows a very high diversity for the shuffled progeny (Ness et al., *Nat. Biotechnol.* 20:1251-1255 (2002)); Nucleotide Exchange and Excision Technology NexT, which exploits a combination of dUTP incorporation followed by treatment with uracil DNA glycosylase and then piperidine to perform endpoint DNA fragmentation (Muller et al., *Nucleic Acids Res.* 33:e117 (2005)).

Further methods include Sequence Homology-Independent Protein Recombination (SHIPREC), in which a linker is used to facilitate fusion between two distantly related or unrelated genes, and a range of chimeras is generated between the two genes, resulting in libraries of single-crossover hybrids (Sieber et al., *Nat. Biotechnol.* 19:456-460 (2001)); Gene Site Saturation Mutagenesis™ (GSSM™), in which the starting materials include a supercoiled double stranded DNA (dsDNA) plasmid containing an insert and two primers which are degenerate at the desired site of mutations (Kretz et al., *Methods Enzymol.* 388:3-11 (2004)); Combinatorial Cassette Mutagenesis (CCM), which involves the use of short oligonucleotide cassettes to replace limited regions with a large number of possible amino acid sequence alterations (Reidhaar-Olson et al. *Methods Enzymol.* 208:564-586 (1991); and Reidhaar-Olson et al. *Science* 241:53-57 (1988)); Combinatorial Multiple Cassette Mutagenesis (CMCM), which is essentially similar to CCM and uses epPCR at high mutation rate to identify hot spots and hot regions and then extension by CMCM to cover a defined region of protein sequence space (Reetz et al., *Angew. Chem. Int. Ed Engl.* 40:3589-3591 (2001)); the Mutator Strains technique, in which conditional is mutator plasmids, utilizing the mutD5 gene, which encodes a mutant subunit of DNA polymerase III, to allow increases of 20 to 4000-X in random and natural mutation frequency during selection and block accumulation of deleterious mutations when selection is not required (Selifonova et al., *Appl. Environ. Microbiol.* 67:3645-3649 (2001)); Low et al., *J. Mol. Biol.* 260:359-3680 (1996)).

Additional exemplary methods include Look-Through Mutagenesis (LTM), which is a multidimensional mutagenesis method that assesses and optimizes combinatorial mutations of selected amino acids (Rajpal et al., *Proc. Natl. Acad. Sci. USA* 102:8466-8471 (2005)); Gene Reassembly, which is a DNA shuffling method that can be applied to multiple genes at one time or to create a large library of chimeras (multiple mutations) of a single gene (Tunable GeneReassembly™ (TGR™) Technology supplied by Verenium Corporation), in Silico Protein Design Automation (PDA), which is an optimization algorithm that anchors the structurally defined protein backbone possessing a particular fold, and searches sequence space for amino acid substitutions that can stabilize the fold and overall protein energetics, and generally works most effectively on proteins with known three-dimensional structures (Hayes et al., *Proc. Natl. Acad. Sci. USA* 99:15926-15931 (2002)); and Iterative Saturation Mutagenesis (ISM), which involves using knowledge of structure/function to choose a likely site for enzyme improvement, performing saturation mutagenesis at chosen site using a mutagenesis method such as Stratagene QuikChange (Stratagene; San Diego Calif.), screening/selecting for desired properties, and, using improved clone(s), starting over at another site and continue repeating until a desired activity is achieved (Reetz et al., *Nat. Protoc.* 2:891-903 (2007); and Reetz et al., *Angew. Chem. Int. Ed Engl.* 45:7745-7751 (2006)).

Any of the aforementioned methods for mutagenesis can be used alone or in any combination. Additionally, any one or combination of the directed evolution methods can be used in conjunction with adaptive evolution techniques, as described herein.

It is understood that modifications which do not substantially affect the activity of the various embodiments of this invention are also provided within the definition of the invention provided herein. Accordingly, the following examples are intended to illustrate but not limit the present invention.

EXAMPLE I

Production of Caprolactone

Several pathways for producing caprolactone are depicted in FIGS. 1-5. Each pathway originates from naturally occurring metabolites. FIG. 1 shows pathways for converting adipate or adipyl-CoA to caprolactone. Adipate is an intermediate produced during the degradation of aromatic and aliphatic ring containing compounds such as cyclohexanol. Biosynthetic pathways for forming adipate and adipyl-CoA are well known in the art (for example, see U.S. Pat. No. 7,799,545). In the pathway shown in FIG. 1, adipate semialdehyde is formed either from adipate via an adipate reductase (Step E) or adipyl-CoA via adipyl-CoA reductase (Step A). Adipate semialdehyde is then reduced to 5-hydroxyhexanoate in Step B. The 6-hydroxyhexanoate intermediate is converted to caprolactone by one of several alternate routes. In one route, 6-hydroxyhexanoate is directly converted to caprolactone by a caprolactone hydrolase (step G). In yet another route, 6-hydroxyhexanoate is activated to its corresponding acyl-CoA, which then cyclizes to caprolactone (step C/D), or cyclizes via a 6-hydroxyhexanoyl-phosphate intermediate (steps J/I). In an alternate route, 6-hydroxyhexanote is activated to 6-hydroxyhexanoyl-phosphate, which is then cyclized to caprolactone (step H/I).

Figure 2:
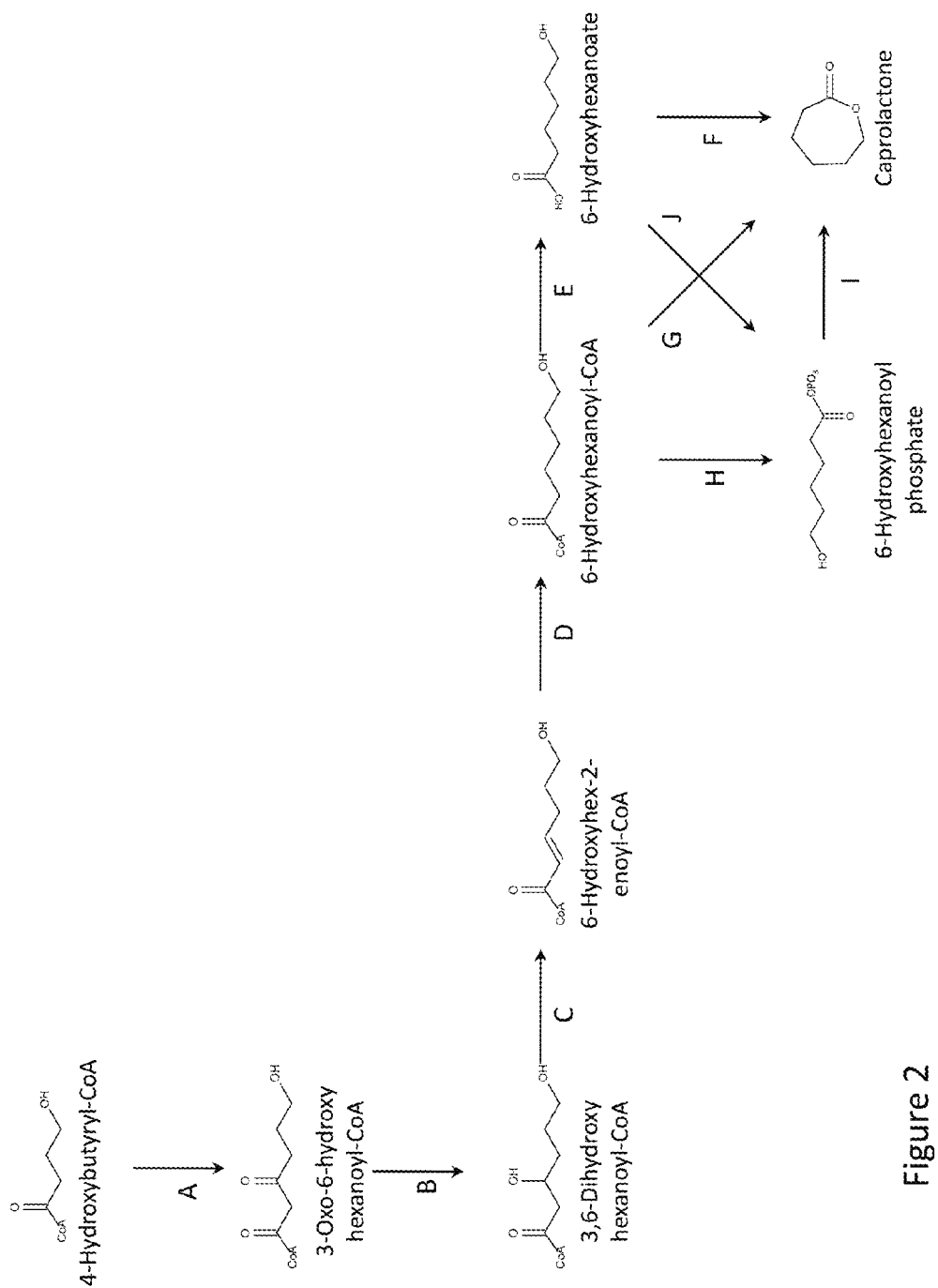
FIG. 2 shows exemplary pathways from 4-hydroxybutyryl-CoA to caprolactone. Enzymes are A. 4-hydroxybutyryl-CoA:acetyl-CoA acyltransferase, B. 3-oxo-6-hydroxyhexanoyl-CoA reductase, C. 3,6-dihydroxyhexanoyl-CoA dehydratase, D. 6-hydroxyhex-2-enoyl-CoA reductase, E. 6-hydroxyhexanoyl-CoA transferase, synthetase or hydrolase, F. 6-hydroxyhexanoate cyclase, G. 6-hydroxyhexanoyl-CoA cyclase or spontaneous, H. phosphotrans-6-hydroxyhexanoylase, I. 6-hydroxyhexanoyl phosphate cyclase or spontaneous, J. 6-hydroxyhexanoate kinase.

A similar series of pathways is shown in FIG. 2. These pathways originate from 4-hydroxybutyryl-CoA, an intermediate in the biosynthesis of poly-hydroxyalkanoates and non-naturally occurring chemicals such as 1,4-butanediol (see U.S. Pat. No. 7,947,483, U.S. Pat. No. 7,229,804). In the first step of FIG. 2 pathways, 4-hydroxybutyryl-CoA and acetyl-CoA are joined by a beta-ketothiolase to form 3-oxo-6-hydroxyhexanoyl-CoA. This intermediate is reduced and dehydrated to 6-hydroxyhex-2-enoyl-CoA (steps B/C). Reduction of 6-hydroxyhex-2-enoyl-CoA yields 6-hydroxyhexanoyl-CoA in Step D. 6-Hydroxyhexanoyl-CoA is directly converted to caprolactone either spontaneously or by an enzyme (step G). Alternately, caprolactone is formed via a phosphate intermediate (steps H/I) and/or 6-hydroxyhexanoate (steps E/J/I or steps E/F).

Figure 3:
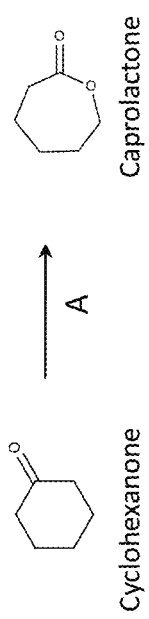
FIG. 3 shows conversion of cyclohexanone to caprolactone by cyclohexanone monooxygenase.

In another embodiment, the caprolactone is derived from cyclohexanone as shown in FIG. 3. The conversion of cyclohexanone to caprolactone by enzymes with cyclohexanone monooxygenase activity is well known in the art (see for example, U.S. Pat. No. 6,790,645 and U.S. Pat. No. 7,105,296). Exemplary pathways for biosynthesizing cyclohexanone from metabolic intermediates are shown in FIGS. 4 and 5.

Figure 4:
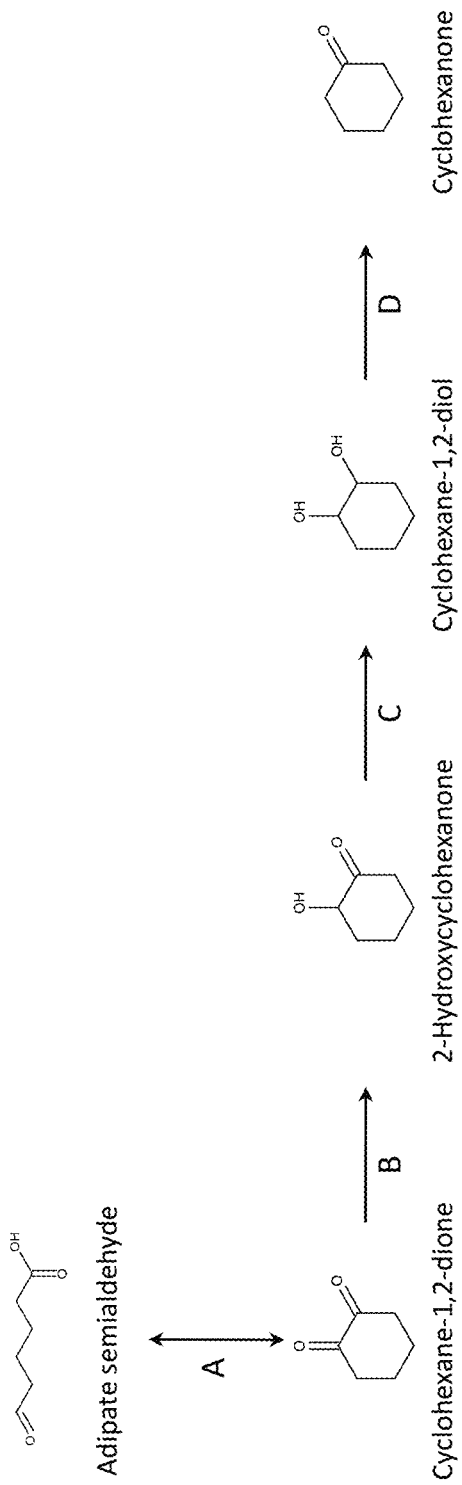
FIG. 4 shows exemplary pathways to cyclohexanone from adipate semialdehyde. Enzymes are A. adipate semialdehyde dehydratase, B. cyclohexane-1,2-dione reductase, C. 2-hydroxycyclohexanone reductase, D. cyclohexane-1,2-diol dehydratase.

FIG. 4 shows a pathway for converting adipate semialdehyde to cyclohexanone in four enzymatic steps. In the first step, adipate semialdehyde is simultaneously dehydrated and cyclized, forming cyclohexane-1,2-dione. Reduction of the two keto groups to alcohol groups is catalyzed by one or more enzymes with cyclohexane-1,2-dione reductase and 2-hydroxycyclohexanone reductase activities. Finally, a diol dehydratase converts cyclohexane-1,2-diol to cyclohexanone.

Figure 5:
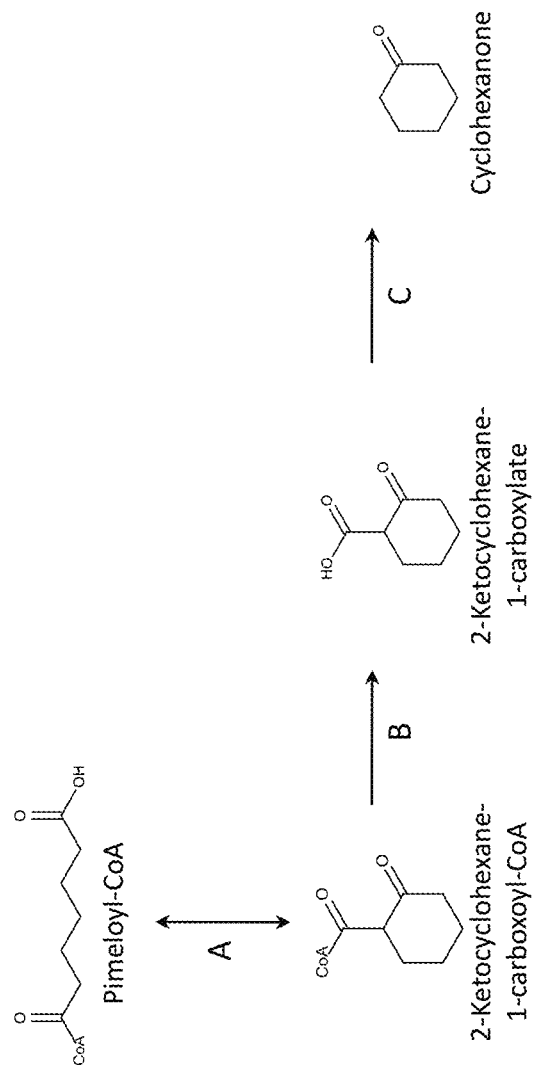
FIG. 5 shows exemplary pathways to cyclohexanone from pimeloyl-CoA. Enzymes are A. 2-ketocyclohexane-1-carboxoyl-CoA hydrolase (acting on C-C), B. 2-ketocyclohexane-1-carboxoyl-CoA transferase, synthetase or hydrolase, C. 2-ketocyclohexane-1-carboxylate decarboxylase.

Cyclohexanone can alternately be synthesized from pimeloyl-CoA as shown in FIG. 5. Pimeloyl-CoA is a naturally occurring intermediate of metabolic pathways including biotin biosynthesis and degradation pathways of aromatic compounds. In the proposed cyclohexanone pathway, pimeloyl-CoA is cyclized to 2-ketocyclohexane-1-carboxyl- CoA by 2-ketocyclohexane-1-carboxyl-CoA hydrolase (acting on C-C). The CoA ester is then converted to 2-ketocyclohexane-1-carboxylate by a CoA synthetase, hydrolase or transferase. Finally decarboxylation of 2-ketocyclohexane-1-carboxylate yields cyclohexanone.

hyde, propionaldehyde, butyraldehyde, and acrolein (Kinoshita et al., *Appl Microbiol Biotechnol* 22:249-254 (1985)). Additional aldehyde reductase candidates are encoded by bdh in *C. saccharoperbutylacetonicum* and Cbei_1722, Cbei_2181 and Cbei_2421 in *C. beijerinckii*.

| | Enzymes | | | | | |
|---|---|---|---|---|---|---|
| EC class | Description | FIG. 1 | FIG. 2 | FIG. 3 | FIG. 4 | FIG. 5 |
| 1.1.1.a | Oxidoreductase (oxo to alcohol) | 1B | 2B | | 4B, 4C | |
| 1.14.13.a | Monooxygenase ($O_2$ incorporating) | | | 3A | | |
| 1.2.1.b | Oxidoreductase (acyl-CoA to aldehyde) | 1A | | | | |
| 1.2.1.e | Oxidoreductase (acid to aldehyde) | 1E | | | | |
| 1.3.1.a | Oxidoreductase (alkene to alkane) | | 2D | | | |
| 2.3.1.a | Phosphotransacylase | 1J | 2H | | | |
| 2.3.1.b | Beta-ketothiolase | | 2A | | | |
| 2.7.2.a | Kinase | 1H | 2J | | | |
| 2.8.3.a | CoA transferase | 1C, 1F | 2E | | | 5B |
| 3.1.1.a | Esterase | 1G | 2F | | | |
| 3.1.2.a | CoA hydrolase | 1F | | | | 5B |
| 3.7.1.a | Hydrolase | | | | 4D | 5A |
| 4.1.1.a | Decarboxylase | | | | | 5C |
| 4.2.1.a | Hydro-lyase | | 2C | | 4A | |
| 6.2.1.a | CoA synthetase | 1C, 1F | 2E | | | 5B |
| N/A | | 1D, 1I | 2G, 2I | | | |

1.1.1.a Alcohol Dehydrogenase

Several reactions shown in FIGS. 1, 2 and 4 are catalyzed by alcohol dehydrogenase enzymes. These reactions include Step B of FIG. 1, Step B of FIG. 2 and Steps B and C of FIG. 4. Exemplary alcohol dehydrogenase enzymes are described in further detail below.

6-Hydroxyhexanoate dehydrogenase (adipate semialdehyde reductase) catalyzes the reduction of adipate semialdehyde to 6-hydroxyhexanoate. Such an enzyme is required in Step B of FIG. 1. Enzymes with this activity are found in organisms that degrade cyclohexanone, and are encoded by chnD of *Acinetobacter* sp. NCIMB9871 (Iwaki et al, *AEM* 65:5158-62 (1999)), *Rhodococcus* sp. Phi2 and *Arthrobacter* sp. BP2 (Brzostowicz et al, *AEM* 69:334-42 (2003)).

| Gene | GenBank ID | GI Number | Organism |
|---|---|---|---|
| chnD | BAC80217.1 | 33284997 | *Acinetobacter* sp. NCIMB9871 |
| chnD | AAN37477.1 | 27657618 | *Arthrobacter* sp. BP2 |
| chnD | AAN37489.1 | 27657631 | *Rhodococcus* sp. Phi2 |

Additional aldehyde reductase enzymes are shown in the table below. AlrA encodes a medium-chain alcohol dehydrogenase for C2-C14 compounds (Tani et al., *Appl. Environ. Microbiol.* 66:5231-5235 (2000)). Other candidates are yqhD and fucO from *E. coli* (Sulzenbacher et al., 342:489-502 (2004)), and bdh I and bdh II from *C. acetobutylicum* (Walter et al., 174:7149-7158 (1992)). YqhD catalyzes the reduction of a wide range of aldehydes using NADPH as the cofactor, with a preference for chain lengths longer than C(3) (Sulzenbacher et al., 342:489-502 (2004); Perez et al., *J Biol. Chem.* 283:7346-7353 (2008)). The adhA gene product from *Zymomonas mobilis* has been demonstrated to have activity on a number of aldehydes including formaldehyde, acetalde-

| Protein | GenBank ID | GI number | Organism |
|---|---|---|---|
| alrA | BAB12273.1 | 9967138 | *Acinetobacter* sp. strain M-1 |
| ADH2 | NP_014032.1 | 6323961 | *Saccharomyces cerevisiae* |
| yqhD | NP_417484.1 | 16130909 | *Escherichia coli* |
| fucO | NP_417279.1 | 16130706 | *Escherichia coli* |
| bdh I | NP_349892.1 | 15896543 | *Clostridium acetobutylicum* |
| bdh II | NP_349891.1 | 15896542 | *Clostridium acetobutylicum* |
| adhA | YP_162971.1 | 56552132 | *Zymomonas mobilis* |
| bdh | BAF45463.1 | 124221917 | *Clostridium saccharoperbutylacetonicum* |
| Cbei_1722 | YP_001308850 | 150016596 | *Clostridium beijerinckii* |
| Cbei_2181 | YP_001309304 | 150017050 | *Clostridium beijerinckii* |
| Cbei_2421 | YP_001309535 | 150017281 | *Clostridium beijerinckii* |

Enzymes exhibiting 4-hydroxybutyrate dehydrogenase activity (EC 1.1.1.61) are also suitable candidates. Such enzymes have been characterized in *Ralstonia eutropha* (Bravo et al., *J Forens Sci*, 49:379-387 (2004)), *Clostridium kluyveri* (Wolff et al., *Protein Expr. Purif.* 6:206-212 (1995)) and *Arabidopsis thaliana* (Breitkreuz et al., *J Biol Chem*, 278:41552-41556 (2003)). The *A. thaliana* enzyme was cloned and characterized in yeast. This enzyme also catalyzes the reduction of glutarate semialdehyde to 5-hydroxyvalerate (WO 2010/068953A2). Yet another gene is the alcohol dehydrogenase adhI from *Geobacillus thermoglucosidasius* (Jeon et al., *J Biotechnol* 135:127-133 (2008)). An enzyme with similar activity is the glutarate semialdehyde reductase enzyme of *Aspergillus terreus*, encoded by ATEG_00539 (WO 2010/068953A2).

| Protein | GenBank ID | GI number | Organism |
|---|---|---|---|
| 4hbd | YP_726053.1 | 113867564 | *Ralstonia eutropha* H16 |
| 4hbd | L21902.1 | 146348486 | *Clostridium kluyveri* DSM 555 |
| 4hbd | Q94B07 | 75249805 | *Arabidopsis thaliana* |

-continued

| Protein | GenBank ID | GI number | Organism |
| --- | --- | --- | --- |
| adhI | AAR91477.1 | 40795502 | Geobacillus thermoglucosidasius |
| ATEG_00539 | XP_001210625.1 | 115491995 | Aspergillus terreus NIH2624 |

Aldehyde reductase gene candidates in *Saccharomyces cerevisiae* include the aldehyde reductases GRE3, ALD2-6 and HFD1, glyoxylate reductases GOR1 and YPL113C and glycerol dehydrogenase GCY1 (WO 2011/022651A1; Atsumi et al., *Nature* 451:86-89 (2008)). The enzyme candidates described previously for catalyzing the reduction of methylglyoxal to acetol or lactaldehyde are also suitable lactaldehyde reductase enzyme candidates.

| Protein | GenBank ID | GI Number | Organism |
| --- | --- | --- | --- |
| GRE3 | P38715.1 | 731691 | Saccharomyces cerevisiae |
| ALD2 | CAA89806.1 | 825575 | Saccharomyces cerevisiae |
| ALD3 | NP_013892.1 | 6323821 | Saccharomyces cerevisiae |
| ALD4 | NP_015019.1 | 6324950 | Saccharomyces cerevisiae |
| ALD5 | NP_010996.2 | 330443526 | Saccharomyces cerevisiae |
| ALD6 | ABX39192.1 | 160415767 | Saccharomyces cerevisiae |
| HFD1 | Q04458.1 | 2494079 | Saccharomyces cerevisiae |
| GOR1 | NP_014125.1 | 6324055 | Saccharomyces cerevisiae |
| YPL113C | AAB68248.1 | 1163100 | Saccharomyces cerevisiae |
| GCY1 | CAA99318.1 | 1420317 | Saccharomyces cerevisiae |

Ketone reductase or alcohol dehydrogenase enzymes that reduce 3-oxoacyl-CoA substrates to their corresponding 3-hydroxyacyl-CoA product are relevant to the pathways depicted in FIG. 2. 3-Oxoacyl-CoA reductase enzymes (EC 1.1.1.35) convert 3-oxoacyl-CoA molecules into 3-hydroxyacyl-CoA molecules and are often involved in fatty acid beta-oxidation or phenylacetate catabolism. For example, subunits of two fatty acid oxidation complexes in *E. coli*, encoded by fadB and fadJ, function as 3-hydroxyacyl-CoA dehydrogenases (Binstock et al., *Methods Enzymol.* 71 Pt C:403-411 (1981)). Given the proximity in *E. coli* of paaH to other genes in the phenylacetate degradation operon (Nogales et al., 153:357-365 (2007)) and the fact that paaH mutants cannot grow on phenylacetate (Ismail et al., *Eur. J Biochem.* 270:3047-3054 (2003)), it is expected that the *E. coli* paaH gene also encodes a 3-hydroxyacyl-CoA dehydrogenase. Additional 3-oxoacyl-CoA enzymes include the gene products of phaC in *Pseudomonas putida* (Olivera et al., *Proc. Natl. Acad. Sci U.S.A* 95:6419-6424 (1998)) and paaC in *Pseudomonas fluorescens* (Di et al., 188:117-125 (2007)). These enzymes catalyze the reversible oxidation of 3-hydroxyadipyl-CoA to 3-oxoadipyl-CoA during the catabolism of phenylacetate or styrene.

Acetoacetyl-CoA reductase participates in the acetyl-CoA fermentation pathway to butyrate in several species of *Clostridia* and has been studied in detail (Jones et al., *Microbiol Rev.* 50:484-524 (1986)). The enzyme from *Clostridium acetobutylicum*, encoded by hbd, has been cloned and functionally expressed in *E. coli* (Youngleson et al., *J Bacteriol.* 171:6800-6807 (1989)). Yet other genes demonstrated to reduce acetoacetyl-CoA to 3-hydroxybutyryl-CoA are phbB from *Zoogloea ramigera* (Ploux et al., *Eur. J Biochem.* 174:177-182 (1988)) and phaB from *Rhodobacter sphaeroides* (Alber et al., *Mol. Microbiol* 61:297-309 (2006)). The former gene is NADPH-dependent, its nucleotide sequence has been determined (Peoples et al., *Mol. Microbiol* 3:349-357 (1989)) and the gene has been expressed in *E. coli*. Substrate specificity studies on the gene led to the conclusion that it could accept 3-oxopropionyl-CoA as a substrate besides acetoacetyl-CoA (Ploux et al., *Eur. J Biochem.* 174:177-182 (1988)). Additional genes include phaB in *Paracoccus denitrificans*, Hbd1 (C-terminal domain) and Hbd2 (N-terminal domain) in *Clostridium kluyveri* (Hillmer and Gottschalk, *Biochim. Biophys. Acta* 3334:12-23 (1974)) and HSD17B10 in *Bos taurus* (Wakil et al., *J Biol. Chem.* 207:631-638 (1954)). The enzyme from *Paracoccus denitrificans* has been functionally expressed and characterized in *E. coli* (Yabutani et al., *FEMS Microbiol Lett.* 133:85-90 (1995)). A number of similar enzymes have been found in other species of *Clostridia* and in *Metallosphaera sedula* (Berg et al., *Science.* 318:1782-1786 (2007)). The enzyme from *Candida tropicalis* is a component of the peroxisomal fatty acid beta-oxidation multifunctional enzyme type 2 (MFE-2). The dehydrogenase B domain of this protein is catalytically active on acetoacetyl-CoA. The domain has been functionally expressed in *E. coli*, a crystal structure is available, and the catalytic mechanism is well-understood (Ylianttila et al., *Biochem Biophys Res Commun* 324:25-30 (2004); Ylianttila et al., *J Mol Biol* 358:1286-1295 (2006)).

| Protein | Genbank ID | GI number | Organism |
| --- | --- | --- | --- |
| fadB | P21177.2 | 119811 | Escherichia coli |
| fadJ | P77399.1 | 3334437 | Escherichia coli |
| paaH | NP_415913.1 | 16129356 | Escherichia coli |
| Hbd2 | EDK34807.1 | 146348271 | Clostridium kluyveri |
| Hbd1 | EDK32512.1 | 146345976 | Clostridium kluyveri |
| phaC | NP_745425.1 | 26990000 | Pseudomonas putida |
| paaC | ABF82235.1 | 106636095 | Pseudomonas fluorescens |
| HSD17B10 | O02691.3 | 3183024 | Bos taurus |
| phbB | P23238.1 | 130017 | Zoogloea ramigera |
| phaB | YP_353825.1 | 77464321 | Rhodobacter sphaeroides |
| phaB | BAA08358 | 675524 | Paracoccus denitrificans |
| Hbd | NP_349314.1 | 15895965 | Clostridium acetobutylicum |
| Hbd | AAM14586.1 | 20162442 | Clostridium beijerinckii |
| Msed_1423 | YP_001191505 | 146304189 | Metallosphaera sedula |
| Msed_0399 | YP_001190500 | 146303184 | Metallosphaera sedula |
| Msed_0389 | YP_001190490 | 146303174 | Metallosphaera sedula |
| Msed_1993 | YP_001192057 | 146304741 | Metallosphaera sedula |
| Fox2 | Q02207 | 399508 | Candida tropicalis |

The conversion of cyclohexane-1,2-dione to a diol can be accomplished by cyclohexane-1,2-diol dehydrogenase (EC 1.1.1.174). This enzymatic activity has been demonstrated in *Acinetobacter* TD63 (Davey et al., *Eur. J Biochem.* 74:115-127 (1977)). It has been indicated that cyclohexanol dehydrogenase (EC 1.1.1.245), an enzyme with a broad substrate range, can catalyze these conversions. Cyclohexanol dehydrogenase enzymes from *Rhodococcus* sp TK6 (Tae-Kang et al., *J. Microbiol. Biotechnol.* 12:39-45 (2002)), a denitrifying *Pseudomonas* sp. (Dangel et al., 152:271-279 (1989)), *Nocardia* sp (Stirling et al., 4:37-40 (1980)) and *Xanthobacter* sp. (Trower et al., 49:1282-1289 (1985)) have all been shown to convert cyclohexan-1,2-diol to cyclohexan-1,2-dione. The gene associated with a cyclohexanol dehydrogenase in *Acinetobacter* sp NCIMB9871 was identified in 2000 (Cheng et al., *J Bacteriol.* 182:4744-4751 (2000)). This enzyme, encoded by chnA, has not been tested for activity on cyclohexan-1,2-dione or cyclohexan-1,2-diol. A BLAST comparison of the *Acinetobacter* ChnA protein sequence identifies genes from other organisms including *Ralstonia metallireducens* (57% identity), and *Pseudomonas putida* (47% identity). A cyclohexanol dehydrogenase gene from *Comamonas testosteroni* has also been expressed and characterized in *E. coli* (Van Beilen et al., 5:174-182 (2003)); a similar gene was also identified in *Xanthobacter flavus* (Van Beilen et al., *Environ. Microbiol* 5:174-182 (2003)). The protein sequences for exemplary gene products can be found using the following GenBank accession numbers shown below.

| Protein | GenBank ID | GI Number | Organism |
|---|---|---|---|
| chnA | BAC80215.1 | 33284995 | *Acinetobacter* sp NCIMB9871 |
| chnA | CAD10799.1 | 16943680 | *Comamonas testosteroni* |
| chnA | CAD10802.1 | 18495819 | *Xanthobacter flavus* |
| Rmet_1335 | YP_583487.1 | 94310277 | *Ralstonia metallireducens* |
| PP_1946 | NP_744098.1 | 26988673 | *Pseudomonas putida* |

Another enzyme which can accomplish this conversion is diacetyl reductase (EC 1.1.1.5). Naturally catalyzing the conversion of diacetyl(2,3-butanedione) to acetoin and subsequent reduction to 2,3-butanediol, two NADPH-dependent diacetyl reductase enzymes from *S. cerevisiae* have been shown to also accept cyclohexan-1,2-dione as a substrate (Heidlas et al., *Eur. J Biochem.* 188:165-174 (1990)). The (S)-specific NADPH-dependent diacetyl reductase from this study was later identified as D-arabinose dehydrogenase, the gene product of ARA1 (Katz et al., 33:163-172 (2003)). The NADH-dependent gene product of BDH1 of *S. cerevisiae* also has diacetyl reductase functionality (Gonzalez et al., 275:35876-35885 (2000)). Several other enzymes with diketone reductase functionality have been identified in yeast, encoded by genes GCY1, YPR1, GRE3, Y1R036c (Johanson et al., *FEMS Yeast Res.* 5:513-525 (2005)). The protein sequences for exemplary gene products can be found using the following GenBank accession numbers shown below.

| Protein | GenBank ID | GI Number | Organism |
|---|---|---|---|
| ARA1 | NP_009707.1 | 6319625 | *Saccharomyces cerevisiae* |
| BDH1 | NP_009341.1 | 6319258 | *Saccharomyces cerevisiae* |
| GCY1 | NP_014763.1 | 6324694 | *Saccharomyces cerevisiae* |
| YPR1 | NP_010656.1 | 6320576 | *Saccharomyces cerevisiae* |
| GRE3 | NP_011972.1 | 6321896 | *Saccharomyces cerevisiae* |
| YIR036c | AAS56566.1 | 45270370 | *Saccharomyces cerevisiae* |

1.2.1.b Oxidoreductase (Acyl-CoA to Aldehyde)

An adipyl-CoA reductase converts adipyl-CoA to adipate semialdehyde in Step A of FIG. 1. Several acyl-CoA reductase enzymes are found in EC class 1.2.1. Exemplary enzymes include fatty acyl-CoA reductase, succinyl-CoA reductase (EC 1.2.1.76), acetyl-CoA reductase, butyryl-CoA reductase and propionyl-CoA reductase (EC 1.2.1.3). Exemplary fatty acyl-CoA reductases enzymes are encoded by acr1 of *Acinetobacter calcoaceticus* (Reiser, *Journal of Bacteriology* 179:2969-2975 (1997)) and *Acinetobacter* sp. M-1 (Ishige et al., *Appl. Environ. Microbiol.* 68:1192-1195 (2002)). Enzymes with succinyl-CoA reductase activity are encoded by sucD of *Clostridium kluyveri* (Sohling, *J. Bacteriol.* 178:871-880 (1996)) and sucD of *P. gingivalis* (Takahashi, *J. Bacteriol* 182:4704-4710 (2000)). Additional succinyl-CoA reductase enzymes participate in the 3-hydroxypropionate/4-hydroxybutyrate cycle of thermophilic archaea including *Metallosphaera sedula* (Berg et al., *Science* 318:1782-1786 (2007)) and *Thermoproteus neutrophilus* (Ramos-Vera et al., *J Bacteriol*, 191:4286-4297 (2009)). The *M. sedula* enzyme, encoded by Msed_0709, is strictly NADPH-dependent and also has malonyl-CoA reductase activity. The *T. neutrophilus* enzyme is active with both NADPH and NADH. The enzyme acylating acetaldehyde dehydrogenase in *Pseudomonas* sp, encoded by bphG, is yet another as it has been demonstrated to oxidize and acylate acetaldehyde, propionaldehyde, butyraldehyde, isobutyraldehyde and formaldehyde (Powlowski, *J. Bacteriol.* 175:377-385 (1993)). In addition to reducing acetyl-CoA to ethanol, the enzyme encoded by adhE in *Leuconostoc mesenteroides* has been shown to oxidize the branched chain compound isobutyraldehyde to isobutyryl-CoA (Kazahaya, *J. Gen. Appl. Microbiol.* 18:43-55 (1972); and Koo et al., *Biotechnol Lett.* 27:505-510 (2005)). Butyraldehyde dehydrogenase catalyzes a similar reaction, conversion of butyryl-CoA to butyraldehyde, in solventogenic organisms such as *Clostridium saccharoperbutylacetonicum* (Kosaka et al., *Biosci Biotechnol Biochem.*, 71:58-68 (2007)). Exemplary propionyl-CoA reductase enzymes include pduP of *Salmonella typhimurium* LT2 (Leal, Arch. Microbiol. 180:353-361 (2003)) and cutE from *E. coli* (Skraly, WO Patent No. 2004/024876). The propionyl-CoA reductase of *Salmonella typhimurium* LT2, which naturally converts propionyl-CoA to propionaldehyde, also catalyzes the reduction of 5-hydroxyvaleryl-CoA to 5-hydroxypentanal (WO 2010/068953A2).

| Protein | GenBank ID | GI Number | Organism |
|---|---|---|---|
| acr1 | YP_047869.1 | 50086359 | *Acinetobacter calcoaceticus* |
| acr1 | AAC45217 | 1684886 | *Acinetobacter baylyi* |
| acr1 | BAB85476.1 | 18857901 | *Acinetobacter* sp. Strain M-1 |
| Msed_0709 | YP_001190808.1 | 146303492 | *Metallosphaera sedula* |
| Tneu_0421 | ACB39369.1 | 170934108 | *Thermoproteus neutrophilus* |
| sucD | P38947.1 | 172046062 | *Clostridium kluyveri* |
| sucD | NP_904963.1 | 34540484 | *Porphyromonas gingivalis* |
| bphG | BAA03892.1 | 425213 | *Pseudomonas* sp |
| adhE | AAV66076.1 | 55818563 | *Leuconostoc mesenteroides* |
| bld | AAP42563.1 | 31075383 | *Clostridium saccharoperbutylacetonicum* |
| pduP | NP_460996 | 16765381 | *Salmonella typhimurium* LT2 |
| eutE | NP_416950 | 16130380 | *Escherichia coli* |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archaeal bacteria (Berg, *Science* 318:1782-1786 (2007); and Thauer, *Science* 318:1732-1733 (2007)). The enzyme utilizes NADPH as a cofactor and has been characterized in *Metallosphaera* and *Sulfolobus* sp. (Alber et al., *J. Bacteriol.* 188: 8551-8559 (2006); and Hugler, *J. Bacteriol.* 184:2404-2410 (2002)). The enzyme is encoded by Msed_0709 in *Metallosphaera sedula* (Alber et al., *J. Bacteriol.* 188:8551-8559 (2006); and Berg, *Science* 318:1782-1786 (2007)). A gene encoding a malonyl-CoA reductase from *Sulfolobus tokodaii* was cloned and heterologously expressed in *E. coli* (Alber et al., *J. Bacteriol* 188:8551-8559 (2006). This enzyme has also been shown to catalyze the conversion of methylmalonyl-CoA to its corresponding aldehyde (WO2007141208 (2007)). Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius* and have been listed below. Yet another candidate for CoA-acylating aldehyde dehydrogenase is the ald gene from *Clostridium beijerinckii* (Toth, *Appl. Environ. Microbiol.*

65:4973-4980 (1999). This enzyme has been reported to reduce acetyl-CoA and butyryl-CoA to their corresponding aldehydes. This gene is very similar to eutE that encodes acetaldehyde dehydrogenase of *Salmonella typhimurium* and *E. coli* (Toth, *Appl. Environ. Microbiol.* 65:4973-4980 (1999).

| Gene | GenBank ID | GI Number | Organism |
|---|---|---|---|
| Msed_0709 | YP_001190808.1 | 146303492 | *Metallosphaera sedula* |
| mcr | NP_378167.1 | 15922498 | *Sulfolobus tokodaii* |
| asd-2 | NP_343563.1 | 15898958 | *Sulfolobus solfataricus* |
| Saci_2370 | YP_256941.1 | 70608071 | *Sulfolobus acidocaldarius* |
| Ald | AAT66436 | 49473535 | *Clostridium beijerinckii* |
| eutE | AAA80209 | 687645 | *Salmonella typhimurium* |
| eutE | NP_416950 | 16130380 | *Escherichia coli* |

1.2.1.e (CAR)

The conversion of an acid to an aldehyde is thermodynamically unfavorable and typically requires energy-rich cofactors and multiple enzymatic steps. For example, in butanol biosynthesis conversion of butyrate to butyraldehyde is catalyzed by activation of butyrate to its corresponding acyl-CoA by a CoA transferase or ligase, followed by reduction to butyraldehyde by a CoA-dependent aldehyde dehydrogenase. Alternately, an acid can be activated to an acyl-phosphate and subsequently reduced by a phosphate reductase. Direct conversion of the acid to aldehyde by a single enzyme is catalyzed by a bifunctional enzyme in the 1.2.1 family. Exemplary enzymes that catalyze these transformations include carboxylic acid reductase, alpha-aminoadipate reductase and retinoic acid reductase.

Carboxylic acid reductase (CAR), found in *Nocardia iowensis*, catalyzes the magnesium, ATP and NADPH-dependent reduction of carboxylic acids to their corresponding aldehydes (Venkitasubramanian et al., *J Biol. Chem.* 282: 478-485 (2007)). The natural substrate of this enzyme is benzoic acid and the enzyme exhibits broad acceptance of aromatic and aliphatic substrates (Venkitasubramanian et al., *Biocatalysis in Pharmaceutical and Biotechnology Industries*. CRC press (2006)). This enzyme, encoded by car, was cloned and functionally expressed in *E. coli* (Venkitasubramanian et al., *J Biol. Chem.* 282:478-485 (2007)). CAR requires post-translational activation by a phosphopantetheine transferase (PPTase) that converts the inactive apo-enzyme to the active holo-enzyme (Hansen et al., *Appl. Environ. Microbiol* 75:2765-2774 (2009)). Expression of the npt gene, encoding a specific PPTase, product improved activity of the enzyme. An enzyme with similar characteristics, alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then reduced by NAD(P)H to yield the aldehyde and AMP. Like CAR, this enzyme utilizes magnesium and requires activation by a PPTase. Enzyme candidates for AAR and its corresponding PPTase are found in *Saccharomyces cerevisiae* (Morris et al., *Gene* 98:141-145 (1991)), *Candida albicans* (Guo et al., *Mol. Genet. Genomics* 269:271-279 (2003)), and *Schizosaccharomyces pombe* (Ford et al., *Curr. Genet.* 28:131-137 (1995)). The AAR from *S. pombe* exhibited significant activity when expressed in *E. coli* (Guo et al., *Yeast* 21:1279-1288 (2004)). The AAR from *Penicillium chrysogenum* accepts S-carboxymethyl-L-cysteine as an alternate substrate, but did not react with adipate, L-glutamate or diaminopimelate (Hijarrubia et al., *J Biol. Chem.* 278:8250-8256 (2003)). The gene encoding the *P. chrysogenum* PPTase has not been identified to date and no high-confidence hits were identified by sequence comparison homology searching.

| Protein | GenBank ID | GI Number | Organism |
|---|---|---|---|
| car | AAR91681.1 | 40796035 | *Nocardia iowensis* |
| npt | ABI83656.1 | 114848891 | *Nocardia iowensis* |
| LYS2 | AAA34747.1 | 171867 | *Saccharomyces cerevisiae* |
| LYS5 | P50113.1 | 1708896 | *Saccharomyces cerevisiae* |
| LYS2 | AAC02241.1 | 2853226 | *Candida albicans* |
| LYS5 | AAO26020.1 | 28136195 | *Candida albicans* |
| Lys1p | P40976.3 | 13124791 | *Schizosaccharomyces pombe* |
| Lys7p | Q10474.1 | 1723561 | *Schizosaccharomyces pombe* |
| Lys2 | CAA74300.1 | 3282044 | *Penicillium chrysogenum* |

Additional car and npt genes can be identified based on sequence homology.

| Gene name | GenBank ID | GI Number | Organism |
|---|---|---|---|
| fadD9 | YP_978699.1 | 121638475 | *Mycobacterium bovis* BCG |
| BCG_2812c | YP_978898.1 | 121638674 | *Mycobacterium bovis* BCG |
| nfa20150 | YP_118225.1 | 54023983 | *Nocardia farcinica* IFM 10152 |
| nfa40540 | YP_120266.1 | 54026024 | *Nocardia farcinica* IFM 10152 |
| SGR_6790 | YP_001828302.1 | 182440583 | *Streptomyces griseus* subsp. *griseus* NBRC 13350 |
| SGR_665 | YP_001822177.1 | 182434458 | *Streptomyces griseus* subsp. *griseus* NBRC 13350 |
| MSMEG_2956 | YP_887275.1 | 118473501 | *Mycobacterium smegmatis* MC2 155 |
| MSMEG_5739 | YP_889972.1 | 118469671 | *Mycobacterium smegmatis* MC2 155 |
| MSMEG_2648 | YP_886985.1 | 118471293 | *Mycobacterium smegmatis* MC2 155 |
| MAP1040c | NP_959974.1 | 41407138 | *Mycobacterium avium* subsp. *paratuberculosis* K-10 |
| MAP2899c | NP_961833.1 | 41408997 | *Mycobacterium avium* subsp. *paratuberculosis* K-10 |
| MMAR_2117 | YP_001850422.1 | 183982131 | *Mycobacterium marinum* M |
| MMAR_2936 | YP_001851230.1 | 183982939 | *Mycobacterium marinum* M |
| MMAR_1916 | YP_001850220.1 | 183981929 | *Mycobacterium marinum* M |
| Tpau_1373 | YP_003646340.1 | 296139097 | *Tsukamurella paurometabola* DSM 20162 |
| Tpau_1726 | YP_003646683.1 | 296139440 | *Tsukamurella paurometabola* DSM 20162 |
| CPCC7001_1320 | ZP_05045132.1 | 254431429 | *Cyanobium* PCC7001 |
| DDBDRAFT_0187729 | XP_636931.1 | 66806417 | *Dictyostelium discoideum* AX4 |

An additional enzyme candidate found in *Streptomyces griseus* is encoded by the griC and griD genes. This enzyme is believed to convert 3-amino-4-hydroxybenzoic acid to 3-amino-4-hydroxybenzaldehyde as deletion of either griC or griD led to accumulation of extracellular 3-acetylamino-4-hydroxybenzoic acid, a shunt product of 3-amino-4-hydroxybenzoic acid metabolism (Suzuki, et al., *J. Antibiot.* 60(6): 380-387 (2007)). Co-expression of griC and griD with SGR_665, an enzyme similar in sequence to the *Nocardia iowensis* npt, can be beneficial.

| Gene name | GenBank Accession No. | GI Number | Organism |
|---|---|---|---|
| griC | YP_001825755.1 | 182438036 | *Streptomyces griseus* subsp. *griseus* NBRC 13350 |
| griD | YP_001825756.1 | 182438037 | *Streptomyces griseus* subsp. *griseus* NBRC 13350 |

1.14.13.a Monooxygenase

Oxidation of cyclohexanone to caprolactone, shown FIG. 3, is catalyzed by cyclohexanone monooxygenase (EC 1.14.13.22). The enzyme encoded by chnB of *Acinetobacter* sp. NCIMB9871 has been extensively studied and it has been overexpressed. Improved expression was obtained when the chnB gene was overexpressed in tandem with its regulator, chnR (Iwaki et al, AEM 65:5158-62 (1999)). Similar enzymes have been characterized in *Acinetobacter calcoaceticus, Rhodococcus* sp. Phi2 and Phi1, *Xanthobacter flavus* and *Acinetobacter* sp. SE19 (Doo et al, *J Biotechnol* 142: 164-9 (2009); Brzostowicz et al, AEM 69:334-42 (2003)). Accession numbers of cyclohexanone monooxygenase enzymes and transcriptional regulators are shown in the table below.

| Gene | GenBank ID | GI Number | Organism |
|---|---|---|---|
| chnB | BAA86293.1 | 6277322 | *Acinetobacter* sp. NCIMB9871 |
| chnB | P12015.2 | 118066 | *Acinetobacter calcoaceticus* |
| chnB | AAN37494.1 | 27657637 | *Rhodococcus* sp. Phi1 |
| chnB | AAN37491.1 | 27657633 | *Rhodococcus* sp. Phi2 |
| chnB | CAD10801.1 | 18495818 | *Xanthobacter flavus* |
| chnB | AAG10026.1 | 9965291 | *Acinetobacter* sp. SE19 |
| chnR | BAA86295.1 | 6277324 | *Acinetobacter* sp. NCIMB9871 |
| chnR | BAA19366 | 1881339 | *Bacillus subtilis* |
| chnR | AAK73166 | 14719380 | *Brevibacerium* sp. HCU |
| chnR | ADY81661.1 | 325122138 | *Acinetobacter calcoaceticus* |
| chnR | AAN37488.1 | 27657630 | *Rhodococcus* sp. Phi2 |
| chnR | AAN37481.1 | 27657622 | *Arthrobacter* sp. BP2 |

2.3.1.a Acyltransferase (Transferring Phosphate Group)

An enzyme with phosphotrans-6-hydroxyhexanoylase activity is required to convert 6-hydroxyhexanoyl-CoA to 6-hydroxyhexanoyl phosphate (Step J of FIG. 1 and Step H of FIG. 2). Exemplary phosphate-transferring acyltransferases include phosphotransacetylase (EC 2.3.1.8) and phosphotransbutyrylase (EC 2.3.1.19). The pta gene from *E. coli* encodes a phosphotransacetylase that reversibly converts acetyl-CoA into acetyl-phosphate (Suzuki, *Biochim. Biophys. Acta* 191:559-569 (1969)). This enzyme can also utilize propionyl-CoA as a substrate, forming propionate in the process (Hesslinger et al., *Mol. Microbiol* 27:477-492 (1998)). Other phosphate acetyltransferases that exhibit activity on propionyl-CoA are found in *Bacillus subtilis* (Rado et al., *Biochim. Biophys. Acta* 321:114-125 (1973)), *Clostridium kluyveri* (Stadtman, *Methods Enzymol* 1:596-599 (1955)), and *Thermotoga maritima* (Bock et al., *J Bacteriol.* 181: 1861-1867 (1999)). Similarly, the ptb gene from *C. acetobutylicum* encodes phosphotransbutyrylase, an enzyme that reversibly converts butyryl-CoA into butyryl-phosphate (Wiesenborn et al., *Appl Environ. Microbiol* 55:317-322 (1989); Walter et al., *Gene* 134:107-111 (1993)). Additional ptb genes are found in butyrate-producing bacterium L2-50 (Louis et al., *J. Bacteriol.* 186:2099-2106 (2004)) and *Bacillus megaterium* (Vazquez et al., *Curr. Microbiol* 42:345-349 (2001)).

| Protein | GenBank ID | GI Number | Organism |
|---|---|---|---|
| pta | NP_416800.1 | 71152910 | *Escherichia coli* |
| pta | P39646 | 730415 | *Bacillus subtilis* |
| pta | A5N801 | 146346896 | *Clostridium kluyveri* |
| pta | Q9X0L4 | 6685776 | *Thermotoga maritima* |
| ptb | NP_349676 | 34540484 | *Clostridium acetobutylicum* |
| ptb | AAR19757.1 | 38425288 | butyrate-producing bacterium L2-50 |
| ptb | CAC07932.1 | 10046659 | *Bacillus megaterium* |

2.3.1.b Beta-Ketothiolase

Beta-ketothiolase enzymes in the EC class 2.3.1 catalyze the condensation of two acyl-CoA substrates. Step A of FIG. 2 requires a beta-ketothiolase to catalyze the condensation of 4-hydroxybutyryl-CoA and acetyl-CoA into 3-oxo-6-hydroxyhexanoyl-CoA. Although this transformation has not been demonstrated in the literature to date, suitable enzymes include 3-oxoadipyl-CoA thiolase (EC 2.3.1.174), acetoacetyl-CoA thiolase (EC 2.3.1.9) and 3-oxopimeloyl-CoA thiolase (EC 2.3.1.16).

3-Oxoadipyl-CoA thiolase (EC 2.3.1.174) converts beta-ketoadipyl-CoA to succinyl-CoA and acetyl-CoA, and is a key enzyme of the beta-ketoadipate pathway for aromatic compound degradation. The enzyme is widespread in soil bacteria and fungi including *Pseudomonas putida* (Harwood et al., *J Bacteriol.* 176:6479-6488 (1994)) and *Acinetobacter calcoaceticus* (Doten et al., *J. Bacteriol.* 169:3168-3174 (1987)). The gene products encoded by pcaF in *Pseudomonas* strain B13 (Kaschabek et al., *J Bacteriol.* 184:207-215 (2002)), phaD in *Pseudomonas putida* U (Olivera et al., *Proc. Natl. Acad. Sci U.S.A* 95:6419-6424 (1998)), paaE in *Pseudomonas fluorescens* ST (Di et al., *Arch. Microbiol* 188: 117-125 (2007)), and paaJ from *E. coli* (Nogales et al., *Microbiology* 153:357-365 (2007)) also catalyze this transformation. Several beta-ketothiolases exhibit significant and selective activities in the oxoadipyl-CoA forming direction including bkt from *Pseudomonas putida*, pcaF and bkt from *Pseudomonas aeruginosa* PAO1, bkt from *Burkholderia ambifaria* AMMD, paaJ from *E. coli*, and phaD from *P. putida*.

| Gene name | GI number | GenBank ID | Organism |
|---|---|---|---|
| paaJ | 16129358 | NP_415915.1 | *Escherichia coli* |
| pcaF | 17736947 | AAL02407 | *Pseudomonas knackmussii* (B13) |
| phaD | 3253200 | AAC24332.1 | *Pseudomonas putida* |
| pcaF | 506695 | AAA85138.1 | *Pseudomonas putida* |
| pcaF | 141777 | AAC37148.1 | *Acinetobacter calcoaceticus* |
| paaE | 106636097 | ABF82237.1 | *Pseudomonas fluorescens* |
| bkt | 115360515 | YP_777652.1 | *Burkholderia ambifaria* AMMD |
| bkt | 9949744 | AAG06977.1 | *Pseudomonas aeruginosa* PAO1 |
| pcaF | 9946065 | AAG03617.1 | *Pseudomonas aeruginosa* PAO1 |

Glutaryl-CoA and acetyl-CoA are condensed to form 3-oxopimeloyl-CoA by oxopimeloyl-CoA:glutaryl-CoA acyltransferase, a beta-ketothiolase (EC 2.3.1.16). An enzyme catalyzing this transformation is found in *Ralstonia eutropha* (formerly known as *Alcaligenes eutrophus*), encoded by genes bktB and bktC (Slater et al., *J. Bacteriol.* 180:1979-1987 (1998); Haywood et al., *FEMS Microbiology Letters* 52:91-96 (1988)). The sequence of the BktB protein is known; however, the sequence of the BktC protein has not been reported. The pim operon of *Rhodopseudomonas palustris* also encodes a beta-ketothiolase, encoded by pimB, predicted to catalyze this transformation in the degradative direction during benzoyl-CoA degradation (Harrison et al., *Microbiology* 151:727-736 (2005)). A beta-ketothiolase enzyme candidate in *S. aciditrophicus* was identified by sequence homology to bktB (43% identity, evalue=1e-93).

| Protein | GenBank ID | GI Number | Organism |
|---|---|---|---|
| bktB | YP_725948 | 11386745 | *Ralstonia eutropha* |
| pimB | CAE29156 | 39650633 | *Rhodopseudomonas palustris* |
| syn_02642 | YP_462685.1 | 85860483 | *Syntrophus aciditrophicus* |

Acetoacetyl-CoA thiolase converts two molecules of acetyl-CoA into acetoacetyl-CoA (EC 2.1.3.9). This activity is encoded by atoB from *E. coli* (Martin et al., *Nat. Biotechnol* 21:796-802 (2003)), thlA and thlB from *Clostridium acetobutylicum* (Hanai et al., *Appl Environ Microbiol* 73:7814-7818 (2007); Winzer et al., *J. Mol. Microbiol Biotechnol* 2:531-541 (2000)), and ERG10 from *S. cerevisiae* (Hiser et al., *J. Biol. Chem.* 269:31383-31389 (1994)).

| Protein | GenBank ID | GI Number | Organism |
|---|---|---|---|
| atoB | NP_416728 | 16130161 | *Escherichia coli* |
| thlA | NP_349476.1 | 15896127 | *Clostridium acetobutylicum* |
| thlB | NP_149242.1 | 15004782 | *Clostridium acetobutylicum* |
| ERG10 | NP_015297 | 6325229 | *Saccharomyces cerevisiae* |

Beta-ketothiolase enzymes catalyzing the formation of beta-ketovalerate from acetyl-CoA and propionyl-CoA may also be able to catalyze the formation of 3-oxo-6-hydroxy-hexanoyl-CoA. *Zoogloea ramigera* possesses two ketothiolases that can form 3-ketovaleryl-CoA from propionyl-CoA and acetyl-CoA and *R. eutropha* has a beta-oxidation ketothiolase that is also capable of catalyzing this transformation (Gruys et al., U.S. Pat. No. 5,958,745 (1999)). The sequences of these genes or their translated proteins have not been reported, but several candidates in *R. eutropha*, *Z. ramigera*, or other organisms can be identified based on sequence homology to bktB from *R. eutropha*. These include:

| Protein | GenBank ID | GI Number | Organism |
|---|---|---|---|
| phaA | YP_725941.1 | 113867452 | *Ralstonia eutropha* |
| h16_A1713 | YP_726205.1 | 113867716 | *Ralstonia eutropha* |
| pcaF | YP_728366.1 | 116694155 | *Ralstonia eutropha* |
| h16_B1369 | YP_840888.1 | 116695312 | *Ralstonia eutropha* |
| h16_A0170 | YP_724690.1 | 113866201 | *Ralstonia eutropha* |
| h16_A0462 | YP_724980.1 | 113866491 | *Ralstonia eutropha* |
| h16_A1528 | YP_726028.1 | 113867539 | *Ralstonia eutropha* |
| h16_B0381 | YP_728545.1 | 116694334 | *Ralstonia eutropha* |
| h16_B0662 | YP_728824.1 | 116694613 | *Ralstonia eutropha* |
| h16_B0759 | YP_728921.1 | 116694710 | *Ralstonia eutropha* |
| h16_B0668 | YP_728830.1 | 116694619 | *Ralstonia eutropha* |
| h16_A1720 | YP_726212.1 | 113867723 | *Ralstonia eutropha* |
| h16_A1887 | YP_726356.1 | 113867867 | *Ralstonia eutropha* |
| phbA | P07097.4 | 135759 | *Zoogloea ramigera* |
| bktB | YP_002005382.1 | 194289475 | *Cupriavidus taiwanensis* |
| Rmet_1362 | YP_583514.1 | 94310304 | *Ralstonia metallidurans* |
| Bphy_0975 | YP_001857210.1 | 186475740 | *Burkholderia phymatum* |

2.7.2.a Phosphotransferase (Carboxy Group Acceptor)

Kinase or phosphotransferase enzymes in the EC class 2.7.2 transform carboxylic acids to phosphonic acids with concurrent hydrolysis of one ATP. Such an enzyme is required for the phosphorylation of 6-hydroxyhexanoate depicted in Step H of FIG. 1 and Step J of FIG. 2. Exemplary enzyme candidates include butyrate kinase (EC 2.7.2.7), isobutyrate kinase (EC 2.7.2.14), aspartokinase (EC 2.7.2.4), acetate kinase (EC 2.7.2.1), glycerate kinase (EC 2.7.1.31) and gamma-glutamyl kinase (EC 2.7.2.11). Butyrate kinase catalyzes the reversible conversion of butyryl-phosphate to butyrate during acidogenesis in *Clostridial* species (Cary et al., *Appl Environ Microbiol* 56:1576-1583 (1990)). The *Clostridium acetobutylicum* enzyme is encoded by either of the two buk gene products (Huang et al., *J Mol. Microbiol Biotechnol* 2:33-38 (2000)). Other butyrate kinase enzymes are found in *C. butyricum* and *C. tetanomorphum* (Twarog et al., *J Bacteriol.* 86:112-117 (1963)). A related enzyme, isobutyrate kinase from *Thermotoga maritima*, was expressed in *E. coli* and crystallized (Diao et al., *J Bacteriol.* 191:2521-2529 (2009); Diao et al., *Acta Crystallogr. D. Biol. Crystallogr.* 59:1100-1102 (2003)). Aspartokinase catalyzes the ATP-dependent phosphorylation of aspartate and participates in the synthesis of several amino acids. The aspartokinase III enzyme in *E. coli*, encoded by lysC, has a broad substrate range and the catalytic residues involved in substrate specificity have been elucidated (Keng et al., *Arch Biochem Biophys* 335:73-81 (1996)). Two additional kinases in *E. coli* are also acetate kinase and gamma-glutamyl kinase. The *E. coli* acetate kinase, encoded by ackA (Skarstedt et al., *J. Biol. Chem.* 251:6775-6783 (1976)), phosphorylates propionate in addition to acetate (Hesslinger et al., *Mol. Microbiol* 27:477-492 (1998)). The *E. coli* gamma-glutamyl kinase, encoded by proB (Smith et al., *J. Bacteriol.* 157:545-551 (1984)), phosphorylates the gamma carbonic acid group of glutamate.

| Protein | GenBank ID | GI Number | Organism |
|---|---|---|---|
| buk1 | NP_349675 | 15896326 | *Clostridium acetobutylicum* |
| buk2 | Q97II1 | 20137415 | *Clostridium acetobutylicum* |
| buk2 | Q9X278.1 | 6685256 | *Thermotoga maritima* |
| lysC | NP_418448.1 | 16131850 | *Escherichia coli* |
| ackA | NP_416799.1 | 16130231 | *Escherichia coli* |
| proB | NP_414777.1 | 16128228 | *Escherichia coli* |

Acetylglutamate kinase phosphorylates acetylated glutamate during arginine biosynthesis. This enzyme is not known to accept alternate substrates; however, several residues of the *E. coli* enzyme involved in substrate binding and phosphorylation have been elucidated by site-directed mutagenesis (Marco-Marin et al., 334:459-476 (2003); Ramon-Maiques et al., *Structure.* 10:329-342 (2002)). The enzyme is encoded by argB in *Bacillus subtilis* and *E. coli* (Parsot et al., *Gene* 68:275-283 (1988)), and ARG5,6 in *S. cerevisiae* (Pauwels et al., *Eur. J Biochem.* 270:1014-1024 (2003)). The ARG5,6 gene of *S. cerevisiae* encodes a polyprotein precursor that is matured in the mitochondrial matrix to become acetylglutamate kinase and acetylglutamylphosphate reductase.

| Protein | GenBank ID | GI Number | Organism |
|---|---|---|---|
| argB | NP_418394.3 | 145698337 | *Escherichia coli* |
| argB | NP_389003.1 | 16078186 | *Bacillus subtilis* |
| ARG5,6 | NP_010992.1 | 6320913 | *Saccharomyces cerevisiae* |

Glycerate kinase (EC 2.7.1.31) activates glycerate to glycerate-2-phosphate or glycerate-3-phosphate. Three classes of glycerate kinase have been identified. Enzymes in class I and II produce glycerate-2-phosphate, whereas the class III enzymes found in plants and yeast produce glycerate-3-phosphate (Bartsch et al., *FEBS Lett.* 582:3025-3028 (2008)). In a recent study, class III glycerate kinase enzymes from *Saccharomyces cerevisiae*, *Oryza sativa* and *Arabidopsis thaliana* were heterologously expressed in *E. coli* and characterized (Bartsch et al., *FEBS Lett.* 582:3025-3028 (2008)). This study also assayed the glxK gene product of *E. coli* for ability to form glycerate-3-phosphate and found that the enzyme can only catalyze the formation of glycerate-2-phosphate, in contrast to previous work (Doughty et al., *J Biol. Chem.* 241:568-572 (1966)).

| Protein | GenBank ID | GI Number | Organism |
| --- | --- | --- | --- |
| glxK | AAC73616.1 | 1786724 | *Escherichia coli* |
| YGR205W | AAS56599.1 | 45270436 | *Saccharomyces cerevisiae* |
| Os01g0682500 | BAF05800.1 | 113533417 | *Oryza sativa* |
| At1g80380 | BAH57057.1 | 227204411 | *Arabidopsis thaliana* |

2.8.3.a CoA Transferase

CoA transferases catalyze the reversible transfer of a CoA moiety from one molecule to another. Several transformations require a CoA transferase to interconvert carboxylic acids and their corresponding acyl-CoA derivatives, including steps C and F of FIG. 1, step E of FIG. 2 and step B of FIG. 5. CoA transferase enzymes have been described in the open literature and represent suitable candidates for these steps. These are described below.

Many transferases have broad specificity and thus can utilize CoA acceptors as diverse as acetate, succinate, propionate, butyrate, 2-methylacetoacetate, 3-ketohexanoate, 3-ketopentanoate, valerate, crotonate, 3-mercaptopropionate, propionate, vinylacetate, butyrate, among others. For example, an enzyme from *Roseburia* sp. A2-183 was shown to have butyryl-CoA:acetate:CoA transferase and propionyl-CoA:acetate:CoA transferase activity (Charrier et al., *Microbiology* 152, 179-185 (2006)). Close homologs can be found in, for example, *Roseburia intestinalis* L1-82, *Roseburia inulinivorans* DSM 16841, *Eubacterium rectale* ATCC 33656. Another enzyme with propionyl-CoA transferase activity can be found in *Clostridium propionicum* (Selmer et al., *Eur J Biochem* 269, 372-380 (2002)). This enzyme can use acetate, (R)-lactate, (S)-lactate, acrylate, and butyrate as the CoA acceptor (Selmer et al., *Eur J Biochem* 269, 372-380 (2002); Schweiger and Buckel, *FEBS Letters*, 171(1) 79-84 (1984)). Close homologs can be found in, for example, *Clostridium novyi* NT, *Clostridium beijerinckii* NCIMB 8052, and *Clostridium botulinum* C str. Eklund. YgfH encodes a propionyl CoA:succinate CoA transferase in *E. coli* (Haller et al., *Biochemistry*, 39(16) 4622-4629). Close homologs can be found in, for example, *Citrobacter youngae* ATCC 29220, *Salmonella enterica* subsp. *arizonae serovar*, and *Yersinia intermedia* ATCC 29909. These proteins are identified below.

| Protein | GenBank ID | GI Number | Organism |
| --- | --- | --- | --- |
| Ach1 | AAX19660.1 | 60396828 | *Roseburia* sp. A2-183 |
| ROSINTL182_07121 | ZP_04743841.2 | 257413684 | *Roseburia intestinalis* |
| ROSEINA2194_03642 | ZP_03755203.1 | 225377982 | *Roseburia inulinivorans* |
| EUBREC_3075 | YP_002938937.1 | 238925420 | *Eubacterium rectale* |
| pct | CAB77207.1 | 7242549 | *Clostridium propionicum* |
| NT01CX_2372 | YP_878445.1 | 118444712 | *Clostridium novyi* NT |
| Cbei_4543 | YP_001311608.1 | 150019354 | *Clostridium beijerinckii* |
| CBC_A0889 | ZP_02621218.1 | 168186583 | *Clostridium botulinum* |
| ygfH | NP_417395.1 | 16130821 | *Escherichia coli* |
| CIT292_04485 | ZP_03838384.1 | 227334728 | *Citrobacter youngae* |
| SARI_04582 | YP_001573497.1 | 161506385 | *Salmonella enterica* |
| yinte0001_14430 | ZP_04635364.1 | 238791727 | *Yersinia intermedia* |

The gene products of cat1, cat2, and cat3 of *Clostridium kluyveri* have been shown to exhibit succinyl-CoA, 4-hydroxybutyryl-CoA, and butyryl-CoA transferase activity, respectively (Seedorf et al., *Proc. Natl. Acad. Sci U.S.A* 105: 2128-2133 (2008); Sohling et al., *J Bacteriol.* 178:871-880 (1996)). Similar CoA transferase activities are also present in *Trichomonas vaginalis* (van Grinsven et al., *J. Biol. Chem.* 283:1411-1418 (2008)) and *Trypanosoma brucei* (Riviere et al., *J. Biol. Chem.* 279:45337-45346 (2004)).

| Protein | GenBank ID | GI Number | Organism |
| --- | --- | --- | --- |
| cat1 | P38946.1 | 729048 | *Clostridium kluyveri* |
| cat2 | P38942.2 | 172046066 | *Clostridium kluyveri* |
| cat3 | EDK35586.1 | 146349050 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |

The glutaconyl-CoA-transferase (EC 2.8.3.12) enzyme from anaerobic bacterium *Acidaminococcus fermentans* reacts with glutaconyl-CoA and 3-butenoyl-CoA (Mack et al., 226:41-51 (1994)). The genes encoding this enzyme are gctA and gctB. This enzyme has reduced but detectable activity with other CoA derivatives including glutaryl-CoA, 2-hydroxyglutaryl-CoA, adipyl-CoA, crotonyl-CoA and acrylyl-CoA (Buckel et al., *Eur. J Biochem.* 118:315-321 (1981)). The enzyme has been cloned and expressed in *E. coli* (Mack et al., supra). Glutaconate CoA-transferase activity has also been detected in *Clostridium sporosphaeroides* and *Clostridium symbiosum*. Additional glutaconate CoA-transferase enzymes can be inferred by homology to the *Acidaminococcus fermentans* protein sequence.

| Protein | GenBank ID | GI Number | Organism |
| --- | --- | --- | --- |
| gctA | CAA57199.1 | 559392 | *Acidaminococcus fermentans* |
| gctB | CAA57200.1 | 559393 | *Acidaminococcus fermentans* |
| gctA | ACJ24333.1 | 212292816 | *Clostridium symbiosum* |
| gctB | ACJ24326.1 | 212292808 | *Clostridium symbiosum* |
| gctA | NP_603109.1 | 19703547 | *Fusobacterium nucleatum* |
| gctB | NP_603110.1 | 19703548 | *Fusobacterium nucleatum* |

A CoA transferase that can utilize acetyl-CoA as the CoA donor is acetoacetyl-CoA transferase, encoded by the *E. coli* atoA (alpha subunit) and atoD (beta subunit) genes (Korolev et al., *Acta Crystallogr. D. Biol. Crystallogr.* 58:2116-2121

(2002); Vanderwinkel et al., 33:902-908 (1968)). This enzyme has a broad substrate range (Sramek et al., Arch Biochem Biophys 171:14-26 (1975)) and has been shown to transfer the CoA moiety to acetate from a variety of branched and linear acyl-CoA substrates, including isobutyrate (Matthies et al., Appl Environ. Microbiol 58:1435-1439 (1992)), valerate (Vanderwinkel et al., Biochem. Biophys. Res. Commun. 33:902-908 (1968)) and butanoate (Vanderwinkel et al., Biochem. Biophys. Res. Commun. 33:902-908 (1968)). This enzyme is induced at the transcriptional level by acetoacetate, so modification of regulatory control may be necessary for engineering this enzyme into a pathway (Pauli et al., Eur. J Biochem. 29:553-562 (1972)). Similar enzymes exist in Corynebacterium glutamicum ATCC 13032 (Duncan et al., 68:5186-5190 (2002)), Clostridium acetobutylicum (Cary et al., Appl Environ Microbiol 56:1576-1583 (1990); Wiesenborn et al., Appl Environ Microbiol 55:323-329 (1989)), and Clostridium saccharoperbutylacetonicum (Kosaka et al., Biosci. Biotechnol Biochem. 71:58-68 (2007)).

| Gene | GI number | GenBank ID | Organism |
|------|-----------|------------|----------|
| atoA | 2492994 | P76459.1 | Escherichia coli |
| atoD | 2492990 | P76458.1 | Escherichia coli |
| actA | 62391407 | YP_226809.1 | Corynebacterium glutamicum |
| cg0592 | 62389399 | YP_224801.1 | Corynebacterium glutamicum |
| ctfA | 15004866 | NP_149326.1 | Clostridium acetobutylicum |
| ctfB | 15004867 | NP_149327.1 | Clostridium acetobutylicum |
| ctfA | 31075384 | AAP42564.1 | Clostridium saccharoperbutylacetonicum |
| ctfB | 31075385 | AAP42565.1 | Clostridium saccharoperbutylacetonicum |

Beta-ketoadipyl-CoA transferase, also known as succinyl-CoA:3:oxoacid-CoA transferase, employs succinate as the CoA acceptor. This enzyme is encoded by pcaI and pcaJ in Pseudomonas putida (Kaschabek et al., J Bacteriol. 184:207-215 (2002)). Similar enzymes are found in Acinetobacter sp. ADP1 (Kowalchuk et al., Gene 146:23-30 (1994)), Streptomyces coelicolor and Pseudomonas knackmussii (formerly sp. B13) (Gobel et al., J Bacteriol. 184:216-223 (2002); Kaschabek et al., J Bacteriol. 184:207-215 (2002)). Additional exemplary succinyl-CoA:3:oxoacid-CoA transferases have been characterized in in Helicobacter pylori (Corthesy-Theulaz et al., J Biol. Chem. 272:25659-25667 (1997)), Bacillus subtilis (Stols et al., Protein Expr. Purif. 53:396-403 (2007)) and Homo sapiens (Fukao, T., et al., Genomics 68:144-151 (2000); Tanaka, H., et al., Mol Hum Reprod 8:16-23 (2002)). Genbank information related to these genes is summarized below.

| Gene | GI number | GenBank ID | Organism |
|------|-----------|------------|----------|
| pcaI | 24985644 | AAN69545.1 | Pseudomonas putida |
| pcaJ | 26990657 | NP_746082.1 | Pseudomonas putida |
| pcaI | 50084858 | YP_046368.1 | Acinetobacter sp. ADP1 |
| pcaJ | 141776 | AAC37147.1 | Acinetobacter sp. ADP1 |
| pcaI | 21224997 | NP_630776.1 | Streptomyces coelicolor |
| pcaJ | 21224996 | NP_630775.1 | Streptomyces coelicolor |
| catI | 75404583 | Q8VPF3 | Pseudomonas knackmussii |
| catJ | 75404582 | Q8VPF2 | Pseudomonas knackmussii |
| HPAG1_0676 | 108563101 | YP_627417 | Helicobacter pylori |
| HPAG1_0677 | 108563102 | YP_627418 | Helicobacter pylori |
| ScoA | 16080950 | NP_391778 | Bacillus subtilis |
| ScoB | 16080949 | NP_391777 | Bacillus subtilis |
| OXCT1 | NP_000427 | 4557817 | Homo sapiens |
| OXCT2 | NP_071403 | 11545841 | Homo sapiens |

3.1.1.a Esterase/Lipase

Enzymes in the EC class 3.1.1 catalyze the hydrolysis and synthesis of ester bonds. Caprolactone hydrolase enzymes required for step G of FIG. 1 and step F of FIG. 2 are found in organisms that degrade cyclohexanone. The chnC gene product of Acinetobacter sp. NCIMB9871 was found to hydrolyze the ester bond of caprolactone, forming 6-hydroxyhexanote (Iwaki et al, AEM 65:5158-62 (1999)). Similar enzymes were identified in Arthrobacter sp. BP2 and Rhodococcus sp. Phi2 (Brzostowicz et al, AEM 69:334-42 (2003)).

| Gene | GenBank ID | GI Number | Organism |
|------|------------|-----------|----------|
| chnC | BAC80218.1 | 33284998 | Acinetobacter sp. NCIMB9871 |
| chnC | AAN37478.1 | 27657619 | Arthrobacter sp. BP2 |
| chnC | AAN37490.1 | 27657632 | Rhodococcus sp. Phi2 |

Formation of caprolactone may also be catalyzed by enzymes that catalyze the interconversion of cyclic lactones and open chain hydroxycarboxylic acids. The L-lactonase from Fusarium proliferatum ECU2002 exhibits lactonase and esterase activities on a variety of lactone substrates (Zhang et al., Appl. Microbiol. Biotechnol. 75:1087-1094 (2007)). The 1,4-lactone hydroxyacylhydrolase (EC 3.1.1.25), also known as 1,4-lactonase or gamma-lactonase, is specific for 1,4-lactones with 4-8 carbon atoms. The gamma lactonase in human blood and rat liver microsomes was purified (Fishbein et al., J Biol Chem 241:4835-4841 (1966)) and the lactonase activity was activated and stabilized by calcium ions (Fishbein et al., J Biol Chem 241:4842-4847 (1966)). The optimal lactonase activities were observed at pH 6.0, whereas high pH resulted in hydrolytic activities (Fishbein and Bessman, J Biol Chem 241:4842-4847 (1966)). Genes from Xanthomonas campestris, Aspergillus niger and Fusarium oxysporum have been annotated as 1,4-lactonase and can be utilized to catalyze the transformation of 4-hydroxybutyrate to GBL (Zhang et al., Appl Microbiol Biotechnol 75:1087-1094 (2007)).

| Gene | Accession No. | GI No. | Organism |
|------|---------------|--------|----------|
| EU596535.1:1..1206 | ACC61057.1 | 183238971 | Fusarium proliferatum |
| xccb100_2516 | YP_001903921.1 | 188991911 | Xanthomonas campestris |
| An16g06620 | CAK46996.1 | 134083519 | Aspergillus niger |
| BAA34062 | BAA34062.1 | 3810873 | Fusarium oxysporum |

Other enzyme candidates for converting 6-hydroxyhexanoate to caprolactone include lipases and esterases (or ester synthases). Lipases (EC 3.1.1.3) typically hydrolyze long-chain carboxylic acid esters, whereas esterases (EC 3.1.1.1) hydrolyze short-chain esters. The amidase from Brevibacterium sp. R312 (EC 3.5.1.4) is a likely enzyme with caprolactone-forming activity. This enzyme was shown to hydrolyze ethylacrylate (Thiery et al., J. Gen. Microbiol., 132:2205-8, 1986; Soubrier et al., Gene, 116:99-104, 1992). The microsomal epoxide hydrolase from Rattus norvegicus (EC 3.3.2.9) is another suitable enzyme (Guengerich et al., Rev. Biochem. Toxicol. 4:5-30, 1982). The protein sequences of these genes are provided below.

| Gene | GenBank ID | GI Number | Organism |
|---|---|---|---|
| amiE | JC1174 | 98711 | Brevibacterium sp. |
| Eph-1 | P07687.1 | 123928 | Rattus norvegicus |

Additional ester synthase genes include the *Acinetobacter* sp. ADP1 atfA encoding a bifunctional enzyme with both wax ester synthase (WS) and acyl-CoA:diacylglycerol acyltransferase (DGAT) activities (Kalscheuer et al. A J Biol Chem 2003, 278: 8075-8082.); the *Simmondsia chinensis* gene AAD38041 encoding a enzyme required for the accumulation of waxes in jojoba seeds (Lardizabal et al. Plant Physiology 2000, 122: 645-655.); the *Alcanivorax borkumensis* atfA1 and atfA2 encoding bifunctional WS/DGAT enzymes (Kalscheuer et al. J Bacteriol 2007, 189: 918-928.); the Fragariaxananassa AAT encoding an alcohol acetyltransferasae (Noichinda et al. FoodSci Technol Res 1999, 5: 239-242.); the Rosa hybrid cultivar AAT1 encoding an alcohol acetyltransferase (Guterman et al. Plant Mol Biol 2006, 60: 555-563.); and the *Saccharomyces cerevisiae* ATF1 and ATF2 encoding alcohol acetyltransferases (Mason et al. Yeast 2000, 16: 1287-1298.); and Ws1 and Ws2 from *Marinobacter hydrocarbonoclasticus* (Holtzapple, E. and Schmidt-Dannert, C., J. Bacteriol. 189 (10), 3804-3812, 2007). The carboxylesterase from *Lactococcus lactis*, encoded by estA, catalyzes the formation of esters from acetyl-CoA and alcohols such as ethanol and methanethiol (Nardi et al. *J. Appl. Microbiol.* 93:994-1002 (2002)). A thermostable carboxylesterase from *Anoxybacillus* sp. PDF1 was recently cloned and characterized (Ay et al, *Prot Expr Purif* 80:74-9 (2011)) but the sequence is not yet available. The alcohol O-acetyltransferase from *Saccharomyces uvarum* converts a wide range of alcohol substrates including branched-chain alcohols to their corresponding acetate esters (Yoshioka and Hashimoto, *Agricul and Biol Chem*, 45:2183-2191 (1981). The gene associated with this activity has not been identified to date. The protein sequences of the enzymes encoded by these genes are provided below.

| Gene | GenBank ID | GI Number | Organism |
|---|---|---|---|
| atfA | Q8GGG1 | 81478805 | *Acinetobacter* sp. ADP 1 |
| AF149919.1:13..1071 | AAD38041 | 5020219 | *Simmondsia chinensis* |
| atfA1 | YP694462 | 110835603 | *Alcanivorax borkumensis* SK2 |
| atfA2 | YP693524 | 110834665 | *Alcanivorax borkumensis* SK2 |
| AAT | AAG13130.1 | 10121328 | *Fragaria x ananassa* |
| AAT1 | Q5I6B5 | 75105208 | *Rosa* hybrid cultivar |
| ATF1 | P40353 | 2506980 | *Saccharomyces cerevisiae* |
| ATF2 | P53296 | 1723729 | *Saccharomyces cerevisiae* |
| Ws2 | ABO21021.1 | 126567232 | *Marinobacter hydrocarbonoclasticus* |
| Ws1 | ABO21020.1 | 126567230 | *Marinobacter hydrocarbonoclasticus* |
| EstA | AAF62859.1 | 7453516 | *Lactococcus lactis* |

The *Homo sapiens* paraoxonase enzymes PON1, PON1 (G3C9), and PON3 (EC 3.1.8.1) possess both arylesterase and organophosphatase activities. PON1 has a common polymorphic site at residue 192, glutamine (R) or arginine (Q) which results in qualitative differences. For example, the R isozyme has a higher esterase activity than the S isozyme (Billecke et al., *Drug Metab Dispos.* 28:1335-1342 (2000)). In *H. sapiens* cells, PON1 resides on high-density lipoprotein (HDL) particles, and its activity and stability require this environment. Wild type and recombinant PON1 enzymes have been functionally expressed in other organisms (Rochu et al., *Biochem. Soc. Trans.* 35:1616-1620 (2007); Martin et al., *Appl. Environ. Microbiol.* (2009)). A directed evolution study of PON1 yielded several mutant enzymes with improved solubility and catalytic properties in *E. coli* (nucleotide accession numbers AY499188-AY499199) (Aharoni et al., *Proc. Natl. Acad. Sci. U.S.A* 101:482-487 (2004)). One recombinant variant from this study, G3C9 (Aharoni et al., *Proc. Natl. Acad. Sci. U.S.A* 101:482-487 (2004)), was recently used in an integrated bioprocess for the pH-dependent production of 4-valerolactone from levulinate (Martin et al., *Appl. Environ. Microbiol.* (2009)). Human PON3 is yet another suitable enzyme (Draganov et al., *J. Lipid Res.* 46:1239-1247 (2005)).

| Gene | Accession No. | GI No. | Organism |
|---|---|---|---|
| PON1 | NP_000437.3 | 19923106 | *Homo sapiens* |
| PON1 (G3C9) | AAR95986.1 | 40850544 | Synthetic variant |
| PON3 | NP_000931.1 | 29788996 | *Homo sapiens* |

Additional ester synthase candidates include the *Candida antarctica* lipase B (Efe et al., *Biotechnol. Bioeng.* 99:1392-1406 (2008)) and EstF1 from *Pseudomonas fluorescens*, encoded by EstF1 (Khalameyzer et al., *Appl. Environ. Microbiol.* 65:477-482 (1999)). Other lipase enzymes from organisms such as *Pseudomonas fluorescens* and *Bacillus subtilis* may also catalyze this transformation. The *B. subtilis* and *P. fluorescens* genes encode triacylglycerol lipase enzymes which have been cloned and characterized in *E. coli* (Dartois et al., *Biochim. Biophys. Acta* 1131:253-260 (1992); Tan et al., *Appl. Environ. Microbiol.* 58:1402-1407 (1992)).

| Gene | Accession No. | GI No. | Organism |
|---|---|---|---|
| calB | P41365.1 | 1170790 | *Candida antarctica* |
| EstF1 | AAC36352.1 | 3641341 | *Pseudomonas fluorescens* |
| lipB | P41773.1 | 1170792 | *Pseudomonas fluorescens* |
| estA | P37957.1 | 7676155 | *Bacillus subtilis* |

3.1.2.a CoA Hydrolase

Enzymes in the 3.1.2 family hydrolyze acyl-CoA molecules to their corresponding acids. Such an enzyme is depicted in Step F of FIG. 1 and Step B of FIG. 5. Several CoA hydrolases have been demonstrated to hydrolyze adipyl-CoA, or alternately accept a broad range of substrates. For example, the enzyme encoded by acot12 from *Rattus norvegicus* brain (Robinson et al., *Biochem. Biophys. Res. Commun.* 71:959-965 (1976)) can react with butyryl-CoA, hexanoyl-CoA and malonyl-CoA. The human dicarboxylic acid thioesterase, encoded by acot8, exhibits activity on glutaryl-CoA, adipyl-CoA, suberyl-CoA, sebacyl-CoA, and dodecanedioyl-CoA (Westin et al., *J. Biol. Chem.* 280:38125-38132 (2005)). The closest *E. coli* homolog to this enzyme, tesB, can also hydrolyze a range of CoA thiolesters (Naggert et al., *J Biol Chem* 266:11044-11050 (1991)). A similar enzyme has also been characterized in the rat liver (Deana R., *Biochem Int* 26:767-773 (1992)). Additional enzymes with hydrolase activity in *E. coli* include ybgC, paaI, and ybdB (Kuznetsova, et al., *FEMS Microbiol Rev,* 2005, 29(2):263-279; Song et al., *J Biol Chem,* 2006, 281(16):11028-38). Though its sequence has not been reported, the enzyme from the mitochondrion of the pea leaf has a broad substrate specificity, with demonstrated activity on acetyl-CoA, propionyl- CoA, butyryl-CoA, palmitoyl-CoA, oleoyl-CoA, succinyl-CoA, and crotonyl-CoA (Zeiher et al., *Plant. Physiol.* 94:20-27 (1990)) The acetyl-CoA hydrolase, ACH1, from *S. cerevisiae* represents another candidate hydrolase (Buu et al., *J. Biol. Chem.* 278:17203-17209 (2003)).

| Gene name | GenBank ID | GI number | Organism |
|---|---|---|---|
| acot12 | NP_570103.1 | 18543355 | *Rattus norvegicus* |
| tesB | NP_414986 | 16128437 | *Escherichia coli* |
| acot8 | CAA15502 | 3191970 | *Homo sapiens* |
| acot8 | NP_570112 | 51036669 | *Rattus norvegicus* |
| tesA | NP_415027 | 16128478 | *Escherichia coli* |
| ybgC | NP_415264 | 16128711 | *Escherichia coli* |
| paaI | NP_415914 | 16129357 | *Escherichia coli* |
| ybdB | NP_415129 | 16128580 | *Escherichia coli* |
| ACH1 | NP_009538 | 6319456 | *Saccharomyces cerevisiae* |

Yet another candidate hydrolase is the glutaconate CoA-transferase from *Acidaminococcus fermentans*. This enzyme was transformed by site-directed mutagenesis into an acyl-CoA hydrolase with activity on glutaryl-CoA, acetyl-CoA and 3-butenoyl-CoA (Mack et al., *FEBS. Lett.* 405:209-212 (1997)).This suggests that the enzymes encoding succinyl-CoA:3-ketoacid-CoA transferases and acetoacetyl-CoA:acetyl-CoA transferases may also serve as candidates for this reaction step but would require certain mutations to change their function.

| Gene name | GenBank ID | GI number | Organism |
|---|---|---|---|
| gctA | CAA57199 | 559392 | *Acidaminococcus fermentans* |
| gctB | CAA57200 | 559393 | *Acidaminococcus fermentans* |

Another CoA hydrolase enzyme is 3-hydroxyisobutyryl-CoA hydrolase which has been described to efficiently catalyze the conversion of 3-hydroxyisobutyryl-CoA to 3-hydroxyisobutyrate during valine degradation (Shimomura et al., *J Biol Chem.* 269:14248-14253 (1994)). Genes encoding this enzyme include hibch of *Rattus norvegicus* (Shimomura et al., Methods Enzymol. 324:229-240 (2000)) and *Homo sapiens* (Shimomura et al., supra). Similar gene candidates can also be identified by sequence homology, including hibch of *Saccharomyces cerevisiae* and BC_2292 of *Bacillus cereus*.

| Gene name | GenBank ID | GI number | Organism |
|---|---|---|---|
| hibch | Q5XIE6.2 | 146324906 | *Rattus norvegicus* |
| hibch | Q6NVY1.2 | 146324905 | *Homo sapiens* |
| hibch | P28817.2 | 2506374 | *Saccharomyces cerevisiae* |
| BC_2292 | AP09256 | 29895975 | *Bacillus cereus* |

3.7.1.a Hydrolase

Cyclohexane-1,2-dione hydrolase is a thiamin-diphosphate and FAD-dependent enzyme (EC 3.7.1.11) catalyzing the conversion of cyclohexane-1,2-dione to adipate semialdehyde. This enzyme has been characterized in *Azoarcus* sp. strain 22Lin, where it participates in cyclohexane-1,2-diol degradation (Steinbeck et al, J Bacteriol, in press (2011); Harder, J., *Arch. Microbiol.* 168:199-203 (1997)). The enzyme also oxidizes adipate semialdehyde to adipate. A similar transformation is catalyzed in the myo-inositol degradation pathway of organisms such as *Bacillus subtilis*, in which the cyclic dione 2,3-diketo-4-deoxy-epi-inositol is hydrolyzed to a linear product, 5-dehydro-2-deoxy-D-gluconate, by a diketodeoxyinositol hydrolase (EC 3.7.1.-). A partially purified protein catalyzing this reaction has been studied in *Klebsiella aerogenes* (Berman et al., *J. Biol. Chem.* 241:800-806 (1966)). A gene has not been associated with this activity to date. The CDH from *Azoarcus* sp. strain 22Lin and close homologs are shown in the table below.

| Protein | GenBank ID | GI Number | Organism |
|---|---|---|---|
| cdh | P0CH62.1 | 306755656 | *Azoarcus* sp. Strain 22Lin |
| Ahas | ZP_04823388.1 | 251780468 | *Clostridium botulinum* |
| ilvB2 | ZP_06013676.1 | 262040433 | *Klebsiella pneumoniae* subsp. *rhinoscleromatis* |
| Deba_0336 | YP_003806306.1 | 302341777 | *Desulfarculus baarsii* DSM 2075 |
| ilvB | AEN91169.1 | 345446152 | *Bacillus megaterium* WSH-002 |

The formation of 2-ketocyclohexane-1-carboxoyl-CoA from pimeloyl-CoA (Step A of FIG. 5) is catalyzed by an enzyme with 2-ketocyclohexane-1-carboxoyl-CoA hydrolase activity. This enzymatic activity has been indicated to occur in the ring-closing direction in *Syntrophus aciditrophicus* during growth on crotonate (Mouttaki et al., *Appl. Environ. Micobiol.* 73:930-938 (2007)). This activity was also demonstrated in cell-free extracts of *S. aciditrophicus* in co-culture with another microbe during growth on benzoate (Elshahed et al., *Appl. Environ. Microbiol.* 67:1728-1738 (2001)). An enzyme catalyzing this activity in the ring-opening direction has been characterized in *Rhodopseudomonas palustris*, where it is encoded by badI (Pelletier et al., *J. Bacteriol.* 180:2330-2336 (1998)). The *R. palustris* enzyme has been expressed in *E. coli* where it was assayed for enzymatic activity in the ring-opening direction; however, such activity was not observed (Egland et al., *Proc. Natl. Acad. Sci U.S.A.* 94:6484-6489 (1997)). Several genes in the *S. aciditrophicus* genome bear sequence homology to the badI gene of *R. palustris* (McInerney et al., *Proc. Natl Acad. Sci U.S.A.* 104:7600-7605 (2007)), including syn_01653 (38%), syn_03076 (33%), syn_02400 (33%), syn_03076 (30%) and syn_01309 (31%).

| Protein | GenBank ID | GI Number | Organism |
|---|---|---|---|
| badI | NP_946006.1 | 39933730 | *Rhodopseudomonas palustris* |
| syn_01653 | YP_463074.1 | 85860872 | *Syntrophus aciditrophicus* |
| syn_01654 | YP_463073.1 | 85860871 | *Syntrophus aciditrophicus* |
| syn_02400 | YP_462924.1 | 85860722 | *Syntrophus aciditrophicus* |
| syn_03076 | YP_463118.1 | 85860916 | *Syntrophus aciditrophicus* |
| syn_01309 | YP_461962.1 | 85859760 | *Syntrophus aciditrophicus* |

Another suitable enzyme candidate for Step A of FIG. 5 is napthoyl-CoA synthetase (EC 4.1.3.36), an enzyme participating in menaquinone biosynthesis. This enzyme catalyzes the ring-closing conversion of succinyl-benzoyl-CoA to 1,4-dihydroxy-2-napthoyl-CoA. The badI gene product of *R. palustris* shares as much as 53% sequence identity with 1,4-dihydroxynapthoyl-CoA synthetase homologs in other organisms (Eberhard et al., *J. Am. Chem. Soc.* 126:7188-7189 (2004)), and enzymes catalyzing this transformation can demonstrate 2-ketocyclohexane-1-carboxyl-CoA hydrolase activity in the ring-closing direction. Such enzymes are found in *Escherichia coli* (Sharma et al., *J. Bacteriol.* 174:5057-5062 (1992)), *Bacillus subtilis* (Driscoll et al., *J. Batceriol.* 174:5063-5071 (1992)), *Staphylococcus aureus* (Ulaganathan et al., *Acta Crstyallogr. Sect. F. Struct. Biol. Cyst. Commun.* 63:908-913 (2007)) and *Geobacillus kaustophilus* (Kanajunia et al., *Acta Crstyallogr. Sect. F. Struct. Biol. Cyst. Commun.* 63:103-105 (2007)). Additionally, structural data is available for the enzymes from *Mycobacterium tuberculosis* (Johnston et al., *Acta Crstyallogr. D. Biol. Crystallogr.* 61:1199-1206 (2005)), *S. aureus* (Ulaganathan et al., supra) and *Geobacillus kaustophilus* (Kanaujia et al., supra).

| Protein | GenBank ID | GI Number | Organism |
|---|---|---|---|
| menB | AAC75322 | 1788597 | *Escherichia coli* K12 sp. MG1655 |
| menB | AAC37016 | 143186 | *Bacillus subtilis* |
| menB | NP_215062 | 15607688 | *Mycobacterium tuberculosis* |
| menB | BAB57207 | 14246815 | *Staphylococcus aureus* |
| menB | BAD77158 | 56381250 | *Geobacillus kaustophilus* |

4.1.1.a Decarboxylase

A decarboxylase enzyme suitable for decarboxylating 2-ketocyclohexane-1-carboxylate (step C of FIG. 5) is the 3-ketoacid decarboxylase, acetoacetate decarboxylase (EC 4.1.1.4). The enzyme from *Clostridium acetobutylicum*, encoded by adc, has a broad substrate specificity and has been shown to decarboxylate numerous alternate substrates including 2-ketocyclohexane carboxylate, 3-oxopentanoate, 2-oxo-3-phenylpropionic acid, 2-methyl-3-oxobutyrate and benzoyl-acetate (Rozzel et al., *J. Am. Chem. Soc.* 106:4937-4941 (1984); Benner and Rozzell, *J. Am. Chem. Soc.* 103:993-994 (1981); Autor et al., *J Biol. Chem.* 245:5214-5222 (1970)). An acetoacetate decarboxylase has also been characterized in *Clostridium beijerinckii* (Ravagnani et al., *Mol. Microbiol* 37:1172-1185 (2000)). The acetoacetate decarboxylase from *Bacillus polymyxa*, characterized in cell-free extracts, also has a broad substrate specificity for 3-keto acids and can decarboxylate 3-oxopentanoate (Matiasek et al., *Curr. Microbiol* 42:276-281 (2001)). The gene encoding this enzyme has not been identified to date and the genome sequence of *B. polymyxa* is not yet available. Another adc is found in *Clostridium saccharoperbutylacetonicum* (Kosaka, et al., *Biosci. Biotechnol Biochem.* 71:58-68 (2007)). Gene candidates in other organisms, including *Clostridium botulinum* and *Bacillus amyloliquefaciens*, can be identified by sequence homology.

| Protein | GenBank ID | GI Number | Organism |
|---|---|---|---|
| adc | NP_149328.1 | 15004868 | *Clostridium acetobutylicum* |
| adc | AAP42566.1 | 31075386 | *Clostridium saccharoperbutylacetonicum* |
| adc | YP_001310906.1 | 150018652 | *Clostridium beijerinckii* |
| CLL_A2135 | YP_001886324.1 | 187933144 | *Clostridium botulinum* |
| RBAM_030030 | YP_001422565.1 | 154687404 | *Bacillus amyloliquefaciens* |

4.2.1.a Hydro-Lyase

Several transformations involving the removal of water are depicted in FIGS. 2 and 4. In Step C of FIG. 2, the dehydration of 3,6-dihydroxyhexanoyl-CoA to 6-hydroxyhex-2-enoyl-CoA is catalyzed by a 3-hydroxyacyl-CoA dehydratase. In FIG. 4, the conversion of cyclohexane-1,2-diol to cyclohexanone (Step D) is catalyzed by a diol dehydratase in EC class 4.2.1. Several relevant dehydratase enzymes have been described in the literature and represent suitable candidates for these steps.

A 3-hydroxyacyl-CoA dehydratase is required for step C of FIG. 2. Enoyl-CoA hydratases (EC 4.2.1.17) catalyze the dehydration of a range of 3-hydroxyacyl-CoA substrates (Roberts et al., *Arch. Microbiol* 117:99-108 (1978); Agnihotri et al., *Bioorg. Med. Chem.* 11:9-20 (2003); Conrad et al., *J Bacteriol.* 118:103-111 (1974)). The enoyl-CoA hydratase of *Pseudomonas putida*, encoded by ech, catalyzes the conversion of 3-hydroxybutyryl-CoA to crotonyl-CoA (Roberts et al., *Arch. Microbiol* 117:99-108 (1978)). This transformation is also catalyzed by the crt gene product of *Clostridium acetobutylicum*, the crt1 gene product of *C. kluyveri*, and other clostridial organisms Atsumi et al., *Metab Eng* 10:305-311 (2008); Boynton et al., *J Bacteriol.* 178:3015-3024 (1996); Hillmer et al., *FEBS Lett.* 21:351-354 (1972)). Additional enoyl-CoA hydratase candidates are phaA and phaB, of *P. putida*, and paaA and paaB from *P. fluorescens* (Olivera et al., *Proc. Natl. Acad. Sci U.S.A* 95:6419-6424 (1998)). The gene product of pimF in *Rhodopseudomonas palustris* is predicted to encode an enoyl-CoA hydratase that participates in pimeloyl-CoA degradation (Harrison et al., *Microbiology* 151:727-736 (2005)). Lastly, a number of *Escherichia coli* genes have been shown to demonstrate enoyl-CoA hydratase functionality including maoC (Park et al., *J Bacteriol.* 185:5391-5397 (2003)), paaF (Ismail et al., *Eur. J Biochem.* 270:3047-3054 (2003); Park et al., *Appl. Biochem. Biotechnol* 113-116:335-346 (2004); Park et al., *Biotechnol Bioeng* 86:681-686 (2004)) and paaG (Ismail et al., *Eur. J Biochem.* 270:3047-3054 (2003); Park and Lee, *Appl. Biochem. Biotechnol* 113-116:335-346 (2004); Park and Yup, *Biotechnol Bioeng* 86:681-686 (2004)).

| Gene | GenBank ID | GI number | Organism |
|---|---|---|---|
| ech | NP_745498.1 | 26990073 | *Pseudomonas putida* |
| crt | NP_349318.1 | 15895969 | *Clostridium acetobutylicum* |
| crt1 | YP_001393856 | 153953091 | *Clostridium kluyveri* |
| phaA | ABF82233.1 | 26990002 | *Pseudomonas putida* |
| phaB | ABF82234.1 | 26990001 | *Pseudomonas putida* |
| paaA | NP_745427.1 | 106636093 | *Pseudomonas fluorescens* |
| paaB | NP_745426.1 | 106636094 | *Pseudomonas fluorescens* |
| maoC | NP_415905.1 | 16129348 | *Escherichia coli* |
| paaF | NP_415911.1 | 16129354 | *Escherichia coli* |
| paaG | NP_415912.1 | 16129355 | *Escherichia coli* |

Alternatively, the *E. coli* gene products of fadA and fadB encode a multienzyme complex involved in fatty acid oxidation that exhibits enoyl-CoA hydratase activity (Yang et al., *Biochemistry* 30:6788-6795 (1991); Yang, *J Bacteriol.* 173:7405-7406 (1991); Nakahigashi et al., *Nucleic Acids Res.* 18:4937 (1990)). Knocking out a negative regulator encoded by fadR can be utilized to activate the fadB gene product (Sato et al., *J Biosci. Bioeng* 103:38-44 (2007)). The fadI and fadJ genes encode similar functions and are naturally expressed under anaerobic conditions (Campbell et al., *Mol. Microbiol* 47:793-805 (2003)).

| Protein | GenBank ID | GI Number | Organism |
|---|---|---|---|
| fadA | YP_026272.1 | 49176430 | *Escherichia coli* |
| fadB | NP_418288.1 | 16131692 | *Escherichia coli* |
| fadI | NP_416844.1 | 16130275 | *Escherichia coli* |
| fadJ | NP_416843.1 | 16130274 | *Escherichia coli* |
| fadR | NP_415705.1 | 16129150 | *Escherichia coli* |

Diol dehydratase enzymes suitable for converting cyclohexane-1,2-diol to cyclohexanone include dihydroxy-acid dehydratase (EC 4.2.1.9), propanediol dehydratase (EC 4.2.1.28), glycerol dehydratase (EC 4.2.1.30) and myo-inositose dehydratase (EC 4.2.1.44).

Adenosylcobalamin-dependent diol dehydratases contain alpha, beta and gamma subunits, which are all required for enzyme function. Exemplary propanediol dehydratase candidates are found in *Klebsiella pneumoniae* (Toraya et al., *Bio-* chem. Biophys. Res. Commun. 69:475-480 (1976); Tobimatsu et al., Biosci. Biotechnol Biochem. 62:1774-1777 (1998)), *Salmonella typhimurium* (Bobik et al., *J Bacteriol.* 179:6633-6639 (1997)), *Klebsiella oxytoca* (Tobimatsu et al., *J Biol. Chem.* 270:7142-7148 (1995)) and *Lactobacillus collinoides* (Sauvageot et al., *FEMS Microbiol Lett.* 209:69-74 (2002)). Methods for isolating diol dehydratase gene candidates in other organisms are well known in the art (e.g. U.S. Pat. No. 5,686,276).

| Protein | GenBank ID | GI Number | Organism |
|---|---|---|---|
| pddC | AAC98386.1 | 4063704 | *Klebsiella pneumoniae* |
| pddB | AAC98385.1 | 4063703 | *Klebsiella pneumoniae* |
| pddA | AAC98384.1 | 4063702 | *Klebsiella pneumoniae* |
| pduC | AAB84102.1 | 2587029 | *Salmonella typhimurium* |
| pduD | AAB84103.1 | 2587030 | *Salmonella typhimurium* |
| pduE | AAB84104.1 | 2587031 | *Salmonella typhimurium* |
| pddA | BAA08099.1 | 868006 | *Klebsiella oxytoca* |
| pddB | BAA08100.1 | 868007 | *Klebsiella oxytoca* |
| pddC | BAA08101.1 | 868008 | *Klebsiella oxytoca* |
| pduC | CAC82541.1 | 18857678 | *Lactobacillus collinoides* |
| pduD | CAC82542.1 | 18857679 | *Lactobacillus collinoides* |
| pduE | CAD01091.1 | 18857680 | *Lactobacillus collinoides* |

Enzymes in the glycerol dehydratase family (EC 4.2.1.30) are also diol dehydratases. Exemplary gene candidates are encoded by gldABC and dhaB123 in *Klebsiella pneumoniae* (World Patent WO 2008/137403) and (Toraya et al., *Biochem. Biophys. Res. Commun.* 69:475-480 (1976)), dhaBCE in *Clostridium pasteuranum* (Macis et al., *FEMS Microbiol Lett.* 164:21-28 (1998)) and dhaBCE in *Citrobacter freundii* (Seyfried et al., *J Bacteriol.* 178:5793-5796 (1996)). Variants of the B12-dependent diol dehydratase from *K. pneumoniae* with 80- to 336-fold enhanced activity were recently engineered by introducing mutations in two residues of the beta subunit (Qi et al., *J. Biotechnol.* 144:43-50 (2009)). Diol dehydratase enzymes with reduced inactivation kinetics were developed by DuPont using error-prone PCR (WO 2004/056963).

| Protein | GenBank ID | GI Number | Organism |
|---|---|---|---|
| gldA | AAB96343.1 | 1778022 | *Klebsiella pneumonia* |
| gldB | AAB96344.1 | 1778023 | *Klebsiella pneumonia* |
| gldC | AAB96345.1 | 1778024 | *Klebsiella pneumoniae* |
| dhaB1 | ABR78884.1 | 150956854 | *Klebsiella pneumoniae* |
| dhaB2 | ABR78883.1 | 150956853 | *Klebsiella pneumoniae* |
| dhaB3 | ABR78882.1 | 150956852 | *Klebsiella pneumoniae* |
| dhaB | AAC27922.1 | 3360389 | *Clostridium pasteuranum* |
| dhaC | AAC27923.1 | 3360390 | *Clostridium pasteuranum* |
| dhaE | AAC27924.1 | 3360391 | *Clostridium pasteuranum* |
| dhaB | P45514.1 | 1169287 | *Citrobacter freundii* |
| dhaC | AAB48851.1 | 1229154 | *Citrobacter freundii* |
| dhaE | AAB48852.1 | 1229155 | *Citrobacter freundii* |

If a B12-dependent diol dehydratase is utilized, heterologous expression of the corresponding reactivating factor is recommended. B12-dependent diol dehydratases are subject to mechanism-based suicide activation by substrates and some downstream products. Inactivation, caused by a tight association with inactive cobalamin, can be partially overcome by diol dehydratase reactivating factors in an ATP-dependent process. Regeneration of the B12 cofactor requires an additional ATP. Diol dehydratase regenerating factors are two-subunit proteins. Exemplary candidates are found in *Klebsiella oxytoca* (Mori et al., *J Biol. Chem.* 272:32034-32041 (1997)), *Salmonella typhimurium* (Bobik et al., *J Bacteriol.* 179:6633-6639 (1997); Chen et al., *J Bacteriol.* 176: 5474-5482 (1994)), *Lactobacillus* collinoides (Sauvageot et al., *FEMS Microbiol Lett.* 209:69-74 (2002)), *Klebsiella pneumonia* (World Patent WO 2008/137403).

| Protein | GenBank ID | GI Number | Organism |
|---|---|---|---|
| ddrA | AAC15871 | 3115376 | *Klebsiella oxytoca* |
| ddrB | AAC15872 | 3115377 | *Klebsiella oxytoca* |
| pduG | AAB84105 | 16420573 | *Salmonella typhimurium* |
| pduH | AAD39008 | 16420574 | *Salmonella typhimurium* |
| pduG | YP_002236779 | 206579698 | *Klebsiella pneumonia* |
| pduH | YP_002236778 | 206579863 | *Klebsiella pneumonia* |
| pduG | CAD01092 | 29335724 | *Lactobacillus collinoides* |
| pduH | AJ297723 | 29335725 | *Lactobacillus collinoides* |

B12-independent diol dehydratase enzymes are glycyl radicals that utilize S-adenosylmethionine (SAM) as a cofactor and function under strictly anaerobic conditions. The glycerol dehydrogenase and corresponding activating factor of *Clostridium butyricum*, encoded by dhaB1 and dhaB2, have been well-characterized (O'Brien et al., *Biochemistry* 43:4635-4645 (2004); Raynaud et al., *Proc. Natl. Acad. Sci U.S.A* 100:5010-5015 (2003)). This enzyme was recently employed in a 1,3-propanediol overproducing strain of *E. coli* and was able to achieve very high titers of product (Tang et al., *Appl. Environ. Microbiol.* 75:1628-1634 (2009)). An additional B12-independent diol dehydratase enzyme and activating factor from *Roseburia inulinivorans* was shown to catalyze the conversion of 2,3-butanediol to 2-butanone (US 2009/09155870).

| Protein | GenBank ID | GI Number | Organism |
|---|---|---|---|
| dhaB1 | AAM54728.1 | 27461255 | *Clostridium butyricum* |
| dhaB2 | AAM54729.1 | 27461256 | *Clostridium butyricum* |
| rdhtA | ABC25539.1 | 83596382 | *Roseburia inulinivorans* |
| rdhtB | ABC25540.1 | 83596383 | *Roseburia inulinivorans* |

Dihydroxy-acid dehydratase (DHAD, EC 4.2.1.9) is a B12-independent enzyme participating in branched-chain amino acid biosynthesis. In its native role, it converts 2,3-dihydroxy-3-methylvalerate to 2-keto-3-methyl-valerate, a precursor of isoleucine. In valine biosynthesis the enzyme catalyzes the dehydration of 2,3-dihydroxy-isovalerate to 2-oxoisovalerate. The DHAD from *Sulfolobus solfataricus* has a broad substrate range and activity of a recombinant enzyme expressed in *E. coli* was demonstrated on a variety of aldonic acids (KIM et al., *J. Biochem.* 139:591-596 (2006)). The *S. solfataricus* enzyme is tolerant of oxygen unlike many diol dehydratase enzymes. The *E. coli* enzyme, encoded by ilvD, is sensitive to oxygen, which inactivates its iron-sulfur cluster (Flint et al., *J. Biol. Chem.* 268:14732-14742 (1993)). Similar enzymes have been characterized in *Neurospora crassa* (Altmiller et al., *Arch. Biochem. Biophys.* 138:160-170 (1970)) and *Salmonella typhimurium* (Armstrong et al., *Biochim. Biophys. Acta* 498:282-293 (1977)). Other groups have shown that the overexpression of one or more Aft proteins or homologs thereof improves DHAD activity (US Patent Application 2011/0183393. In *Saccharomyces cerevisiae*, the Aft1 and Aft2 proteins are transcriptional activators that regulate numerous proteins related to the acquisition, compartmentalization, and utilization of iron.

| Protein | GenBank ID | GI Number | Organism |
|---|---|---|---|
| ilvD | NP_344419.1 | 15899814 | *Sulfolobus solfataricus* |
| ilvD | AAT48208.1 | 48994964 | *Escherichia coli* |

| Protein | GenBank ID | GI Number | Organism |
| --- | --- | --- | --- |
| ilvD | NP_462795.1 | 16767180 | Salmonella typhimurium |
| ilvD | XP_958280.1 | 85090149 | Neurospora crassa |
| Aft1 | P22149.2 | 1168370 | Saccharomyces cerevisiae |
| Aft2 | Q08957.1 | 74583775 | Saccharomyces cerevisiae |

The diol dehydratase myo-inosose-2-dehydratase (EC 4.2.1.44) is another exemplary candidate. Myo-inosose is a six-membered ring containing adjacent alcohol groups. A purified enzyme encoding myo-inosose-2-dehydratase functionality has been studied in *Klebsiella aerogenes* in the context of myo-inositol degradation (Berman et al., *J Biol. Chem.* 241:800-806 (1966)), but has not been associated with a gene to date. The myo-inosose-2-dehydratase of *Sinorhizobium fredii* was cloned and functionally expressed in *E. coli* (Yoshida et al., *Biosci. Biotechnol. Biochem.* 70:2957-2964 (2006)). A similar enzyme from *B. subtilis*, encoded by iolE, has also been studied (Yoshida et al., *Microbiology* 150:571-580 (2004)).

| Protein | GenBank ID | GI Number | Organism |
| --- | --- | --- | --- |
| iolE | P42416.1 | 1176989 | Bacillus subtilis |
| iolE | AAX24114.1 | 60549621 | Sinorhizobium fredii |

6.2.1.a CoA Synthetase

The conversion of acyl-CoA substrates to their acid products can be catalyzed by a CoA acid-thiol ligase or CoA synthetase in the 6.2.1 family of enzymes. Several transformations require a CoA synthetase to interconvert carboxylic acids and their corresponding acyl-CoA derivatives, including steps C and F of FIG. 1, step E of FIG. 2 and step B of FIG. 5. Enzymes catalyzing these exact transformations have not been characterized to date; however, several enzymes with broad substrate specificities have been described in the literature.

ADP-forming acetyl-CoA synthetase (ACD, EC 6.2.1.13) is an enzyme that couples the conversion of acyl-CoA esters to their corresponding acids with the concomitant synthesis of ATP. ACD I from *Archaeoglobus fulgidus*, encoded by AF1211, was shown to operate on a variety of linear and branched-chain substrates including isobutyrate, isopentanoate, and fumarate (Musfeldt et al., *J Bacteriol.* 184:636-644 (2002)). A second reversible ACD in *Archaeoglobus fulgidus*, encoded by AF1983, was also shown to have a broad substrate range with high activity on cyclic compounds phenylacetate and indoleacetate (Musfeldt and Schonheit, *J Bacteriol.* 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch Microbiol* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al, supra). Directed evolution or engineering can be used to modify this enzyme to operate at the physiological temperature of the host organism. The enzymes from *A. fulgidus, H. marismortui* and *P. aerophilum* have all been cloned, functionally expressed, and characterized in *E. coli* (Brasen and Schonheit, supra; Musfeldt and Schonheit, *J Bacteriol.* 184: 636-644 (2002)). An additional candidate is succinyl-CoA synthetase, encoded by sucCD of *E. coli* and LSC1 and LSC2 genes of *Saccharomyces cerevisiae*. These enzymes catalyze the formation of succinyl-CoA from succinate with the concomitant consumption of one ATP in a reaction which is reversible in vivo (Buck et al., *Biochemistry* 24:6245-6252 (1985)). The acyl CoA ligase from *Pseudomonas putida* has been demonstrated to work on several aliphatic substrates including acetic, propionic, butyric, valeric, hexanoic, heptanoic, and octanoic acids and on aromatic compounds such as phenylacetic and phenoxyacetic acids (Fernandez-Valverde et al., *Appl. Environ. Microbiol.* 59:1149-1154 (1993)). A related enzyme, malonyl CoA synthetase (6.3.4.9) from *Rhizobium leguminosarum* could convert several diacids, namely, ethyl-, propyl-, allyl-, isopropyl-, dimethyl-, cyclopropyl-, cyclopropylmethylene-, cyclobutyl-, and benzylmalonate into their corresponding monothioesters (Pohl et al., *J. Am. Chem. Soc.* 123:5822-5823 (2001)).

| Protein | GenBank ID | GI Number | Organism |
| --- | --- | --- | --- |
| AF1211 | NP_070039.1 | 11498810 | Archaeoglobus fulgidus |
| AF1983 | NP_070807.1 | 11499565 | Archaeoglobus fulgidus |
| scs | YP_135572.1 | 55377722 | Haloarcula marismortui |
| PAE3250 | NP_560604.1 | 18313937 | Pyrobaculum aerophilum str. IM2 |
| sucC | NP_415256.1 | 16128703 | Escherichia coli |
| sucD | AAC73823.1 | 1786949 | Escherichia coli |
| LSC1 | NP_014785 | 6324716 | Saccharomyces cerevisiae |
| LSC2 | NP_011760 | 6321683 | Saccharomyces cerevisiae |
| paaF | AAC24333.2 | 22711873 | Pseudomonas putida |
| matB | AAC83455.1 | 3982573 | Rhizobium leguminosarum |

Another candidate enzyme is 6-carboxyhexanoate-CoA ligase, also known as pimeloyl-CoA ligase (EC 6.2.1.14), which naturally activates pimelate to pimeloyl-CoA during biotin biosynthesis in gram-positive bacteria. The enzyme from *Pseudomonas mendocina*, cloned into *E. coli*, was shown to accept the alternate substrates hexanedioate and nonanedioate (Binieda et al., *Biochem. J* 340 (Pt 3):793-801 (1999)). Other candidates are found in *Bacillus subtilis* (Bower et al., *J Bacteriol.* 178:4122-4130 (1996)) and *Lysinibacillus sphaericus* (formerly *Bacillus sphaericus*) (Ploux et al., *Biochem. J* 287 (Pt 3):685-690 (1992)).

| Protein | GenBank ID | GI Number | Organism |
| --- | --- | --- | --- |
| bioW | NP_390902.2 | 50812281 | Bacillus subtilis |
| bioW | CAA10043.1 | 3850837 | Pseudomonas mendocina |
| bioW | P22822.1 | 115012 | Bacillus sphaericus |

Additional CoA-ligases include the rat dicarboxylate-CoA ligase for which the sequence is yet uncharacterized (Vamecq et al., *Biochem. J* 230:683-693 (1985)), either of the two characterized phenylacetate-CoA ligases from *P. chrysogenum* (Lamas-Maceiras et al., *Biochem. J* 395:147-155 (2006); Wang et al., 360:453-458 (2007)), the phenylacetate-CoA ligase from *Pseudomonas putida* (Martinez-Blanco et al., *J Biol Chem* 265:7084-7090 (1990)) and the 6-carboxyhexanoate-CoA ligase from *Bacillus subtilis* (Bower et al. *J Bacteriol* 178(14):4122-4130 (1996)). Acetoacetyl-CoA synthetases from *Mus musculus* (Hasegawa et al., *Biochim Biophys Acta* 1779:414-419 (2008)) and *Homo sapiens* (Ohgami et al., *Biochem. Pharmacol.* 65:989-994 (2003)) naturally catalyze the ATP-dependent conversion of acetoacetate into acetoacetyl-CoA.

| Gene | Accession No. | GI No. | Organism |
|---|---|---|---|
| phl | CAJ15517.1 | 77019264 | Penicillium chrysogenum |
| phlB | ABS19624.1 | 152002983 | Penicillium chrysogenum |
| paaF | AAC24333.2 | 22711873 | Pseudomonas putida |
| bioW | NP 390902.2 | 50812281 | Bacillus subtilis |
| AACS | NP 084486.1 | 21313520 | Mus musculus |
| AACS | NP 076417.2 | 31982927 | Homo sapiens |

No EC

Formation of caprolactone from 6-hydroxyhexanoyl-CoA (step D of FIG. 1 and step F of FIG. 2) either occurs spontaneously or is catalyzed by enzymes having 6-hydroxyhexanoyl-CoA cyclase or alcohol transferase activity. Several enzymes with alcohol transferase activity were demonstrated in Examples 1-10 of U.S. Pat. No. 7,901,915. These include Novozyme 435 (immobilized lipase B from *Candida antarctica*, Sigma), Lipase C2 from *Candida cylindracea* (Alphamerix Ltd), lipase from *Pseudomonas fluorescens* (Alphamerix Ltd), L-aminoacylase ex *Aspergillus* spp., and protease ex *Aspergillus oryzae*. Such enzymes were shown to form methyl acrylate and ethyl acrylate from acrylyl-CoA and methanol or ethanol, respectively. Similar alcohol transferase enzymes can also be used to form cyclic esters such as caprolactone. Other suitable candidates include esterase enzymes in EC class 3.1.1, described above. Additional candidates include O-acyltransferases that transfer acyl groups from acyl-CoA to alcohols. Suitable O-acyltransferases include serine O-acetyltransferase (EC 2.3.1.30) such as cysE of *E. coli*, homoserine O-acetyltransferase (EC 2.3.1.31) enzymes such as met2 of *Saccharomyces cerevisiae*, or carnitine O-acyltransferases (EC 2.3.1.21) such as Cpt1a of *Rattus norvegicus* (Langin et al *Gene* 49:283-93 (1986); Denk et al, *J Gen Microbiol* 133:515-25 (1987); de Vries et al, *Biochem* 36:5285-92 (1997)).

| Gene | Accession No. | GI No. | Organism |
|---|---|---|---|
| Met2 | NP_014122.1 | 6324052 | Saccharomyces cerevisiae |
| cysE | NP_418064.1 | 16131478 | Escherichia coli |
| Cpt1a | NP_113747.2 | 162287173 | Rattus norvegicus |

Cyclization of 6-hydroxyhexanoyl-phosphate to caprolactone (Step I of FIGS. 1 and 2) can either occur spontaneously or by an enzyme with 6-hydroxyhexanoyl phosphate cyclase activity. An exemplary enzyme for this transformation is acyl-phosphate:glycerol-3-phosphate acyltransferase, encoded by plsY of *Streptococcus pneumoniae* (Lu et al, *J Biol Chem* 282:11339-46 (2007)). Although this enzyme catalyzes an intermolecular reaction, it could also catalyze the intramolecular ester-forming reaction to caprolactone. Genes encoding similar enzymes are listed in the table below. Alcohol transferase enzymes and esterase enzymes described above are also suitable candidates.

| Gene | Accession No. | GI No. | Organism |
|---|---|---|---|
| plsY | P0A4P9.1 | 61250558 | Streptococcus pneumoniae |
| plsY | YP_001035186.1 | 125718053 | Streptococcus sanguinis |
| ykaC | NP_267134.1 | 15672960 | Lactococcus lactis |
| plsY | NP_721591.1 | 24379636 | Streptococcus mucans |

EXAMPLE II

Exemplary Hydrogenase and CO Dehydrogenase Enzymes for Extracting Reducing Equivalents from Syngas and Exemplary Reductive TCA Cycle Enzymes Enzymes of the reductive TCA cycle useful in the non-naturally occurring microbial organisms of the present invention include one or more of ATP-citrate lyase and three $CO_2$-fixing enzymes: isocitrate dehydrogenase, alpha-ketoglutarate:ferredoxin oxidoreductase, pyruvate:ferredoxin oxidoreductase. The presence of ATP-citrate lyase or citrate lyase and alpha-ketoglutarate:ferredoxin oxidoreductase indicates the presence of an active reductive TCA cycle in an organism. Enzymes for each step of the reductive TCA cycle are shown below.

ATP-citrate lyase (ACL, EC 2.3.3.8), also called ATP citrate synthase, catalyzes the ATP-dependent cleavage of citrate to oxaloacetate and acetyl-CoA. ACL is an enzyme of the RTCA cycle that has been studied in green sulfur bacteria *Chlorobium limicola* and *Chlorobium tepidum*. The alpha(4) beta(4) heteromeric enzyme from *Chlorobium limicola* was cloned and characterized in *E. coli* (Kanao et al., *Eur. J. Biochem.* 269:3409-3416 (2002). The *C. limicola* enzyme, encoded by aclAB, is irreversible and activity of the enzyme is regulated by the ratio of ADP/ATP. A recombinant ACL from *Chlorobium tepidum* was also expressed in *E. coli* and the holoenzyme was reconstituted in vitro, in a study elucidating the role of the alpha and beta subunits in the catalytic mechanism (Kim and Tabita, *J. Bacteriol.* 188:6544-6552 (2006). ACL enzymes have also been identified in *Balnearium lithotrophicum*, *Sulfurihydrogenibium subterraneum* and other members of the bacterial phylum Aquificae (Hugler et al., *Environ. Microbiol.* 9:81-92 (2007)). This activity has been reported in some fungi as well. Exemplary organisms include *Sordaria macrospora* (Nowrousian et al., *Curr. Genet.* 37:189-93 (2000), *Aspergillus nidulans*, *Yarrowia lipolytica* (Hynes and Murray, *Eukaryotic Cell*, July: 1039-1048, (2010) and *Aspergillus niger* (Meijer et al. *J. Ind. Microbiol. Biotechnol.* 36:1275-1280 (2009). Other candidates can be found based on sequence homology. Information related to these enzymes is tabulated below:

| Protein | GenBank ID | GI Number | Organism |
|---|---|---|---|
| aclA | BAB21376.1 | 12407237 | Chlorobium limicola |
| aclB | BAB21375.1 | 12407235 | Chlorobium limicola |
| aclA | AAM72321.1 | 21647054 | Chlorobium tepidum |
| aclB | AAM72322.1 | 21647055 | Chlorobium tepidum |
| aclA | ABI50076.1 | 114054981 | Balnearium lithotrophicum |
| aclB | ABI50075.1 | 114054980 | Balnearium lithotrophicum |
| aclA | ABI50085.1 | 114055040 | Sulfurihydrogenibium subterraneum |
| aclB | ABI50084.1 | 114055039 | Sulfurihydrogenibium subterraneum |
| aclA | AAX76834.1 | 62199504 | Sulfurimonas denitrificans |
| aclB | AAX76835.1 | 62199506 | Sulfurimonas denitrificans |
| acl1 | XP_504787.1 | 50554757 | Yarrowia lipolytica |
| acl2 | XP_503231.1 | 50551515 | Yarrowia lipolytica |
| SPBC1703.07 | NP_596202.1 | 19112994 | Schizosaccharomyces pombe |
| SPAC22A12.16 | NP_593246.1 | 19114158 | Schizosaccharomyces pombe |
| acl1 | CAB76165.1 | 7160185 | Sordaria macrospora |
| acl2 | CAB76164.1 | 7160184 | Sordaria macrospora |
| aclA | CBF86850.1 | 259487849 | Aspergillus nidulans |
| aclB | CBF86848 | 259487848 | Aspergillus nidulans |

In some organisms the conversion of citrate to oxaloacetate and acetyl-CoA proceeds through a citryl-CoA intermediate and is catalyzed by two separate enzymes, citryl-CoA synthetase (EC 6.2.1.18) and citryl-CoA lyase (EC 4.1.3.34) (Aoshima, M., *Appl. Microbiol. Biotechnol.* 75:249-255 (2007). Citryl-CoA synthetase catalyzes the activation of citrate to citryl-CoA. The *Hydrogenobacter thermophilus* enzyme is composed of large and small subunits encoded by ccsA and ccsB, respectively (Aoshima et al., *Mol. Micrbiol.* 52:751-761 (2004)). The citryl-CoA synthetase of *Aquifex aeolicus* is composed of alpha and beta subunits encoded by sucC1 and sucD1 (Hugler et al., *Environ. Microbiol.* 9:81-92 (2007)). Citryl-CoA lyase splits citryl-CoA into oxaloacetate and acetyl-CoA. This enzyme is a homotrimer encoded by ccl in *Hydrogenobacter thermophilus* (Aoshima et al., *Mol. Microbiol.* 52:763-770 (2004)) and aq_150 in *Aquifex aeolicus* (Hugler et al., supra (2007)). The genes for this mechanism of converting citrate to oxaloacetate and citryl-CoA have also been reported recently in *Chlorobium tepidum* (Eisen et al., PNAS 99(14): 9509-14 (2002).

| Protein | GenBank ID | GI Number | Organism |
| --- | --- | --- | --- |
| ccsA | BAD17844.1 | 46849514 | *Hydrogenobacter thermophilus* |
| ccsB | BAD17846.1 | 46849517 | *Hydrogenobacter thermophilus* |
| sucC1 | AAC07285 | 2983723 | *Aquifex aeolicus* |
| sucD1 | AAC07686 | 2984152 | *Aquifex aeolicus* |
| ccl | BAD17841.1 | 46849510 | *Hydrogenobacter thermophilus* |
| aq_150 | AAC06486 | 2982866 | *Aquifex aeolicus* |
| CT0380 | NP_661284 | 21673219 | *Chlorobium tepidum* |
| CT0269 | NP_661173.1 | 21673108 | *Chlorobium tepidum* |
| CT1834 | AAM73055.1 | 21647851 | *Chlorobium tepidum* |

Oxaloacetate is converted into malate by malate dehydrogenase (EC 1.1.1.37), an enzyme which functions in both the forward and reverse direction. *S. cerevisiae* possesses three copies of malate dehydrogenase, MDH1 (McAlister-Henn and Thompson, *J. Bacteriol.* 169:5157-5166 (1987), MDH2 (Minard and McAlister-Henn, *Mol. Cell. Biol.* 11:370-380 (1991); Gibson and McAlister-Henn, *J. Biol. Chem.* 278: 25628-25636 (2003)), and MDH3 (Steffan and McAlister-Henn, *J. Biol. Chem.* 267:24708-24715 (1992)), which localize to the mitochondrion, cytosol, and peroxisome, respectively. *E. coli* is known to have an active malate dehydrogenase encoded by mdh.

| Protein | GenBank ID | GI Number | Organism |
| --- | --- | --- | --- |
| MDH1 | NP_012838 | 6322765 | *Saccharomyces cerevisiae* |
| MDH2 | NP_014515 | 116006499 | *Saccharomyces cerevisiae* |
| MDH3 | NP_010205 | 6320125 | *Saccharomyces cerevisiae* |
| Mdh | NP_417703.1 | 16131126 | *Escherichia coli* |

Fumarate hydratase (EC 4.2.1.2) catalyzes the reversible hydration of fumarate to malate. The three fumarases of *E. coli*, encoded by fumA, fumB and fumC, are regulated under different conditions of oxygen availability. FumB is oxygen sensitive and is active under anaerobic conditions. FumA is active under microaerobic conditions, and FumC is active under aerobic growth conditions (Tseng et al., *J. Bacteriol.* 183:461-467 (2001); Woods et al., *Biochim. Biophys. Acta* 954:14-26 (1988); Guest et al., *J. Gen. Microbiol.* 131:2971-2984 (1985)). *S. cerevisiae* contains one copy of a fumarase-encoding gene, FUM1, whose product localizes to both the cytosol and mitochondrion (Sass et al., *J. Biol. Chem.* 278: 45109-45116 (2003)). Additional fumarase enzymes are found in *Campylobacter jejuni* (Smith et al., *Int. J. Biochem. Cell. Biol.* 31:961-975 (1999)), *Thermus thermophilus* (Mizobata et al., *Arch. Biochem. Biophys.* 355:49-55 (1998)) and *Rattus norvegicus* (Kobayashi et al., *J. Biochem.* 89:1923-1931 (1981)). Similar enzymes with high sequence homology include fum1 from *Arabidopsis thaliana* and fumC from *Corynebacterium glutamicum*. The MmcBC fumarase from *Pelotomaculum thermopropionicum* is another class of fumarase with two subunits (Shimoyama et al., *FEMS Microbiol. Lett.* 270:207-213 (2007)).

| Protein | GenBank ID | GI Number | Organism |
| --- | --- | --- | --- |
| fumA | NP_416129.1 | 16129570 | *Escherichia coli* |
| fumB | NP_418546.1 | 16131948 | *Escherichia coli* |
| fumC | NP_416128.1 | 16129569 | *Escherichia coli* |
| FUM1 | NP_015061 | 6324993 | *Saccharomyces cerevisiae* |
| fumC | Q8NRN8.1 | 39931596 | *Corynebacterium glutamicum* |
| fumC | 069294.1 | 9789756 | *Campylobacter jejuni* |
| fumC | P84127 | 75427690 | *Thermus thermophilus* |
| fumH | P14408.1 | 120605 | *Rattus norvegicus* |
| MmcB | YP_001211906 | 147677691 | *Pelotomaculum thermopropionicum* |
| MmcC | YP_001211907 | 147677692 | *Pelotomaculum thermopropionicum* |

Fumarate reductase catalyzes the reduction of fumarate to succinate. The fumarate reductase of *E. coli*, composed of four subunits encoded by frdABCD, is membrane-bound and active under anaerobic conditions. The electron donor for this reaction is menaquinone and the two protons produced in this reaction do not contribute to the proton gradient (Iverson et al., *Science* 284:1961-1966 (1999)). The yeast genome encodes two soluble fumarate reductase isozymes encoded by FRDS1 (Enomoto et al., *DNA Res.* 3:263-267 (1996)) and FRDS2 (Muratsubaki et al., *Arch. Biochem. Biophys.* 352: 175-181 (1998)), which localize to the cytosol and promitochondrion, respectively, and are used during anaerobic growth on glucose (Arikawa et al., *FEMS Microbiol. Lett.* 165:111-116 (1998)).

| Protein | GenBank ID | GI Number | Organism |
| --- | --- | --- | --- |
| FRDS1 | P32614 | 418423 | *Saccharomyces cerevisiae* |
| FRDS2 | NP_012585 | 6322511 | *Saccharomyces cerevisiae* |
| frdA | NP_418578.1 | 16131979 | *Escherichia coli* |
| frdB | NP_418577.1 | 16131978 | *Escherichia coli* |
| frdC | NP_418576.1 | 16131977 | *Escherichia coli* |
| frdD | NP_418475.1 | 16131877 | *Escherichia coli* |

The ATP-dependent acylation of succinate to succinyl-CoA is catalyzed by succinyl-CoA synthetase (EC 6.2.1.5). The product of the LSC1 and LSC2 genes of *S. cerevisiae* and the sucC and sucD genes of *E. coli* naturally form a succinyl-CoA synthetase complex that catalyzes the formation of succinyl-CoA from succinate with the concomitant consumption of one ATP, a reaction which is reversible in vivo (Buck et al., *Biochemistry* 24:6245-6252 (1985)). These proteins are identified below:

| Protein | GenBank ID | GI Number | Organism |
| --- | --- | --- | --- |
| LSC1 | NP_014785 | 6324716 | *Saccharomyces cerevisiae* |
| LSC2 | NP_011760 | 6321683 | *Saccharomyces cerevisiae* |
| sucC | NP_415256.1 | 16128703 | *Escherichia coli* |
| sucD | AAC73823.1 | 1786949 | *Escherichia coli* |

Alpha-ketoglutarate:ferredoxin oxidoreductase (EC 1.2.7.3), also known as 2-oxoglutarate synthase or 2-oxoglutarate:ferredoxin oxidoreductase (OFOR), forms alpha-ketoglutarate from $CO_2$ and succinyl-CoA with concurrent consumption of two reduced ferredoxin equivalents. OFOR and pyruvate:ferredoxin oxidoreductase (PFOR) are members of a diverse family of 2-oxoacid:ferredoxin (flavodoxin) oxidoreductases which utilize thiamine pyrophosphate, CoA and iron-sulfur clusters as cofactors and ferredoxin, flavodoxin and FAD as electron carriers (Adams et al., *Archaea. Adv. Protein Chem.* 48:101-180 (1996)). Enzymes in this class are reversible and function in the carboxylation direction in organisms that fix carbon by the RTCA cycle such as *Hydrogenobacter thermophilus, Desulfobacter hydrogenophilus* and *Chlorobium* species (Shiba et al. 1985; Evans et al., *Proc. Natl. Acad. Sci. U.S.A.* 55:92934 (1966); Buchanan, 1971). The two-subunit enzyme from *H. thermophilus*, encoded by korAB, has been cloned and expressed in *E. coli* (Yun et al., *Biochem. Biophys. Res. Commun.* 282:589-594 (2001)). A five subunit OFOR from the same organism with strict substrate specificity for succinyl-CoA, encoded by forDABGE, was recently identified and expressed in *E. coli* (Yun et al., *Biochem. Biophys. Res. Commun.* 292:280-286 (2002)). The kinetics of CO2 fixation of both *H. thermophilus* OFOR enzymes have been characterized (Yamamoto et al., *Extremophiles* 14:79-85 (2010)). A CO2-fixing OFOR from *Chlorobium thiosulfatophilum* has been purified and characterized but the genes encoding this enzyme have not been identified to date. Enzyme candidates in *Chlorobium* species can be inferred by sequence similarity to the *H. thermophilus* genes. For example, the *Chlorobium limicola* genome encodes two similar proteins. Acetogenic bacteria such as *Moorella thermoacetica* are predicted to encode two OFOR enzymes. The enzyme encoded by Moth_0034 is predicted to function in the CO2-assimilating direction. The genes associated with this enzyme, Moth_0034 have not been experimentally validated to date but can be inferred by sequence similarity to known OFOR enzymes.

OFOR enzymes that function in the decarboxylation direction under physiological conditions can also catalyze the reverse reaction. The OFOR from the thermoacidophilic archaeon *Sulfolobus* sp. strain 7, encoded by ST2300, has been extensively studied (Zhang et al., supra, 1996). A plasmid-based expression system has been developed for efficiently expressing this protein in *E. coli* (Fukuda et al., *Eur. J. Biochem.* 268:5639-5646 (2001)) and residues involved in substrate specificity were determined (Fukuda and Wakagi, *Biochim. Biophys. Acta* 1597:74-80 (2002)). The OFOR encoded by Ape1472/Ape1473 from *Aeropyrum pernix* str. K1 was recently cloned into *E. coli*, characterized, and found to react with 2-oxoglutarate and a broad range of 2-oxoacids (Nishizawa et al., *FEBS Lett.* 579:2319-2322 (2005)). Another exemplary OFOR is encoded by oorDABC in *Helicobacter pylori* (Hughes et al., *J. Bacteriol.* 180:1119-1128 (1998)). An enzyme specific to alpha-ketoglutarate has been reported in *Thauera aromatics* (Dorner and Boll, *J. Bacteriol.* 184 (14), 3975-83 (2002)). A similar enzyme can be found in *Rhodospirillum rubrum* by sequence homology. A two subunit enzyme has also been identified in *Chlorobium tepidum* (Eisen et al., *Proc. Natl. Acad. Sci. USA* 99(14): 9509-9514 (2002)).

| Protein | GenBank ID | GI Number | Organism |
|---|---|---|---|
| korA | BAB21494 | 12583691 | *Hydrogenobacter thermophilus* |
| korB | BAB21495 | 12583692 | *Hydrogenobacter thermophilus* |
| forD | BAB62132.1 | 14970994 | *Hydrogenobacter thermophilus* |
| forA | BAB62133.1 | 14970995 | *Hydrogenobacter thermophilus* |
| forB | BAB62134.1 | 14970996 | *Hydrogenobacter thermophilus* |
| forG | BAB62135.1 | 14970997 | *Hydrogenobacter thermophilus* |
| forE | BAB62136.1 | 14970998 | *Hydrogenobacter thermophilus* |
| Clim_0204 | ACD89303.1 | 189339900 | *Chlorobium limicola* |
| Clim_0205 | ACD89302.1 | 189339899 | *Chlorobium limicola* |
| Clim_1123 | ACD90192.1 | 189340789 | *Chlorobium limicola* |
| Clim_1124 | ACD90193.1 | 189340790 | *Chlorobium limicola* |
| Moth_1984 | YP 430825.1 | 83590816 | *Moorella thermoacetica* |
| Moth_1985 | YP 430826.1 | 83590817 | *Moorella thermoacetica* |
| Moth_0034 | YP 428917.1 | 83588908 | *Moorella thermoacetica* |
| ST2300 | NP_378302.1 | 15922633 | *Sulfolobus sp. strain 7* |
| Ape1472 | BAA80470.1 | 5105156 | *Aeropyrum pernix* |
| Ape1 473 | BAA80471.2 | 116062794 | *Aeropyrum pernix* |
| oorD | NP_207383.1 | 15645213 | *Helicobacter pylori* |
| oorA | NP_207384.1 | 15645214 | *Helicobacter pylori* |
| oorB | NP_207385.1 | 15645215 | *Helicobacter pylori* |
| oorC | NP_207386.1 | 15645216 | *Helicobacter pylori* |
| CT0163 | NP_661069.1 | 21673004 | *Chlorobium tepidum* |
| CT0162 | NP_661068.1 | 21673003 | *Chlorobium tepidum* |
| korA | CAA12243.2 | 19571179 | *Thauera aromatics* |
| korB | CAD27440.1 | 19571178 | *Thauera aromatics* |
| Rru_A2721 | YP_427805.1 | 83594053 | *Rhodospirillum rubrum* |
| Rru_A2722 | YP_427806.1 | 83594054 | *Rhodospirillum rubrum* |

Isocitrate dehydrogenase catalyzes the reversible decarboxylation of isocitrate to 2-oxoglutarate coupled to the reduction of $NAD(P)^+$. IDH enzymes in *Saccharomyces cerevisiae* and *Escherichia coli* are encoded by IDP1 and icd, respectively (Haselbeck and McAlister-Henn, *J. Biol. Chem.* 266:2339-2345 (1991); Nimmo, *Biochem. J.* 234:317-2332 (1986)). The reverse reaction in the reductive TCA cycle, the reductive carboxylation of 2-oxoglutarate to isocitrate, is favored by the NADPH-dependent $CO_2$-fixing IDH from *Chlorobium limicola* and was functionally expressed in *E. coli* (Kanao et al., *Eur. J. Biochem.* 269:1926-1931 (2002)). A similar enzyme with 95% sequence identity is found in the *C. tepidum* genome in addition to some other candidates listed below.

| Protein | GenBank ID | GI Number | Organism |
|---|---|---|---|
| Icd | ACI84720.1 | 209772816 | *Escherichia coli* |
| IDP1 | AAA34703.1 | 171749 | *Saccharomyces cerevisiae* |
| Idh | BAC00856.1 | 21396513 | *Chlorobium limicola* |
| Icd | AAM71597.1 | 21646271 | *Chlorobium tepidum* |
| icd | NP_952516.1 | 39996565 | *Geobacter sulfurreducens* |
| icd | YP_393560. | 78777245 | *Sulfurimonas denitrificans* |

In *H. thermophilus* the reductive carboxylation of 2-oxoglutarate to isocitrate is catalyzed by two enzymes: 2-oxoglutarate carboxylase and oxalosuccinate reductase. 2-Oxoglutarate carboxylase (EC 6.4.1.7) catalyzes the ATP-dependent carboxylation of alpha-ketoglutarate to oxalosuccinate (Aoshima and Igarashi, *Mol. Microbiol.* 62:748-759 (2006)). This enzyme is a large complex composed of two subunits. Biotinylation of the large (A) subunit is required for enzyme function (Aoshima et al., *Mol. Microbiol.* 51:791-798 (2004)). Oxalosuccinate reductase (EC 1.1.1.-) catalyzes the NAD-dependent conversion of oxalosuccinate to D-threo-isocitrate. The enzyme is a homodimer encoded by icd in *H. thermophilus*. The kinetic parameters of this enzyme indicate that the enzyme only operates in the reductive carboxylation direction in vivo, in contrast to isocitrate dehydrogenase enzymes in other organisms (Aoshima and Igarashi, *J. Bacteriol.* 190:2050-2055 (2008)). Based on sequence homology, gene candidates have also been found in *Thiobacillus denitrificans* and *Thermocrinis albus*.

| Protein | GenBank ID | GI Number | Organism |
|---|---|---|---|
| cfiA | BAF34932.1 | 116234991 | Hydrogenobacter thermophilus |
| cfiB | BAF34931.1 | 116234990 | Hydrogenobacter thermophilus |
| Icd | BAD02487.1 | 38602676 | Hydrogenobacter thermophilus |
| Tbd_1556 | YP_315314 | 74317574 | Thiobacillus denitrificans |
| Tbd_1555 | YP_315313 | 74317573 | Thiobacillus denitrificans |
| Tbd_0854 | YP_314612 | 74316872 | Thiobacillus denitrificans |
| Thal_0268 | YP_003473030 | 289548042 | Thermocrinis albus |
| Thal_0267 | YP_003473029 | 289548041 | Thermocrinis albus |
| Thal_0646 | YP_003473406 | 289548418 | Thermocrinis albus |

Aconitase (EC 4.2.1.3) is an iron-sulfur-containing protein catalyzing the reversible isomerization of citrate and isocitrate via the intermediate cis-aconitate. Two aconitase enzymes are encoded in the *E. coli* genome by acnA and acnB. AcnB is the main catabolic enzyme, while AcnA is more stable and appears to be active under conditions of oxidative or acid stress (Cunningham et al., *Microbiology* 143 (Pt 12):3795-3805 (1997)). Two isozymes of aconitase in *Salmonella typhimurium* are encoded by acnA and acnB (Horswill and Escalante-Semerena, *Biochemistry* 40:4703-4713 (2001)). The *S. cerevisiae* aconitase, encoded by ACO1, is localized to the mitochondria where it participates in the TCA cycle (Gangloff et al., *Mol. Cell. Biol.* 10:3551-3561 (1990)) and the cytosol where it participates in the glyoxylate shunt (Regev-Rudzki et al., *Mol. Biol. Cell.* 16:4163-4171 (2005)).

| Protein | GenBank ID | GI Number | Organism |
|---|---|---|---|
| acnA | AAC7438.1 | 1787531 | Escherichia coli |
| acnB | AAC73229.1 | 2367097 | Escherichia coli |
| acnA | NP_460671.1 | 16765056 | Salmonella typhimurium |
| HP0779 | NP_207572.1 | 15645398 | Helicobacter pylori 26695 |
| H16_B0568 | CAJ95365.1 | 113529018 | Ralstonia eutropha |
| DesfrDRAFT_3783 | ZP_07335307.1 | 303249064 | Desulfovibrio fructosovorans JJ |
| Suden_1040 (acnB) | ABB44318.1 | 78497778 | Sulfurimonas denitrificans |
| Hydth_0755 | AD045152.1 | 308751669 | Hydrogenobacter thermophilus |
| CT0543 (acn) | AAM71785.1 | 21646475 | Chlorobium tepidum |
| Clim_2436 | YP_001944436.1 | 189347907 | Chlorobium limicola |
| Clim_0515 | ACD89607.1 | 189340204 | Chlorobium limicola |
| acnB | NP_459163.1 | 16763548 | Salmonella typhimurium |
| ACO1 | AAA34389.1 | 170982 | Saccharomyces cerevisiae |

Pyruvate:ferredoxin oxidoreductase (PFOR) catalyzes the reversible oxidation of pyruvate to form acetyl-CoA. The PFOR from *Desulfovibrio africanus* has been cloned and expressed in *E. coli* resulting in an active recombinant enzyme that was stable for several days in the presence of oxygen (Pieulle et al., *J. Bacteriol.* 179:5684-5692 (1997)). Oxygen stability is relatively uncommon in PFORs and is believed to be conferred by a 60 residue extension in the polypeptide chain of the *D. africanus* enzyme. Two cysteine residues in this enzyme form a disulfide bond that protects it against inactivation in the form of oxygen. This disulfide bond and the stability in the presence of oxygen has been found in other *Desulfovibrio* species also (Vita et al., Biochemistry, 47: 957-64 (2008)). The *M. thermoacetica* PFOR is also well characterized (Menon and Ragsdale, *Biochemistry* 36:8484-8494 (1997)) and was shown to have high activity in the direction of pyruvate synthesis during autotrophic growth (Furdui and Ragsdale, *J. Biol. Chem.* 275:28494-28499 (2000)). Further, *E. coli* possesses an uncharacterized open reading frame, ydbK, encoding a protein that is 51% identical to the *M. thermoacetica* PFOR. Evidence for pyruvate oxidoreductase activity in *E. coli* has been described (Blaschkowski et al., *Eur. J. Biochem.* 123:563-569 (1982)). PFORs have also been described in other organisms, including *Rhodobacter capsulatas* (Yakunin and Hallenbeck, Biochimica et Biophysica Acta 1409 (1998) 39-49 (1998)) and *Choloboum tepidum* (Eisen et al., *Proc. Natl. Acad. Sci. USA* 99(14): 9509-14 (2002)). The five subunit PFOR from *H. thermophilus*, encoded by porEDABG, was cloned into *E. coli* and shown to function in both the decarboxylating and $CO_2$-assimilating directions (Ikeda et al., *Biochem. Biophys. Res. Commun.* 340:76-82 (2006) 2006; Yamamoto et al., *Extremophiles* 14:79-85 (2010)). Homologs also exist in *C. carboxidivorans* P7. Several additional PFOR enzymes are described in the following review (Ragsdale, S. W., *Chem. Rev.* 103:2333-2346 (2003)). Finally, flavodoxin reductases (e.g., fqrB from *Helicobacter pylori* or *Campylobacter jejuni*) (St Maurice et al., *J. Bacteriol.* 189:4764-4773 (2007)) or Rnf-type proteins (Seedorf et al., *Proc. Natl. Acad. Sci. U.S.A.* 105:2128-2133 (2008); and Herrmann, *J. Bacteriol* 190:784-791 (2008)) provide a means to generate NADH or NADPH from the reduced ferredoxin generated by PFOR. These proteins are identified below.

| Protein | GenBank ID | GI Number | Organism |
|---|---|---|---|
| DesfrDRAFT_0121 | ZP_07331646.1 | 303245362 | Desulfovibrio fructosovorans JJ |
| Por | CAA70873.1 | 1770208 | Desulfovibrio africanus |
| por | YP_012236.1 | 46581428 | Desulfovibrio vulgaris str. Hildenborough |
| Dde 3237 | ABB40031.1 | 78220682 | DesulfoVibrio desulfuricans G20 |
| Ddes 0298 | YP_002478891.1 | 220903579 | Desulfovibrio desulfuricans subsp. desulfuricans str. ATCC 27774 |
| Por | YP_428946.1 | 83588937 | Moorella thermoacetica |
| YdbK | NP_415896.1 | 16129339 | Escherichia coli |
| nifJ (CT1628) | NP_662511.1 | 21674446 | Chlorobium tepidum |
| CJE1649 | YP_179630.1 | 57238499 | Campylobacter jejuni |
| nifJ | ADE85473.1 | 294476085 | Rhodobacter capsulatus |
| porE | BAA95603.1 | 7768912 | Hydrogenobacter thermophilus |
| porD | BAA95604.1 | 7768913 | Hydrogenobacter thermophilus |
| porA | BAA95605.1 | 7768914 | Hydrogenobacter thermophilus |
| porB | BAA95606.1 | 776891 | Hydrogenobacter thermophilus |
| porG | BAA95607.1 | 7768916 | Hydrogenobacter thermophilus |
| FqrB | YP_001482096.1 | 157414840 | Campylobacter jejuni |
| HP1164 | NP_207955.1 | 15645778 | Helicobacter pylori |
| RnfC | EDK33306.1 | 146346770 | Clostridium kluyveri |
| RnfD | EDK33307.1 | 146346771 | Clostridium kluyveri |
| RnfG | EDK33308.1 | 146346772 | Clostridium kluyveri |
| RnfE | EDK33309.1 | 146346773 | Clostridium kluyveri |
| RnfA | EDK33310.1 | 146346774 | Clostridium kluyveri |
| RnfB | EDK33311.1 | 146346775 | Clostridium kluyveri |

The conversion of pyruvate into acetyl-CoA can be catalyzed by several other enzymes or their combinations thereof. For example, pyruvate dehydrogenase can transform pyruvate into acetyl-CoA with the concomitant reduction of a molecule of NAD into NADH. It is a multi-enzyme complex that catalyzes a series of partial reactions which results in acylating oxidative decarboxylation of pyruvate. The enzyme comprises of three subunits: the pyruvate decarboxylase (E1), dihydrolipoamide acyltransferase (E2) and dihydrolipoamide dehydrogenase (E3). This enzyme is naturally present in several organisms, including *E. coli* and *S. cerevisiae*. In the *E. coli* enzyme, specific residues in the E1 component are responsible for substrate specificity (Bisswanger, J. Biol. Chem. 256:815-82 (1981); Bremer, Eur. J. Biochem. 8:535-540 (1969); Gong et al., J. Biol. Chem. 275:13645-13653 (2000)). Enzyme engineering efforts have improved the *E. coli* PDH enzyme activity under anaerobic conditions (Kim et al., J. Bacteriol. 190:3851-3858 (2008); Kim et al., Appl. Environ. Microbiol. 73:1766-1771 (2007); Zhou et al., Biotechnol. Lett. 30:335-342 (2008)). In contrast to the *E. coli* PDH, the *B. subtilis* complex is active and required for growth under anaerobic conditions (Nakano et al., *J. Bacteriol.* 179: 6749-6755 (1997)). The *Klebsiella pneumoniae* PDH, characterized during growth on glycerol, is also active under anaerobic conditions (5). Crystal structures of the enzyme complex from bovine kidney (18) and the E2 catalytic domain from *Azotobacter vinelandii* are available (4). Yet another enzyme that can catalyze this conversion is pyruvate formate lyase. This enzyme catalyzes the conversion of pyruvate and CoA into acetyl-CoA and formate. Pyruvate formate lyase is a common enzyme in prokaryotic organisms that is used to help modulate anaerobic redox balance. Exemplary enzymes can be found in *Escherichia coli* encoded by pflB (Knappe and Sawers, FEMS. Microbiol Rev. 6:383-398 (1990)), *Lactococcus lactis* (Melchiorsen et al., Appl Microbiol Biotechnol 58:338-344 (2002)), and *Streptococcus mutans* (Takahashi-Abbe et al., Oral. Microbiol Immunol. 18:293-297 (2003)). *E. coli* possesses an additional pyruvate formate lyase, encoded by tdcE, that catalyzes the conversion of pyruvate or 2-oxobutanoate to acetyl-CoA or propionyl-CoA, respectively (Hesslinger et al., Mol. Microbiol 27:477-492 (1998)). Both pflB and tdcE from *E. coli* require the presence of pyruvate formate lyase activating enzyme, encoded by pflA. Further, a short protein encoded by yfiD in *E. coli* can associate with and restore activity to oxygen-cleaved pyruvate formate lyase (Vey et al., Proc. Natl. Acad. Sci. U.S.A. 105:16137-16141 (2008). Note that pflA and pflB from *E. coli* were expressed in *S. cerevisiae* as a means to increase cytosolic acetyl-CoA for butanol production as described in WO/2008/080124. Additional pyruvate formate lyase and activating enzyme candidates, encoded by pfl and act, respectively, are found in *Clostridium pasteurianum* (Weidner et al., J Bacteriol. 178:2440-2444 (1996)).

Further, different enzymes can be used in combination to convert pyruvate into acetyl-CoA. For example, in *S. cerevisiae*, acetyl-CoA is obtained in the cytosol by first decarboxylating pyruvate to form acetaldehyde; the latter is oxidized to acetate by acetaldehyde dehydrogenase and subsequently activated to form acetyl-CoA by acetyl-CoA synthetase. Acetyl-CoA synthetase is a native enzyme in several other organisms including *E. coli* (Kumari et al., J. Bacteriol. 177: 2878-2886 (1995)), *Salmonella enterica* (Starai et al., Microbiology 151:3793-3801 (2005); Starai et al., J. Biol. Chem. 280:26200-26205 (2005)), and *Moorella thermoacetica* (described already). Alternatively, acetate can be activated to form acetyl-CoA by acetate kinase and phosphotransacetylase. Acetate kinase first converts acetate into acetyl-phosphate with the accompanying use of an ATP molecule. Acetyl-phosphate and CoA are next converted into acetyl-CoA with the release of one phosphate by phosphotransacetylase. Both acetate kinase and phosphotransacetlyase are well-studied enzymes in several *Clostridia* and *Methanosarcina thermophila*.

Yet another way of converting pyruvate to acetyl-CoA is via pyruvate oxidase. Pyruvate oxidase converts pyruvate into acetate, using ubiquione as the electron acceptor. In *E. coli*, this activity is encoded by poxB. PoxB has similarity to pyruvate decarboxylase of *S. cerevisiae* and *Zymomonas mobilis*. The enzyme has a thiamin pyrophosphate cofactor (Koland and Gennis, Biochemistry 21:4438-4442 (1982)); O'Brien et al., Biochemistry 16:3105-3109 (1977); O'Brien and Gennis, J. Biol. Chem. 255:3302-3307 (1980)) and a flavin adenine dinucleotide (FAD) cofactor. Acetate can then be converted into acetyl-CoA by either acetyl-CoA synthetase or by acetate kinase and phosphotransacetylase, as described earlier. Some of these enzymes can also catalyze the reverse reaction from acetyl-CoA to pyruvate.

For enzymes that use reducing equivalents in the form of NADH or NADPH, these reduced carriers can be generated by transferring electrons from reduced ferredoxin. Two enzymes catalyze the reversible transfer of electrons from reduced ferredoxins to $NAD(P)^+$, ferredoxin:$NAD^+$ oxidoreductase (EC 1.18.1.3) and ferredoxin:$NADP^+$ oxidoreductase (FNR, EC 1.18.1.2). Ferredoxin:$NADP^+$ oxidoreductase (FNR, EC 1.18.1.2) has a noncovalently bound FAD cofactor that facilitates the reversible transfer of electrons from NADPH to low-potential acceptors such as ferredoxins or flavodoxins (Blaschkowski et al., *Eur. J. Biochem.* 123:563-569 (1982); Fujii et al., 1977). The *Helicobacter pylori* FNR, encoded by HP1164 (fqrB), is coupled to the activity of pyruvate:ferredoxin oxidoreductase (PFOR) resulting in the pyruvate-dependent production of NADPH (St. Maurice et al., *J Bacteriol.* 189(13):4764-4773 (2007)). An analogous enzyme is found in *Campylobacter jejuni* (St. Maurice et al., supra, 2007). A ferredoxin:$NADP^+$ oxidoreductase enzyme is encoded in the *E. coli* genome by fpr (Bianchi et al., *J Bacteriol.* 175:1590-1595 (1993)). Ferredoxin:$NAD^+$ oxidoreductase utilizes reduced ferredoxin to generate NADH from $NAD^+$. In several organisms, including *E. coli*, this enzyme is a component of multifunctional dioxygenase enzyme complexes. The ferredoxin:$NAD^+$ oxidoreductase of *E. coli*, encoded by hcaD, is a component of the 3-phenylproppionate dioxygenase system involved in involved in aromatic acid utilization (Diaz et al., *J. Bacteriol.* 180:2915-2923 (1998)). NADH:ferredoxin reductase activity was detected in cell extracts of *Hydrogenobacter thermophilus* strain TK-6, although a gene with this activity has not yet been indicated (Yoon et al. 2006). NADP oxidoreductase of *C. kluyveri*, encoded by nfnAB, catalyzes the concomitant reduction of ferredoxin and NAD+ with two equivalents of NADPH (Wang et al, *J. Bacteriol.* 192: 5115-5123 (2010)). Finally, the energy-conserving membrane-associated Rnf-type proteins (Seedorf et al., *Proc. Natl. Acad. Sci. U.S.A.* 105:2128-2133 (2008); Herrmann et al., *J. Bacteriol.* 190: 784-791 (2008)) provide a means to generate NADH or NADPH from reduced ferredoxin. Additional ferredoxin:NAD(P)+ oxidoreductases have been annotated in *Clostridium carboxydivorans* P7 and *Clostridium ljungdahli*.

| Protein | GenBank ID | GI Number | Organism |
|---|---|---|---|
| HP1164 | NP_207955.1 | 15645778 | Helicobacter pylori |
| RPA3954 | CAE29395.1 | 39650872 | Rhodopseudomonas palustris |
| fpr | BAH29712.1 | 225320633 | Hydrogenobacter thermophilus |
| yumC | NP_391091.2 | 255767736 | Bacillus subtilis |
| CJE0663 | AAW35824.1 | 57167045 | Campylobacter jejuni |
| fpr | P28861.4 | 399486 | Escherichia coli |
| hcaD | AAC75595.1 | 1788892 | Escherichia coli |
| LOC100282643 | NP_001149023.1 | 226497434 | Zea mays |
| NfnA | YP_001393861.1 | 153953096 | Clostridium kluyveri |
| NfnB | YP_001393862.1 | 153953097 | Clostridium kluyveri |
| RnfC | EDK33306.1 | 146346770 | Clostridium kluyveri |
| RnfD | EDK33307.1 | 146346771 | Clostridium kluyveri |
| RnfG | EDK33308.1 | 146346772 | Clostridium kluyveri |
| RnfE | EDK33309.1 | 146346773 | Clostridium kluyveri |
| RnfA | EDK33310.1 | 146346774 | Clostridium kluyveri |
| RnfB | EDK33311.1 | 146346775 | Clostridium kluyveri |
| CcarbDRAFT_2639 | ZP_05392639.1 | 255525707 | Clostridium carboxidivorans P7 |
| CcarbDRAFT_2638 | ZP_05392638.1 | 255525706 | Clostridium carboxidivorans P7 |
| CcarbDRAFT_2636 | ZP_05392636.1 | 255525704 | Clostridium carboxidivorans P7 |
| CcarbDRAFT_5060 | ZP_05395060.1 | 255528241 | Clostridium carboxidivorans P7 |
| CcarbDRAFT_2450 | ZP_05392450.1 | 255525514 | Clostridium carboxidivorans P7 |
| CcarbDRAFT_1084 | ZP_05391084.1 | 255524124 | Clostridium carboxidivorans P7 |
| CLJU_c11410 (RnfB) | ADK14209.1 | 300434442 | Clostridium ljungdahli |
| CLJU_c11400 (RnfA) | ADK14208.1 | 300434441 | Clostridium ljungdahli |
| CLJU_c11390 (RnfE) | ADK14207.1 | 300434440 | Clostridium ljungdahli |
| CLJU_c11380 (RnfG) | ADK14206.1 | 300434439 | Clostridium ljungdahli |
| CLJU_c11370 (RnfD) | ADK14205.1 | 300434438 | Clostridium ljungdahli |
| CLJU_c11360 (RnfC) | ADK14204.1 | 300434437 | Clostridium ljungdahli |

Ferredoxins are small acidic proteins containing one or more iron-sulfur clusters that function as intracellular electron carriers with a low reduction potential. Reduced ferredoxins donate electrons to Fe-dependent enzymes such as ferredoxin-NADP$^+$ oxidoreductase, pyruvate:ferredoxin oxidoreductase (PFOR) and 2-oxoglutarate:ferredoxin oxidoreductase (OFOR). The H. thermophilus gene fdx1 encodes a [4Fe-4S]-type ferredoxin that is required for the reversible carboxylation of 2-oxoglutarate and pyruvate by OFOR and PFOR, respectively (Yamamoto et al., Extremophiles 14:79-85 (2010)). The ferredoxin associated with the Sulfolobus solfataricus 2-oxoacid:ferredoxin reductase is a monomeric dicluster [3Fe-4S][4Fe-4S] type ferredoxin (Park et al., J Biochem Mol Biol. 39:46-54 (2006)). While the gene associated with this protein has not been fully sequenced, the N-terminal domain shares 93% homology with the zfx ferredoxin from S. acidocaldarius. The E. coli genome encodes a soluble ferredoxin of unknown physiological function, fdx. Some evidence indicates that this protein can function in iron-sulfur cluster assembly (Takahashi and Nakamura, J Biochem. 126:917-926 (1999)). Additional ferredoxin proteins have been characterized in Helicobacter pylori (Mukhopadhyay et al., J Bacteriol. 185:2927-2935 (2003)) and Campylobacter jejuni (van Vliet et al., FEMS Microbiol Lett. 196:189-193 (2001)). A 2Fe-2S ferredoxin from Clostridium pasteurianum has been cloned and expressed in E. coli (Fujinaga and Meyer, Biochemical and Biophysical Research Communications, 192(3):1115-1122 (1993)). Acetogenic bacteria such as Moorella thermoacetica, Clostridium carboxidivorans P7, Clostridium ljungdahli and Rhodospirillum rubrum are predicted to encode several ferredoxins, listed in the table below.

| Protein | GenBank ID | GI Number | Organism |
|---|---|---|---|
| fdx1 | BAE02673.1 | 68163284 | Hydrogenobacter thermophilus |
| M11214.1 | AAA83524.1 | 144806 | Clostridium pasteurianum |
| Zfx | AAY79867.1 | 68566938 | Sulfolobus acidocalarius |
| Fdx | AAC75578.1 | 1788874 | Escherichia coli |
| hp_0277 | AAD07340.1 | 2313367 | Helicobacter pylori |
| fdxA | CAL34484.1 | 112359698 | Campylobacter jejuni |
| Moth_0061 | ABC18400.1 | 83571848 | Moorella thermoacetica |
| Moth_1200 | ABC19514.1 | 83572962 | Moorella thermoacetica |
| Moth_1888 | ABC20188.1 | 83573636 | Moorella thermoacetica |
| Moth_2112 | ABC20404.1 | 83573852 | Moorella thermoacetica |
| Moth_1037 | ABC19351.1 | 83572799 | Moorella thermoacetica |
| CcarbDRAFT_4383 | ZP_5394383.1 | 255527515 | Clostridium carboxidivorans P7 |
| CcarbDRAFT_2958 | ZP_05392958.1 | 255526034 | Clostridium carboxidivorans P7 |
| CcarbDRAFT_2281 | ZP_05392281.1 | 255525342 | Clostridium carboxidivorans P7 |
| CcarbDRAFT_5296 | ZP_05395295.1 | 255528511 | Clostridium carboxidivorans P7 |
| CcarbDRAFT_1615 | ZP_05391615.1 | 255524662 | Clostridium carboxidivorans P7 |
| CcarbDRAFT_1304 | ZP_05391304.1 | 255524347 | Clostridium carboxidivorans P7 |
| cooF | AAG29808.1 | 11095245 | Carboxydothermus hydrogenoformans |
| fdxN | CAA35699.1 | 46143 | Rhodobacter capsulatus |
| Rru_A2264 | ABC23064.1 | 83576513 | Rhodospirillum rubrum |
| Rru_A1916 | ABC22716.1 | 83576165 | Rhodospirillum rubrum |
| Rru_A2026 | ABC22826.1 | 83576275 | Rhodospirillum rubrum |
| cooF | AAC45122.1 | 1498747 | Rhodospirillum rubrum |
| fdxN | AAA26460.1 | 152605 | Rhodospirillum rubrum |
| Alvin_2884 | ADC63789.1 | 288897953 | Allochromatium vinosum DSM 180 |
| fdx | YP_002801146.1 | 226946073 | Azotobacter vinelandii DJ |
| CKL_3790 | YP_001397146.1 | 153956381 | Clostridium kluyveri DSM 555 |
| fer1 | NP_949965.1 | 39937689 | Rhodopseudomonas palustris CGA009 |
| fdx | CAA12251.1 | 3724172 | Thauera aromatics |

| Protein | GenBank ID | GI Number | Organism |
| --- | --- | --- | --- |
| CHY_2405 | YP_361202.1 | 78044690 | Carboxydothermus hydrogenoformans |
| fer | YP_359966.1 | 78045103 | Carboxydothermus hydrogenoformans |
| fer | AAC83945.1 | 1146198 | Bacillus subtilis |
| fdx1 | NP_249053.1 | 15595559 | Pseudomonas aeruginosa PA01 |
| yfhL | AP_003148.1 | 89109368 | Escherichia coli K-12 |
| CLJU_c00930 | ADK13195.1 | 300433428 | Clostridium ljungdahli |
| CLJU_c00010 | ADK13115.1 | 300433348 | Clostridium ljungdahli |
| CLJU_c01820 | ADK13272.1 | 300433505 | Clostridium ljungdahli |
| CLJU_c17980 | ADK14861.1 | 300435094 | Clostridium ljungdahli |
| CLJU_c17970 | ADK14860.1 | 300435093 | Clostridium ljungdahli |
| CLJU_c22510 | ADK15311.1 | 300435544 | Clostridium ljungdahli |
| CLJU_c26680 | ADK15726.1 | 300435959 | Clostridium ljungdahli |
| CLJU_c29400 | ADK15988.1 | 300436221 | Clostridium ljungdahli |

Succinyl-CoA transferase catalyzes the conversion of succinyl-CoA to succinate while transferring the CoA moiety to a CoA acceptor molecule. Many transferases have broad specificity and can utilize CoA acceptors as diverse as acetate, succinate, propionate, butyrate, 2-methylacetoacetate, 3-ketohexanoate, 3-ketopentanoate, valerate, crotonate, 3-mercaptopropionate, propionate, vinylacetate, and butyrate, among others.

The conversion of succinate to succinyl-CoA can be carried by a transferase which does not require the direct consumption of an ATP or GTP. This type of reaction is common in a number of organisms. The conversion of succinate to succinyl-CoA can also be catalyzed by succinyl-CoA:Acetyl-CoA transferase. The gene product of cat1 of *Clostridium kluyveri* has been shown to exhibit succinyl-CoA:acetyl-CoA transferase activity (Sohling and Gottschalk, *J. Bacteriol.* 178:871-880 (1996)). In addition, the activity is present in *Trichomonas vaginalis* (van Grinsven et al., *J Biol Chem.* 283:1411-1418 (2008)) and *Trypanosoma brucei* (Riviere et al., *J. Biol. Chem.* 279(44):45337-45346 (2004)). The succinyl-CoA:acetate CoA-transferase from *Acetobacter aceti*, encoded by aarC, replaces succinyl-CoA synthetase in a variant TCA cycle (Mullins et al., *J. Bacteriol.* 190(14):4933-4940 (2008)). Similar succinyl-CoA transferase activities are also present in *Trichomonas vaginalis* (van Grinsven et al., supra, 2008), *Trypanosoma brucei* (Riviere et al., supra, 2004) and *Clostridium kluyveri* (Sohling and Gottschalk, supra, 1996). The beta-ketoadipate:succinyl-CoA transferase encoded by pcaI and pcaJ in *Pseudomonas putida* is yet another candidate (Kaschabek et al., *J. Bacteriol.* 184(1):207-215 (2002)). The aforementioned proteins are identified below.

| Protein | GenBank ID | GI Number | Organism |
| --- | --- | --- | --- |
| cat1 | P38946.1 | 729048 | Clostridium kluyveri |
| TVAG_395550 | XP_001330176 | 123975034 | Trichomonas vaginalis G3 |
| Tb11.02.0290 | XP_828352 | 71754875 | Trypanosoma brucei |
| pcaI | AAN69545.1 | 24985644 | Pseudomonas putida |
| pcaJ | NP_746082.1 | 26990657 | Pseudomonas putida |
| aarC | ACD85596.1 | 189233555 | Acetobacter aceti |

An additional exemplary transferase that converts succinate to succinyl-CoA while converting a 3-ketoacyl-CoA to a 3-ketoacid is succinyl-CoA:3:ketoacid-CoA transferase (EC 2.8.3.5). Exemplary succinyl-CoA:3:ketoacid-CoA transferases are present in *Helicobacter pylori* (Corthesy-Theulaz et al., *J. Biol. Chem.* 272(41):25659-25667 (1997)), *Bacillus subtilis*, and *Homo sapiens* (Fukao et al., *Genomics* 68(2): 144-151 (2000); Tanaka et al., *Mol. Hum. Reprod.* 8(1):16-23 (2002)). The aforementioned proteins are identified below.

| Protein | GenBank ID | GI Number | Organism |
| --- | --- | --- | --- |
| HPAG1_0676 | YP_627417 | 108563101 | Helicobacter pylori |
| HPAG1_0677 | YP_627418 | 108563102 | Helicobacter pylori |
| ScoA | NP_391778 | 16080950 | Bacillus subtilis |
| ScoB | NP_391777 | 16080949 | Bacillus subtilis |
| OXCT1 | NP_000427 | 4557817 | Homo sapiens |
| OXCT2 | NP_071403 | 11545841 | Homo sapiens |

Converting succinate to succinyl-CoA by succinyl-CoA:3:ketoacid-CoA transferase requires the simultaneous conversion of a 3-ketoacyl-CoA such as acetoacetyl-CoA to a 3-ketoacid such as acetoacetate. Conversion of a 3-ketoacid back to a 3-ketoacyl-CoA can be catalyzed by an acetoacetyl-CoA:acetate:CoA transferase. Acetoacetyl-CoA:acetate:CoA transferase converts acetoacetyl-CoA and acetate to acetoacetate and acetyl-CoA, or vice versa. Exemplary enzymes include the gene products of atoAD from *E. coli* (Hanai et al., *Appl Environ Microbiol* 73:7814-7818 (2007), ctfAB from *C. acetobutylicum* (Jojima et al., *Appl Microbiol Biotechnol* 77:1219-1224 (2008), and ctfAB from *Clostridium saccharoperbutylacetonicum* (Kosaka et al., *Biosci. Biotechnol Biochem.* 71:58-68 (2007)) are shown below.

| Protein | GenBank ID | GI Number | Organism |
| --- | --- | --- | --- |
| AtoA | NP_416726.1 | 2492994 | Escherichia coli |
| AtoD | NP_416725.1 | 2492990 | Escherichia coli |
| CtfA | NP_149326.1 | 15004866 | Clostridium acetobutylicum |
| CtfB | NP_149327.1 | 15004867 | Clostridium acetobutylicum |
| CtfA | AAP42564.1 | 31075384 | Clostridium saccharoperbutylacetonicum |
| CtfB | AAP42565.1 | 31075385 | Clostridium saccharoperbutylacetonicum |

Yet another possible CoA acceptor is benzylsuccinate. Succinyl-CoA:(R)-Benzylsuccinate CoA-Transferase functions as part of an anaerobic degradation pathway for toluene in organisms such as *Thauera aromatica* (Leutwein and Heider, *J. Bact.* 183(14) 4288-4295 (2001)). Homologs can be found in *Azoarcus* sp. T, *Aromatoleum aromaticum* EbN1, and *Geobacter metallireducens* GS-15. The aforementioned proteins are identified below.

| Protein | GenBank ID | GI Number | Organism |
| --- | --- | --- | --- |
| bbsE | AAF89840 | 9622535 | Thauera aromatics |
| Bbsf | AAF89841 | 9622536 | Thauera aromatics |
| bbsE | AAU45405.1 | 52421824 | Azoarcus sp. T |
| bbsF | AAU45406.1 | 52421825 | Azoarcus sp. T |

| Protein | GenBank ID | GI Number | Organism |
|---|---|---|---|
| bbsE | YP_158075.1 | 56476486 | *Aromatoleum aromaticum* EbN1 |
| bbsF | YP_158074.1 | 56476485 | *Aromatoleum aromaticum* EbN1 |
| Gmet_1521 | YP_384480.1 | 78222733 | *Geobacter metallireducens* GS-15 |
| Gmet_1522 | YP_384481.1 | 78222734 | *Geobacter metallireducens* GS-15 |

Additionally, ygfH encodes a propionyl CoA:succinate CoA transferase in *E. coli* (Haller et al., *Biochemistry*, 39(16) 4622-4629). Close homologs can be found in, for example, *Citrobacter youngae* ATCC 29220, *Salmonella enterica* subsp. *arizonae serovar*, and *Yersinia intermedia* ATCC 29909. The aforementioned proteins are identified below.

| Protein | GenBank ID | GI Number | Organism |
|---|---|---|---|
| ygfH | NP_417395.1 | 16130821 | *Escherichia coli* str. K-12 substr. MG1655 |
| CIT292_04485 | ZP_03838384.1 | 227334728 | *Citrobacter youngae* ATCC 29220 |
| SARI_04582 | YP_001573497.1 | 161506385 | *Salmonella enterica* subsp. *arizonae serovar* |
| yinte0001_14430 | ZP_04635364.1 | 238791727 | *Yersinia intermedia* ATCC 29909 |

Citrate lyase (EC 4.1.3.6) catalyzes a series of reactions resulting in the cleavage of citrate to acetate and oxaloacetate. The enzyme is active under anaerobic conditions and is composed of three subunits: an acyl-carrier protein (ACP, gamma), an ACP transferase (alpha), and a acyl lyase (beta). Enzyme activation uses covalent binding and acetylation of an unusual prosthetic group, 2'-(5"-phosphoribosyl)-3-'-dephospho-CoA, which is similar in structure to acetyl-CoA. Acylation is catalyzed by CitC, a citrate lyase synthetase. Two additional proteins, CitG and CitX, are used to convert the apo enzyme into the active holo enzyme (Schneider et al., *Biochemistry* 39:9438-9450 (2000)). Wild type *E. coli* does not have citrate lyase activity; however, mutants deficient in molybdenum cofactor synthesis have an active citrate lyase (Clark, *FEMS Microbiol. Lett.* 55:245-249 (1990)). The *E. coli* enzyme is encoded by citEFD and the citrate lyase synthetase is encoded by citC (Nilekani and SivaRaman, *Biochemistry* 22:4657-4663 (1983)). The *Leuconostoc mesenteroides* citrate lyase has been cloned, characterized and expressed in *E. coli* (Bekal et al., *J. Bacteriol.* 180:647-654 (1998)). Citrate lyase enzymes have also been identified in enterobacteria that utilize citrate as a carbon and energy source, including *Salmonella typhimurium* and *Klebsiella pneumoniae* (Bott, *Arch. Microbiol.* 167: 78-88 (1997); Bott and Dimroth, *Mol. Microbiol.* 14:347-356 (1994)). The aforementioned proteins are tabulated below.

| Protein | GenBank ID | GI Number | Organism |
|---|---|---|---|
| citF | AAC73716.1 | 1786832 | *Escherichia coli* |
| Cite | AAC73717.2 | 87081764 | *Escherichia coli* |
| citD | AAC73718.1 | 1786834 | *Escherichia coli* |
| citC | AAC73719.2 | 87081765 | *Escherichia coli* |
| citG | AAC73714.1 | 1786830 | *Escherichia coli* |
| citX | AAC73715.1 | 1786831 | *Escherichia coli* |
| citF | CAA71633.1 | 2842397 | *Leuconostoc mesenteroides* |
| citE | CAA71632.1 | 2842396 | *Leuconostoc mesenteroides* |
| citD | CAA71635.1 | 2842395 | *Leuconostoc mesenteroides* |
| citC | CAA71636.1 | 3413797 | *Leuconostoc mesenteroides* |
| citG | CAA71634.1 | 2842398 | *Leuconostoc mesenteroides* |
| citX | CAA71634.1 | 2842398 | *Leuconostoc mesenteroides* |
| citF | NP_459613.1 | 16763998 | *Salmonella typhimurium* |
| citE | AAL19573.1 | 16419133 | *Salmonella typhimurium* |
| citD | NP_459064.1 | 16763449 | *Salmonella typhimurium* |
| citC | NP_459616.1 | 16764001 | *Salmonella typhimurium* |
| citG | NP_459611.1 | 16763996 | *Salmonella typhimurium* |
| citX | NP_459612.1 | 16763997 | *Salmonella typhimurium* |
| citF | CAA56217.1 | 565619 | *Klebsiella pneumoniae* |
| cite | CAA56216.1 | 565618 | *Klebsiella pneumoniae* |
| citD | CAA56215.1 | 565617 | *Klebsiella pneumoniae* |
| citC | BAH66541.1 | 238774045 | *Klebsiella pneumoniae* |
| citG | CAA56218.1 | 565620 | *Klebsiella pneumoniae* |
| citX | AAL60463.1 | 18140907 | *Klebsiella pneumoniae* |

Acetate kinase (EC 2.7.2.1) catalyzes the reversible ATP-dependent phosphorylation of acetate to acetylphosphate. Exemplary acetate kinase enzymes have been characterized in many organisms including *E. coli*, *Clostridium acetobutylicum* and *Methanosarcina thermophila* (Ingram-Smith et al., *J. Bacteriol.* 187:2386-2394 (2005); Fox and Roseman, *J. Biol. Chem.* 261:13487-13497 (1986); Winzer et al., *Microbioloy* 143 (Pt 10):3279-3286 (1997)). Acetate kinase activity has also been demonstrated in the gene product of *E. coli* purT (Marolewski et al., *Biochemistry* 33:2531-2537 (1994). Some butyrate kinase enzymes (EC 2.7.2.7), for example buk1 and buk2 from *Clostridium acetobutylicum*, also accept acetate as a substrate (Hartmanis, M. G., *J. Biol. Chem.* 262:617-621 (1987)).

| Protein | GenBank ID | GI Number | Organism |
|---|---|---|---|
| ackA | NP_416799.1 | 16130231 | *Escherichia coli* |
| Ack | AAB18301.1 | 1491790 | *Clostridium acetobutylicum* |
| Ack | AAA72042.1 | 349834 | *Methanosarcina thermophile* |
| purT | AAC74919.1 | 1788155 | *Escherichia coli* |
| buk1 | NP_349675 | 15896326 | *Clostridium acetobutylicum* |
| buk2 | Q97II1 | 20137415 | *Clostridium acetobutylicum* |

The formation of acetyl-CoA from acetylphosphate is catalyzed by phosphotransacetylase (EC 2.3.1.8). The pta gene from *E. coli* encodes an enzyme that reversibly converts acetyl-CoA into acetyl-phosphate (Suzuki, T., *Biochim. Biophys. Acta* 191:559-569 (969)). Additional acetyltransferase enzymes have been characterized in *Bacillus subtilis* (Rado and Hoch, *Biochim. Biophys. Acta* 321:114-125 (1973), *Clostridium kluyveri* (Stadtman, E., *Methods Enzymol.* 1:5896-599 (1955), and *Thermotoga maritima* (Bock et al., *J. Bacteriol.* 181:1861-1867 (1999)). This reaction is also catalyzed by some phosphotranbutyrylase enzymes (EC 2.3.1.19) including the ptb gene products from *Clostridium acetobutylicum* (Wiesenborn et al., *App. Environ. Microbiol.* 55:317-322 (1989); Walter et al., *Gene* 134:107-111 (1993)). Additional ptb genes are found in butyrate-producing bacterium L2-50 (Louis et al., *J. Bacteriol.* 186:2099-2106 (2004) and *Bacillus megaterium* (Vazquez et al., *Curr. Microbiol.* 42:345-349 (2001).

| Protein | GenBank ID | GI Number | Organism |
|---|---|---|---|
| Pta | NP_416800.1 | 71152910 | *Escherichia coli* |
| Pta | P39646 | 730415 | *Bacillus subtilis* |

| Protein | GenBank ID | GI Number | Organism |
|---------|-----------|-----------|----------|
| Pta | A5N801 | 146346896 | Clostridium kluyveri |
| Pta | Q9X0L4 | 6685776 | Thermotoga maritima |
| Ptb | NP_349676 | 34540484 | Clostridium acetobutylicum |
| Ptb | AAR19757.1 | 38425288 | butyrate-producing bacterium L2-50 |
| Ptb | CAC07932.1 | 10046659 | Bacillus megaterium |

The acylation of acetate to acetyl-CoA is catalyzed by enzymes with acetyl-CoA synthetase activity. Two enzymes that catalyze this reaction are AMP-forming acetyl-CoA synthetase (EC 6.2.1.1) and ADP-forming acetyl-CoA synthetase (EC 6.2.1.13). AMP-forming acetyl-CoA synthetase (ACS) is the predominant enzyme for activation of acetate to acetyl-CoA. Exemplary ACS enzymes are found in *E. coli* (Brown et al., *J. Gen. Microbiol.* 102:327-336 (1977)), *Ralstonia eutropha* (Priefert and Steinbuchel, *J. Bacteriol.* 174:6590-6599 (1992)), *Methanothermobacter thermautotrophicus* (Ingram-Smith and Smith, Archaea 2:95-107 (2007)), *Salmonella enterica* (Gulick et al., *Biochemistry* 42:2866-2873 (2003)) and *Saccharomyces cerevisiae* (Jogl and Tong, *Biochemistry* 43:1425-1431 (2004)). ADP-forming acetyl-CoA synthetases are reversible enzymes with a generally broad substrate range (Musfeldt and Schonheit, *J. Bacteriol.* 184:636-644 (2002)). Two isozymes of ADP-forming acetyl-CoA synthetases are encoded in the *Archaeoglobus fulgidus* genome by are encoded by AF1211 and AF1983 (Musfeldt and Schonheit, supra (2002)). The enzyme from *Haloarcula marismortui* (annotated as a succinyl-CoA synthetase) also accepts acetate as a substrate and reversibility of the enzyme was demonstrated (Brasen and Schonheit, *Arch. Microbiol.* 182:277-287 (2004)). The ACD encoded by PAE3250 from hyperthermophilic crenarchaeon *Pyrobaculum aerophilum* showed the broadest substrate range of all characterized ACDs, reacting with acetate, isobutyryl-CoA (preferred substrate) and phenylacetyl-CoA (Brasen and Schonheit, supra (2004)). Directed evolution or engineering can be used to modify this enzyme to operate at the physiological temperature of the host organism. The enzymes from *A. fulgidus, H. marismortui* and *P. aerophilum* have all been cloned, functionally expressed, and characterized in *E. coli* (Brasen and Schonheit, supra (2004); Musfeldt and Schonheit, supra (2002)). Additional candidates include the succinyl-CoA synthetase encoded by sucCD in *E. coli* (Buck et al., *Biochemistry* 24:6245-6252 (1985)) and the acyl-CoA ligase from *Pseudomonas putida* (Fernandez-Valverde et al., *Appl. Environ. Microbiol.* 59:1149-1154 (1993)). The aforementioned proteins are tabulated below.

| Protein | GenBank ID | GI Number | Organism |
|---------|-----------|-----------|----------|
| acs | AAC77039.1 | 1790505 | Escherichia coli |
| acoE | AAA21945.1 | 141890 | Ralstonia eutropha |
| acs1 | ABC87079.1 | 86169671 | Methanothermobacter thermautotrophicus |
| acs1 | AAL23099.1 | 16422835 | Salmonella enterica |
| ACS1 | Q01574.2 | 257050994 | Saccharomyces cerevisiae |
| AF1211 | NP_070039.1 | 11498810 | Archaeoglobus fulgidus |
| AF1983 | NP_070807.1 | 11499565 | Archaeoglobus fulgidus |
| scs | YP_135572.1 | 55377722 | Haloarcula marismortui |
| PAE3250 | NP_560604.1 | 18313937 | Pyrobaculum aerophilum str. IM2 |
| sucC | NP_415256.1 | 16128703 | Escherichia coli |
| sucD | AAC73823.1 | 1786949 | Escherichia coli |
| paaF | AAC24333.2 | 22711873 | Pseudomonas putida |

The product yields per C-mol of substrate of microbial cells synthesizing reduced fermentation products such as caprolactone, are limited by insufficient reducing equivalents in the carbohydrate feedstock. Reducing equivalents, or electrons, can be extracted from synthesis gas components such as CO and $H_2$ using carbon monoxide dehydrogenase (CODH) and hydrogenase enzymes, respectively. The reducing equivalents are then passed to acceptors such as oxidized ferredoxins, oxidized quinones, oxidized cytochromes, NAD(P)+, water, or hydrogen peroxide to form reduced ferredoxin, reduced quinones, reduced cytochromes, NAD(P)H, $H_2$, or water, respectively. Reduced ferredoxin and NAD(P)H are particularly useful as they can serve as redox carriers for various Wood-Ljungdahl pathway and reductive TCA cycle enzymes.

A combined feedstock strategy where syngas is combined with a sugar-based feedstock or other carbon substrate can greatly improve the theoretical yields. In this co-feeding approach, syngas components $H_2$ and CO can be utilized by the hydrogenase and CO dehydrogenase to generate reducing equivalents, that can be used to power chemical production pathways in which the carbons from sugar or other carbon substrates will be maximally conserved and the theoretical yields improved. In case of caprolactone production from glucose or sugar, the theoretical yields improve from XX mol caprolactone per mol of glucose to YY mol caprolactone per mol of glucose. Such improvements provide environmental and economic benefits and greatly enhance sustainable chemical production.

Herein below the enzymes and the corresponding genes used for extracting redox from synags components are described. CODH is a reversible enzyme that interconverts CO and $CO_2$ at the expense or gain of electrons. The natural physiological role of the CODH in ACS/CODH complexes is to convert $CO_2$ to CO for incorporation into acetyl-CoA by acetyl-CoA synthase. Nevertheless, such CODH enzymes are suitable for the extraction of reducing equivalents from CO due to the reversible nature of such enzymes. Expressing such CODH enzymes in the absence of ACS allows them to operate in the direction opposite to their natural physiological role (i.e., CO oxidation).

In *M. thermoacetica, C. hydrogenoformans, C. carboxidivorans* P7, and several other organisms, additional CODH encoding genes are located outside of the ACS/CODH operons. These enzymes provide a means for extracting electrons (or reducing equivalents) from the conversion of carbon monoxide to carbon dioxide. The *M. thermoacetica* gene (Genbank Accession Number: YP_430813) is expressed by itself in an operon and is believed to transfer electrons from CO to an external mediator like ferredoxin in a "Ping-pong" reaction. The reduced mediator then couples to other reduced nicolinamide adenine dinucleotide phosphate (NAD(P)H) carriers or ferredoxin-dependent cellular processes (Ragsdale, *Annals of the New York Academy of Sciences* 1125:129-136 (2008)). The genes encoding the *C. hydrogenoformans* CODH-II and CooF, a neighboring protein, were cloned and sequenced (Gonzalez and Robb, *FEMS Microbiol Lett.* 191:243-247 (2000)). The resulting complex was membrane-bound, although cytoplasmic fractions of CODH-II were shown to catalyze the formation of NADPH suggesting an anabolic role (Svetlitchnyi et al., *J Bacteriol.* 183:5134-5144 (2001)). The crystal structure of the CODH-II is also available (Dobbek et al., *Science* 293:1281-1285 (2001)). Similar ACS-free CODH enzymes can be found in a diverse array of organisms including *Geobacter metallireducens* GS-15, *Chlorobium phaeobacteroides* DSM 266, *Clostridium cellulolyticum* H10, *Desulfovibrio desulfuricans* subsp. *desulfuricans* str. ATCC 27774, *Pelobacter carbinolicus* DSM 2380, and *Campylobacter curvus* 525.92.

| Protein | GenBank ID | GI Number | Organism |
|---|---|---|---|
| CODH (putative) | YP_430813 | 83590804 | Moorella thermoacetica |
| CODH-II (CooS-II) | YP_358957 | 78044574 | Carboxydothermus hydrogenoformans |
| CooF | YP_358958 | 78045112 | Carboxydothermus hydrogenoformans |
| CODH (putative) | ZP_05390164.1 | 255523193 | Clostridium carboxidivorans P7 |
| CcarbDRAFT_0341 | ZP_05390341.1 | 255523371 | Clostridium carboxidivorans P7 |
| CcarbDRAFT_1756 | ZP_05391756.1 | 255524806 | Clostridium carboxidivorans P7 |
| CcarbDRAFT_2944 | ZP_05392944.1 | 255526020 | Clostridium carboxidivorans P7 |
| CODH | YP_384856.1 | 78223109 | Geobacter metallireducens GS-15 |
| Cpha266_0148 (cytochrome c) | YP_910642.1 | 119355998 | Chlorobium phaeobacteroides DSM 266 |
| Cpha266_0149 (CODH) | YP_910643.1 | 119355999 | Chlorobium phaeobacteroides DSM 266 |
| Ccel_0438 | YP_002504800.1 | 220927891 | Clostridium cellulolyticum H10 |
| Ddes_0382 (CODH) | YP_002478973.1 | 220903661 | Desulfovibrio desulfuricans subsp. desulfuricans str. ATCC 27774 |
| Ddes_0381 (CooC) | YP_002478972.1 | 220903660 | Desulfovibrio desulfuricans subsp. desulfuricans str. ATCC 27774 |
| Pcar_0057 (CODH) | YP_355490.1 | 7791767 | Pelobacter carbinolicus DSM 2380 |
| Pcar_0058 (CooC) | YP_355491.1 | 7791766 | Pelobacter carbinolicus DSM 2380 |
| Pcar_0058 (HypA) | YP_355492.1 | 7791765 | Pelobacter carbinolicus DSM 2380 |
| CooS (CODH) | YP_001407343.1 | 154175407 | Campylobacter curvus 525.92 |
| CLJU_c09110 | ADK13979.1 | 300434212 | Clostridium ljungdahli |
| CLJU_c09100 | ADK13978.1 | 300434211 | Clostridium ljungdahli |
| CLJU_c09090 | ADK13977.1 | 300434210 | Clostridium ljungdahli |

In some cases, hydrogenase encoding genes are located adjacent to a CODH. In *Rhodospirillum rubrum*, the encoded CODH/hydrogenase proteins form a membrane-bound enzyme complex that has been indicated to be a site where energy, in the form of a proton gradient, is generated from the conversion of CO and $H_2O$ to $CO_2$ and $H_2$ (Fox et al., *J Bacteriol.* 178:6200-6208 (1996)). The CODH-I of *C. hydrogenoformans* and its adjacent genes have been proposed to catalyze a similar functional role based on their similarity to the *R. rubrum* CODH/hydrogenase gene cluster (Wu et al., *PLoS Genet.* 1:e65 (2005)). The *C. hydrogenoformans* CODH-I was also shown to exhibit intense CO oxidation and $CO_2$ reduction activities when linked to an electrode (Parkin et al., *J Am. Chem. Soc.* 129:10328-10329 (2007)). The protein sequences of exemplary CODH and hydrogenase genes can be identified by the following GenBank accession numbers.

| Protein | GenBank ID | GI Number | Organism |
|---|---|---|---|
| CODH-I (CooS-I) | YP_360644 | 78043418 | Carboxydothermus hydrogenoformans |
| CooF | YP_360645 | 78044791 | Carboxydothermus hydrogenoformans |
| HypA | YP_360646 | 78044340 | Carboxydothermus hydrogenoformans |
| CooH | YP_360647 | 78043871 | Carboxydothermus hydrogenoformans |
| CooU | YP_360648 | 78044023 | Carboxydothermus hydrogenoformans |
| CooX | YP_360649 | 78043124 | Carboxydothermus hydrogenoformans |
| CooL | YP_360650 | 78043938 | Carboxydothermus hydrogenoformans |

-continued

| Protein | GenBank ID | GI Number | Organism |
|---|---|---|---|
| CooK | YP_360651 | 78044700 | Carboxydothermus hydrogenoformans |
| CooM | YP_360652 | 78043942 | Carboxydothermus hydrogenoformans |
| CooC | YP_360654.1 | 78043296 | Carboxydothermus hydrogenoformans |
| CooA-1 | YP_360655.1 | 78044021 | Carboxydothermus hydrogenoformans |
| CooL | AAC45118 | 1515468 | Rhodospirillum rubrum |
| CooX | AAC45119 | 1515469 | Rhodospirillum rubrum |
| CooU | AAC45120 | 1515470 | Rhodospirillum rubrum |
| CooH | AAC45121 | 1498746 | Rhodospirillum rubrum |
| CooF | AAC45122 | 1498747 | Rhodospirillum rubrum |
| CODH (CooS) | AAC45123 | 1498748 | Rhodospirillum rubrum |
| CooC | AAC45124 | 1498749 | Rhodospirillum rubrum |
| CooT | AAC45125 | 1498750 | Rhodospirillum rubrum |
| CooJ | AAC45126 | 1498751 | Rhodospirillum rubrum |

Native to *E. coli* and other enteric bacteria are multiple genes encoding up to four hydrogenases (Sawers, G., Antonie Van Leeuwenhoek 66:57-88 (1994); Sawers et al., *J Bacteriol.* 164:1324-1331 (1985); Sawers and Boxer, *Eur. J Biochem.* 156:265-275 (1986); Sawers et al., *J Bacteriol.* 168:398-404 (1986)). Given the multiplicity of enzyme activities, *E. coli* or another host organism can provide sufficient hydrogenase activity to split incoming molecular hydrogen and reduce the corresponding acceptor. *E. coli* possesses two uptake hydrogenases, Hyd-1 and Hyd-2, encoded by the hyaABCDEF and hybOABCDEFG gene clusters, respectively (Lukey et al., J. Biol. Chem. 285(6):3928-3938 (2010)). Hyd-1 is oxygen-tolerant, irreversible, and is coupled to quinone reduction via the hyaC cytochrome.

Hyd-2 is sensitive to $O_2$, reversible, and transfers electrons to the periplasmic ferredoxin hybA which, in turn, reduces a quinone via the hybB integral membrane protein. Reduced quinones can serve as the source of electrons for fumarate reductase in the reductive branch of the TCA cycle. Reduced ferredoxins can be used by enzymes such as NAD(P)H:ferredoxin oxidoreductases to generate NADPH or NADH. They can alternatively be used as the electron donor for reactions such as pyruvate ferredoxin oxidoreductase, AKG ferredoxin oxidoreductase, and 5,10-methylene-H4folate reductase.

| Protein | GenBank ID | GI Number | Organism |
|---|---|---|---|
| HyaA | AAC74057.1 | 1787206 | Escherichia coli |
| HyaB | AAC74058.1 | 1787207 | Escherichia coli |
| HyaC | AAC74059.1 | 1787208 | Escherichia coli |
| HyaD | AAC74060.1 | 1787209 | Escherichia coli |
| HyaE | AAC74061.1 | 1787210 | Escherichia coli |
| HyaF | AAC74062.1 | 1787211 | Escherichia coli |
| HybO | AAC76033.1 | 1789371 | Escherichia coli |
| HybA | AAC76032.1 | 1789370 | Escherichia coli |
| HybB | AAC76031.1 | 2367183 | Escherichia coli |
| HybC | AAC76030.1 | 1789368 | Escherichia coli |
| HybD | AAC76029.1 | 1789367 | Escherichia coli |
| HybE | AAC76028.1 | 1789366 | Escherichia coli |
| HybF | AAC76027.1 | 1789365 | Escherichia coli |
| HybG | AAC76026.1 | 1789364 | Escherichia coli |

The hydrogen-lyase systems of E. coli include hydrogenase 3, a membrane-bound enzyme complex using ferredoxin as an acceptor, and hydrogenase 4 that also uses a ferredoxin acceptor. Hydrogenase 3 and 4 are encoded by the hyc and hyf gene clusters, respectively. Hydrogenase 3 has been shown to be a reversible enzyme (Maeda et al., Appl Microbiol Biotechnol 76(5):1035-42 (2007)). Hydrogenase activity in E. coli is also dependent upon the expression of the hyp genes whose corresponding proteins are involved in the assembly of the hydrogenase complexes (Jacobi et al., Arch. Microbiol 158:444-451 (1992); Rangarajan et al., J. Bacteriol. 190: 1447-1458 (2008)).

| Protein | GenBank ID | GI Number | Organism |
|---|---|---|---|
| HycA | NP_417205 | 16130632 | Escherichia coli |
| HycB | NP_417204 | 16130631 | Escherichia coli |
| HycC | NP_41720316 | 130630 | Escherichia coli |
| HycD | NP_41720216 | 130629 | Escherichia coli |
| HycE | NP_41720116 | 130628 | Escherichia coli |
| HycF | NP_41720016 | 130627 | Escherichia coli |
| HycG | NP_41719916 | 130626 | Escherichia coli |
| HycH | NP_41719816 | 130625 | Escherichia coli |
| HycI | NP_41719716 | 130624 | Escherichia coli |
| HyfA | NP_416976 | 90111444 | Escherichia coli |
| HyfB | NP_416977 | 16130407 | Escherichia coli |
| HyfC | NP_416978 | 90111445 | Escherichia coli |
| HyfD | NP_416979 | 16130409 | Escherichia coli |
| HyfE | NP_416980 | 16130410 | Escherichia coli |
| HyfF | NP_416981 | 16130411 | Escherichia coli |
| HyfG | NP_416982 | 16130412 | Escherichia coli |
| HyfH | NP_416983 | 16130413 | Escherichia coli |
| HyfI | NP_416984 | 16130414 | Escherichia coli |
| HyfJ | NP_416985 | 90111446 | Escherichia coli |
| HyfR | NP_416986 | 90111447 | Escherichia coli |
| HypA | NP_417206 | 16130633 | Escherichia coli |
| HypB | NP_417207 | 16130634 | Escherichia coli |
| HypC | NP_417208 | 16130635 | Escherichia coli |
| HypD | NP_417209 | 16130636 | Escherichia coli |
| HypE | NP_417210 | 226524740 | Escherichia coli |
| HypF | NP_417192 | 16130619 | Escherichia coli |

The M. thermoacetica hydrogenases are suitable for a host that lacks sufficient endogenous hydrogenase activity. M. thermoacetica can grow with $CO_2$ as the exclusive carbon source indicating that reducing equivalents are extracted from $H_2$ to enable acetyl-CoA synthesis via the Wood-Ljungdahl pathway (Drake, H. L., J. Bacteriol. 150:702-709 (1982); Drake and Daniel, Res. Microbiol. 155:869-883 (2004); Kellum and Drake, J. Bacteriol. 160:466-469 (1984)) (see FIG. 6). M. thermoacetica has homologs to several hyp, hyc, and hyf genes from E. coli. The protein sequences encoded for by these genes are identified by the following GenBank accession numbers.

Proteins in M. thermoacetica whose genes are homologous to the E. coli hyp genes are shown below.

| Protein | GenBank ID | GI Number | Organism |
|---|---|---|---|
| Moth_2175 | YP_431007 | 83590998 | Moorella thermoacetica |
| Moth_2176 | YP_431008 | 83590999 | Moorella thermoacetica |
| Moth_2177 | YP_431009 | 83591000 | Moorella thermoacetica |
| Moth_2178 | YP_431010 | 83591001 | Moorella thermoacetica |
| Moth_2179 | YP_431011 | 83591002 | Moorella thermoacetica |
| Moth_2180 | YP_431012 | 83591003 | Moorella thermoacetica |
| Moth_2181 | YP_431013 | 83591004 | Moorella thermoacetica |

Proteins in M. thermoacetica that are homologous to the E. coli Hydrogenase 3 and/or 4 proteins are listed in the following table.

| Protein | GenBank ID | GI Number | Organism |
|---|---|---|---|
| Moth_2182 | YP_431014 | 83591005 | Moorella thermoacetica |
| Moth_2183 | YP_431015 | 83591006 | Moorella thermoacetica |
| Moth_2184 | YP_431016 | 83591007 | Moorella thermoacetica |
| Moth_2185 | YP_431017 | 83591008 | Moorella thermoacetica |
| Moth_2186 | YP_431018 | 83591009 | Moorella thermoacetica |
| Moth_2187 | YP_431019 | 83591010 | Moorella thermoacetica |
| Moth_2188 | YP_431020 | 83591011 | Moorella thermoacetica |
| Moth_2189 | YP_431021 | 83591012 | Moorella thermoacetica |
| Moth_2190 | YP_431022 | 83591013 | Moorella thermoacetica |
| Moth_2191 | YP_431023 | 83591014 | Moorella thermoacetica |
| Moth_2192 | YP_431024 | 83591015 | Moorella thermoacetica |

In addition, several gene clusters encoding hydrogenase functionality are present in M. thermoacetica and their corresponding protein sequences are provided below.

| Protein | GenBank ID | GI Number | Organism |
|---|---|---|---|
| Moth_0439 | YP_429313 | 83589304 | Moorella thermoacetica |
| Moth_0440 | YP_429314 | 83589305 | Moorella thermoacetica |
| Moth_0441 | YP_429315 | 83589306 | Moorella thermoacetica |
| Moth_0442 | YP_429316 | 83589307 | Moorella thermoacetica |
| Moth_0809 | YP_429670 | 83589661 | Moorella thermoacetica |
| Moth_0810 | YP_429671 | 83589662 | Moorella thermoacetica |
| Moth_0811 | YP_429672 | 83589663 | Moorella thermoacetica |
| Moth_0812 | YP_429673 | 83589664 | Moorella thermoacetica |
| Moth_0814 | YP_429674 | 83589665 | Moorella thermoacetica |
| Moth_0815 | YP_429675 | 83589666 | Moorella thermoacetica |
| Moth_0816 | YP_429676 | 83589667 | Moorella thermoacetica |
| Moth_1193 | YP_430050 | 83590041 | Moorella thermoacetica |
| Moth_1194 | YP_430051 | 83590042 | Moorella thermoacetica |
| Moth_1195 | YP_430052 | 83590043 | Moorella thermoacetica |
| Moth_1196 | YP_430053 | 83590044 | Moorella thermoacetica |
| Moth_1717 | YP_430562 | 83590553 | Moorella thermoacetica |
| Moth_1718 | YP_430563 | 83590554 | Moorella thermoacetica |
| Moth_1719 | YP_430564 | 83590555 | Moorella thermoacetica |
| Moth_1883 | YP_430726 | 83590717 | Moorella thermoacetica |
| Moth_1884 | YP_430727 | 83590718 | Moorella thermoacetica |
| Moth_1885 | YP_430728 | 83590719 | Moorella thermoacetica |
| Moth_1886 | YP_430729 | 83590720 | Moorella thermoacetica |
| Moth_1887 | YP_430730 | 83590721 | Moorella thermoacetica |
| Moth_1888 | YP_430731 | 83590722 | Moorella thermoacetica |
| Moth_1452 | YP_430305 | 83590296 | Moorella thermoacetica |

-continued

| Protein | GenBank ID | GI Number | Organism |
|---|---|---|---|
| Moth_1453 | YP_430306 | 83590297 | *Moorella thermoacetica* |
| Moth_1454 | YP_430307 | 83590298 | *Moorella thermoacetica* |

*Ralstonia eutropha* H16 uses hydrogen as an energy source with oxygen as a terminal electron acceptor. Its membrane-bound uptake [NiFe]-hydrogenase is an "O2-tolerant" hydrogenase (Cracknell, et al. Proc Nat Acad Sci, 106(49) 20681-20686 (2009)) that is periplasmically-oriented and connected to the respiratory chain via a b-type cytochrome (Schink and Schlegel, *Biochim. Biophys. Acta,* 567, 315-324 (1979); Bernhard et al., *Eur. J. Biochem.* 248, 179-186 (1997)). *R. eutropha* also contains an $O_2$-tolerant soluble hydrogenase encoded by the Hox operon which is cytoplasmic and directly reduces NAD+ at the expense of hydrogen (Schneider and Schlegel, *Biochim. Biophys. Acta* 452, 66-80 (1976); Burgdorf, *J. Bact.* 187(9) 3122-3132(2005)). Soluble hydrogenase enzymes are additionally present in several other organisms including *Geobacter sulfurreducens* (Coppi, *Microbiology* 151, 1239-1254 (2005)), *Synechocystis* str. PCC 6803 (Germer, *J. Biol. Chem.,* 284(52), 36462-36472 (2009)), and *Thiocapsa roseopersicina* (Rakhely, *Appl. Environ. Microbiol.* 70(2) 722-728 (2004)). The *Synechocystis* enzyme is capable of generating NADPH from hydrogen. Overexpression of both the Hox operon from *Synechocystis* str. PCC 6803 and the accessory genes encoded by the Hyp operon from *Nostoc* sp. PCC 7120 led to increased hydrogenase activity compared to expression of the Hox genes alone (Germer, *J. Biol. Chem.* 284(52), 36462-36472 (2009)).

| Protein | GenBank ID | GI Number | Organism |
|---|---|---|---|
| HoxF | NP_942727.1 | 38637753 | *Ralstonia eutropha* H16 |
| HoxU | NP_942728.1 | 38637754 | *Ralstonia eutropha* H16 |
| HoxY | NP_942729.1 | 38637755 | *Ralstonia eutropha* H16 |
| HoxH | NP_942730.1 | 38637756 | *Ralstonia eutropha* H16 |
| HoxW | NP_942731.1 | 38637757 | *Ralstonia eutropha* H16 |
| HoxI | NP_942732.1 | 38637758 | *Ralstonia eutropha* H16 |
| HoxE | NP_953767.1 | 39997816 | *Geobacter sulfurreducens* |
| HoxF | NP_953766.1 | 39997815 | *Geobacter sulfurreducens* |
| HoxU | NP_953765.1 | 39997814 | *Geobacter sulfurreducens* |
| HoxY | NP_953764.1 | 39997813 | *Geobacter sulfurreducens* |
| HoxH | NP_953763.1 | 39997812 | *Geobacter sulfurreducens* |
| GSU2717 | NP_953762.1 | 39997811 | *Geobacter sulfurreducens* |
| HoxE | NP_441418.1 | 16330690 | *Synechocystis* str. PCC 6803 |
| HoxF | NP_441417.1 | 16330689 | *Synechocystis* str. PCC 6803 |
| Unknown function | NP_441416.1 | 16330688 | *Synechocystis* str. PCC 6803 |
| HoxU | NP_441415.1 | 16330687 | *Synechocystis* str. PCC 6803 |
| HoxY | NP_441414.1 | 16330686 | *Synechocystis* str. PCC 6803 |
| Unknown function | NP_441413.1 | 16330685 | *Synechocystis* str. PCC 6803 |
| Unknown function | NP_441412.1 | 16330684 | *Synechocystis* str. PCC 6803 |
| HoxH | NP_441411.1 | 16330683 | *Synechocystis* str. PCC 6803 |
| HypF | NP_484737.1 | 17228189 | *Nostoc* sp. PCC 7120 |
| HypC | NP_484738.1 | 17228190 | *Nostoc* sp. PCC 7120 |
| HypD | NP_484739.1 | 17228191 | *Nostoc* sp. PCC 7120 |
| Unknown function | NP_484740.1 | 17228192 | *Nostoc* sp. PCC 7120 |
| HypE | NP_484741.1 | 17228193 | *Nostoc* sp. PCC 7120 |
| HypA | NP_484742.1 | 17228194 | *Nostoc* sp. PCC 7120 |
| HypB | NP_484743.1 | 17228195 | *Nostoc* sp. PCC 7120 |
| Hox1E | AAP50519.1 | 37787351 | *Thiocapsa roseopersicina* |
| Hox1F | AAP50520.1 | 37787352 | *Thiocapsa roseopersicina* |
| Hox1U | AAP50521.1 | 37787353 | *Thiocapsa roseopersicina* |
| Hox1Y | AAP50522.1 | 37787354 | *Thiocapsa roseopersicina* |
| Hox1H | AAP50523.1 | 37787355 | *Thiocapsa roseopersicina* |

Genes encoding hydrogenase enzymes from *C. ljungdahli* are shown below.

| Protein | GenBank ID | GI Number | Organism |
|---|---|---|---|
| CLJU_c20290 | ADK15091.1 | 300435324 | *Clostridium ljungdahli* |
| CLJU_c07030 | ADK13773.1 | 300434006 | *Clostridium ljungdahli* |
| CLJU_c07040 | ADK13774.1 | 300434007 | *Clostridium ljungdahli* |
| CLJU_c07050 | ADK13775.1 | 300434008 | *Clostridium ljungdahli* |
| CLJU_c07060 | ADK13776.1 | 300434009 | *Clostridium ljungdahli* |
| CLJU_c07070 | ADK13777.1 | 300434010 | *Clostridium ljungdahli* |
| CLJU_c07080 | ADK13778.1 | 300434011 | *Clostridium ljungdahli* |
| CLJU_c14730 | ADK14541.1 | 300434774 | *Clostridium ljungdahli* |
| CLJU_c14720 | ADK14540.1 | 300434773 | *Clostridium ljungdahli* |
| CLJU_c14710 | ADK14539.1 | 300434772 | *Clostridium ljungdahli* |
| CLJU_c14700 | ADK14538.1 | 300434771 | *Clostridium ljungdahli* |
| CLJU_c28670 | ADK15915.1 | 300436148 | *Clostridium ljungdahli* |
| CLJU_c28660 | ADK15914.1 | 300436147 | *Clostridium ljungdahli* |
| CLJU_c28650 | ADK15913.1 | 300436146 | *Clostridium ljungdahli* |
| CLJU_c28640 | ADK15912.1 | 300436145 | *Clostridium ljungdahli* |

Several enzymes and the corresponding genes used for fixing carbon dioxide to either pyruvate or phosphoenolpyruvate to form the TCA cycle intermediates, oxaloacetate or malate are described below.

Carboxylation of phosphoenolpyruvate to oxaloacetate is catalyzed by phosphoenolpyruvate carboxylase. Exemplary PEP carboxylase enzymes are encoded by ppc in *E. coli* (Kai et al., *Arch. Biochem. Biophys.* 414:170-179 (2003), ppcA in *Methylobacterium extorquens* AM1 (Arps et al., *J. Bacteriol.* 175:3776-3783 (1993), and ppc in *Corynebacterium glutamicum* (Eikmanns et al., *Mol. Gen. Genet.* 218:330-339 (1989).

| Protein | GenBank ID | GI Number | Organism |
|---|---|---|---|
| Ppc | NP_418391 | 16131794 | *Escherichia coli* |
| ppcA | AAB58883 | 28572162 | *Methylobacterium extorquens* |
| Ppc | ABB53270 | 80973080 | *Corynebacterium glutamicum* |

An alternative enzyme for converting phosphoenolpyruvate to oxaloacetate is PEP carboxykinase, which simultaneously forms an ATP while carboxylating PEP. In most organisms PEP carboxykinase serves a gluconeogenic function and converts oxaloacetate to PEP at the expense of one ATP. *S. cerevisiae* is one such organism whose native PEP carboxykinase, PCK1, serves a gluconeogenic role (Valdes-Hevia et al., *FEBS Lett.* 258:313-316 (1989). *E. coli* is another such organism, as the role of PEP carboxykinase in producing oxaloacetate is believed to be minor when compared to PEP carboxylase, which does not form ATP, possibly due to the higher $K_m$ for bicarbonate of PEP carboxykinase (Kim et al., *Appl. Environ. Microbiol.* 70:1238-1241 (2004)). Nevertheless, activity of the native *E. coli* PEP carboxykinase from PEP towards oxaloacetate has been recently demonstrated in ppc mutants of *E. coli* K-12 (Kwon et al., *J. Microbiol. Biotechnol.* 16:1448-1452 (2006)). These strains exhibited no growth defects and had increased succinate production at high $NaHCO_3$ concentrations. Mutant strains of *E. coli* can adopt Pck as the dominant CO2-fixing enzyme following adaptive evolution (Zhang et al. 2009). In some organisms, particularly rumen bacteria, PEP carboxykinase is quite efficient in producing oxaloacetate from PEP and generating ATP. Examples of PEP carboxykinase genes that have been cloned into *E. coli* include those from *Mannheimia succiniciproducens* (Lee et al., *Biotechnol. Bioprocess Eng.* 7:95-99 (2002)), *Anaerobiospirillum succiniciproducens* (Laivenieks et al., *Appl. Environ. Microbiol.* 63:2273-2280 (1997), and *Actinobacillus succinogenes* (Kim et al. supra). The PEP carboxykinase enzyme encoded by *Haemophilus influenza* is effective at forming oxaloacetate from PEP.

| Protein | GenBank ID | GI Number | Organism |
|---|---|---|---|
| PCK1 | NP_013023 | 6322950 | *Saccharomyces cerevisiae* |
| pck | NP_417862.1 | 16131280 | *Escherichia coli* |
| pckA | YP_089485.1 | 52426348 | *Mannheimia succiniciproducens* |
| pckA | 009460.1 | 3122621 | *Anaerobiospirillum succiniciproducens* |
| pckA | Q6W6X5 | 75440571 | *Actinobacillus succinogenes* |
| pckA | P43923.1 | 1172573 | *Haemophilus influenza* |

Pyruvate carboxylase (EC 6.4.1.1) directly converts pyruvate to oxaloacetate at the cost of one ATP. Pyruvate carboxylase enzymes are encoded by PYC1 (Walker et al., *Biochem. Biophys. Res. Commun.* 176:1210-1217 (1991) and PYC2 (Walker et al., supra) in *Saccharomyces cerevisiae*, and pyc in *Mycobacterium smegmatis* (Mukhopadhyay and Purwantini, *Biochim. Biophys. Acta* 1475:191-206 (2000)).

| Protein | GenBank ID | GI Number | Organism |
|---|---|---|---|
| PYC1 | NP_011453 | 6321376 | *Saccharomyces cerevisiae* |
| PYC2 | NP_009777 | 6319695 | *Saccharomyces cerevisiae* |
| Pyc | YP_890857.1 | 118470447 | *Mycobacterium smegmatis* |

Malic enzyme can be applied to convert $CO_2$ and pyruvate to malate at the expense of one reducing equivalent. Malic enzymes for this purpose can include, without limitation, malic enzyme (NAD-dependent) and malic enzyme (NADP-dependent). For example, one of the *E. coli* malic enzymes (Takeo, *J. Biochem.* 66:379-387 (1969)) or a similar enzyme with higher activity can be expressed to enable the conversion of pyruvate and $CO_2$ to malate. By fixing carbon to pyruvate as opposed to PEP, malic enzyme allows the high-energy phosphate bond from PEP to be conserved by pyruvate kinase whereby ATP is generated in the formation of pyruvate or by the phosphotransferase system for glucose transport. Although malic enzyme is typically assumed to operate in the direction of pyruvate formation from malate, overexpression of the NAD-dependent enzyme, encoded by maeA, has been demonstrated to increase succinate production in *E. coli* while restoring the lethal Δpfl-ΔldhA phenotype under anaerobic conditions by operating in the carbon-fixing direction (Stols and Donnelly, *Appl. Environ. Microbiol.* 63(7) 2695-2701 (1997)). A similar observation was made upon overexpressing the malic enzyme from *Ascaris suum* in *E. coli* (Stols et al., *Appl. Biochem. Biotechnol.* 63-65(1), 153-158 (1997)). The second *E. coli* malic enzyme, encoded by maeB, is NADP-dependent and also decarboxylates oxaloacetate and other alpha-keto acids (Iwakura et al., *J. Biochem.* 85(5):1355-65 (1979)).

| Protein | GenBank ID | GI Number | Organism |
|---|---|---|---|
| maeA | NP_415996 | 90111281 | *Escherichia coli* |
| maeB | NP_416958 | 16130388 | *Escherichia coli* |
| NAD-ME | P27443 | 126732 | *Ascaris suum* |

The enzymes used for converting oxaloacetate (formed from, for example, PEP carboxylase, PEP carboxykinase, or pyruvate carboxylase) or malate (formed from, for example, malic enzyme or malate dehydrogenase) to succinyl-CoA via the reductive branch of the TCA cycle are malate dehydrogenase, fumarate dehydratase (fumarase), fumarate reductase, and succinyl-CoA transferase. The genes for each of the enzymes are described herein above.

Enzymes, genes and methods for engineering pathways from succinyl-CoA to various products into a microorganism are now known in the art. The additional reducing equivalents obtained from CO and/or $H_2$, as disclosed herein, improve the yields of caprolactone when utilizing carbohydrate-based feedstock. For example, caprolactone can be produced from succinyl-CoA via conversion of adipyl-CoA to caprolactone. Exemplary enzymes for the conversion succinyl-CoA to caprolactone include an adipyl-CoA reductase, an adipate semialdehyde reductase, a 6-hydroxyhexanoyl-CoA transferase, a 6-hydroxyhexanoyl-CoA synthetase, a 6-hydroxyhexanoyl-CoA cyclase, an adipate reductase, a 6-hydroxyhexanoate cyclase, a 6-hydroxyhexanoate kinase, and/or a 6-hydroxyhexanoyl phosphate cyclase (see FIG. 1 steps A/B/C/D; A/B/H/I; A/B/G; E/B/C/D; E/B/H/I; or EB/G).

EXAMPLE III

Methods for Handling CO and Anaerobic Cultures

This example describes methods used in handling CO and anaerobic cultures.

A. Handling of CO in Small Quantities for Assays and Small Cultures.

CO is an odorless, colorless and tasteless gas that is a poison. Therefore, cultures and assays that utilized CO required special handling. Several assays, including CO oxidation, acetyl-CoA synthesis, CO concentration using myoglobin, and CO tolerance/utilization in small batch cultures, called for small quantities of the CO gas that were dispensed and handled within a fume hood. Biochemical assays called for saturating very small quantities (<2 mL) of the biochemical assay medium or buffer with CO and then performing the assay. All of the CO handling steps were performed in a fume hood with the sash set at the proper height and blower turned on; CO was dispensed from a compressed gas cylinder and the regulator connected to a Schlenk line. The latter ensures that equal concentrations of CO were dispensed to each of several possible cuvettes or vials. The Schlenk line was set up containing an oxygen scrubber on the input side and an oil pressure release bubbler and vent on the other side. Assay cuvettes were both anaerobic and CO-containing. Therefore, the assay cuvettes were tightly sealed with a rubber stopper and reagents were added or removed using gas-tight needles and syringes. Secondly, small (~50 mL) cultures were grown with saturating CO in tightly stoppered serum bottles. As with the biochemical assays, the CO-saturated microbial cultures were equilibrated in the fume hood using the Schlenk line setup. Both the biochemical assays and microbial cultures were in portable, sealed containers and in small volumes making for safe handling outside of the fume hood. The compressed CO tank was adjacent to the fume hood.

Typically, a Schlenk line was used to dispense CO to cuvettes, each vented. Rubber stoppers on the cuvettes were pierced with 19 or 20 gage disposable syringe needles and were vented with the same. An oil bubbler was used with a CO tank and oxygen scrubber. The glass or quartz spectrophotometer cuvettes have a circular hole on top into which a Kontes stopper sleeve, Sz7 774250-0007 was fitted. The CO detector unit was positioned proximal to the fume hood.

B. Handling of CO in Larger Quantities Fed to Large-Scale Cultures.

Fermentation cultures are fed either CO or a mixture of CO and $H_2$ to simulate syngas as a feedstock in fermentative production. Therefore, quantities of cells ranging from 1 liter to several liters can include the addition of CO gas to increase the dissolved concentration of CO in the medium. In these circumstances, fairly large and continuously administered quantities of CO gas are added to the cultures. At different points, the cultures are harvested or samples removed. Alternatively, cells are harvested with an integrated continuous flow centrifuge that is part of the fermenter.

The fermentative processes are carried out under anaerobic conditions. In some cases, it is uneconomical to pump oxygen or air into fermenters to ensure adequate oxygen saturation to provide a respiratory environment. In addition, the reducing power generated during anaerobic fermentation may be needed in product formation rather than respiration. Furthermore, many of the enzymes for various pathways are oxygen-sensitive to varying degrees. Classic acetogens such as *M. thermoacetica* are obligate anaerobes and the enzymes in the Wood-Ljungdahl pathway are highly sensitive to irreversible inactivation by molecular oxygen. While there are oxygen-tolerant acetogens, the repertoire of enzymes in the Wood-Ljungdahl pathway might be incompatible in the presence of oxygen because most are metallo-enzymes, key components are ferredoxins, and regulation can divert metabolism away from the Wood-Ljungdahl pathway to maximize energy acquisition. At the same time, cells in culture act as oxygen scavengers that moderate the need for extreme measures in the presence of large cell growth.

C. Anaerobic Chamber and Conditions.

Exemplary anaerobic chambers are available commercially (see, for example, Vacuum Atmospheres Company, Hawthorne Calif.; MBraun, Newburyport Mass.). Conditions included an $O_2$ concentration of 1 ppm or less and 1 atm pure $N_2$. In one example, 3 oxygen scrubbers/catalyst regenerators were used, and the chamber included an $O_2$ electrode (such as Teledyne; City of Industry Calif.). Nearly all items and reagents were cycled four times in the airlock of the chamber prior to opening the inner chamber door. Reagents with a volume >5 mL were sparged with pure $N_2$ prior to introduction into the chamber. Gloves are changed twice/yr and the catalyst containers were regenerated periodically when the chamber displays increasingly sluggish response to changes in oxygen levels. The chamber's pressure was controlled through one-way valves activated by solenoids. This feature allowed setting the chamber pressure at a level higher than the surroundings to allow transfer of very small tubes through the purge valve.

The anaerobic chambers achieved levels of $O_2$ that were consistently very low and were needed for highly oxygen sensitive anaerobic conditions. However, growth and handling of cells does not usually require such precautions. In an alternative anaerobic chamber configuration, platinum or palladium can be used as a catalyst that requires some hydrogen gas in the mix. Instead of using solenoid valves, pressure release can be controlled by a bubbler. Instead of using instrument-based $O_2$ monitoring, test strips can be used instead.

D. Anaerobic Microbiology.

Small cultures were handled as described above for CO handling. In particular, serum or media bottles are fitted with thick rubber stoppers and aluminum crimps are employed to seal the bottle. Medium, such as Terrific Broth, is made in a conventional manner and dispensed to an appropriately sized serum bottle. The bottles are sparged with nitrogen for ~30 min of moderate bubbling. This removes most of the oxygen from the medium and, after this step, each bottle is capped with a rubber stopper (such as Bellco 20 mm septum stoppers; Bellco, Vineland, N.J.) and crimp-sealed (Bellco 20 mm). Then the bottles of medium are autoclaved using a slow (liquid) exhaust cycle. At least sometimes a needle can be poked through the stopper to provide exhaust during autoclaving; the needle needs to be removed immediately upon removal from the autoclave. The sterile medium has the remaining medium components, for example buffer or antibiotics, added via syringe and needle. Prior to addition of reducing agents, the bottles are equilibrated for 30-60 minutes with nitrogen (or CO depending upon use). A reducing agent such as a 100×150 mM sodium sulfide, 200 mM cysteine-HCl is added. This is made by weighing the sodium sulfide into a dry beaker and the cysteine into a serum bottle, bringing both into the anaerobic chamber, dissolving the sodium sulfide into anaerobic water, then adding this to the cysteine in the serum bottle. The bottle is stoppered immediately as the sodium sulfide solution generates hydrogen sulfide gas upon contact with the cysteine. When injecting into the culture, a syringe filter is used to sterilize the solution. Other components are added through syringe needles, such as B12 (10 µM cyanocobalamin), nickel chloride ($NiCl_2$, 20 microM final concentration from a 40 mM stock made in anaerobic water in the chamber and sterilized by autoclaving or by using a syringe filter upon injection into the culture), and ferrous ammonium sulfate (final concentration needed is 100 µM—made as 100-1000× stock solution in anaerobic water in the chamber and sterilized by autoclaving or by using a syringe filter upon injection into the culture). To facilitate faster growth under anaerobic conditions, the 1 liter bottles were inoculated with 50 mL of a preculture grown anaerobically. Induction of the pA1-lacO1 promoter in the vectors was performed by addition of isopropyl β-D-1-thiogalactopyranoside (IPTG) to a final concentration of 0.2 mM and was carried out for about 3 hrs.

Large cultures can be grown in larger bottles using continuous gas addition while bubbling. A rubber stopper with a metal bubbler is placed in the bottle after medium addition and sparged with nitrogen for 30 minutes or more prior to setting up the rest of the bottle. Each bottle is put together such that a sterile filter will sterilize the gas bubbled in and the hoses on the bottles are compressible with small C clamps. Medium and cells are stirred with magnetic stir bars. Once all medium components and cells are added, the bottles are incubated in an incubator in room air but with continuous nitrogen sparging into the bottles.

EXAMPLE IV

CO Oxidation (CODH) Assay

This example describes assay methods for measuring CO oxidation (CO dehydrogenase; CODH).

The 7 gene CODH/ACS operon of *Moorella thermoacetica* was cloned into *E. coli* expression vectors. The intact ~10 kbp DNA fragment was cloned, and it is likely that some of the genes in this region are expressed from their own endogenous promoters and all contain endogenous ribosomal binding sites. These clones were assayed for CO oxidation, using an assay that quantitatively measures CODH activity. Antisera to the M. thermoacetica gene products was used for Western blots to estimate specific activity. M. thermoacetica is Gram positive, and ribosome binding site elements are expected to work well in E. coli. This activity, described below in more detail, was estimated to be ~1/50th of the M. thermoacetica specific activity. It is possible that CODH activity of recombinant E. coli cells could be limited by the fact that M. thermoacetica enzymes have temperature optima around 55° C. Therefore, a mesophilic CODH/ACS pathway could be advantageous such as the close relative of Moorella that is mesophilic and does have an apparently intact CODH/ACS operon and a Wood-Ljungdahl pathway, Desulfitobacterium hafniense. Acetogens as potential host organisms include, but are not limited to, Rhodospirillum rubrum, Moorella thermoacetica and Desulfitobacterium hafniense.

CO oxidation is both the most sensitive and most robust of the CODH/ACS assays. It is likely that an E. coli-based syngas using system will ultimately need to be about as anaerobic as Clostridial (i.e., Moorella) systems, especially for maximal activity. Improvement in CODH should be possible but will ultimately be limited by the solubility of CO gas in water.

Initially, each of the genes was cloned individually into expression vectors. Combined expression units for multiple subunits/1 complex were generated. Expression in E. coli at the protein level was determined. Both combined M. thermoacetica CODH/ACS operons and individual expression clones were made.

CO oxidation assay. This assay is one of the simpler, reliable, and more versatile assays of enzymatic activities within the Wood-Ljungdahl pathway and tests CODH (Seravalli et al., Biochemistry 43:3944-3955 (2004)). A typical activity of M. thermoacetica CODH specific activity is 500 U at 55° C. or ~60 U at 25° C. This assay employs reduction of methyl viologen in the presence of CO. This is measured at 578 nm in stoppered, anaerobic, glass cuvettes.

In more detail, glass rubber stoppered cuvettes were prepared after first washing the cuvette four times in deionized water and one time with acetone. A small amount of vacuum grease was smeared on the top of the rubber gasket. The cuvette was gassed with CO, dried 10 min with a 22 Ga. needle plus an exhaust needle. A volume of 0.98 mlL of reaction buffer (50 mM Hepes, pH 8.5, 2 mM dithiothreitol (DTT) was added using a 22 Ga. needle, with exhaust needled, and 100% C0. Methyl viologen ($CH_3$ viologen) stock was 1 M in water. Each assay used 20 microliters for 20 mM final concentration. When methyl viologen was added, an 18 Ga needle (partial) was used as a jacket to facilitate use of a Hamilton syringe to withdraw the $CH_3$ viologen. 4-5 aliquots were drawn up and discarded to wash and gas equilibrate the syringe. A small amount of sodium dithionite (0.1 M stock) was added when making up the $CH_3$ viologen stock to slightly reduce the $CH_3$ viologen. The temperature was equilibrated to 55° C. in a heated Olis spectrophotometer (Bogart Ga.). A blank reaction ($CH_3$ viologen+buffer) was run first to measure the base rate of $CH_3$ viologen reduction. Crude E. coli cell extracts of ACS90 and ACS91 (CODH-ACS operon of M. thermoacetica with and without, respectively, the first cooC). 10 microliters of extract were added at a time, mixed and assayed. Reduced $CH_3$ viologen turns purple. The results of an assay are shown in Table I.

TABLE I

Crude extract CO Oxidation Activities.

| | | | |
|---|---|---|---|
| ACS90 | 7.7 mg/ml | ACS91 | 11.8 mg/ml |
| Mta98 | 9.8 mg/ml | Mta99 | 11.2 mg/ml |

| Extract | Vol | OD/ | U/ml | U/mg |
|---|---|---|---|---|
| ACS90 | 10 microliters | 0.073 | 0.376 | 0.049 |
| ACS91 | 10 microliters | 0.096 | 0.494 | 0.042 |
| Mta99 | 10 microliters | 0.0031 | 0.016 | 0.0014 |
| ACS90 | 10 microliters | 0.099 | 0.51 | 0.066 |
| Mta99 | 25 microliters | 0.012 | 0.025 | 0.0022 |
| ACS91 | 25 microliters | 0.215 | 0.443 | 0.037 |
| Mta98 | 25 microliters | 0.019 | 0.039 | 0.004 |
| ACS91 | 10 microliters | 0.129 | 0.66 | 0.056 |

Averages

| | |
|---|---|
| ACS90 | 0.057 U/mg |
| ACS91 | 0.045 U/mg |
| Mta99 | 0.0018 U/mg |

Mta98/Mta99 are E. coli MG1655 strains that express methanol methyltransferase genes from M. thermoacetica and, therefore, are negative controls for the ACS90 ACS91 E. coli strains that contain M. thermoacetica CODH operons.

If ~1% of the cellular protein is CODH, then these figures would be approximately 100× less than the 500 U/mg activity of pure M. thermoacetica CODH. Actual estimates based on Western blots are 0.5% of the cellular protein, so the activity is about 50× less than for M. thermoacetica CODH. Nevertheless, this experiment demonstrates CO oxidation activity in recombinant E. coli with a much smaller amount in the negative controls. The small amount of CO oxidation ($CH_3$ viologen reduction) seen in the negative controls indicates that E. coli may have a limited ability to reduce $CH_3$ viologen.

Figure 8:
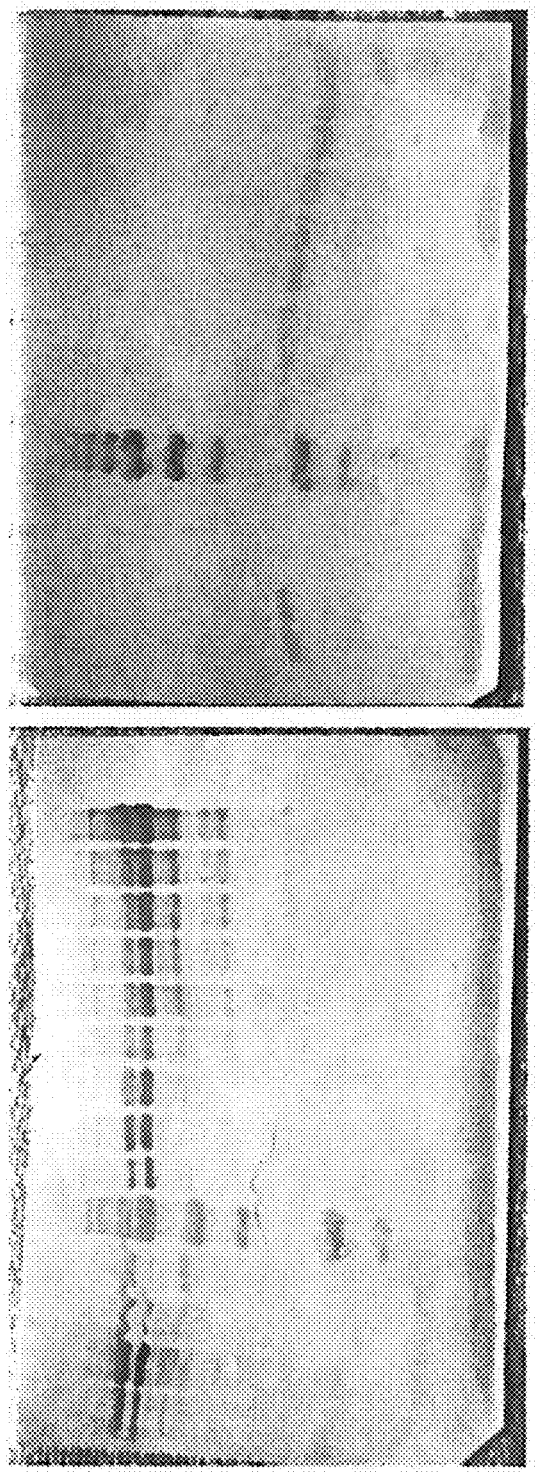
FIG. 8 shows Western blots of 10 micrograms ACS90 (lane 1), ACS91 (lane 2), Mta98/99 (lanes 3 and 4) cell extracts with size standards (lane 5) and controls of *M. thermoacetica* CODH (Moth_1202/1203) or Mtr (Moth_1197) proteins (50, 150, 250, 350, 450, 500, 750, 900, and 1000 ng).

To estimate the final concentrations of CODH and Mtr proteins, SDS-PAGE followed by Western blot analyses were performed on the same cell extracts used in the CO oxidation, ACS, methyltransferase, and corrinoid Fe—S assays. The antisera used were polyclonal to purified M. thermoacetica CODH-ACS and Mtr proteins and were visualized using an alkaline phosphatase-linked goat-anti-rabbit secondary antibody. The Westerns were performed and results are shown in FIG. 8. The amounts of CODH in ACS90 and ACS91 were estimated at 50 ng by comparison to the control lanes. Expression of CODH-ACS operon genes including 2 CODH subunits and the methyltransferase were confirmed via Western blot analysis. Therefore, the recombinant E. coli cells express multiple components of a 7 gene operon. In addition, both the methyltransferase and corrinoid iron sulfur protein were active in the same recombinant E. coli cells. These proteins are part of the same operon cloned into the same cells.

Figure 9:
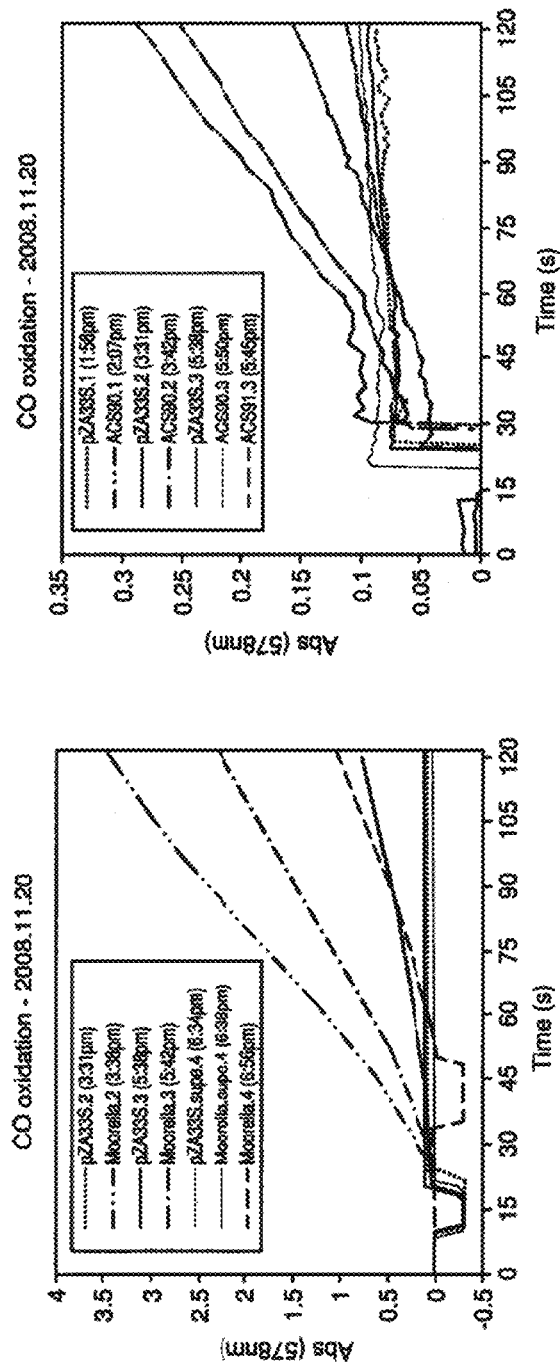
FIG. 9 shows CO oxidation assay results. Cells (*M. thermoacetica* or *E. coli* with the CODH/ACS operon; ACS90 or ACS91 or empty vector: pZA33S) were grown and extracts prepared. Assays were performed at 55° C. at various times on the day the extracts were prepared. Reduction of methylviologen was followed at 578 nm over a 120 sec time course.

The CO oxidation assays were repeated using extracts of Moorella thermoacetica cells for the positive controls. Though CODH activity in E. coli ACS90 and ACS91 was measurable, it was at about 130-150× lower than the M. thermoacetica control. The results of the assay are shown in FIG. 9. Briefly, cells (M. thermoacetica or E. coli with the CODH/ACS operon; ACS90 or ACS91 or empty vector: pZA33S) were grown and extracts prepared as described herein. Assays were performed as described above at 55° C. at various times on the day the extracts were prepared. Reduction of methylviologen was followed at 578 nm over a 120 sec time course.

These results describe the CO oxidation (CODH) assay and results. Recombinant E. coli cells expressed CO oxidation activity as measured by the methyl viologen reduction assay.

EXAMPLE V

E. coli CO Tolerance Experiment and CO Concentration Assay

Myoglobin Assay

This example describes the tolerance of E. coli for high concentrations of CO.

To test whether or not E. coli can grow anaerobically in the presence of saturating amounts of CO, cultures were set up in 120 ml serum bottles with 50 ml of Terrific Broth medium (plus reducing solution, $NiCl_2$, $Fe(II)NH_4SO_4$, cyanocobalamin, IPTG, and chloramphenicol) as described above for anaerobic microbiology in small volumes. One half of these bottles were equilibrated with nitrogen gas for 30 min. and one half was equilibrated with CO gas for 30 min. An empty vector (pZA33) was used as a control, and cultures containing the pZA33 empty vector as well as both ACS90 and ACS91 were tested with both $N_2$ and CO. All were inoculated and grown for 36 hrs with shaking (250 rpm) at 37° C. At the end of the 36 hour period, examination of the flasks showed high amounts of growth in all. The bulk of the observed growth occurred overnight with a long lag.

Given that all cultures appeared to grow well in the presence of CO, the final CO concentrations were confirmed. This was performed using an assay of the spectral shift of myoglobin upon exposure to CO. Myoglobin reduced with sodium dithionite has an absorbance peak at 435 nm; this peak is shifted to 423 nm with CO. Due to the low wavelength and need to record a whole spectrum from 300 nm on upwards, quartz cuvettes must be used. CO concentration is measured against a standard curve and depends upon the Henry's Law constant for CO of maximum water solubility=970 micromolar at 20° C. and 1 atm.

For the myoglobin test of CO concentration, cuvettes were washed 10× with water, 1× with acetone, and then stoppered as with the CODH assay. $N_2$ was blown into the cuvettes for ~10 min. A volume of 1 ml of anaerobic buffer (HEPES, pH 8.0, 2 mM DTT) was added to the blank (not equilibrated with CO) with a Hamilton syringe. A volume of 10 microliter myoglobin (~1 mM—can be varied, just need a fairly large amount) and 1 microliter dithionite (20 mM stock) were added. A CO standard curve was made using CO saturated buffer added at 1 microliter increments. Peak height and shift was recorded for each increment. The cultures tested were pZA33/CO, ACS90/CO, and ACS91/CO. Each of these was added in 1 microliter increments to the same cuvette. Midway through the experiment a second cuvette was set up and used. The results are shown in Table II.

TABLE II

| Strain and Growth Conditions | Carbon Monoxide Concentrations, 36 hrs. Final CO concentration (micromolar) |
|---|---|
| pZA33-CO | 930 |
| ACS90-CO | 638 |
|  | 494 |
|  | 734 |
|  | 883 |
| ave | 687 |
| SD | 164 |
| ACS91-CO | 728 |

TABLE II-continued

| Strain and Growth Conditions | Carbon Monoxide Concentrations, 36 hrs. Final CO concentration (micromolar) |
|---|---|
|  | 812 |
|  | 760 |
|  | 611 |
| ave. | 728 |
| SD | 85 |

The results shown in Table II indicate that the cultures grew whether or not a strain was cultured in the presence of CO or not. These results indicate that E. coli can tolerate exposure to CO under anaerobic conditions and that E. coli cells expressing the CODH-ACS operon can metabolize some of the CO.

These results demonstrate that E. coli cells, whether expressing CODH/ACS or not, were able to grow in the presence of saturating amounts of CO. Furthermore, these grew equally well as the controls in nitrogen in place of CO. This experiment demonstrated that laboratory strains of E. coli are insensitive to CO at the levels achievable in a syngas project performed at normal atmospheric pressure. In addition, preliminary experiments indicated that the recombinant E. coli cells expressing CODH/ACS actually consumed some CO, probably by oxidation to carbon dioxide.

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A method for producing caprolactone, said method comprising culturing a non-naturally occurring microorganism for a sufficient period of time to produce caprolactone, wherein said caprolactone is produced at an intracellular concentration of about 0.1 mM to about 200 mM, wherein said non-naturally occurring microorganism comprises a caprolactone pathway comprising at least one exogenous nucleic acid encoding a caprolactone pathway enzyme expressed in a sufficient amount to produce caprolactone and wherein said caprolactone pathway comprises a pathway selected from:
(1) 1D, 1A, 1B, and 1C;
(2) 1E, 1B, 1C and 1D;
(3) 1F, 1A, 1B, 1C and 1D;
(4) 1F, 1E, 1B, 1C and 1D;
(5) 1A, 1B and 1G;
(6) 1E, 1B and 1G;
(7) 1F, 1A, 1B and 1G;
(8) 1F, 1E, 1B and 1G;
(9) 1A, 1B, 1C, 1J and 1I;
(10) 1E, 1B, 1C, 1J and 1I;
(11) 1F, 1A, 1B, 1C, 1J and 1I;
(12) 1F, 1E, 1B, 1C, 1J and 1I;
(13) 1A, 1B, 1H and 1I;
(14) 1E, 1B, 1H and 1I;
(15) 1F, 1A, 1B, 1H and 1I;
(16) 1F, 1E, 1B, 1H and 1I;
(17) 2A, 2B, 2C, 2D, 2E and 2F;
(18) 2A, 2B, 2C, 2D and 2G;

(19) 2A, 2B, 2C, 2D, 2E, 2J and 2I;
(20) 2A, 2B, 2C, 2D, 2H and 2I;
(21) 4A, 4B, 4C, 4D and 3A; and
(22) 5A, 5B, 5C an 3A, wherein 1A is an adipyl-CoA reductase, wherein 1B is an adipate semialdehyde reductase, wherein 1C is a 6-hydroxyhexanoyl-CoA transferase or a 6-hydroxyhexanoyl-CoA synthetase, wherein 1D is a 6-hydroxyhexanoyl-CoA cyclase or spontaneous cyclization, wherein 1E is an adipate reductase, wherein 1F is an adipyl-CoA transferase, an adipyl-CoA synthetase or an adipyl-CoA hydrolase, wherein 1G is a 6-hydroxyhexanoate cyclase, wherein 1H is a 6-hydroxyhexanoate kinase, wherein 1I is a 6-hydroxyhexanoyl phosphate cyclase or spontaneous cyclization, wherein 1J is a phosphotrans-6-hydroxyhexanoylase, wherein 2A is a 4-hydroxybutyryl-CoA:acetyl-CoA acyltransferase, wherein 2B is a 3-oxo-6-hydroxyhexanoyl-CoA reductase, wherein 2C is a 3,6-dihydroxyhexanoyl-CoA dehydratase, wherein 2D is a 6-hydroxyhex-2-enoyl-CoA reductase, wherein 2E is a 6-hydroxyhexanoyl-CoA transferase, a 6-hydroxyhexanoyl-CoA synthetase or a 6-hydroxyhexanoyl-CoA hydrolase, wherein 2F is a 6-hydroxyhexanoate cyclase, wherein 2G is a 6-hydroxyhexanoyl-CoA cyclase or spontaneous cyclization, wherein 2H is a phosphotrans-6-hydroxyhexanoylase, wherein 2I is a 6-hydroxyhexanoyl phosphate cyclase or spontaneous cyclization, wherein 2J is a 6-hydroxyhexanoate kinase, wherein 3A is a cyclohexanone monooxygenase, wherein 4A is an adipate semialdehyde dehydratase, wherein 4B is a cyclohexane-1,2-dione reductase, wherein 4C is a 2-hydroxycyclohexanone reductase, wherein 4D is a cyclohexane-1,2-diol dehydratase, wherein 5A is a 2-ketocyclohexane-1-carboxoyl-CoA hydrolase (acting on C-C), wherein 5B is a 2-ketocyclohexane-1-carboxoyl-CoA transferase, a 2-ketocyclohexane-1-carboxoyl-CoA synthetase or a 2-ketocyclohexane-1-carboxoyl-CoA hydrolase, and wherein 5C is a 2-ketocyclohexane-1-carboxylate decarboxylase.

2. The method of claim 1, wherein said intracellular concentration of said caprolactone is about 3 mM to about 150 mM.

3. The method of claim 1, wherein said intracellular concentration of said caprolactone is about 8 mM to about 100 mM.

4. The method of claim 1, wherein said caprolactone is separated from other components in said culture.

5. The method of claim 4, wherein said separating comprises extraction, continuous liquid-liquid extraction, pervaporation, membrane filtration, membrane separation, reverse osmosis, electrodialysis, distillation, crystallization, centrifugation, extractive filtration, ion exchange chromatography, absorption chromatography, or ultrafiltration.

6. The method of claim 1, wherein said microbial organism comprises two, three, four, five, six or seven exogenous nucleic acids each encoding a caprolactone pathway enzyme.

7. The method of claim 1, wherein said microbial organism comprises exogenous nucleic acids encoding each of the enzymes of at least one of the pathways selected from (1)-(22).

8. The method of claim 1, wherein said culturing is performed in a fermentation broth comprising glucose.

9. The method of claim 1, wherein said culturing is performed in a fermentation broth comprising methanol.

10. The method of claim 1, wherein said non-naturally occurring microbial further comprises:

(i) a reductive TCA pathway comprising at least one exogenous nucleic acid encoding a reductive TCA pathway enzyme, wherein said at least one exogenous nucleic acid is selected from an ATP-citrate lyase, citrate lyase, a citryl-CoA synthetase, a citryl-CoA, a fumarate reductase, and an alpha-ketoglutarate:ferredoxin oxidoreductase;

(ii) a reductive TCA pathway comprising at least one exogenous nucleic acid encoding a reductive TCA pathway enzyme, wherein said at least one exogenous nucleic acid is selected from a pyruvate:ferredoxin oxidoreductase, a phosphoenolpyruvate carboxylase, a phosphoenolpyruvate carboxykinase, a CO dehydrogenase, and an H2 hydrogenase; or (iii) at least one exogenous nucleic acid encodes an enzyme selected from a CO dehydrogenase, an H2 hydrogenase, and combinations thereof.

11. The method of claim 1, wherein said exogenous nucleic acid is a heterologous nucleic acid.

12. The method of claim 1, wherein said non-naturally occurring microorganism is generated in *E. coli*.

13. Bioderived caprolactone synthesized from the method of claim 1 having a carbon-12, carbon-13 and carbon-14 isotope ratio that reflects an atmospheric carbon dioxide uptake source.

14. A composition comprising at least 3 mM caprolactone and a viable non-naturally occurring microbial organism having a caprolactone pathway and comprising at least one exogenous nucleic acid encoding a caprolactone pathway enzyme expressed in a sufficient amount to produce caprolactone, wherein said caprolactone pathway comprises a pathway selected from:

(1) 1D, 1A, 1B, and 1C;
(2) 1E, 1B, 1C and 1D;
(3) 1F, 1A, 1B, 1C and 1D;
(4) 1F, 1E, 1B, 1C and 1D;
(5) 1A, 1B and 1G;
(6) 1E, 1B and 1G;
(7) 1F, 1A, 1B and 1G;
(8) 1F, 1E, 1B and 1G;
(9) 1A, 1B, 1C, 1J and 1I;
(10) 1E, 1B, 1C, 1J and 1I;
(11) 1F, 1A, 1B, 1C, 1J and 1I;
(12) 1F, 1E, 1B, 1C, 1J and 1I;
(13) 1A, 1B, 1H and 1I;
(14) 1E, 1B, 1H and 1I;
(15) 1F, 1A, 1B, 1H and 1I;
(16) 1F, 1E, 1B, 1H and 1I;
(17) 2A, 2B, 2C, 2D, 2E and 2F;
(18) 2A, 2B, 2C, 2D and 2G;
(19) 2A, 2B, 2C, 2D, 2E, 2J and 2I;
(20) 2A, 2B, 2C, 2D, 2H and 2I;
(21) 4A, 4B, 4C, 4D and 3A; and
(22) 5A, 5B, 5C an 3A, wherein 1A is an adipyl-CoA reductase, wherein 1B is an adipate semialdehyde reductase, wherein 1C is a 6-hydroxyhexanoyl-CoA transferase or a 6-hydroxyhexanoyl-CoA synthetase, wherein 1D is a 6-hydroxyhexanoyl-CoA cyclase or spontaneous cyclization, wherein 1E is an adipate reductase, wherein 1F is an adipyl-CoA transferase, an adipyl-CoA synthetase or an adipyl-CoA hydrolase, wherein 1G is a 6-hydroxyhexanoate cyclase, wherein 1H is a 6-hydroxyhexanoate kinase, wherein 1I is a 6-hydroxyhexanoyl phosphate cyclase or spontaneous cyclization, wherein 1J is a phosphotrans-6-hydroxyhexanoylase, wherein 2A is a 4-hydroxybutyryl-CoA:acetyl-CoA acyltransferase, wherein 2B is a 3-oxo-6-hydroxyhexanoyl-CoA reductase, wherein 2C is a 3,6-dihydroxyhexanoyl-CoA dehydratase, wherein 2D is a 6-hydroxyhex-2-enoyl-CoA reductase, wherein 2E is a 6-hydroxyhexanoyl-CoA transferase, a 6-hydroxyhexanoyl-CoA synthetase or a 6-hydroxyhexanoyl-CoA hydrolase, wherein 2F is a 6-hydroxyhexanoate cyclase, wherein 2G is a 6-hydroxyhexanoyl-CoA cyclase or spontaneous cyclization, wherein 2H is a phosphotrans-6-hydroxyhexanoylase, wherein 2I is a 6-hydroxyhexanoyl phosphate cyclase or spontaneous cyclization, wherein 2J is a 6-hydroxyhexanoate kinase, wherein 3A is a cyclohexanone monooxygenase, wherein 4A is an adipate semialdehyde dehydratase, wherein 4B is a cyclohexane-1,2-dione reductase, wherein 4C is a 2-hydroxycyclohexanone reductase, wherein 4D is a cyclohexane-1,2-diol dehydratase, wherein 5A is a 2-ketocyclohexane-1-carboxoyl-CoA hydrolase (acting on C-C), wherein 5B is a 2-ketocyclohexane-1-carboxoyl-CoA transferase, a 2-ketocyclohexane-1-carboxoyl-CoA synthetase or a 2-ketocyclohexane-1-carboxoyl-CoA hydrolase, and wherein 5C is a 2-ketocyclohexane-1-carboxylate decarboxylase.

15. The composition of claim 14, wherein said composition is a fermentation broth.

16. The composition of claim 14, wherein said caprolactone is present at an amount of at least 10 mM, 20 mM, 50 mM, or 80 mM.

17. The composition of claim 14, wherein said caprolactone comprises bioderived caprolactone.

18. The composition of claim 14, wherein said microbial organism comprises two, three, four, five, six or seven exogenous nucleic acids each encoding a caprolactone pathway enzyme.

19. The composition of claim 14, wherein said microbial organism comprises exogenous nucleic acids encoding each of the enzymes of at least one of the pathways selected from (1)-(22).

20. The composition of claim 14, wherein said non-naturally occurring microorganism is generated in *E. coli*.

* * * * *